United States Patent
Agbandje-McKenna et al.

(10) Patent No.: US 11,905,524 B2
(45) Date of Patent: Feb. 20, 2024

(54) AAV CHIMERAS

(71) Applicant: University of Florida Research Foundation, Incorporated, Gainesville, FL (US)

(72) Inventors: Mavis Agbandje-McKenna, Gainesville, FL (US); Mario Mietzsch, Gainesville, FL (US); Robert McKenna, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/978,657

(22) PCT Filed: Mar. 6, 2019

(86) PCT No.: PCT/US2019/021048
§ 371 (c)(1),
(2) Date: Sep. 4, 2020

(87) PCT Pub. No.: WO2019/173538
PCT Pub. Date: Sep. 12, 2019

(65) Prior Publication Data
US 2020/0407753 A1     Dec. 31, 2020

Related U.S. Application Data

(60) Provisional application No. 62/639,466, filed on Mar. 6, 2018.

(51) Int. Cl.
*C07H 21/02* (2006.01)
*C12N 15/861* (2006.01)

(52) U.S. Cl.
CPC .. *C12N 15/861* (2013.01); *C12N 2750/14143* (2013.01); *C12N 2750/14151* (2013.01)

(58) Field of Classification Search
None
See application file for complete search history.

(56) References Cited

U.S. PATENT DOCUMENTS 6,491,907 B1 * 12/2002 Rabinowitz ............... A61P 1/18
977/804
2003/0040101 A1    2/2003 Wilson et al.
(Continued)

FOREIGN PATENT DOCUMENTS

| CN | 1461805 A | 12/2003 |
| CN | 101724608 A | 6/2010 |

(Continued)

OTHER PUBLICATIONS

Hickman et al., "Structural Unity among Viral Origin Binding Proteins: Crystal Structure of the Nuclease Domain of Adeno-Associated Virus Rep," Molecular Cell, vol. 10: 327-337 (Year: 2002).*

(Continued)

*Primary Examiner* — M Franco G Salvoza
(74) *Attorney, Agent, or Firm* — Wolf, Greenfield & Sacks, P.C.

(57) ABSTRACT

Provided herein are compositions and methods for packaging a recombinant adeno-associated vims (rAAV) particle comprising using inverted terminal repeats (ITRs) and rep genes of different serotypes and/or using chimeric rep genes.

5 Claims, 22 Drawing Sheets

Specification includes a Sequence Listing.

(56) References Cited

U.S. PATENT DOCUMENTS

2003/0148506 A1     8/2003    Kotin et al.
2013/0109742 A1*   5/2013    Hewitt .................... C12N 7/00
                                                                                    435/235.1

FOREIGN PATENT DOCUMENTS

WO     WO 2003/104392 A2    12/2003
WO     WO 2011/088081 A1     7/2011
WO     WO 2017/100674 A1     6/2017

OTHER PUBLICATIONS

Extended European Search Report dated Feb. 4, 2022 for Application No. EP19764877.7.
Hewitt et al., Creating a novel origin of replication through modulating DNA-protein interfaces. PLoS One. Jan. 22, 2010;5(1):e8850. doi: 10.1371/journal.pone.0008850.
Mietzsch et al., Improved Genome Packaging Efficiency of Adeno-associated Virus Vectors Using Rep Hybrids. J Virol. Sep. 9, 2021;95(19):e0077321. doi: 10.1128/JVI.00773-21. Epub Jul. 21, 2021.
Yoon et al., Amino-terminal domain exchange redirects origin-specific interactions of adeno-associated virus rep78 in vitro. J Virol. Apr. 2001;75(7):3230-9. doi: 10.1128/JVI.75.7.3230-3239.2001.
Invitation to Pay Additional Fees dated May 9, 2019 in connection with Application No. PCT/US2019/021048.
International Search Report and Written Opinion dated Jul. 5, 2019 in connection with Application No. PCT/US2019/021048.
International Preliminary Report on Patentability dated Sep. 17, 2020 in connection with Application No. PCT/US2019/021048.
Chiorini et al., Adeno-associated virus (AAV) type 5 Rep protein cleaves a unique terminal resolution site compared with other AAV serotypes. J Virol. May 1999;73(5):4293-8. doi: 10.1128/JVI.73.5.4293-4298.1999.
Rabinowitz et al., Cross-packaging of a single adeno-associated virus (AAV) type 2 vector genome into multiple AAV serotypes enables transduction with broad specificity. J Virol. Jan. 2002;76(2):791-801. doi: 10.1128/jvi.76.2.791-801.2002.
Mori et al., Two novel adeno-associated viruses from cynomolgus monkey: psuedotyping characterization of capsid protein. Virology. Dec. 20, 2004;330(2):375-383. doi: 10.1016/j.virol.2004.10.012.
Smith et al., An adeno-associated virus (AAV) initiator protein, Rep78, catalyzes the cleavage and ligation of single-stranded AAV ori DNA. J Virol. Apr. 2000;74(7):3122-3129. doi: 10.1128/jvi.74.7.3122-3129.2000.
Grimm et al., Liver transduction with recombinant adeno-associated virus is primarily restricted by capsid serotype not vector genotype. J Virol. Jan. 2006;80(1):426-39. doi: 10.1128/JVI.80.1.426-439.2006.

\* cited by examiner

|  | AAV1 | AAV2 | AAV3 | AAV4 | AAV5 | AAV6 | AAV7 | AAV8 | AAV9 |
|---|---|---|---|---|---|---|---|---|---|
| AAV1 |  | 81.6 | 85.1 | 77.7 | 56.3 | 81.6 | 95.9 | N/A | N/A |
| AAV2 | 87.3 |  | 82.3 | 81.1 | 54.5 | 100 | 83.6 | N/A | N/A |
| AAV3 | 88.5 | 88.9 |  | 78.5 | 55.1 | 82.3 | 87.8 | N/A | N/A |
| AAV4 | 89.8 | 90.2 | 92.6 |  | 54.5 | 81.1 | 80.4 | N/A | N/A |
| AAV5 | 57.7 | 58.0 | 58.0 | 58.3 |  | 54.4 | 55.1 | N/A | N/A |
| AAV6 | 99.4 | 87.3 | 88.5 | 89.4 | 58.0 |  | 83.6 | N/A | N/A |
| AAV7 | 97.6 | 88.3 | 89.6 | 90.2 | 58.3 | 97.6 |  | N/A | N/A |
| AAV8 | 95.0 | 85.4 | 87.2 | 87.7 | 57.2 | 95.0 | 96.0 |  | N/A |
| AAV9 | N/A | N/A | N/A | N/A | N/A | N/A | N/A |  |  |

ITR DNA sequence identity [%]

Rep78 amino acid sequence identity [%]

FIG. 5

| Rep variant plasmid | genome packaging efficiency |
|---|---|
| R2V1 | reference |
| R2n1V1 | 1.7-fold higher |
| R2d1V1 | 4.9-fold higher |
| R2h1V1 | 3.8-fold higher |

| Rep variant plasmid | genome packaging efficiency |
|---|---|
| R1c2V1 | 3.0-fold higher |
| R1nc2V1 | 1.4-fold higher |
| R1dc2V1 | 2.0-fold higher |
| R1hc2V1 | 4.5-fold higher |

FIG. 7B

| | AAV1 expression plasmids (all encode the AAV1 cap gene) | | |
|---|---|---|---|
| plasmid name | description of rep gene | VP expression | genome packaging efficiency |
| pR1c2V1 | AAV1 rep gene (ATG start codon) with AAV2 Rep C-terminus (aa 371-621) | similar to pR2V1 | 3.0-fold higher than pR2V1 |
| pR1hc2V1 | AAV1 rep gene (ATG start codon) with AAV2 Rep helicase domain (aa 243-370) + C-terminus (aa 371-621) | similar to pR2V1 | 4.5-fold higher than pR2V1 |
| pR2d1V1 | AAV2 rep gene (ACG start codon) with AAV1 Rep DNA-binding domain (aa 103-242) | similar to pR2V1 | 4.9-fold higher than pR2V1 |
| pR2h1V1 | AAV2 rep gene (ACG start codon) with AAV1 Rep helicase domain (aa 243-370) | similar to pR2V1 | 3.8-fold higher than pR2V1 |
| variants to be tested | | | |
| pR1y2V1 | AAV1 rep gene (ATG start codon) with AAV2 Rep p40 region (aa 371-529) | | |
| pR1z2V1 | AAV1 rep gene (ATG start codon) with AAV2 zinc finger domain (aa 530-621) | | |
| pR1hy2V1 | AAV1 rep gene (ATG start codon) with AAV2 Rep helicase domain (aa 243-370) + AAV2 Rep p40 region (aa 371-529) | | |
| pR1hz2V1 | AAV1 rep gene (ATG start codon) with AAV2 Rep helicase domain (aa 243-370) + AAV2 zinc finger domain (aa 530-621) | | |
| pR2dy1V1 | AAV2 rep gene (ACG start codon) with AAV1 Rep DNA-binding domain (aa 103-242) + AAV1 Rep p40 region (aa 371-530) | | |
| pR2dz1V1 | AAV2 rep gene (ACG start codon) with AAV1 Rep DNA-binding domain (aa 103-242) + AAV1 zinc finger domain (aa 531-623) | | |

FIG. 8

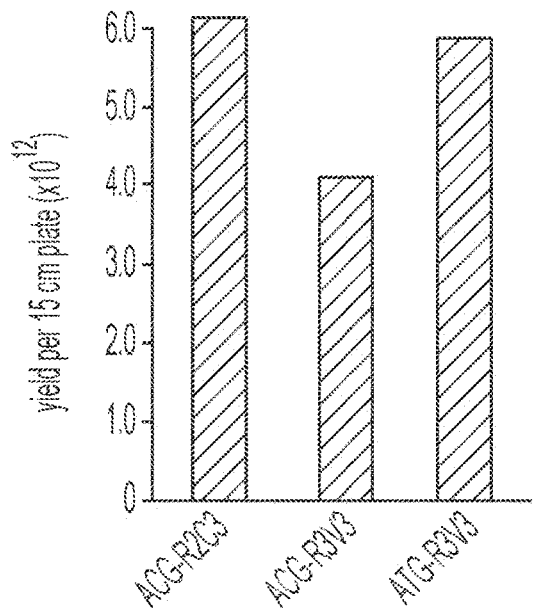

FIG. 9C

| AAV3 expression plasmids (all contain AAV3 cap gene) | |
|---|---|
| plasmid name | description of rep gene |
| pR2V3 | AAV2 rep gene (ACG start codon) |
| pACG-R3V3 | AAV3 rep gene (ACG start codon) |
| pATG-R3V3 | AAV3 rep gene (ATG start codon) |
| pR1c2V3 | AAV1 rep gene (ACG start codon) with AAV2 Rep C-terminus (aa 371-621) |
| pR1hc2V3 | AAV1 rep gene (ATG start codon) with AAV2 Rep helicase domain (aa 243-370) + C-terminus (aa 371-621) |
| pR2d1V3 | AAV2 rep gene (ACG start codon) with AAV1 Rep DNA-binding domain (aa 103-242) |
| pR2h1V3 | AAV2 rep gene (ACG start codon) with AAV1 Rep helicase domain (aa 243-370) |
| pR8d1c2V3 | AAV8 rep gene (ATG start codon) with AAV1 Rep DNA-binding domain (aa 103-242) + AAV2 C-terminus (aa 371-621) |
| pR3h2V3 | AAV3 rep gene (ATG start codon) with AAV2 Rep helicase domain (aa 243-370) |
| pR3d2V3 | AAV3 rep gene (ATG start codon) with AAV2 Rep DNA-binding domain (aa 103-242) |
| variants to be tested | |

FIG. 9D

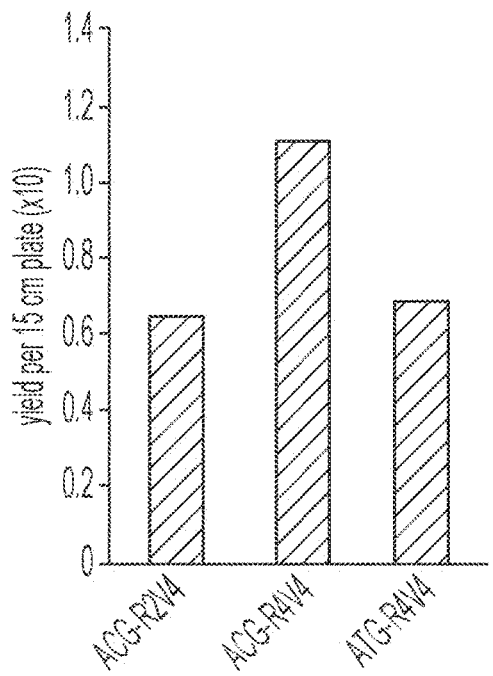

FIG. 10C

| AAV4 expression plasmids (all contain AAV4 cap gene) | |
|---|---|
| plasmid name | description of rep gene |
| pR2V4 | AAV2 rep gene (ACG start codon) |
| pACG-R4V4 | AAV4 rep gene (ACG start codon) |
| pATG-R4V4 | AAV4 rep gene (ATG start codon) |
| pR1c2V4 | AAV1 rep gene (ACG start codon) with AAV2 Rep C-terminus (aa 371-621) |
| pR1hc2V4 | AAV1 rep gene (ATG start codon) with AAV2 Rep helicase domain (aa 243-370) + C-terminus (aa 371-621) |
| pR2d1V4 | AAV2 rep gene (ACG start codon) with AAV1 Rep DNA-binding domain (aa 103-242) |
| pR2h1V4 | AAV2 rep gene (ACG start codon) with AAV1 Rep helicase domain (aa 243-370) |
| pR8d1c2V4 | AAV8 rep gene (ATG start codon) with AAV1 Rep DNA-binding domain (aa 103-242) + AAV2 C-terminus (aa 371-621) |
| pR4h2V4 | AAV4 rep gene (ACG start codon) with AAV2 Rep helicase domain (aa 243-370) |
| pR4d2V4 | AAV4 rep gene (ACG start codon) with AAV2 Rep DNA-binding domain (aa 103-242) |
| | variants to be tested |

FIG. 10D

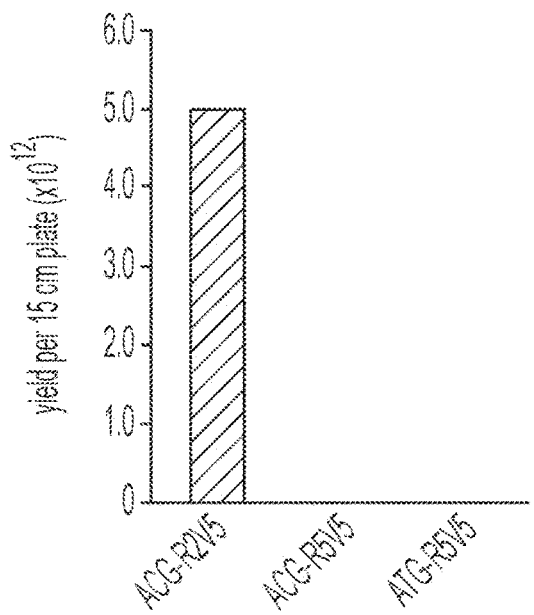

FIG. 11C

| AAV5 expression plasmids (all contain AAV5 cap gene) | |
|---|---|
| plasmid name | description of rep gene |
| pR2V5 | AAV2 rep gene (ACG start codon) |
| pACG-R5V5 | AAV5 rep gene (ACG start codon) |
| pATG-R5V5 | AAV5 rep gene (ATG start codon) |
| pR1c2V5 | AAV1 rep gene (ACG start codon) with AAV2 Rep C-terminus (aa 371-621) |
| pR1hc2V5 | AAV1 rep gene (ATG start codon) with AAV2 Rep helicase domain (aa 243-370) + C-terminus (aa 371-621) |
| pR2d1V5 | AAV2 rep gene (ACG start codon) with AAV1 Rep DNA-binding domain (aa 103-242) |
| pR2h1V5 | AAV2 rep gene (ACG start codon) with AAV1 Rep helicase domain (aa 243-370) |
| pR8d1c2V5 | AAV8 rep gene (ATG start codon) with AAV1 Rep DNA-binding domain (aa 103-242) + AAV2 C-terminus (aa 371-621) |
| pR5h2V5 | AAV5 rep gene (ACG start codon) with AAV2 Rep helicase domain (aa 243-370) |
| pR5d2V5 | AAV5 rep gene (ACG start codon) with AAV2 Rep DNA-binding domain (aa 103-242) |
| variants to be tested | |

FIG. 11D

| Rep variant plasmid | genome packaging efficiency |
|---|---|
| R2V6 | reference |
| R8d1c2V6 | ~2.9-fold higher |
| R1hc2V6 | ~2.4-fold higher |

FIG. 12B

| plasmid name | AAV1 expression plasmids (all encode the AAV1 cap gene) | | |
|---|---|---|---|
| | description of rep gene | VP expression | genome packaging efficiency |
| pR8d1c2V6 | AAV8 rep gene (ATG start codon) with AAV1 Rep DNA-binding domain (aa 103-242) + AAV2 Rep C-terminus (aa 371-621) | similar to pR2V6 | 2.9-fold higher than pR2V6 |
| pR1hc2V6 | AAV1 rep gene (ATG start codon) with AAV2 Rep helicase domain (aa 243-370) + C-terminus (aa 371-621) | similar to pR2V6 | 2.4-fold higher than pR2V6 |
| variants to be tested | | | |
| pR8d1y2V6 | AAV8 rep gene (ATG start codon) with AAV1 Rep DNA-binding domain (aa 103-242) + AAV2 Rep p40 region (aa 371-529) | | |
| pR8d1z2V6 | AAV8 rep gene (ATG start codon) with AAV1 Rep DNA-binding domain (aa 103-242) + AAV2 zinc finger domain (aa 530-621) | | |
| pR1hy2V6 | AAV1 rep gene (ATG start codon) with AAV2 Rep helicase domain (aa 243-370) + AAV2 Rep p40 region (aa 371-529) | | |
| pR1hz2V6 | AAV1 rep gene (ATG start codon) with AAV2 Rep helicase domain (aa 243-370) + AAV2 zinc finger domain (aa 530-621) | | |

FIG. 12C

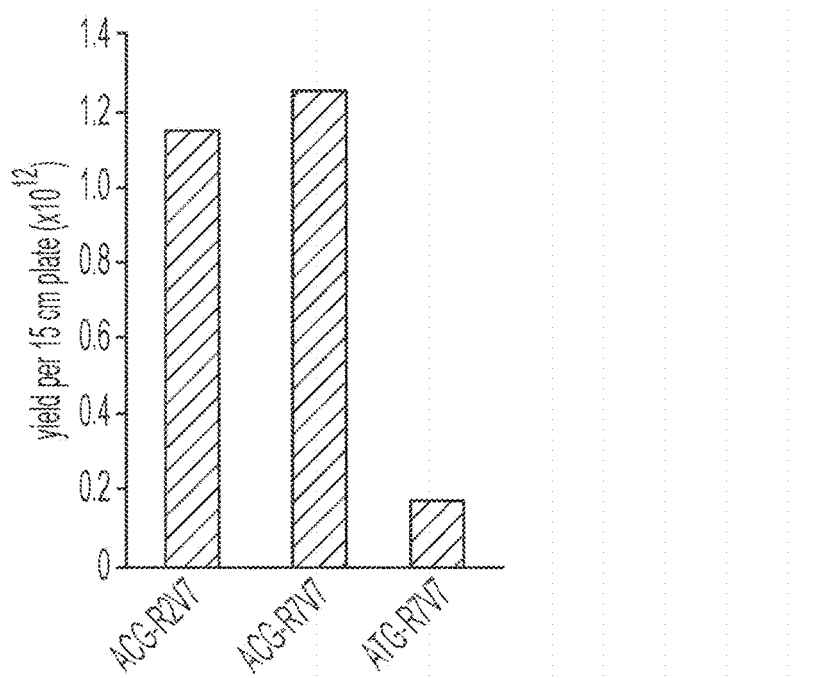

FIG. 13C

| AAV7 expression plasmids (all contain AAV7 cap gene) |  |
|---|---|
| plasmid name | description of rep gene |
| pR2V7 | AAV2 rep gene (ACG start codon) |
| pACG-R7V7 | AAV6 rep gene (ACG start codon) |
| pATG-R7V7 | AAV6 rep gene (ATG start codon) |
| pR1c2V7 | AAV1 rep gene (ACG start codon) with AAV2 Rep C-terminus (aa 371-621) |
| pR1hc2V7 | AAV1 rep gene (ATG start codon) with AAV2 Rep helicase domain (aa 243-370) + C-terminus (aa 371-621) |
| pR2d1V7 | AAV2 rep gene (ACG start codon) with AAV1 Rep DNA-binding domain (aa 103-242) |
| pR2h1V7 | AAV2 rep gene (ACG start codon) with AAV1 Rep helicase domain (aa 243-370) |
| pR8d1c2V7 | AAV8 rep gene (ATG start codon) with AAV1 Rep DNA-binding domain (aa 103-242) + AAV2 C-terminus (aa 371-621) |
| pR7hc2V7 | AAV7 rep gene (ACG start codon) with AAV2 Rep helicase domain (aa 243-370) + AAV2 C-terminus (aa 371-621) |
| pR7dc2V7 | AAV7 rep gene (ACG start codon) with AAV2 Rep DNA-binding domain (aa 103-242) + AAV2 C-terminus (aa 371-621) |
| | variants to be tested |

FIG. 13D

| plasmid name | description of rep gene | VP expression | genome packaging |
|---|---|---|---|
| pR8d1c2V8 | AAV8 rep gene (ATG start codon) with AAV1 Rep DNA-binding domain (aa 103-242) + AAV2 Rep C-terminus (aa 371-621) | high, similar to pR2V8 | higher than pR2V8 (~3 fold) |
| pR1c2V8 | AAV1 rep gene (ATG start codon) with AAV2 Rep C-terminus (aa 371-621) | high, similar to pR2V8 | higher than pR2V8 (~4 fold) |
| pR8p1f2c2V8 | AAV8 rep gene (ATG start codon) with six nucleotide deletions in the AAV8 DNA-binding domain + AAV2 Rep C-terminus (aa 371-621) | high, similar to pR2V8 | higher than pR2V8 (~4 fold) |

FIG. 16A

```
SEQ ID NO: 186   Query   AAGTCCATGGTGCTAGGCCCGCTTCCTGAGTCAGATTCGGGGAAAAGCTGGTCCAGACCAT
SEQ ID NO: 187   Sbjct   AAGTCCATGGTGCTAGGCCCGCTTCCTGAGTCAGATTCGGGGAAAAGCTGGTCCAGACCAT Query   CTACCTGGGGGTCGAGCCCCACCTTGCCCAACTGGTTCGGGTGACCAAGAGCGTA
                 Sbjct   CTACCTGGGGGTCGAGCCCCACCTTGCCCAACTGGTTCGGGTGACCAAAGAGCGGGTA Query   ATGGGCCCCGGCGGCGGGGGGAACAAGGTGGTGGACGAGTGCTACATCCCCAACTACCTCCTG
                 Sbjct   ATGGGCCCCGGCGGCGGGGGGAACAAGGTGGTGGACGAGTGCTACATCCCCAACTACCTCCTG
```

FIG. 16B

ID NO: 125 (and
AAV CHIMERAS

RELATED APPLICATIONS

This application is a national stage filing under 35 U.S.C. § 371 of International Patent Application Serial No. PCT/US2019/021048, filed Mar. 6, 2019, which claims the benefit of U.S. Provisional Application No. 62/639,466, filed on Mar. 6, 2018, each of which is incorporated herein by reference in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 4, 2020, is named U119670055US01-SEQ-PRW.txt, and is 92 bytes in size.

BACKGROUND

Adeno-associated virus (AAV) particles are commonly used for research and also for gene therapy applications, including several in clinical development.

Methods and compositions for producing recombinant adeno-associated virus (rAAV) particles, in both small and large scale, are useful for research, pre-clinical, and clinical applications.

SUMMARY

Recombinant AAV particle production can involve culturing cells, introducing to those cells AAV genes and genes of interest that are desired to be packaged in rAAV particles, and allowing the cells to package (or produce) rAAV particles. Cells that package or produce rAAV particles are also referred to herein as "producer cells." AAV genes that are introduced to a producer cell generally include rep, cap, helper genes and inverted terminal repeats (ITRs) which flank one or more genes of interest. In the last decade numerous AAV cap genes from multiple natural serotypes and variants have been utilized for different gene therapy applications. In contrast, variation of rep and ITR sequences and how they influence rAAV particle packaging has not been explored. This application is related, at least in part, to the finding that both rep and ITR sequences can be varied to improve the packaging of rAAV particles of difference serotypes. In some embodiments, recombinant Rep proteins (e.g., chimeric Rep proteins) and/or genes encoding them as described in this application can be used in the production of rAAV particles comprising recombinant rAAV nucleic acids including one or more genes of interest flanked by ITR sequences (e.g., of different serotypes) as described in this application.

Accordingly, in one aspect, provided herein is a composition comprising a nucleic acid comprising a rep gene, wherein the rep gene is chimeric. In some embodiments, a rep gene comprises an N-terminus and a C-terminus (c). In some embodiments, an N terminus comprises an N-terminus domain (n), a DNA binding domain (d), and a helicase domain (h). In some embodiments, a C terminus comprises a NLS/p40 promoter domain (y) and a Zinc finger domain (z). In some embodiments, a rep gene is of serotype AAV1, AAV2, AAV3, AAV4, AAV6, AAV12, AAV13, AAV1 and AAV2, or AAV5 and AAV2, or is chimeric.

In some embodiments, an N terminus is of AAV1 serotype and the C terminus is of AAV2 serotype. In some embodiments, an N terminus is of AAV2 serotype and the C terminus is of AAV1 serotype. In some embodiments, an N terminus is of AAV2 serotype and the C terminus is of AAV5 serotype. In some embodiments, an N terminus is of AAV5 serotype and the C terminus is of AAV2 serotype.

In some embodiments, n, d, y, and z domains are of AAV2 serotype and an h domain is of AAV1 serotype. In some embodiments, n, h, y, and z domains are of AAV2 serotype and a d domain is of AAV1 serotype. In some embodiments, d, h, y, and z domains are of AAV2 serotype and a n domain is of AAV1 serotype. In some embodiments, n, d, and h domains are of AAV1 serotype and y and z domains are of AAV1 serotype. In some embodiments, d and h domains are of AAV1 serotype and n, y and z domains are of AAV2 serotype. In some embodiments, n and d domains are of AAV1 serotype and h, y, and z domains is of AAV2 serotype.

In some embodiments, n, d, and h domains are of AAV2 serotype and y and z domains are of AAV3 serotype. In some embodiments, a rep gene having n, d, and h domains are of AAV2 serotype and y and z domains are of AAV3 serotype has a start codon of sequence ACG. In some embodiments, a rep gene is of AAV3 serotype, and has a start codon of sequence ATG.

In some embodiments, a rep gene is of AAV4 serotype, and has a start codon of sequence ACG.

In some embodiments, a rep gene is of AAV2 serotype, and has a start codon of sequence ACG.

In some embodiments, n and h domains are of AAV8 serotype and d, y and z domains are of AAV2 serotype. In some embodiments, n and d domains are of AAV1 serotype and h, y, and z domains are of AAV2 serotype.

In some embodiments, a rep gene is of AAV2 serotype, and has a start codon of sequence ACG. In some embodiments, a rep gene is of AAV7 serotype, and has a start codon of sequence ACG.

In some embodiments, n and h domains are of AAV8 serotype and the d, y, and z domains are of AAV2 serotype, and a rep gene has a start codon of sequence ATG. In some embodiments, n, h and d domains are of AAV1 serotype and the y and z domains are of AAV2 serotype, and a rep gene has a start codon of sequence ATG. In some embodiments, n and h domains are of AAV8 serotype, the following nucleotides are deleted in the d domain: T574, C592, C607, A637, G644, AND C657 according to SEQ ID NO: 125 (and resulting in SEQ ID NO: 126), y and z domains are of AAV2 serotype, and a rep gene has a start codon of sequence ATG.

In some embodiments, any one of the compositions described herein further comprises a nucleic acid comprising a cap gene. The cap gene may be of any serotype (e.g., 1, 2, 3, 4, 5, 6, 7, 8, 9, 10, 11, 12, or 13).

In some embodiments, the nucleic acid comprising the rep gene and the nucleic acid comprising the cap gene are comprised by a nucleic acid vector. In some embodiments, a nucleic acid vector comprising nucleic acid comprising a rep gene and the nucleic acid comprising a cap gene further comprises a nucleic acid comprising a pair of ITRs. In some embodiments, a gene of interest is flanked by the pair of ITRs.

Accordingly, in one aspect, provided herein is a method of packaging a recombinant adeno-associated virus (AAV) particle comprising contacting a cell that expresses a rep gene of a first serotype with a recombinant nucleic acid that comprises a pair of inverted terminal repeats (ITRs) of a second serotype. In some embodiments, a rep gene is expressed by transfecting or infecting the cell with a nucleic acid encoding the rep gene. In some embodiments, a rep gene is chimeric. A chimeric rep gene is one that comprises corresponding nucleic acid bases of more than AAV one serotype. In some embodiments, a rep gene is of serotype 1, 2, 3, 4, 6, 12, 13, 1 and 2, or 5 and 2.

In some embodiments of any one of the methods disclosed herein, Rep proteins encoded by a rep gene of serotype 1 and 2 comprise amino acids of serotype 1 in the N terminus and amino acids of serotype 2 in the C terminus. In some embodiments, Rep proteins encoded by a rep gene of serotype 1 and 2 comprise amino acids of serotype 2 in the N terminus and amino acids of serotype 1 in the C terminus. In some embodiments, Rep proteins encoded by a rep gene of serotype 2 and 5 comprise amino acids of serotype 2 in the N terminus and amino acids of serotype 5 in the C terminus. In some embodiments, Rep proteins encoded by a rep gene of serotype 5 and 2 comprise amino acids of serotype 5 in the N terminus and amino acids of serotype 2 in the C terminus.

In some embodiments of any one of the methods disclosed herein, the first serotype of the rep gene is serotype 1. In some embodiments, the first serotype of the rep gene is serotype 1, and the second serotype of the ITRs is serotype 1, 2, 3, 4, or 7. In some embodiments, the first serotype of the rep gene is serotype 1, and the second serotype of the ITRs is serotype 1. In some embodiments, the first serotype of the rep gene is serotype 1, and the second serotype of the ITRs is serotype 2. In some embodiments, the first serotype of the rep gene is serotype 1, and the second serotype of the ITRs is serotype 3. In some embodiments, the first serotype of the rep gene is serotype 1, and the second serotype of the ITRs is serotype 4. In some embodiments, the first serotype of the rep gene is serotype 1, and the second serotype of the ITRs is serotype 7.

In some embodiments of any one of the methods disclosed herein, the second serotype of the ITRs is serotype 6. In some embodiments of any one of the methods disclosed herein, the second serotype of the ITRs is serotype 6, and the first serotype of the rep gene is serotype 2, 3, 4, 6, 12, or 13. In some embodiments of any one of the methods disclosed herein, the second serotype of the ITRs is serotype 6, and the first serotype of the rep gene is serotype 2. In some embodiments of any one of the methods disclosed herein, the second serotype of the ITRs is serotype 6, and the first serotype of the rep gene is serotype 3. In some embodiments of any one of the methods disclosed herein, the second serotype of the ITRs is serotype 6, and the first serotype of the rep gene is serotype 4. In some embodiments of any one of the methods disclosed herein, the second serotype of the ITRs is serotype 6, and the first serotype of the rep gene is serotype 6. In some embodiments of any one of the methods disclosed herein, the second serotype of the ITRs is serotype 6, and the first serotype of the rep gene is serotype 12. In some embodiments of any one of the methods disclosed herein, the second serotype of the ITRs is serotype 6, and the first serotype of the rep gene is serotype 13.

In some embodiments of any one of the methods disclosed herein, the second serotype of the ITRs is serotype 1. In some embodiments of any one of the methods disclosed herein, the second serotype of the ITRs is serotype 1, and the first serotype of the rep gene is serotype 2, 3, 4, 12, or 13. In some embodiments of any one of the methods disclosed herein, the second serotype of the ITRs is serotype 1, and the first serotype of the rep gene is serotype 2. In some embodiments of any one of the methods disclosed herein, the second serotype of the ITRs is serotype 1, and the first serotype of the rep gene is serotype 3. In some embodiments of any one of the methods disclosed herein, the second serotype of the ITRs is serotype 1, and the first serotype of the rep gene is serotype 4. In some embodiments of any one of the methods disclosed herein, the second serotype of the ITRs is serotype 1, and the first serotype of the rep gene is serotype 12. In some embodiments of any one of the methods disclosed herein, the second serotype of the ITRs is serotype 1, and the first serotype of the rep gene is serotype 13.

In some embodiments, the Rep proteins encoded by a rep gene of serotype 1 and 2 comprise amino acids of serotype 1 in the N terminus and amino acids of serotype 2 in the C terminus, and the second serotype of the ITRs is serotype 1. In some embodiments, the Rep proteins encoded by a rep gene of serotype 1 and 2 comprise amino acids of serotype 1 in the N terminus and amino acids of serotype 2 in the C terminus, and the second serotype of the ITRs is serotype 6.

In some embodiments, the Rep proteins encoded by a rep gene of serotype 2 and 1 comprise amino acids of serotype 2 in the N terminus and amino acids of serotype 1 in the C terminus, and the second serotype of the ITRs is serotype 1. In some embodiments, the Rep proteins encoded by a rep gene of serotype 2 and 1 comprise amino acids of serotype 2 in the N terminus and amino acids of serotype 1 in the C terminus, and the second serotype of the ITRs is serotype 6.

In some embodiments, the Rep proteins encoded by a rep gene of serotype 2 and 5 comprise amino acids of serotype 2 in the N terminus and amino acids of serotype 5 in the C terminus, and the second serotype of the ITRs is serotype 2.

In some embodiments, the Rep proteins encoded by a rep gene of serotype 5 and 2 comprise amino acids of serotype 5 in the N terminus and amino acids of serotype 2 in the C terminus, and the second serotype of the ITRs is serotype 5.

In some embodiments, n, d, y, and z domains are of AAV2 serotype and an h domain is of AAV1 serotype. In some embodiments, n, h, y, and z domains are of AAV2 serotype and a d domain is of AAV1 serotype. In some embodiments, d, h, y, and z domains are of AAV2 serotype and a n domain is of AAV1 serotype. In some embodiments, n, d, and h domains are of AAV1 serotype and y and z domains are of AAV1 serotype. In some embodiments, d and h domains are of AAV1 serotype and n, y and z domains are of AAV2 serotype. In some embodiments, n and d domains are of AAV1 serotype and h, y, and z domains are of AAV2 serotype.

In some embodiments, n, d, and h domains are of AAV2 serotype and y and z domains are of AAV3 serotype. In some embodiments, a rep gene having n, d, and h domains are of AAV2 serotype and y and z domains are of AAV3 serotype has a start codon of sequence ACG. In some embodiments, a rep gene is of AAV3 serotype, and has a start codon of sequence ATG.

In some embodiments, a rep gene is of AAV4 serotype, and has a start codon of sequence ACG.

In some embodiments, a rep gene is of AAV2 serotype, and has a start codon of sequence ACG.

In some embodiments, n and h domains are of AAV8 serotype and d, y and z domains are of AAV2 serotype. In some embodiments, n and d domains are of AAV1 serotype and h, y, and z domains are of AAV2 serotype.

In some embodiments, a rep gene is of AAV2 serotype, and has a start codon of sequence ACG. In some embodiments, a rep gene is of AAV7 serotype, and has a start codon of sequence ACG.

In some embodiments, n and h domains are of AAV8 serotype and the d, y, and z domains are of AAV2 serotype, and a rep gene has a start codon of sequence ATG. In some embodiments, n, h and d domains are of AAV1 serotype and the y and z domains are of AAV2 serotype, and a rep gene has a start codon of sequence ATG. In some embodiments, n and h domains are of AAV8 serotype, the following nucleotides are deleted in the d domain: T574, C592, C607, A637, G644, AND C657 according to SEQ ID NO: 125 (and resulting in SEQ ID NO: 126), y and z domains are of AAV2 serotype, and a rep gene has a start codon of sequence ATG.

In some embodiments, any one of the compositions described herein further comprises a nucleic acid comprising a cap gene. The cap gene may be of any serotype (e.g., 1, 2, 3, 4, 5, 6, 7, 8, 9, 10, 11, 12, or 13)

In some embodiments of any one of the methods disclosed herein, a cells is also contacted with a recombinant nucleic acid that comprises a cap gene. In some embodiments of any one of the methods disclosed herein, a cell that expresses a rep gene and is contacted with a recombinant nucleic acid that comprises a pair of inverted terminal repeats (ITRs) of a second serotype also expresses a cap gene.

In some aspects, the present application also provides a cell comprising a rep gene of a first serotype and a pair of ITRs of a second serotype. A cell as provided herein may comprise any one of the combinations of ITRs and rep genes disclosed herein. In some embodiments, any one of the cells provided herein further comprises a cap gene.

BRIEF DESCRIPTION OF THE DRAWINGS

The following drawings form part of the present specification and are included to further demonstrate certain aspects of the present application, which can be better understood by reference to one or more of these drawings in combination with the detailed description of specific embodiments presented herein. It is to be understood that the data illustrated in the drawings in no way limit the scope of the application.

FIG. 5 shows percent sequence identity analysis for AAV ITR and Rep78 for AAV serotypes 1-9.

FIGS. 7A-7B show characterization and optimization of the rep gene for AAV1 vector production. FIG. 7A shows examples of AAV plasmid designs with variations in the rep gene. pR2V1 denotes a plasmid with a cap gene of AAV1 sequence, and a rep gene of AAV2 sequence. pR2h1V1 denotes a plasmid with a cap gene of AAV1 sequence, and a rep gene of AAV2 sequence with the exception that the helicase domain (h) is of AAV1 sequence. pR2d1V1 denotes a plasmid with a cap gene of AAV1 sequence, and a rep gene of AAV2 sequence with the exception that the DNA binding domain (d) is of AAV1 sequence. pR2n1V1 denotes a plasmid with a cap gene of AAV1 sequence, and a rep gene of AAV2 sequence with the exception that the N-terminus domain (n) is of AAV1 sequence. pR1c2V1 denotes a plasmid with a cap gene of AAV1 sequence, and a rep gene of AAV1 sequence with the exception that the C terminus (c), which consists of the NLS/p40 promoter domain (y) and the zinc-finger domain (z) is of AAV2 sequence. pR1hc2V1 denotes a plasmid with a cap gene of AAV1 sequence, and a rep gene of AAV1 sequence with the exception that the C terminus (c) and the helicase domain (h) are of AAV2 sequence. pR1dc2V1 denotes a plasmid with a cap gene of AAV1 sequence, and a rep gene of AAV1 sequence with the exception that the DNA binding domain (d), and the C terminus (c) are of AAV2 sequence. pR1nc2V1 denotes a plasmid with a cap gene of AAV1 sequence, and a rep gene of AAV1 sequence with the exception that the N-terminus domain (n), and the C terminus (c) are of AAV2 sequence.

FIG. 7B shows the genome packaging efficiencies of the plasmids shown in FIG. 7A. The genome packaging efficiency is calculated as the amount of genome packaged in a rAAV particle compared to a particle with capsid proteins of serotype 1 and rep proteins of serotype 2 (reference).

FIG. 8 provides an overview of the newly generated AAV1 production plasmids and their phenotype. The plasmid names, descriptions of rep genes, VP expressions, and genome packaging efficiencies are shown.

FIGS. 9A-9D provide characterization and optimization of the rep gene for AAV3 vector production. FIG. 9A is a schematic showing examples of the AAV2 and AAV3 rep variations with either the naturally occurring ACG start codon, or a ATG start codon. FIG. 9B shows expression of capsid proteins or VP proteins and Rep proteins for the plasmids shown in FIG. 9A. AAV3 Rep78 is not visible with the ACG start codon. FIG. 9C provides yield of vector genomes per 15 cm plate ($\times 10^{12}$) of ACG-R2C3, ACG-R3V3, and ATG-R3V3 as shown in FIG. 9A. FIG. 9D is a chart showing the plasmid names and descriptions of the AAV3 expression plasmids tested.

FIGS. 10A-10D provide characterization and optimization of the rep gene for AAV4 vector production. FIG. 10A is a schematic showing examples of the AAV2 and AAV4 rep variations with either the naturally occurring ACG start codon, or a ATG start codon. FIG. 10B shows expression of capsid proteins or VP proteins and Rep proteins for the plasmids shown in FIG. 10A. The asterisk denotes known cross-reactivity of the A1 antibody. FIG. 10C provides yield of vector genomes per 15 cm plate ($\times 10^{12}$) of ACG-R2C3, ACG-R3V3, and ATG-R3V3 as shown in FIG. 10A.4. FIG. 10D is a chart showing the names and descriptions of AAV4 expression plasmids.

FIGS. 11A-11D provide characterization and optimization of the rep gene for AAV5 vector production. FIG. 11A is a schematic showing examples of the AAV2 and AAV5 rep variations with either the naturally occurring ACG start codon, or a ATG start codon. FIG. 11B shows expression of capsid proteins or VP proteins and Rep proteins for the plasmids shown in FIG. 10A. AAV5 Rep78 is not visible with the ACG start codon. FIG. 11C shows the plasmid yield per 15 cm plate ($\times 10^{12}$) of ACG-R2V5, ACG-R5V5, and ATG-R5V5. FIG. 10D is a chart showing the names and descriptions of AAV5 expression plasmids, all of which contain the AAV5 cap gene.

FIGS. 12A-12C provide characterization and optimization of the rep gene for AAV6 vector production. FIG. 12A shows expression of capsid proteins or VP proteins and Rep proteins for denoted plasmids, as well as their yields relative to the control (untransfected cells). FIG. 12B provides genome packaging efficiency for R8d1c3V6 and R1hc2V6 relative to R2V6. FIG. 12C is a chart showing the names and descriptions of AAV6 expression plasmids.

FIGS. 13A-13D provide characterization and optimization of the rep gene for AAV7 vector production. FIG. 13A is a schematic showing examples of the AAV2 and AAV7 rep variations with either the naturally occurring ACG start codon, or a ATG start codon. FIG. 13B shows expression of capsid proteins or VP proteins and Rep proteins for the plasmids shown in FIG. 13A. FIG. 13C shows the plasmid yield per 15 cm plate ($\times 10^{12}$) of ACG-R2V7, ACG-R7V7, and ATG-R7V7. FIG. 13D is a chart showing the names and descriptions of AAV7 expression plasmids.

FIG. 14A shows the plasmid yield per 15 cm plate (gp) for R2V8, R8c2V8, R1c2V8, R8n1c2V8, R8d1c2V8, and R8h1c2V8. FIG. 14B shows schematics of example AAV1, AAV2 and AAV8 rep variations.

FIG. 16A is a chart showing the names and descriptions of AAV8 expression plasmids, along with their genome packaging efficiencies and expression of VP proteins relative to pR2V8.

FIG. 16B shows nucleotides are deleted in the DNA binding (d) domain of AAV8 for the last hybrid listed in FIG. 16A.

DETAILED DESCRIPTION

To package rAAV particles, the viral genome that is found between two flanking ITRs is replaced with one or more genes of interest along with one or more control sequences (e.g., a promoter). Generally, when constructing rAAV particles, a gene to be packaged is flanked by cis-active ITRs while the rep and cap genes, which are in encoded in the wild-type genome, can be supplied in trans. The cap gene encodes capsid proteins that encapsidate packaged genetic material. The rep gene encodes proteins involved in replication of viral DNA. In the last decade, numerous AAV cap genes from multiple natural serotypes and variants have been utilized for different gene therapy applications. Generally, ITRs and rep gene of serotype 2 are used for packaging rAAV particles of various serotypes. The present application provides novel methods and compositions for packaging rAAV particles using ITRs and rep genes of different serotypes. As used herein, "packaging of rAAV particles" implies packing of nucleic acid sequences that are flanked by ITRs, which may comprises one or more genes of interest, into rAAV particles.

The inventors of the present application have explored how the sequences of ITRs and rep genes can be varied to improve the packaging of rAAV particles. Accordingly, provided herein are compositions of nucleic acids (e.g., comprised in vectors such as plasmids) that comprise ITRs and/or rep of different serotypes, including chimeric rep genes, for use in transfecting a producer cell, as well as cells that express a Rep proteins of a serotype that is different from the serotype of the ITRs used in producing rAAV particles. As defined herein, a "chimeric" AAV gene (e.g., rep or cap), also referred to as a "hybrid" AAV gene, or chimeric" AAV protein (e.g., Rep (e.g., Rep78, Rep68, Rep52, or Rep40) or capsid protein (e.g., VP1, VP2, and VP3)), also referred to as a "hybrid" AAV protein, is gene or protein having nucleotides or amino acids of more than one AAV serotype, respectively.

Methods of using ITRs and rep genes of different serotypes to improve rAAV particle packaging are also disclosed herein. In some embodiments, chimeric ITRs and/or chimeric rep genes are used for rAAV particle packaging.

AAV Structure

The AAV genome is built of single-stranded deoxyribonucleic acid (ssDNA), which is either positive- or negative-sensed. At each end of the DNA strand is an inverted terminal repeat (ITR). Between the ITRs are two open reading frames (ORFs): rep and cap. The cap ORF contains overlapping nucleotide sequences of capsid proteins: VP1, VP2 and VP3, which interact together to form a capsid of an icosahedral symmetry. The serotype of an AAV particle is attributed to the sequence of comprising capsid proteins.

Figures 1, 2:
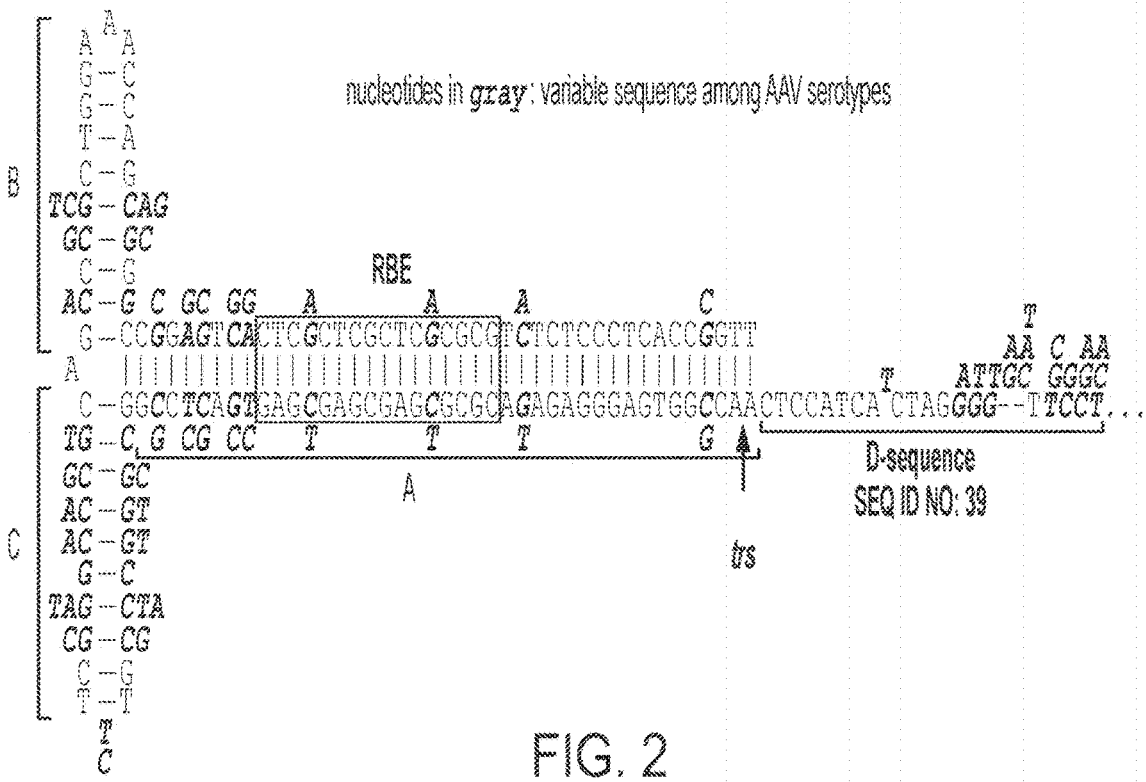
FIG. 1 shows alignment of rep and ITR sequences of AAV serotypes 1-13.
FIG. 2 shows a structure of an AAV ITR with variations in base pairs found between different AAV serotypes. RBE: Rep binding element where AAV Rep78 and Rep68 proteins bind.

FIG. 2 shows the structure of an AAV ITR. Each AAV ITR forms a hairpin, which contributes to so-called self-priming that allows primase-independent synthesis of the second DNA strand. ITRs are required for integration of AAV DNA into host DNA, efficient encapsidation and generation of a fully assembled DNAse-resistant AAV particle. ITRs are generally considered to be required in cis next to the one or more genes that are desired to be packaged into a rAAV particle. SEQ ID NOs: 1-7 correspond to examples of wild-type ITR sequences of serotypes 1-7 (AAV1-AAV7), respectively.

```
Example sequence of wild-type AAV1 ITR:
                                  (SEQ ID NO: 1)
ttgcccactccctctctgcgcgctcgctcgctcggtggggcctgcggacc aaaggtccgcagacggcagagctctgctctgccggccccaccgagcgagc gagcgcgcagagagggagtgggcaactccatcactaggggtaatcgc Example sequence of wild-type AAV2 ITR:
                                  (SEQ ID NO: 2)
ttggccactccctctctgcgcgctcgctcgctcactgaggccgggcgacc aaaggtcgcccgacgcccgggctttgcccgggcggcctcagtgagcgagc gagcgcgcagagagggagtggccaactccatcactaggggttcct Example sequence of wild-type AAV3 ITR:
                                  (SEQ ID NO: 3)
tggccactccctctatgcgcactcgctcgctcggtggggcctggcgacca aaggtcgccagacggacgtgctttgcacgtccggccccaccgagcgagcg agtgcgcatagagggagtggccaactccatcactagaggtatggca Example sequence of wild-type AAV4 ITR:
                                  (SEQ ID NO: 4)
ttggccactccctctatgcgcgctcgctcactcactcggccctggagacc aaaggtctccagactgccggcctctggccggcagggccgagtgagtgagc gagcgcgcatagagggagtggccaactccatcatctaggtttgcccac Example sequence of wild-type AAV5 ITR:
                                  (SEQ ID NO: 5)
ctctccccctgtcgcgttcgctcgctcgctggctcgtttgggggggtgg cagctcaaagagctgccagacgacggccctctggccgtcgcccccccaaa cgagccagcgagcgagcgaacgcgacaggggggagagtgccacactctca agcaaggggggttttgtaagcagtgat
```

Example sequence of wild-type AAV6 ITR:
(SEQ ID NO: 6)
ttggccactccctctctgcgcgctcgctcgctcactgaggccgggcgacc aaaggtcgcccgacgcccgggctttgcccgggcggcctcagtgagcgagc gagcgcgcagagagggagtggccaactccatcactagggggttcct Example sequence of wild-type AAV7 ITR:
(SEQ ID NO: 7)
ttggccactccctctatgcgcgctcgctcgctcggtggggcctgcggacc aaaggtccgcagacggcagagctctgctctgccggccccaccgagcgagc gagcgcgcatagagggagtggccaactccatcactaggggtaccgc The rep ORF is composed of four overlapping genes encoding Rep proteins required for the AAV life cycle. The names of the four Rep proteins depict their sizes in kilodaltons (kDa): Rep78, Rep68, Rep52 and Rep40. Rep78 and Rep68 bind the hairpin formed by the ITR in the self-priming act and cleave at a specific region, designated terminal resolution site, within the hairpin. All four Rep proteins bind to ATP and possess helicase activity. They upregulate the transcription from the p40 promoter, and downregulate both p5 and p19 promoter activity.

SEQ ID NOs: 8-20 correspond to example sequences of wild-type AAV rep genes of serotypes 1-13, respectively.

SEQ ID NOs: 21-33 correspond to example sequences of wild-type AAV Rep78 protein of serotypes 1-13, respectively. Rep78 has 621 amino acids. Rep68 comprises of amino acids 1-529 of Rep78 and a sequence LARGHSL (SEQ ID NO: 38) in the C terminus. Rep52 comprises amino acids 225-621 of Rep78. Rep40 comprises of amino acids 225-621 of Rep78 and LARGHSL (SEQ ID NO: 38) in the C terminus.

(SEQ ID NO: 8)
atgccgggcttctacgagatcgtgatcaaggtgccgagcgacctggacgagcacctgccgggcatttctgactcgtttgtgagctggg tggccgagaaggaatgggagctgccccccggattctgacatggatctgaatctgattgagcaggcacccctgaccgtggccgagaag ctgcagcgcgacttcctggtccaatggcgccgcgtgagtaaggccccggaggccctcttctttgttcagttcgagaagggcgagtcct acttccacctccatattctggtggagaccacgggggtcaaatccatggtgctgggccgcttcctgagtcagattagggacaagctggtg cagaccatctaccgcgggatcgagccgaccctgcccaactggttcgcggtgaccaagacgcgtaatggcgccggaggggggaac aaggtggtggacgagtgctacatcccccaactacctcctgcccaagactcagcccgagctgcagtgggcgtggactaacatggagga gtatataagcgcctgtttgaacctggccgagcgcaaacggctcgtggcgcagcacctgacccacgtcagccagacccaggagcaga acaaggagaatctgaacccccaattctgacgcgcctgtcatccggtcaaaaacctccgcgcgctacatggagctggtcgggtggctgg tggaccggggcatcacctccgagaagcagtggatccaggaggaccaggcctcgtacatctccttcaacgccgcttccaactcgcggt cccagatcaaggccgctctggacaatgccggcaagatcatggcgctgaccaaatccgcgcccgactacctggtaggccccgctccg cccgcggacattaaaaccaaccgcatctaccgcatcctggagctgaacggctacgaacctgcctacgccggctccgtctttctcggct gggcccagaaaaggttcggggaagcgcaacaccatctggctgtttgggccggccaccacgggcaagaccaacatcgcggaagccat cgcccacgccgtgccttctacggctgcgtcaactggaccaatgagaacttttcccttcaatgattgcgtcgacaagatggtgatctggtg ggaggagggcaagatgacggccaaggtcgtggagtccgccaaggccattctcggcggcagcaaggtgcgcgtggaccaaaagtg caagtcgtccgcccagatcgaccccaccccgtgatcgtcacctccaacaccaacatgtgcgccgtgattgacgggaacagcacca ccttcgagcaccagcagccgttgcaggaccggatgttcaaatttgaactcacccgccgtctggagcatgactttggcaaggtgacaaa gcaggaagtcaaagagttcttccgctgggcgcaggatcacgtgaccgaggtggcgcatgagttctacgtcagaaagggtggagcca acaaaagacccgccccgatgacgcggataaaagcgagcccaagcgggcctgccctcagtcgcggatccatcgacgtcagacg cggaaggagctccggtggactttgccgacaggtaccaaaacaaatgttctcgtcacgcgggcatgcttcagatgctgtttccctgcaag acatgcgagagaatgaatcagaatttcaacatttgcttcacgcacgggacgagagactgttcagagtgcttccccggcgtgtcagaatc tcaaccggtcgtcagaaaggacgtatcggaaactctgtgccattcatcatctgctggggcgggctcccgagattgcttgctcggcct gcgatctggtcaacgtggacctggatgactgtgtttctgagcaataa Example of wild-type AAV2 rep nucleic acid sequence:
(SEQ ID NO: 9)
atgccggggttttacgagattgtgattaaggtccccagcgaccttgacgggcatctgcccggcatttctgacagctttgtgaactgggtg gccgagaaggaatgggagttgccgccagattctgacatggatctgaatctgattgagcaggcacccctgaccgtggccgagaagctg cagcgcgactttctgacggaatggcgccgtgtgagtaaggccccggaggcccttttctttgtgcaatttgagaagggagagagctactt ccacatgcacgtgctcgtggaaaccaccggggtgaaatccatggttttgggacgtttcctgagtcagattcgcgaaaaactgattcaga gaatttaccgcgggatcgagccgactttgccaaactggttcgcggtcacaaagaccagaaatggcgccggaggcgggaacaaggt ggtggatgagtgctacatccccaattacttgctccccaaaacccagcctgagctccagtgggcgtggactaatatggaacagtatttaa -continued

```
gcgcctgtttgaatctcacggagcgtaaacggttggtggcgcagcatctgacgcacgtgtcgcagacgcaggagcagaacaaagag
aatcagaatcccaattctgatgcgccggtgatcagatcaaaaacttcagccaggtacatggagctggtcgggtggctcgtggacaagg
ggattacctcggagaagcagtggatccaggaggaccaggcctcatacatctccttcaatgcggcctccaactcgcggtcccaaatcaa
ggctgccttggacaatgcgggaaagattatgagcctgactaaaaccgcccccgactacctggtgggccagcagcccgtggaggaca
tttccagcaatcggatttataaaattttggaactaaacgggtacgatccccaatatgcggcttccgtctttctgggatgggccacgaaaaa
gttcggcaagaggaacaccatctggctgtttgggcctgcaactaccgggaagaccaacatcgcggaggccatagcccacactgtgc
ccttctacgggtgcgtaaactggaccaatgagaactttcccttcaacgactgtgtcgacaagatggtgatctggtgggaggaggggaa
gatgaccgccaaggtcgtggagtcggccaaagccattctcggaggaagcaaggtgcgcgtggaccagaaatgcaagtcctcggcc
cagatagacccgactcccgtgatcgtcacctccaacaccaacatgtgcgccgtgattgacgggaactcaacgaccttcgaacaccag
cagccgttgcaagaccggatgttcaaatttgaactcacccgccgtctggatcatgactttgggaaggtcaccaagcaggaagtcaaag
acttttccggtgggcaaaggatcacgtggttgaggtggagcatgaattctacgtcaaaaagggtggagccaagaaaagacccgccc
ccagtgacgcagatataagtgagcccaaacgggtgcgcgagtcagttgcgcagccatcgacgtcagacgcggaagcttcgatcaac
tacgcagacaggtaccaaaacaaatgttctcgtcacgtgggcatgaatctgatgctgtttccctgcagacaatgcgagagaatgaatca
gaattcaaatatctgcttcactcacggacagaaagactgtttagagtgctttcccgtgtcagaatctcaacccgtttctgtcgtcaaaaagg
cgtatcagaaactgtgctacattcatcatatcatgggaaaggtgccagacgcttgcactgcctgcgatctggtcaatgtggatttggatga
ctgcatctttgaacaataa
```

Example of wild-type AAV3 rep nucleic acid sequence:

(SEQ ID NO: 10)

```
atgccggggttctacgagattgtcctgaaggtcccgagtgacctggacgagcacctgccgggcatttctaactcgtttgttaactgggtg
gccgagaaggaatgggagctgccgccggattctgacatggatccgaatctgattgagcaggcacccctgaccgtggccgaaaagct
tcagcgcgagttcctggtggagtggcgccgcgtgagtaaggccccggaggccctcttttttgtccagttcgaaaaggggagaccta
cttccacctgcacgtgctgattgagaccatcggggtcaaatccatggtggtcggccgctacgtgagccagattaaagagaagctggtg
accgcatctaccgcgggtcgagccgcagcttccgaactggttcgcggtgaccaaaacgcgaaatggcgccgggggcgggaac
aaggtggtggacgactgctacatccccaactacctgctcccaagacccagcccgagctccagtgggcgtggactaacatggacca
gtatttaagcgcctgtttgaatctcgcggagcgtaaacggctggtggcgcagcatctgacgcacgtgtcgcagacgcaggagcagaa
caaagagaatcagaaccccaattctgacgcgccggtcatcaggtcaaaaacctcagccaggtacatggagctggtcgggtggctggt
ggaccgcgggatcacgtcagaaaagcaatggattcaggaggaccaggcctcgtacatctccttcaacgccgcctccaactcgcggtc
ccagatcaaggccgcgctggacaatgcctccaagatcatgagcctgacaaagacggctccggactacctggtgggcagcaacccg
ccggaggacattaccaaaaatcggatctaccaaatcctggagctgaacgggtacgatccgcagtacgcggcctccgtcacctgggct
gggcgcaaaagaagacgggaagaggaacaccatctggctctagggccggccacgacgggtaaaaccaacatcgcggaagccat
cgcccacgccgtgcccactacggctgcgtaaactggaccaatgagaactacccacaacgattgcgtcgacaagatggtgatctggt
gggaggagggcaagatgacggccaaggtcgtggagagcgccaaggccattctgggcggaagcaaggtgcgcgtggaccaaaag
tgcaagtcatcggcccagatcgaacccactcccgtgatcgtcacctccaacaccaacatgtgcgccgtgattgacgggaacagcacc
accacgagcatcagcagccgctgcaggaccggatgataaatttgaacttacccgccgtaggaccatgactagggaaggtcaccaa
acaggaagtaaaggactattccggtgggcaccgatcacgtgactgacgtggctcatgagactacgtcagaaagggtggagctaaga
aacgccccgcctccaatgacgcggatgtaagcgagccaaaacggcagtgcacgtcacttgcgcagccgacaacgtcagacgcgga
agcaccggcggactacgcggacaggtaccaaaacaaatgactcgtcacgtgggcatgaatctgatgcataccctgtaaaacatgcg
agagaatgaatcaaataccaatgtctgattacgcatggtcaaagagactgtggggaatgcaccctggaatgtcagaatctcaacccgt
ttctgtcgtcaaaaagaagacttatcagaaactgtgtccaattcatcatatcctgggaagggcacccgagattgcctgttcggcctgcgat
aggccaatgtggacaggatgactgtgatctgagcaataa
```

-continued

Example of wild-type AAV4 rep nucleic acid sequence:

(SEQ ID NO: 11)

atgccggggactacgagatcgtgctgaaggtgcccagcgacctggacgagcacctgcccggcatttctgactatagtgagctgggt ggccgagaaggaatgggagctgccgccggattctgacatggacttgaatctgattgagcaggcacccctgaccgtggccgaaaagc tgcaacgcgagacctggtcgagtggcgccgcgtgagtaaggccccggaggccctcactagtccagacgagaaggggggacagct acaccacctgcacatcctggtggagaccgtgggcgtcaaatccatggtggtgggccgctacgtgagccagattaaagagaagctgg tgacccgcatctaccgcggggtcgagccgcagatccgaactggacgcggtgaccaagacgcgtaatggcgccggaggcgggaa caaggtggtggacgactgctacatccccaactacctgctccccaagacccagcccgagctccagtgggcgtggactaacatggacc agtatataagcgcctgatgaatctcgcggagcgtaaacggctggtggcgcagcatctgacgcacgtgtcgcagacgcaggagcaga acaaggaaaaccagaaccccaattctgacgcgccggtcatcaggtcaaaaacctccgccaggtacatggagctggtcgggtggctg gtggaccgcgggatcacgtcagaaaagcaatggatccaggaggaccaggcgtcctacatctccttcaacgccgcctccaactcgcg gtcacaaatcaaggccgcgctggacaatgcctccaaaatcatgagcctgacaaagacggctccggactacctggtgggccagaacc cgccggaggacataccagcaaccgcatctaccgaatcctcgagatgaacgggtacgatccgcagtacgcggcctccgtcacctgg gctgggcgcaaaagaagacgggaagaggaacaccatctggctctagggccggccacgacgggtaaaaccaacatcgcggaagc catcgcccacgccgtgcccactacggctgcgtgaactggaccaatgagaactaccgacaacgattgcgtcgacaagatggtgatct ggtggaggagggcaagatgacggccaaggtcgtagagagcgccaaggccatcctgggcggaagcaaggtgcgcgtggaccaa aagtgcaagtcatcggcccagatcgacccaactcccgtgatcgtcacctccaacaccaacatgtgcgcggtcatcgacggaaactcg accaccacgagcaccaacaaccactccaggaccggatgacaagacgagctcaccaagcgcctggagcacgactaggcaaggtc accaagcaggaagtcaaagactattccggtgggcgtcagatcacgtgaccgaggtgactcacgagattacgtcagaaagggtgga gctagaaagaggcccgcccccaatgacgcagatataagtgagcccaagcgggcctgtccgtcagagcgcagccatcgacgtcaga cgcggaagctccggtggactacgcggacaggtaccaaaacaaatgactcgtcacgtgggtatgaatctgatgattaccctgccggc aatgcgagagaatgaatcagaatgtggacatttgcttcacgcacgggtcatggactgtgccgagtgcttccccgtgtcagaatctcaa cccgtgtctgtcgtcagaaagcggacgtatcagaaactgtgtccgattcatcacatcatggggagggcgcccgaggtggcctgctcg gcctgcgaactggccaatgtggacttggatgactgtgacatggaacaataa Example of wild-type AAV5 rep nucleic acid sequence:

(SEQ ID NO: 12)

atggctaccttctatgaagtcattgttcgcgtcccatttgacgtggaggaacatctgcctggaatttctgacagctttgtggactgggtaac tggtcaaatttgggagctgcctccagagtcagatttaaatttgactctggttgaacagcctcagttgacggtggctgatagaattcgccgc gtgttcctgtacgagtggaacaaattttccaagcaggagtccaaattctttgtgcagtttgaaaagggatctgaatattttcatctgcacac gcttgtggagacctccggcatctcttccatggtcctcggccgctacgtgagtcagattcgcgcccagctggtgaaagtggtcttccagg gaattgaacccagatcaacgactgggtcgccatcaccaaggtaaagaagggcggagccaataaggtggtggattctgggtatattc ccgcctacctgctgccgaaggtccaaccggagcttcagtgggcgtggacaaacctggacgagtataaattggccgccctgaatctgg aggagcgcaaacggctcgtcgcgcagtttctggcagaatcctcgcagcgctcgcaggaggcggcttcgcagcgtgagttctcggct gacccggtcatcaaaagcaagacttcccagaaatacatggcgctcgtcaactggctcgtggagcacggcatcacttccgagaagcag tggatccaggaaaatcaggagagctacctctccttcaactccaccggcaactctcggagccagatcaaggccgcgctcgacaacgc gaccaaaattatgagtctgacaaaaagcgcggtggactacctcgtgggagctccgttcccgaggacatttcaaaaaacagaatctgg caaatttttgagatgaatggctacgacccggcctacgcgggatccatcctctacggctggtgtcagcgctccttcaacaagaggaacac cgtctggctctacggacccgccacgaccggcaagaccaacatcgcggaggccatcgcccacactgtgcccttttacggctgcgtgaa ctggaccaatgaaaactttccctttaatgactgtgtggacaaaatgctcatttggtgggaggagggaaagatgaccaacaaggtggttg aatccgccaaggccatcctgggggctcaaaggtgcgggtcgatcagaaatgtaaatcctctgttcaaattgattctaccctgtcattg taacttccaatacaaacatgtgtgtggtggtggatgggaattccacgacctttgaacaccagcagccgctggaggaccgcatgttcaaa tttgaactgactaagcggctcccgccagattttggcaagattactaagcaggaagtcaaggactttttttgcttgggcaaaggtcaatcag -continued gtgccggtgactcacgagtttaaagttcccagggaattggcgggaactaaaggggcggagaaatctctaaaacgcccactgggtgac gtcaccaatactagctataaaagtctggagaagcgggccaggctctcatttgttcccgagacgcctcgcagttcagacgtgactgttgat cccgctcctctgcgaccgctcaattggaattcaaggtatgattgcaaatgtgactatcatgctcaatttgacaacatttctaacaaatgtgat gaatgtgaatatttgaatcggggcaaaaatggatgtatctgtcacaatgtaactcactgtcaaatttgtcatgggattccccctgggaaa aggaaaacttgtcagattttggggattttgacgatgccaataaagaacagtaa Example of wild-type AAV6 rep nucleic acid sequence:

(SEQ ID NO: 13)

atgccggggttttacgagattgtgattaaggtccccagcgaccttgacgagcatctgcccggcatttctgacagctttgtgaactgggtg gccgagaaggaatgggagttgccgccagattctgacatggatctgaatctgattgagcaggcacccctgaccgtggccgagaagctg cagcgcgacttcctggtccagtggcgccgcgtgagtaaggccccggaggccctcttctttgttcagttcgagaagggcgagtcctactt ccacctccatattctggtggagaccacgggggtcaaatccatggtgctgggccgcttcctgagtcagattagggacaagctggtgcag accatctaccgcgggatcgagccgaccctgcccaactggttcgcggtgaccaagacgcgtaatggcgccggagggggaacaag gtggtggacgagtgctacatccccaactacctcctgcccaagactcagcccgagctgcagtgggcgtggactaacatggaggagtat ataagcgcgtgtttaaacctggccgagcgcaaacggctcgtggcgcacgacctgacccacgtcagccagacccaggagcagaaca aggagaatctgaaccccaattctgacgcgcctgtcatccggtcaaaaacctccgcacgctacatggagctggtcgggtggctggtgg accggggcatcacctccgagaagcagtggatccaggaggaccaggcctcgtacatctccttcaacgccgcctccaactcgcggtcc cagatcaaggccgctctggacaatgccggcaagatcatggcgctgaccaaatccgcgcccgactacctggtaggccccgctccgcc cgccgacattaaaaccaaccgcatttaccgcatcctggagctgaacggctacgacctgcctacgccggctccgtctttctcggctgg gcccagaaaaggttcggaaaacgcaacaccatctggctgtttgggccggccaccacgggcaagaccaacatcgcggaagccatcg cccacgccgtgcccttctacgctgcgtcaactggaccaatgagaactttccccttcaacgattgcgtcgacaagatggtgatctggtgg gaggagggcaagatgacggccaaggtcgtggagtccgccaaggccattctcggcggcagcaaggtgcgcgtggaccaaaagtgc aagtcgtccgcccagatcgatccccaccccgtgatcgtcacctccaacaccaacatgtgcgccgtgattgacgggaacagcaccacc ttcgagcaccagcagccgttgcaggaccggatgttcaaatttgaactcacccgccgtctggagcatgactttggcaaggtgacaaagc aggaagtcaaagagttcttccgctgggcgcaggatcacgtgaccgaggtggcgcatgagttctacgtcagaaagggtggagccaac aagagacccgcccccgatgacgcggataaaagcgagcccaagcgggcctgcccctcagtcgcggatccatcgacgtcagacgcg gaaggagctccggtggactttgccgacaggtaccaaaacaaatgttctcgtcacgcgggcatgcttcagatgctgtttccctgcaaaac atgcgagagaatgaatcagaatttcaacatttgcttcacgcacgggaccagagactgttcagaatgttttccccggcgtgtcagaatctca accggtcgtcagaagaggacgtatcggaaactctgtgccattcatcatctgctggggcgggctcccgagattgcttgctcggcctgc gatctggtcaacgtggatctggatgactgtgtttctgagcaataa Example of wild-type AAV7 rep nucleic acid sequence:

(SEQ ID NO: 14)

atgccggggtttctacgagatcgtgatcaaggtgccgagcgacctggacgagcacctgccgggcatttctgactcgtttgtgaactgggt ggccgagaaggaatgggagctgccccccggattctgacatggatctgaatctgatcgagcaggcacccctgaccgtggccgagaag ctgcagcgcgacttcctggtccaatggcgccgcgtgagtaaggccccggaggccctgttctttgttcagttcgagaagggcgagagct acttccaccttcacgttctggtggagaccacgggggtcaagtccatggtgctaggccgcttcctgagtcagattcgggagaagctggtc cagaccatctaccgcggggtcgagcccacgctgcccaactggttcgcggtgaccaagacgcgtaatggcgccggcggggggaac aaggtggtggacgagtgctacatccccaactacctcctgcccaagacccagcccgagctgcagtgggcgtggactaacatggagga gtatataagcgcgtgtttgaacctggccgaacgcaaacggctcgtggcgcagcacctgacccacgtcagccagacgcaggagcag aacaaggagaatctgaaccccaattctgacgcgcccgtgatcaggtcaaaaacctccgcgcgctacatggagctggtcgggtggctg gtggaccggggcatcacctccgagaagcagtggatccaggaggaccaggcctcgtacatctccttcaacgccgcctccaactcgcg gtcccagatcaaggccgcgctggacaatgccggcaagatcatggcgctgaccaaatccgcgcccgactacctggtggggccctcg ctgccccgcgacattaaaaccaaccgcatctaccgcatcctggagctgaacgggtacgatcctgcctacgccggctccgtctttctcg gctgggcccagaaaaggttcgggaagcgcaacaccatctggctgtttgggccgccaccaccggcaagaccaacattgcggaagc -continued catcgcccacgccgtgcccttctacggctgcgtcaactggaccaatgagaactttcccttcaacgattgcgtcgacaagatggtgatct ggtgggaggagggcaagatgacggccaaggtcgtggagtccgccaaggccattctcggcggcagcaaggtgcgcgtggaccaaa agtgcaagtcgtccgcccagatcgaccccaccccgtgatcgtcacctccaacaccaacatgtgcgccgtgattgacgggaacagca ccaccttcgagcaccagcagccgttgcaggaccggatgttcaaatttgaactcacccgccgtctggagcacgactttggcaaggtgac gaagcaggaagtcaaagagttcttccgctgggccagtgatcacgtgaccgaggtggcgcatgagttctacgtcagaaagggcggag ccagcaaaagacccgcccccgatgacgcggatataagcgagcccaagcgggcctgcccctcagtcgcggatccatcgacgtcaga cgcggaaggagctccggtggactttgccgacaggtaccaaaacaaatgttctcgtcacgcgggcatgattcagatgctgtttccctgca aaacgtgcgagagaatgaatcagaatttcaacatttgcttcacacacggggtcagagactgtttagagtgtttccccggcgtgtcagaat ctcaaccggtcgtcagaaaaagacgtatcggaaactctgcgcgattcatcatctgctggggcgggcgcccgagattgcttgctcggc ctgcgacctggtcaacgtggacctggacgactgcgtttctgagcaataa Example of wild-type AAV8 rep nucleic acid sequence:

(SEQ ID NO: 15)

atgccgggcttctacgagatcgtgatcaaggtgccgagcgacctggacgagcacctgccgggcatttctgactcgtttgtgaactggg tggccgagaaggaatgggagctgccccggattctgacatggatcggaatctgatcgagcaggcacccctgaccgtggccgagaa gctgcagcgcgacttcctggtccaatggcgccgcgtgagtaaggccccggaggccctcttctttgttcagttcgagaagggcgagag ctactttcacctgcacgttctggtcgagaccacgggggtcaagtccatggtgctaggccgcttcctgagtcagattcgggaaaagcttg gtccagaccatctaccgcggggtcgagcccaccttgcccaactggttcgcggtgaccaaagacgcggtaatggcgccggcggg ggggaacaaggtggtggacgagtgctacatccccaactacctcctgcccaagactcagcccgagctgcagtgggcgtggactaaca tggaggagtatataagcgcgtgcttgaacctggccgagcgcaaacggctcgtggcgcagcacctgacccacgtcagccagacgca ggagcagaacaaggagaatctgaaccccaattctgacgcgcccgtgatcaggtcaaaaacctccgcgcgctatatggagctggtcg ggtggctggtggaccggggcatcacctccgagaagcagtggatccaggaggaccaggcctcgtacatctccttcaacgccgcctcc aactcgcggtcccagatcaaggccgcgctggacaatgccggcaagatcatggcgctgaccaaatccgcgcccgactacctggtgg ggccctcgctgccgcggacattacccagaaccgcatctaccgcatcctcgctctcaacggctacgaccctgcctacgccggctccg tctttctcggctgggctcagaaaaagttcgggaaacgcaacaccatctggctgtttggacccgccaccaccggcaagaccaacattgc ggaagccatcgcccacgccgtgcccttctacggctgcgtcaactggaccaatgagaactttcccttcaatgattgcgtcgacaagatgg tgatctggtgggaggagggcaagatgacggccaaggtcgtggagtccgccaaggccattctcggcggcagcaaggtgcgcgtgga ccaaaagtgcaagtcgtccgcccagatcgaccccaccccgtgatcgtcacctccaacaccaacatgtgcgccgtgattgacgggaa cagcaccaccttcgagcaccagcagcctccaggaccggatgtttaagttcgaactcacccgccgtctggagcacgactttggcaag gtgacaaagcaggaagtcaaagagttcttccgctgggccagtgatcacgtgaccgaggtggcgcatgagttttacgtcagaaagggc ggagccagcaaaagacccgcccccgatgacgcggataaaagcgagcccaagcgggcctgcccctcagtcgcggatccatcgacg tcagacgcggaaggagctccggtggactttgccgacaggtaccaaaacaaatgttctcgtcacgcgggcatgcttcagatgctgtttcc ctgcaaaacgtgcgagagaatgaatcagaatttcaacatttgcttcacacacggggtcagagactgctcagagtgtttccccggcgtgt cagaatctcaaccggtcgtcagaaagaggacgtatcggaaactctgtgcgattcatcatctgctggggcgggctcccgagattgcttg ctcggcctgcgatctggtcaacgtggacctggatgactgtgtttctgagcaataa Example of wild-type AAVrH.8 rep nucleic acid sequence:

(SEQ ID NO: 16)

atgccgggcttctacgagattgtgatcaaggtgccgagcgacctggacgagcacctgccgggcatttctgactcttttgtgaactgggt ggccgagaaggaatgggagctgccccggattctgacatggatcggaatctgatcgagcaggcacccctgaccgtggccgagaag ctgtagcgcgacttcctggtccaatggcgccgcgtgagtaaggccccggaggccctcttctttgttcagttcgagaagggcgagagct actttcacctgcacgttctggtcgagaccacgggggtcaagtccatggtgctaggccgcttcctgagtcagattcgggagaagctggtc cagaccatctaccgcgggatcgagccgaccctgcccaactggttcgcggtgaccaagacgcgtaatggcgccggcgggggggaac aaggtggtggacgagtgctacatccccaactacctcctgcccaagactcagcccgagctgcagtgggcgtggactaacatggagga -continued gtatataagcgcgtgcttgaacctggccgagcgcaaacggctcgtggcgcagcacctgacccacgtcagccagacgcaggagcag aacaaggagaatctgaaccccaattctgacgcgcccgtgatcaggtcaaaaacctccgcgcgctacatggagctggtcgggtggctg gtggaccggggcatcacctccgagaagcagtggatccaggaggaccaggcctcgtacatctccttcaacgccgcctccaactcgcg gtcccagatcaaggccgcgctggacaatgccggcaagatcatggcgctgaccaaatccgcgcccgactacctggtaggcccttcact tccggtggacattacgcagaaccgcatctaccgcatcctgcagctcaacggctacgaccctgcctacgccggctccgtctttctcggct gggcacaaaagaagttcggaaaacgcaacaccatctggctgtttgggccggccaccacgggaaagaccaacatcgcagaagccat tgcccacgccgtgcccttctacggctgcgtcaactggaccaatgagaactttcccttcaacgattgcgtcgacaagatggtgatctggtg ggaggagggcaagatgacggccaaggtcgtggagtccgccaaggccattctcggcggcagcaaggtgcgcgtggaccaaaagtg caagtcgtccgcccagatcgaccccactcccgtgatcgtcacctccaacaccaacatgtgcgccgtgattgacgggaacagcaccac cttcgagcaccagcagcctctccaggaccggatgtttaagttcgaactcacccgccgtctggagcacgactttggcaaggtgacaaag caggaagtcaaagagttcttccgctgggccagtgatcacgtgaccgaggtggcgcatgagttttacgtcagaaagggcggagccag caaaagacccgcccccgatgacgcggataaaagcgagcccaagcgggcctgcccctcagtcgcggatccatcgacgtcagacgc ggaaggagctccggtggactttgccgacaggtaccaaaacaaatgttctcgtcacgcgggcatgcttcagatgctgcttccctgcaaa acgtgcgagagaatgaatcagaatttcaacatttgcttcacacacggggtcagagactgctcagagtgtttccccggcgtgtcagaatct caaccggtcgtcagaaagaggacgtatcggaaactctgtgcgattcatcatctgctggggcgggctcccgagattgcttgctcggcct gcgatctggtcaacgtggacctggatgactgtgtttctgagcaataa Example of wild-type AAV10 rep nucleic acid sequence:

(SEQ ID NO: 17)
atgccgggcttctacgagatcgtgatcaaggtgccgagcgacctggacgagcacctgccgggcatttctgactcgtttgtgaactggg tggccgagaaggaatgggagctgcccccggattctgacatggatcggaatctgatcgagcaggcaccccctgaccgtggccgagaa gctgcagcgcgacttcctggtccactggcgccgcgtgagtaaggccccggaggccctcttctttgttcagttcgagaagggcgagtcc tactttcacctgcacgttctggtcgagaccacgggggtcaagtccatggtcctgggccgcttcctgagtcagatcagagacaggctggt gcagaccatctaccgcggggtagagcccacgctgcccaactggttcgcggttgaccaagacgcgaaatggcgccggcgggggaa caaggtggtggacgagtgctacatccccaactacctcctgcccaagacgcagcccgagctgcagtgggcgtggactaacatggagg agtatataagcgcgtgtctgaacctcgcggagcgtaaacggctcgtggcgcagcacctgacccacgtcagccagacgcaggagca gaacaaggagaatctgaaccccgaattctgacgcgcccgtgatcaggtcaaaaacctccgcgcgctacatggagctggtcgggtggct ggtggaccggggcatcacctccgagaagcagtggatccaggaggaccaggcctcgtacatctccttcaacgccgcctccaactcgc ggtcccagatcaaggccgcgctggacaatgccggaaagatcatggcgctgaccaaatccgcgcccgactacctggtaggcccgtcc ttacccgcggacattaaggccaaccgcatctaccgcatcctggagctcaacggctacgaccccgcctacgccggctccgtcttcctgg gctgggcgcagaaaaagttcggtaaaaggaatacaatttggctgttcgggcccgccaccaccggcaagaccaacatcgcggaagcc atcgcccacgccgtgcccttctacggctgcgtcaactggaccaatgagaactttcccttcaacgattgcgtcgacaagatggtgatctg gtgggaggagggcaagatgacggccaaggtcgtggagtccgccaaggccattctgggcggaagcaaggtgcgcgtcgaccaaaa gtgcaagtcctcggcccagatcgaccccacgcccgtgatcgtcacctccaacaccaacatgtgcgccgtgatcgacgggaacagca ccaccttcgagcaccagcagccctgcaggaccgcatgttcaagttcgagctcacccgccgtctggagcacgactttggcaaggtga ccaagcaggaagtcaaagagttcttccgctgggctcaggatcacgtgactgaggtgacgcatgagttctacgtcagaaagggcggag ccaccaaaagacccgcccccagtgacgcggatataagcgagcccaagcgggcctgcccctcagttgcggagccatcgacgtcaga cgcggaagcaccggtggactttgcggacaggtaccaaaacaaatgttctcgtcacgcgggcatgcttcagatgctgtttccctgcaag acatgcgagagaatgaatcagaatttcaacgtctgcttcacgcacggggtcagagactgctcagagtgcttccccggcgcgtcagaat ctcaacctgtcgtcagaaaaagacgtatcagaaactgtgcgcgattcatcatctgctggggcgggcacccgagattgcgtgttcggc ctgcgatctcgtcaacgtggacttggatgactgtgtttctgagcaataa Example of wild-type AAV11 rep nucleic acid sequence:

(SEQ ID NO: 18)

atgccgggcttctacgagatcgtgatcaaggtgccgagcgacctggacgagcacctgccgggcatttctgactcgttgtgaactggg tggccgagaaggaatgggagctgcccccggattctgacatggatcggaatctgatcgagcaggcacccctgaccgtggccgagaa gctgcagcgcgacttcctggtccactggcgccgcgtgagtaaggccccggaggccctcttctttgttcagttcgagaagggcgagtcc tacttccacctccacgttctcgtcgagaccacgggggtcaagtccatggtcctgggccgcttcctgagtcagatcagagacaggctggt gcagaccatctaccgcggggtcgagcccacgctgcccaactggttcgcggtgaccaagacgcgaaatggcgccggcggggggaa caaggtggtggacgagtgctacatccccaactacctcctgcccaagacccagcccgagctgcagtgggcgtggactaacatggagg agtatataagcgcgtgtctaaacctcgcggagcgtaaacggctcgtggcgcagcacctgaccacgtcagccagacgcaggagca gaacaaggagaatctgaacccgaattctgacgcgcccgtgatcaggtcaaaaacctccgcgcgctacatggagctggtcgggtggct ggtggaccggggcatcacctccgagaagcagtggatccaggaggaccaggcctcgtacatctccttcaacgccgcctccaactcgc ggtcccagatcaaggccgcgctggacaatgccggaaagatcatggcgctgaccaaatccgcgcccgactacctggtaggcccgtcc ttacccgcggacattaaggccaaccgcatctaccgcatcctggagctcaacggctacgaccccgcctacgccggctccgtcttcctgg gctgggcgcagaaaaagttcggtaaacgcaacaccatctggctgtttgggcccgccaccaccggcaagaccaacatcgcggaagc catagcccacgccgtgcccttctacggctgcgtgaactggaccaatgagaactttcccttcaacgattgcgtcgacaagatggtgatct ggtgggaggagggcaagatgaccgccaaggtcgtggagtccgccaaggccattctgggcggaagcaaggtgcgcgtggaccaaa agtgcaagtcctcggcccagatcgaccccacgcccgtgatcgtcacctccaacaccaacatgtgcgccgtgatcgacgggaacagc accaccttcgagcaccagcagccgctgcaggaccgcatgttcaagttcgagctcacccgccgtctggagcacgactttggcaaggtg accaagcaggaagtcaaagagttcttccgctgggctcaggatcacgtgactgaggtggcgcatgagttctacgtcagaaagggcgga gccaccaaaagacccgcccccagtgacgcggatataagcgagcccaagcgggcctgcccctcagttccggagccatcgacgtcag acgcggaagcaccggtggactttgcggacaggtaccaaaacaaatgttctcgtcacgcgggcatgcttcagatgctgtttccctgcaa gacatgcgagagaatgaatcagaatttcaacgtctgcttcacgcacggggtcagagactgctcagagtgcttccccggcgcgtcaga atctcaacccgtcgtcagaaaaagacgtatcagaaactgtgcgcgattcatcatctgctggggcgggcacccgagattgcgtgttcg gcctgcgatctcgtcaacgtggacttggatgactgtgtttctgagcaataa Example of wild-type AAV12 rep nucleic acid sequence:

(SEQ ID NO: 19)

atgccggggttctacgaggtggtgatcaaggtgccccagcgacctggacgagcacctgccccggcatttctgactccttttgtgaactggg tggccgagaaggaatgggagttgccccccggattctgacatggatcagaatctgattgagcaggcacccctgaccgtggccgagaag ctgcagcgcgagttcctggtggaatgggccgagtgagtaaatttctggaggccaagttattgtgcagtttgaaaaggggggactcgta cttcatttgcatattctgattgaaattaccggcgtgaaatccatggtggtgggccgctacgtgagtcagattagggataaactgatccag cgcatctaccgcggggtcgagcccccagctgcccaactggttcgcggtcacaaagacccgaaatggcgccggaggcgggaacaag gtggtggacgagtgctacatccccaactacctgctccccaaggtccagcccgagcttcagtgggcgtggactaacatggaggagtat ataagcgcctgttgaacctcgcggagcgtaaacggctcgtggcgcagcacctgacgcacgtctcccagacccaggagggcgaca aggagaatctgaacccgaattctgacgcgccggtgatccggtcaaaaacctccgccaggtacatggagctggtcgggtggctggtg gacaagggcatcacgtccgagaagcagtggatccaggaggaccaggcctcgtacatctccttcaacgcggcctccaactcccggtc gcagatcaaggcggccctggacaatgcctccaaaatcatgagcctcaccaaaacggctccggactatctcatcgggcagcagcccg tgggggacattaccaccaaccggatctacaaaatcctggaactgaacgggtacgaccccagtacgccgcctccgtcttctctcggctg ggcccagaaaaagtttggaaagcgcaacaccatctggctgtttgggcccgccaccaccggcaagaccaacatcgcggaagccatc gcccacgcggtccccttctacggctgcgtcaactggaccaatgagaactttcccttcaacgactgcgtcgacaaaatggtgatttggtg ggaggagggcaagatgaccgccaaggtcgtagagtccgccaaggccattctgggcggcagcaaggtgcgcgtggaccaaaaatg caaggcctctgcgcagatcgacccacccccgtgatcgtcacctccaacaccaacatgtgcgccgtgattgacgggaacagcacca ccttcgagcaccagcagcccctgcaggaccggatgttcaagtttgaactcacccgccgcctcgaccacgactttggcaaggtcacca -continued agcaggaagtcaaggactttttccggtgggcggctgatcacgtgactgacgtggctcatgagttttacgtcacaaagggtggagctaa gaaaaggcccgcccctctgacgaggatataagcgagcccaagcggccgcgcgtgtcatttgcgcagccggagacgtcagacgc ggaagctcccggagacttcgccgacaggtaccaaaacaaatgttctcgtcacgcgggtatgctgcagatgctcttccctgcaagacg tgcgagagaatgaatcagaattccaacgtctgcttcacgcacggtcagaaagattgcggggagtgctttcccgggtcagaatctcaac cggtttctgtcgtcagaaaaacgtatcagaaactgtgcatccttcatcagctccggggggcacccgagatcgcctgctctgcttgcgac caactcaaccccgatttggacgattgccaatttgagcaataa Example of wild-type AAV13 rep nucleic acid sequence:
(SEQ ID NO: 20)

atgccgggattctacgagattgtcctgaaggtgcccagcgacctggacgagcacctgcctggcatttctgactcttttgtaaactgggtg gcggagaaggaatgggagctgccgccggattctgacatggatctgaatctgattgagcaggcacccctaaccgtggccgaaaagct gcaacgcgaattcctggtcgagtggcgccgcgtgagtaaggccccggaggccctcttcttttgttcagttcgagaaggggggacagcta cttccacctacacattctggtggagaccgtgggcgtgaaatccatggtggtgggccgctacgtgagccagattaaagagaagctggtg acccgcatctaccgcggggtcgagccgcagcttccgaactggttcgcggtgaccaagacgcgtaatggcgccggaggcgggaaca aggtggtggacgactgctacatccccaactacctgctccccaagacccagcccgagctccagtgggcgtggactaatatggaccagt atttaagcgcctgtttgaatctcgcggagcgtaaacggctggtggcgcagcatctgacgcacgtgtcgcagacgcaggagcagaaca agagaaccagaatcccaattctgacgcgccggtgatcagatcaaaaacctccgcgaggtacatggagctggtcgggtggctggtg gaccgcgggatcacgtcagaaaagcaatggatccaggaggaccaggcctcttacatctccttcaacgccgcctccaactcgcggtca caaatcaaggccgcactggacaatgcctccaaatttatgagcctgacaaaaacggctccggactacctggtggggaaacaacccgccg gaggacattaccagcaaccggatctacaaaatcctcgagatgaacgggtacgatccgcagtacgcggcctccgtcttcctgggctgg gcgcaaaagaagttcgggaagaggaacaccatctggctctttgggccggccacgacgggtaaaaccaacatcgctgaagctatcgc ccacgccgtgcccttttacggctgcgtgaactggaccaatgagaactttccgttcaacgattgcgtcgacaagatggtgatctggtggg aggagggcaagatgacggccaaggtcgtggagtccgccaaggccattctgggcggaagcaaggtgcgcgtggaccaaaagtgca agtcatcggcccagatcgacccaactcccgtcatcgtcacctccaacaccaacatgtgcgcggtcatcgacggaaattccaccacctt cgagcaccaacaaccactccaagaccggatgttcaagttcgagctcaccaagcgcctggagcacgactttggcaaggtcaccaagc aggaagtcaaggacttttccggtgggcgtcagatcacgtgactgaggtgtctcacgagttttacgtcagaaagggtggagctagaaa gaggcccgcccccaatgacgcagatataagtgagcccaagcgggcctgtccgtcagttgcgcagccatcgacgtcagacgcggaa gctccggtggactacgcggacaggtaccaaaacaaatgttctcgtcacgtgggcatgaatctgatgcttttccctgccggcaatgcga gagaatgaatcagaatgtggacatttgcttcacgcacggggtcatggactgtgccgagtgcttccccgtgtcagaatctcaacccgtgt ctgtcgtcagaaagcggacatatcagaaactgtgtccgattcatcacatcatggggagggcgcccgaggtggcttgttcggcctgcga tctggccaatgtggacttggatgactgtgacatggagcaataa Example of wild-type AAV1 Rep78 amino acid sequence:
(SEQ ID NO: 21)

MPGFYEIVIKVPSDLDEHLPGISDSFVSWVAEKEWELPPDSDMDLNLIEQAPLTVAEK

LQRDFLVQWRRVSKAPEALFFVQFEKGESYFHLHILVETTGVKSMVLGRFLSQIRDK

LVQTIYRGIEPTLPNWFAVTKTRNGAGGGNKVVDECYIPNYLLPKTQPELQWAWTN

MEEYISACLNLAERKRLVAQHLTHVSQTQEQNKENLNPNSDAPVIRSKTSARYMELV

GWLVDRGITSEKQWIQEDQASYISFNAASNSRSQIKAALDNAGKIMALTKSAPDYLV

GPAPPADIKTNRIYRILELNGYEPAYAGSVFLGWAQKRFGKRNTIWLFGPATTGKTNI

AEAIAHAVPFYGCVNWTNENFPFNDCVDKMVIWWEEGKMTAKVVESAKAILGGSK

VRVDQKCKSSAQIDPTPVIVTSNTNMCAVIDGNSTTFEHQQPLQDRMFKFELTRRLE

HDFGKVTKQEVKEFFRWAQDHVTEVAHEFYVRKGGANKRPAPDDADKSEPKRACP

-continued

SVADPSTSDAEGAPVDFADRYQNKCSRHAGMLQMLFPCKTCERMNQNFNICFTHGT

RDCSECFPGVSESQPVVRKRTYRKLCAIHHLLGRAPEIACSACDLVNVDLDDCVSEQ

Example of wild-type AAV2 Rep78 amino acid sequence: (SEQ ID NO: 22)

MPGFYEIVIKVPSDLDGHLPGISDSFVNWVAEKEWELPPDSDMDLNLIEQAPLTVAE

KLQRDFLTEWRRVSKAPEALFFVQFEKGESYFHMHVLVETTGVKSMVLGRFLSQIRE

KLIQRIYRGIEPTLPNWFAVTKTRNGAGGGNKVVDECYIPNYLLPKTQPELQWAWTN

MEQYLSACLNLTERKRLVAQHLTHVSQTQEQNKENQNPNSDAPVIRSKTSARYMEL

VGWLVDKGITSEKQWIQEDQASYISFNAASNSRSQIKAALDNAGKIMSLTKTAPDYL

VGQQPVEDISSNRIYKILELNGYDPQYAASVFLGWATKKFGKRNTIWLFGPATTGKT

NIAEAIAHTVPFYGCVNWTNENFPFNDCVDKMVIWWEEGKMTAKVVESAKAILGGS

KVRVDQKCKSSAQIDPTPVIVTSNTNMCAVIDGNSTTFEHQQPLQDRMFKFELTRRL

DHDFGKVTKQEVKDFFRWAKDHVVEVEHEFYVKKGGAKKRPAPSDADISEPKRVR

ESVAQPSTSDAEASINYADRYQNKCSRHVGMNLMLFPCRQCERMNQNSNICFTHGQ

KDCLECFPVSESQPVSVVKKAYQKLCYIHHIMGKVPDACTACDLVNVDLDDCIFEQ

Example of wild-type AAV3 Rep78 amino acid sequence: (SEQ ID NO: 23)

MPGFYEIVLKVPSDLDEHLPGISNSFVNWVAEKEWELPPDSDMDPNLIEQAPLTVAE

KLQREFLVEWRRVSKAPEALFFVQFEKGETYFHLHVLIETIGVKSMVVGRYVSQIKE

KLVTRIYRGVEPQLPNWFAVTKTRNGAGGGNKVVDDCYlPNYLLPKTQPELQWAW

TNMDQYLSACLNLAERKRLVAQHLTHVSQTQEQNKENQNPNSDAPVIRSKTSARYM

ELVGWLVDRGITSEKQWIQEDQASYISFNAASNSRSQIKAALDNASKIMSLTKTAPD

YLVGSNPPEDITKNRIYQILELNGYDPQYAASVFLGWAQKKFGKRNTIWLFGPATTG

KTNIAEAIAHAVPFYGCVNWTNENFPFNDCVDKMVIWWEEGKMTAKVVESAKAIL

GGSKVRVDQKCKSSAQIEPTPVIVTSNTNMCAVIDGNSTTFEHQQPLQDRMFKFELT

RRLDHDFGKVTKQEVKDFFRWASDHVTDVAHEFYVRKGGAKKRPASNDADVSEPK

RQCTSLAQPTTSDAEAPADYADRYQNKCSRHVGMNLMLFPCKTCERMNQISNVCFT

HGQRDCGECFPGMSESQPVSVVKKKTYQKLCPIHHILGRAPEIACSACDLANVDLDD

CVSEQ

Example of wild-type AAV4 Rep78 amino acid sequence: (SEQ ID NO: 24)

MPGFYEIVLKVPSDLDEHLPGISDSFVSWVAEKEWELPPDSDMDLNLIEQAPLTVAE

KLQREFLVEWRRVSKAPEALFFVQFEKGDSYFHLHILVETVGVKSMVVGRYVSQIKE

KLVTRIYRGVEPQLPNWFAVTKTRNGAGGGNKVVDDCYlPNYLLPKTQPELQWAW

TNMDQYISACLNLAERKRLVAQHLTHVSQTQEQNKENQNPNSDAPVIRSKTSARYM

ELVGWLVDRGITSEKQWIQEDQASYISFNAASNSRSQIKAALDNASKIMSLTKTAPD

YLVGQNPPEDISSNRIYRILEMNGYDPQYAASVFLGWAQKKFGKRNTIWLFGPATTG

KTNIAEAIAHAVPFYGCVNWTNENFPFNDCVDKMVIWWEEGKMTAKVVESAKAIL

GGSKVRVDQKCKSSAQIDPTPVIVTSNTNMCAVIDGNSTTFEHQQPLQDRMFKFELT

KRLEHDFGKVTKQEVKDFFRWASDHVTEVTHEFYVRKGGARKRPAPNDADISEPKR

ACPSVAQPSTSDAEAPVDYADRYQNKCSRHVGMNLMLFPCRQCERMNQNVDICFT

HGVMDCAECFPVSESQPVSVVRKRTYQKLCPIHHIMGRAPEVACSACELANVDLDD

CDMEQ

Example of wild-type AAV5 Rep78 amino acid sequence: (SEQ ID NO: 25)

MATFYEVIVRVPFDVEEHLPGISDSFVDWVTGQIWELPPESDLNLTLVEQPQLTVADR

IRRVFLYEWNKFSKQESKFFVQFEKGSEYFHLHTLVETSGISSMVLGRYVSQIRAQLV

KVVFQGIEPQINDWVAITKVKKGGANKVVDSGYIPAYLLPKVQPELQWAWTNLDEY

KLAALNLEERKRLVAQFLAESSQRSQEAASQREFSADPVIKSKTSQKYMALVNWLV

EHGITSEKQWIQENQESYLSFNSTGNSRSQIKAALDNATKIMSLTKSAVDYLVGSSVP

EDISKNRIWQIFEMNGYDPAYAGSILYGWCQRSFNKRNTVWLYGPATTGKTNIAEAI

AHTVPFYGCVNWTNENFPFNDCVDKMLIWWEEGKMTNKVVESAKAILGGSKVRVD

QKCKSSVQIDSTPVIVTSNTNMCVVVDGNSTTFEHQQPLEDRMFKFELTKRLPPDFG

KITKQEVKDFFAWAKVNQVPVTHEFKVPRELAGTKGAEKSLKRPLGDVTNTSYKSL

EKRARLSFVPETPRSSDVTVDPAPLRPLNWNSRYDCKCDYHAQFDNISNKCDECEYL

NRGKNGCICHNVTHCQICHGIPPWEKENLSDFGDFDDANKEQ

Example of wild-type AAV6 Rep78 amino acid sequence: (SEQ ID NO: 26)

MPGFYEIVIKVPSDLDEHLPGISDSFVNWVAEKEWELPPDSDMDLNLIEQAPLTVAEK

LQRDFLVQWRRVSKAPEALFFVQFEKGESYFHLHILVETTGVKSMVLGRFLSQIRDK

LVQTIYRGIEPTLPNWFAVTKTRNGAGGGNKVVDECYIPNYLLPKTQPELQWAWTN

MEEYISACLNLAERKRLVAHDLTHVSQTQEQNKENLNPNSDAPVIRSKTSARYMELV

GWLVDRGITSEKQWIQEDQASYISFNAASNSRSQIKAALDNAGKIMALTKSAPDYLV

GPAPPADIKTNRIYRILELNGYDPAYAGSVFLGWAQKRFGKRNTIWLFGPATTGKTNI

AEAIAHAVPFYGCVNWTNENFPFNDCVDKMVIWWEEGKMTAKVVESAKAILGGSK

VRVDQKCKSSAQIDPTPVIVTSNTNMCAVIDGNSTTFEHQQPLQDRMFKFELTRRLE

HDFGKVTKQEVKEFFRWAQDHVTEVAHEFYVRKGGANKRPAPDDADKSEPKRACP

SVADPSTSDAEGAPVDFADRYQNKCSRHAGMLQMLFPCKTCERMNQNFNICFTHGT

RDCSECFPGVSESQPVVRKRTYRKLCAIHHLLGRAPEIACSACDLVNVDLDDCVSEQ

Example of wild-type AAV7 Rep78 amino acid sequence: (SEQ ID NO: 27)

MPGFYEIVIKVPSDLDEHLPGISDSFVNWVAEKEWELPPDSDMDLNLIEQAPLTVAEK

LQRDFLVQWRRVSKAPEALFFVQFEKGESYFHLHVLVETTGVKSMVLGRFLSQIREK

LVQTIYRGVEPTLPNWFAVTKTRNGAGGGNKVVDECYIPNYLLPKTQPELQWAWTN

MEEYISACLNLAERKRLVAQHLTHVSQTQEQNKENLNPNSDAPVIRSKTSARYMELV

GWLVDRGITSEKQWIQEDQASYISFNAASNSRSQIKAALDNAGKIMALTKSAPDYLV

GPSLPADIKTNRIYRILELNGYDPAYAGSVFLGWAQKKFGKRNTIWLFGPATTGKTNI

AEAIAHAVPFYGCVNWTNENFPFNDCVDKMVIWWEEGKMTAKVVESAKAILGGSK

VRVDQKCKSSAQIDPTPVIVTSNTNMCAVIDGNSTTFEHQQPLQDRMFKFELTRRLE

HDFGKVTKQEVKEFFRWASDHVTEVAHEFYVRKGGASKRPAPDDADISEPKRACPS

VADPSTSDAEGAPVDFADRYQNKCSRHAGMIQMLFPCKTCERMNQNFNICFTHGVR

DCLECFPGVSESQPVVRKKTYRKLCAIHHLLGRAPEIACSACDLVNVDLDDCVSEQ

Example of wild-type AAV8 Rep78 amino acid sequence: (SEQ ID NO: 28)

MPGFYEIVIKVPSDLDEHLPGISDSFVNWVAEKEWELPPDSDMDRNLIEQAPLTVAEK

LQRDFLVQWRRVSKAPEALFFVQFEKGESYFHLHVLVETTGVKSMVLGRFLSQIREK

LGPDHLPAGSSPTLPNWFAVTKDAVMAPAGGNKVVDECYIPNYLLPKTQPELQWA

WTNMEEYISACLNLAERKRLVAQHLTHVSQTQEQNKENLNPNSDAPVIRSKTSARY

```
MELVGWLVDRGITSEKQWIQEDQASYISFNAASNSRSQIKAALDNAGKIMALTKSAP

DYLVGPSLPADITQNRIYRILALNGYDPAYAGSVFLGWAQKKFGKRNTIWLFGPATT

GKTNIAEAIAHAVPFYGCVNWTNENFPFNDCVDKMVIWWEEGKMTAKVVESAKAI

LGGSKVRVDQKCKSSAQIDPTPVIVTSNTNMCAVIDGNSTTFEHQQPLQDRMFKFEL

TRRLEHDFGKVTKQEVKEFFRWASDHVTEVAHEFYVRKGGASKRPAPDDADKSEP

KRACPSVADPSTSDAEGAPVDFADRYQNKCSRHAGMLQMLFPCKTCERMNQNFNIC

FTHGVRDCSECFPGVSESQPVVRKRTYRKLCAIHHLLGRAPEIACSACDLVNVDLDD

CVSEQ
```

Example of wild-type AAVrh.8 Rep78 amino acid sequence: (SEQ ID NO: 29)

```
MPGFYEIVIKVPSDLDEHLPGISDSFVNWVAEKEWELPPDSDMDRNLIEQAPLTVAEK

LQRDFLVQWRRVSKAPEALFFVQFEKGESYFHLHVLVETTGVKSMVLGRFLSQIREK

LVQTIYRGIEPTLPNWFAVTKTRNGAGGGNKVVDECYIPNYLLPKTQPELQWAWTN

MEEYISACLNLAERKRLVAQHLTHVSQTQEQNKENLNPNSDAPVIRSKTSARYMELV

GWLVDRGITSEKQWIQEDQASYISFNAASNSRSQIKAALDNAGKIMALTKSAPDYLV

GPSLPVDITQNRIYRILQLNGYDPAYAGSVFLGWAQKKFGKRNTIWLFGPATTGKTNI

AEAIAHAVPFYGCVNWTNENFPFNDCVDKMVIWWEEGKMTAKVVESAKAILGGSK

VRVDQKCKSSAQIDPTPVIVTSNTNMCAVIDGNSTTFEHQQPLQDRMFKFELTRRLE

HDFGKVTKQEVKEFFRWASDHVTEVAHEFYVRKGGASKRPAPDDADKSEPKRACP

SVADPSTSDAEGAPVDFADRYQNKCSRHAGMLQMLLPCKTCERMNQNFNICFTHG

VRDCSECFPGVSESQPVVRKRTYRKLCAIHHLLGRAPEIACSACDLVNVDLDDCVSE

Q
```

Example of wild-type AAV10 Rep78 amino acid sequence: (SEQ ID NO: 30)

```
MPGFYEIVIKVPSDLDEHLPGISDSFVNWVAEKEWELPPDSDMDRNLIEQAPLTVAEK

LQRDFLVHWRRVSKAPEALFFVQFEKGESYFHLHVLVETTGVKSMVLGRFLSQIRDR

LVQTIYRGVEPTLPNWFAVTKTRNGAGGGNKVVDECYIPNYLLPKTQPELQWAWTN

MEEYISACLNLAERKRLVAQHLTHVSQTQEQNKENLNPNSDAPVIRSKTSARYMELV

GWLVDRGITSEKQWIQEDQASYISFNAASNSRSQIKAALDNAGKIMALTKSAPDYLV

GPSLPADIKANRIYRILELNGYDPAYAGSVFLGWAQKKFGKRNTIWLFGPATTGKTNI

AEAIAHAVPFYGCVNWTNENFPFNDCVDKMVIWWEEGKMTAKVVESAKAILGGSK

VRVDQKCKSSAQIDPTPVIVTSNTNMCAVIDGNSTTFEHQQPLQDRMFKFELTRRLE

HDFGKVTKQEVKEFFRWAQDHVTEVTHEFYVRKGGATKRPAPSDADISEPKRACPS

VAEPSTSDAEAPVDFADRYQNKCSRHAGMLQMLFPCKTCERMNQNFNVCFTHGVR

DCSECFPGASESQPVVRKKTYQKLCAIHHLLGRAPEIACSACDLVNVDLDDCVSEQ
```

Example of wild-type AAV11 Rep78 amino acid sequence: (SEQ ID NO: 31)

```
MPGFYEIVIKVPSDLDEHLPGISDSFVNWVAEKEWELPPDSDMDRNLIEQAPLTVAEK

LQRDFLVHWRRVSKAPEALFFVQFEKGESYFHLHVLVETTGVKSMVLGRFLSQIRDR

LVQTIYRGVEPTLPNWFAVTKTRNGAGGGNKVVDECYIPNYLLPKTQPELQWAWTN
```

-continued

```
MEEYISACLNLAERKRLVAQHLTHVSQTQEQNKENLNPNSDAPVIRSKTSARYMELV
GWLVDRGITSEKQWIQEDQASYISFNAASNSRSQIKAALDNAGKIMALTKSAPDYLV
GPSLPADIKANRIYRILELNGYDPAYAGSVFLGWAQKKFGKRNTIWLFGPATTGKTNI
AEAIAHAVPFYGCVNWTNENFPFNDCVDKMVIWWEEGKMTAKVVESAKAILGGSK
VRVDQKCKSSAQIDPTPVIVTSNTNMCAVIDGNSTTFEHQQPLQDRMFKFELTRRLE
HDFGKVTKQEVKEFFRWAQDHVTEVAHEFYVRKGGATKRPAPSDADISEPKRACPS
VPEPSTSDAEAPVDFADRYQNKCSRHAGMLQMLFPCKTCERMNQNFNVCFTHGVR
DCSECFPGASESQPVVRKKTYQKLCAIHHLLGRAPEIACSACDLVNVDLDDCVSEQ
```

Example of wild-type AAV12 Rep78 amino acid sequence:  (SEQ ID NO: 32)

```
MPGFYEVVIKVPSDLDEHLPGISDSFVNWVAEKEWELPPDSDMDQNLIEQAPLTVAE
KLQREFLVEWRRVSKFLEAKFFVQFEKGDSYFHLHILIEITGVKSMVVGRYVSQIRDK
LIQRIYRGVEPQLPNWFAVTKTRNGAGGGNKVVDECYIPNYLLPKVQPELQWAWTN
MEEYISACLNLAERKRLVAQHLTHVSQTQEGDKENLNPNSDAPVIRSKTSARYMELV
GWLVDKGITSEKQWIQEDQASYISFNAASNSRSQIKAALDNASKIMSLTKTAPDYLIG
QQPVGDITTNRIYKILELNGYDPQYAASVFLGWAQKKFGKRNTIWLFGPATTGKTNI
AEAIAHAVPFYGCVNWTNENFPFNDCVDKMVIWWEEGKMTAKVVESAKAILGGSK
VRVDQKCKASAQIDPTPVIVTSNTNMCAVIDGNSTTFEHQQPLQDRMFKFELTRRLD
HDFGKVTKQEVKDFFRWAADHVTDVAHEFYVTKGGAKKRPAPSDEDISEPKRPRVS
FAQPETSDAEAPGDFADRYQNKCSRHAGMLQMLFPCKTCERMNQNSNVCFTHGQK
DCGECFPGSESQPVSVVRKTYQKLCILHQLRGAPEIACSACDQLNPDLDDCQFEQ
```

Example of wild-type AAV13 Rep78 amino acid sequence:  (SEQ ID NO: 33)

```
MPGFYEIVLKVPSDLDEHLPGISDSFVNWVAEKEWELPPDSDMDLNLIEQAPLTVAE
KLQREFLVEWRRVSKAPEALFFVQFEKGDSYFHLHILVETVGVKSMVVGRYVSQIKE
KLVTRIYRGVEPQLPNWFAVTKTRNGAGGGNKVVDDCY1PNYLLPKTQPELQWAW
TNMDQYLSACLNLAERKRLVAQHLTHVSQTQEQNKENQNPNSDAPVIRSKTSARYM
ELVGWLVDRGITSEKQWIQEDQASYISFNAASNSRSQIKAALDNASKFMSLTKTAPD
YLVGNNPPEDITSNRIYKILEMNGYDPQYAASVFLGWAQKKFGKRNTIWLFGPATTG
KTNIAEAIAHAVPFYGCVNWTNENFPFNDCVDKMVIWWEEGKMTAKVVESAKAIL
GGSKVRVDQKCKSSAQIDPTPVIVTSNTNMCAVIDGNSTTFEHQQPLQDRMFKFELT
KRLEHDFGKVTKQEVKDFFRWASDHVTEVSHEFYVRKGGARKRPAPNDADISEPKR
ACPSVAQPSTSDAEAPVDYADRYQNKCSRHVGMNLMLFPCRQCERMNQNVDICFT
HGVMDCAECFPVSESQPVSVVRKRTYQKLCPIHHIMGRAPEVACSACDLANVDLDD
CDMEQ
```

As defined herein, a rep gene or Rep protein comprises an N-terminus and a C-terminus (c), wherein the N terminus comprises an N-terminus domain (n), a DNA binding domain (d), and a helicase domain (h), and C terminus (c) comprises a NLS/p40 promoter domain (y) and a Zinc finger domain (z). Table 1 provides example sequences of these domains for different AAV serotypes.

TABLE 1

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| AAV1 | DNA | n | 1-306 | ATGCCGGGCTTCTACGAGATCGTGATC AAGGTGCCGAGCGACCTGGACGAGCA CCTGCCGGGCATTTCTGACTCGTTTGTG AGCTGGGTGGCCGAGAAGGAATGGGA GCTGCCCCCGGATTCTGACATGGATCT GAATCTGATTGAGCAGGCACCCCTGAC CGTGGCCGAGAAGCTGCAGCGCGACTT CCTGGTCCAATGGCGCCGCGTGAGTAA GGCCCCGGAGGCCCTCTTCTTTGTTCA GTTCGAGAAGGGCGAGTCCTACTTCCA CCTCCATATTCTGGTGGAGACCACGGG GGTCAAATCC | 40 |
| | | d | 307-726 | ATGGTGCTGGGCCGCTTCCTGAGTCAG ATTAGGGACAAGCTGGTGCAGACCATC TACCGCGGGATCGAGCCGACCCTGCCC AACTGGTTCGCGGTGACCAAGACGCGT AATGGCGCCGGAGGGGGGAACAAGGT GGTGGACGAGTGCTACATCCCCAACTA CCTCCTGCCCAAGACTCAGCCCGAGCT GCAGTGGGCGTGGACTAACATGGAGG AGTATATAAGCGCCTGTTTGAACCTGG CCGAGCGCAAACGGCTCGTGGCGCAG CACCTGACCCACGTCAGCCAGACCCAG GAGCAGAACAAGGAGAATCTGAACCC CAATTCTGACGCGCCTGTCATCCGGTC AAAAACCTCCGCGCGCTACATGGAGCT GGTCGGGTGGCTGGTGGACCGGGGCAT CACCTCCGAGAAGCAGTGG | 41 |
| | | h | 727-1107 | ATCCAGGAGGACCAGGCCTCGTACATC TCCTTCAACGCCGCTTCCAACTCGCGG TCCCAGATCAAGGCCGCTCTGGACAAT GCCGGCAAGATCATGGCGCTGACCAA ATCCGCGCCCGACTACCTGGTAGGCCC CGCTCCGCCCGCGGACATTAAAACCAA CCGCATCTACCGCATCCTGGAGCTGAA CGGCTACGAACCTGCCTACGCCGGCTC CGTCTTTCTCGGCTGGGCCCAGAAAAG GTTCGGGAAGCGCAACACCATCTGGCT GTTTGGGCCGGCCACCACGGGCAAGAC CAACATCGCGGAAGCCATCGCCCACGC CGTGCCCTTCTACGGCTGCGTCAACTG GACCAATGAGAACTTTCCCTTCAATGA TTGC | 42 |
| | | c | 1108-1872 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA ACATGTGCGCCGTGATTGACGGGAACA GCACCACCTTCGAGCACCAGCAGCCGT TGCAGGACCGGATGTTCAAATTTGAAC TCACCCGCCGTCTGGAGCATGACTTTG GCAAGGTGACAAAGCAGGAAGTCAAA GAGTTCTTCCGCTGGGCGCAGGATCAC GTGACCGAGGTGGCGCATGAGTTCTAC GTCAGAAAGGGTGGAGCCAACAAAAG ACCCGCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAATGTTCTCGTCACG CGGGCATGCTTCAGATGCTGTTTCCCT GCAAGACATGCGAGAGAATGAATCAG AATTTCAACATTTGCTTCACGCACGGG ACGAGAGACTGTTCAGAGTGCTTCCCC | 43 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | GGCGTGTCAGAATCTCAACCGGTCGTC AGAAAGAGGACGTATCGGAAACTCTG TGCCATTCATCATCTGCTGGGGCGGGC TCCCGAGATTGCTTGCTCGGCCTGCGA TCTGGTCAACGTGGACCTGGATGACTG TGTTTCTGAGCAATAA | |
| | | y | 1108-1602 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA ACATGTGCGCCGTGATTGACGGGAACA GCACCACCTTCGAGCACCAGCAGCCGT TGCAGGACCGGATGTTCAAATTTGAAC TCACCCGCCGTCTGGAGCATGACTTTG GCAAGGTGACAAAGCAGGAAGTCAAA GAGTTCTTCCGCTGGGCGCAGGATCAC GTGACCGAGGTGGCGCATGAGTTCTAC GTCAGAAAGGGTGGAGCCAACAAAAG ACCCGCCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAA | 44 |
| | | z | 1603-1872 | TGTTCTCGTCACGCGGGCATGCTTCAG ATGCTGTTTCCCTGCAAGACATGCGAG AGAATGAATCAGAATTTCAACATTTGC TTCACGCACGGGACGAGAGACTGTTCA GAGTGCTTCCCCGGCGTGTCAGAATCT CAACCGGTCGTCAGAAAGAGGACGTA TCGGAAACTCTGTGCCATTCATCATCT GCTGGGGCGGGCTCCCGAGATTGCTTG CTCGGCCTGCGATCTGGTCAACGTGGA CCTGGATGACTGTGTTTCTGAGCAATA A | 45 |
| | PRT | n | 1-102 | MPGFYEIVIKVPSDLDEHLPGISDSFVSW VAEKEWELPPDSDMDLNLIEQAPLTVAE KLQRDFLVQWRRVSKAPEALFFVQFEK GESYFHLHILVETTGVKS | 46 |
| | | d | 103-242 | MVLGRFLSQIRDKLVQTIYRGIEPTLPNW FAVTKTRNGAGGGNKVVDECYIPNYLLP KTQPELQWAWTNMEEYISACLNLAERK RLVAQHLTHVSQTQEQNKENLNPNSDA PVIRSKTSARYMELVGWLVDRGITSEKQ W | 47 |
| | | h | 243-369 | IQEDQASYISFNAASNSRSQIKAALDNAG KIMALTKSAPDYLVGPAPPADIKTNRIYR ILELNGYEPAYAGSVFLGWAQKRFGKR NTIWLFGPATTGKTNIAEAIAHAVPFYGC VNWTNENFPFNDC | 48 |
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGANKRPAPDDADKSEP KRACPSVADPSTSDAEGAPVDFADRYQN KCSRHAGMLQMLFPCKTCERMNQNFNI CFTHGTRDCSECFPGVSESQPVVRKRTY RKLCAIHHLLGRAPEIACSACDLVNVDL DDCVSEQ | 49 |
| | | y | 370-534 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGANKRPAPDDADKSEP KRACPSVADPSTSDAEGAPVDFADRYQN K | 50 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | z | 535-623 | CSRHAGMLQMLFPCKTCERMNQNFNIC FTHGTRDCSECFPGVSESQPVVRKRTYR KLCAIHHLLGRAPEIACSACDLVNVDLD DCVSEQ | 51 |
| AAV2 | DNA | n | 1-306 | ACGCCGGGGTTTTACGAGATTGTGATT AAGGTCCCCAGCGACCTTGACGAGCAT CTGCCCGGCATTTCTGACAGCTTTGTG AACTGGGTGGCCGAGAAGGAATGGGA GTTGCCGCCAGATTCTGACATGGATCT GAATCTGATTGAGCAGGCACCCCTGAC CGTGGCCGAGAAGCTGCAGCGCGACTT TCTGACGGAATGGCGCCGTGTGAGTAA GGCCCCGGAGGCCCTTTTCTTTGTGCA ATTTGAGAAGGGAGAGAGCTACTTCCA CATGCACGTGCTCGTGGAAACCACCGG GGTGAAATCC | 52 |
| | | d | 307-726 | ATGGTTTTGGGACGTTTCCTGAGTCAG ATTCGCGAAAAACTGATTCAGAGAATT TACCGCGGGATCGAGCCGACTTTGCCA AACTGGTTCGCGGTCACAAAGACCAGA AATGGCGCCGGAGGCGGGAACAAGGT GGTGGATGAGTGCTACATCCCCAATTA CTTGCTCCCCAAAACCCAGCCTGAGCT CCAGTGGGCGTGGACTAATATGGAACA GTATTTAAGCGCCTGTTTGAATCTCAC GGAGCGTAAACGGTTGGTGGCGCAGC ATCTGACGCACGTGTCGCAGACGCAGG AGCAGAACAAAGAGAATCAGAATCCC AATTCTGATGCGCCGGTGATCAGATCA AAAACTTCAGCCAGGTACATGGAGCTG GTCGGGTGGCTCGTGGACAAGGGGATT ACCTCGGAGAAGCAGTGG | 53 |
| | | h | 727-1107 | ATCCAGGAGGACCAGGCCTCATACATC TCCTTCAATGCGGCCTCCAACTCGCGG TCCCAAATCAAGGCTGCCTTGGACAAT GCGGGAAAGATTATGAGCCTGACTAA AACCGCCCCCGACTACCTGGTGGGCCA GCAGCCCGTGGAGGACATTTCCAGCAA TCGGATTTATAAAATTTTGGAACTAAA CGGGTACGATCCCCAATATGCGGCTTC CGTCTTTCTGGGATGGGCCACGAAAAA GTTCGGCAAGAGGAACACCATCTGGCT GTTTGGGCCTGCAACTACCGGGAAGAC CAACATCGCGGAGGCCATAGCCCACAC TGTGCCCTTCTACGGGTGCGTAAACTG GACCAATGAGAACTTTCCCTTCAACGA CTGT | 54 |
| | | c | 1108-1866 | GTCGACAAGATGGTGATCTGGTGGGAG GAGGGGAAGATGACCGCCAAGGTCGT GGAGTCGGCCAAAGCCATTCTCGGAGG AAGCAAGGTGCGCGTGGACCAGAAAT GCAAGTCCTCGGCCCAGATAGACCCGA CTCCCGTGATCGTCACCTCCAACACCA ACATGTGCGCCGTGATTGACGGGAACT CAACGACCTTCGAACACCAGCAGCCGT TGCAAGACCGGATGTTCAAATTTGAAC TCACCCGCCGTCTGGATCATGACTTTG GGAAGGTCACCAAGCAGGAAGTCAAA GACTTTTTCCGGTGGGCAAAGGATCAC GTGGTTGAGGTGGAGCATGAATTCTAC GTCAAAAAGGGTGGAGCCAAGAAAAG ACCCGCCCCCAGTGACGCAGATATAAG TGAGCCCAAACGGGTGCGCGAGTCAGT TGCGCAGCCATCGACGTCAGACGCGGA AGCTTCGATCAACTACCAGAGCAGGTA CCAAAACAAATGTTCTCGTCACGTGGG CATGAATCTGATGCTGTTTCCCTGCAG ACAATGCGAGAGAATGAATCAGAATT CAAATATCTGCTTCACTCACGGACAGA AAGACTGTTTAGAGTGCTTTCCCGTGT | 55 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | CAGAATCTCAACCCGTTTCTGTCGTCA AAAAGGCGTATCAGAAACTGTGCTACA TTCATCATATCATGGGAAAGGTGCCAG ACGCTTGCACTGCCTGCGATCTGGTCA ATGTGGATTTGGATGACTGCATCTTTG AACAATAA | |
| | | y | 1108-1599 | GTCGACAAGATGGTGATCTGGTGGGAG GAGGGGAAGATGACCGCCAAGGTCGT GGAGTCGGCCAAAGCCATTCTCGGAGG AAGCAAGGTGCGCGTGGACCAGAAAT GCAAGTCCTCGGCCCAGATAGACCCGA CTCCCGTGATCGTCACCTCCAACACCA ACATGTGCGCCGTGATTGACGGGAACT CAACGACCTTCGAACACCAGCAGCCGT TGCAAGACCGGATGTTCAAATTTGAAC TCACCCGCCGTCTGGATCATGACTTTG GGAAGGTCACCAAGCAGGAAGTCAAA GACTTTTTCCGGTGGGCAAAGGATCAC GTGGTTGAGGTGGAGCATGAATTCTAC GTCAAAAAGGGTGGAGCCAAGAAAAG ACCCGCCCCCAGTGACGCAGATATAAG TGAGCCCAAACGGGTGCGCGAGTCAGT TGCGCAGCCATCGACGTCAGACGCGGA AGCTTCGATCAACTACGCAGACAGGTA CCAAAACAAA | 56 |
| | | z | 1600-1866 | TGTTCTCGTCACGTGGGCATGAATCTG ATGCTGTTTCCCTGCAGACAATGCGAG AGAATGAATCAGAATTCAAATATCTGC TTCACTCACGGACAGAAAGACTGTTTA GAGTGCTTTCCCGTGTCAGAATCTCAA CCCGTTTCTGTCGTCAAAAAGGCGTAT CAGAAACTGTGCTACATTCATCATATC ATGGGAAAGGTGCCAGACGCTTGCACT GCCTGCGATCTGGTCAATGTGGATTTG GATGACTGCATCTTTGAACAATAA | 57 |
| | PRT | n | 1-102 | TPGFYEIVIKVPSDLDGHLPGISDSFVNW VAEKEWELPPDSDMDLNLIEQAPLTVAE KLQRDFLTEWRRVSKAPEALFFVQFEKG ESYFHMHVLVETTGVKS | 58 |
| | | d | 103-242 | MVLGRFLSQIREKLIQRIYRGIEPTLPNWF AVTKTRNGAGGGNKVVDECYIPNYLLP KTQPELQWAWTNMEQYLSACLNLTERK RLVAQHLTHVSQTQEQNKENQNPNSDA PVIRSKTSARYMELVGWLVDKGITSEKQ W | 59 |
| | | h | 243-369 | IQEDQASYISFNAASNSRSQIKAALDNAG KIMSLTKTAPDYLVGQQPVEDISSNRIYK ILELNGYDPQYAASVFLGWATKKFGKR NTIWLFGPATTGKTNIAEAIAHTVPFYGC VNWTNENFPFNDC | 60 |
| | | c | 370-621 | VDKMVIWWEEGKMTAKVVESAKAILG GSKVRVDQKCKSSAQIDPTPVIVTSNTN MCAVIDGNSTTFEHQQPLQDRMFKFELT RRLDHDFGKVTKQEVKDFFRWAKDHV VEVEHEFYVKKGGAKKRPAPSDADISEP KRVRESVAQPSTSDAEASINYADRYQNK CSRHVGMNLMLFPCRQCERMNQNSNIC FTHGQKDCLECFPVSESQPVSVVKKAYQ KLCYIHHIMGKVPDACTACDLVNVDLD DCIFEQ | 61 |
| | | y | 370-533 | VDKMVIWWEEGKMTAKVVESAKAILG GSKVRVDQKCKSSAQIDPTPVIVTSNTN MCAVIDGNSTTFEHQQPLQDRMFKFELT RRLDHDFGKVTKQEVKDFFRWAKDHV VEVEHEFYVKKGGAKKRPAPSDADISEP KRVRESVAQPSTSDAEASINYADRYQNK | 62 |
| | | z | 534-621 | CSRHVGMNLMLFPCRQCERMNQNSNIC FTHGQKDCLECFPVSESQPVSVVKKAYQ KLCYIHHIMGKVPDACTACDLVNVDLD DCIFEQ | 63 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| AAV3 | DNA | n | 1-306 | ATGCCGGGGTTCTACGAGATTGTCCTG AAGGTCCCGAGTGACCTGGACGAGCA CCTGCCGGGCATTTCTAACTCGTTTGTT AACTGGGTGGCCGAGAAGGAATGGGA GCTGCCGCCGGATTCTGACATGGATCC GAATCTGATTGAGCAGGCACCCCTGAC CGTGGCCGAAAAGCTTCAGCGCGAGTT CCTGGTGGAGTGGCGCCGCGTGAGTAA GGCCCCGGAGGCCCTCTTTTTTGTCCA GTTCGAAAAGGGGGAGACCTACTTCCA CCTGCACGTGCTGATTGAGACCATCGG GGTCAAATCC | 64 |
| | | d | 307-726 | ATGGTGGTCGGCCGCTACGTGAGCCAG ATTAAAGAGAAGCTGGTGACCCGCATC TACCGCGGGGTCGAGCCGCAGCTTCCG AACTGGTTCGCGGTGACCAAAACGCGA AATGGCGCCGGGGGCGGGAACAAGGT GGTGGACGACTGCTACATCCCCAACTA CCTGCTCCCCAAGACCCAGCCCGAGCT CCAGTGGGCGTGGACTAACATGGACCA GTATTTAAGCGCCTGTTTGAATCTCGC GGGAGCGTAAACGGCTGGTGGCGCAGC ATCTGACGCACGTGTCGCAGACGCAGG AGCAGAACAAAGAGAATCAGAACCCC AATTCTGACGCGCCGGTCATCAGGTCA AAAACCTCAGCCAGGTACATGGAGCTG GTCGGGTGGCTGGTGGACCGCGGGATC ACGTCAGAAAAGCAATGG | 65 |
| | | h | 727-1107 | ATTCAGGAGGACCAGGCCTCGTACATC TCCTTCAACGCCGCCTCCAACTCGCGG TCCCAGATCAAGGCCGCGCTGGACAAT GCCTCCAAGATCATGAGCCTGACAAAG ACGGCTCCGGACTACCTGGTGGGCAGC AACCCGCCGGAGGACATTACCAAAAA TCGGATCTACCAAATCCTGGAGCTGAA CGGGTACGATCCGCAGTACGCGGCCTC CGTCTTCCTGGGCTGGGCGCAAAAGAA GTTCGGGAAGAGGAACACCATCTGGCT CTTTGGGCCGGCCACGACGGGTAAAAC CAACATCGCGGAAGCCATCGCCCACGC CGTGCCCTTCTACGGCTGCGTAAACTG GACCAATGAGAACTTTCCCTTCAACGA TTGC | 66 |
| | | c | 1108-1875 | GTCGACAAGATGGTGATCTGGTGGGAG GAGGGCAAGATGACGGCCAAGGTCGT GGAGAGCGCCAAGGCCATTCTGGGCG GAAGCAAGGTGCGCGTGGACCAAAAG TGCAAGTCATCGGCCCAGATCGAACCC ACTCCCGTGATCGTCACCTCCAACACC AACATGTGCGCCGTGATTGACGGGAAC AGCACCACCTTCGAGCATCAGCAGCCG CTGCAGGACCGGATGTTTAAATTTGAA CTTACCCGCCGTTTGGACCATGACTTT GGGAAGGTCACCAAACAGGAAGTAAA GGACTTTTTCCGGTGGGCTTCCGATCA CGTGACTGACGTGGCTCATGAGTTCTA CGTCAGAAAGGGTGGAGCTAAGAAAC GCCCCGCCTCCAATGACGCGGATGTAA GCGAGCCAAAACGGCAGTGCACGTCA CTTGCGCAGCCGACAACGTCAGACGCG GAAGCACCGGCGGACTACGCGGACAG GTACCAAAACAAATGTTCTCGTCACGT GGGCATGAATCTGATGCTTTTTCCCTGT AAAACATGCGAGAGAATGAATCAAAT TTCCAATGTCTGTTTTACGCATGGTCAA AGAGACTGTGGGGAATGCTTCCCTGGA ATGTCAGAATCTCAACCCGTTTCTGTC | 67 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | y | 1108-1599 | GTCAAAAAGAAGACTTATCAGAAACT GTGTCCAATTCATCATATCCTGGGAAG GGCACCCGAGATTGCCTGTTCGGCCTG CGATTTGGCCAATGTGGACTTGGATGA CTGTGTTTCTGAGCAATAA GTCGACAAGATGGTGATCTGGTGGGAG GAGGGCAAGATGACGGCCAAGGTCGT GGAGAGCGCCAAGGCCATTCTGGGCG GAAGCAAGGTGCGCGTGGACCAAAAG TGCAAGTCATCGGCCCAGATCGAACCC ACTCCCGTGATCGTCACCTCCAACACC AACATGTGCGCCGTGATTGACGGGAAC AGCACCACCTTCGAGCATCAGCAGCCG CTGCAGGACCGGATGTTTAAATTTGAA CTTACCCGCCGTTTGGACCATGACTTT GGGAAGGTCACCAAACAGGAAGTAAA GGACTTTTTCCGGTGGGCTTCCGATCA CGTGACTGACGTGGCTCATGAGTTCTA CGTCAGAAAGGGTGGAGCTAAGAAAC GCCCCGCCTCCAATGACGCGGATGTAA GCGAGCCAAAACGGCAGTGCACGTCA CTTGCGCAGCCGACAACGTCAGACGCG GAAGCACCGGCGGACTACGCGGACAG GTACCAAAACAAA | 68 |
| | | z | 1600-1875 | TGTTCTCGTCACGTGGGCATGAATCTG ATGCTTTTTCCCTGTAAAACATGCGAG AGAATGAATCAAATTTCCAATGTCTGT TTTACGCATGGTCAAAGAGACTGTGGG GAATGCTTCCCTGGAATGTCAGAATCT CAACCCGTTTCTGTCGTCAAAAAGAAG ACTTATCAGAAACTGTGTCCAATTCAT CATATCCTGGGAAGGGCACCCGAGATT GCCTGTTCGGCCTGCGATTTGGCCAAT GTGGACTTGGATGACTGTGTTTCTGAG CAATAA | 69 |
| | PRT | n | 1-102 | MPGFYEIVLKVPSDLDEHLPGISNSFVNW VAEKEWELPPDSDMDPNLIEQAPLTVAE KLQREFLVEWRRVSKAPEALFFVQFEKG ETYFHLHVLIETIGVKS | 70 |
| | | d | 103-242 | MVVGRYVSQIKEKLVTRIYRGVEPQLPN WFPAVTKTRNGAGGGNKVVDDCYIPNYL LPKTQPELQWAWTNMDQYLSACLNLAE RKRLVAQHLTHVSQTQEQNKENQPNS DAPVIRSKTSARYMELVGWLVDRGITSE KQW | 71 |
| | | h | 243-369 | IQEDQASYISFNAASNSRSQIKAALDNAS KIMSLTKTAPDYLVGSNPPEDITKNRIYQ ILELNGYDPQYAASVFLGWAQKKFGKR NTIWLFGPATTGKTNIAEAIAHAVPFYGC VNWTNENFPFNDC | 72 |
| | | c | 370-624 | VDKMVIWWEEGKMTAKVVESAKAILG GSKVRVDQKCKSSAQIEPTPVIVTSNTN MCAVIDGNSTTFEHQQPLQDRMFKFELT RRLDHDFGKVTKQEVKDFFRWASDHVT DVAHEFYVRKGGAKKRPASNDADVSEP KRQCTSLAQPTTSDAEAPADYADRYQN KCSRHVGMNLMLFPCKTCERMNQISNV CFTHGQRDCGECFPGMSESQPVSVVKKK TYQKLCPIHHILGRAPEIACSACDLANVD LDDCVSEQ | 73 |
| | | y | 370-533 | VDKMVIWWEEGKMTAKVVESAKAILG GSKVRVDQKCKSSAQIEPTPVIVTSNTN MCAVIDGNSTTFEHQQPLQDRMFKFELT RRLDHDFGKVTKQEVKDFFRWASDHVT DVAHEFYVRKGGAKKRPASNDADVSEP KRQCTSLAQPTTSDAEAPADYADRYQN K | 74 |
| | | z | 534-624 | CSRHVGMNLMLFPCKTCERMNQISNVC FTHGQRDCGECFPGMSESQPVSVVKKKT YQKLCPIHHILGRAPEIACSACDLANVDL DDCVSEQ | 75 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| AAV4 | DNA | n | 1-306 | ACGCCGGGGTTCTACGAGATCGTGCTG AAGGTGCCCAGCGACCTGGACGAGCA CCTGCCCGGCATTTCTGACTCTTTTGTG AGCTGGGTGGCCGAGAAGGAATGGGA GCTGCCGCCGGATTCTGACATGGACTT GAATCTGATTGAGCAGGCACCCCTGAC CGTGGCCGAAAAGCTGCAACGCGAGTT CCTGGTCGAGTGGCGCCGCGTGAGTAA GGCCCCGGAGGCCCTCTTCTTTGTCCA GTTCGAGAAGGGGGACAGCTACTTCCA CCTGCACATCCTGGTGGAGACCGTGGG CGTCAAATCC | 76 |
| | | d | 307-726 | ATGGTGGTGGGCCGCTACGTGAGCCAG ATTAAAGAGAAGCTGGTGACCCGCATC TACCGCGGGGTCGAGCCGCAGCTTCCG AACTGGTTCGCGGTGACCAAGACGCGT AATGGCGCCGGAGGCGGGAACAAGGT GGTGGACGACTGCTACATCCCCAACTA CCTGCTCCCCAAGACCCAGCCCGAGCT CCAGTGGGCGTGGACTAACATGGACCA GTATATAAGCGCCTGTTTGAATCTCGC GGGAGCGTAAACGGCTGGTGGCGCAGC ATCTGACGCACGTGTCGCAGACGCAGG AGCAGAACAAGGAAAACCAGAACCCC AATTCTGACGCGCCGGTCATCAGGTCA AAAACCTCCGCCAGGTACATGGAGCTG GTCGGGTGGCTGGTGGACCGCGGGATC ACGTCAGAAAAGCAATGG | 77 |
| | | h | 727-1107 | ATCCAGGAGGACCAGGCGTCCTACATC TCCTTCAACGCCGCCTCCAACTCGCGG TCACAAATCAAGGCCGCGCTGGACAAT GCCTCCAAAATCATGAGCCTGACAAAG ACGGCTCCGGACTACCTGGTGGGCCAG AACCCGCCGGAGGACATTTCCAGCAAC CGCATCTACCGAATCCTGGAGATGAAC GGGTACGATCCGCAGTACGCGGCCTCC GTCTTCCTGGGCTGGGCGCAAAAGAAG TTCGGGAAGAGGAACACCATCTGGCTC TTTGGGCCGGCCACGACGGGTAAAACC AACATCGCGGAAGCCATCGCCCACGCC GTGCCCTTCTACGGCTGCGTGAACTGG ACCAATGAGAACTTTCCGTTCAACGAT TGC | 78 |
| | | c | 1108-1872 | GTCGACAAGATGGTGATCTGGTGGGAG GAGGGCAAGATGACGGCCAAGGTCGT AGAGAGCGCCAAGGCCATCCTGGGCG GAAGCAAGGTGCGCGTGGACCAAAAG TGCAAGTCATCGGCCCAGATCGACCCA ACTCCCGTGATCGTCACCTCCAACACC AACATGTGCGCGGTCATCGACGGAAAC TCGACCACCTTCGAGCACCAACAACCA CTCCAGGACCGGATGTTCAAGTTCGAG CTCACCAAGCGCCTGGAGCACGACTTT GGCAAGGTCACCAAGCAGGAAGTCAA AGACTTTTTCCGGTGGCGTCAGATCA CGTGACCGAGGTGACTCACGAGTTTTA CGTCAGAAAGGGTGGAGCTAGAAAGA GGCCCGCCCCAATGACGCAGATATAA GTGAGCCCAAGCGGGCCTGTCCGTCAG TTGCGCAGCCATCGACGTCAGACGCGG AAGCTCCGGTGGACTACGCGGACAGGT ACCAAAACAAATGTTCTCGTCACGTGG GTATGAATCTGATGCTTTTTCCCTGCCG GCAATGCGAGAGAATGAATCAGAATG TGGACATTTGCTTCACGCACGGGGTCA TGGACTGTGCCGAGTGCTTCCCCGTGT CAGAATCTCAACCCGTGTCTGTCGTCA GAAAGCGGACGTATCAGAAACTGTGTC CGATTCATCACATCATGGGGAGGGCGC CCGAGGTGGCCTGCTCGGCCTGCGAAC | 79 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | y | 1108-1599 | TGGCCAATGTGGACTTGGATGACTGTG ACATGGAACAATAA GTCGACAAGATGGTGATCTGGTGGGAG GAGGGCAAGATGACGGCCAAGGTCGT AGAGAGCGCCAAGGCCATCCTGGGCG GAAGCAAGGTGCGCGTGGACCAAAAG TGCAAGTCATCGGCCCAGATCGACCCA ACTCCCGTGATCGTCACCTCCAACACC AACATGTGCGCGGTCATCGACGGAAAC TCGACCACCTTCGAGCACCAACAACCA CTCCAGGACCGGATGTTCAAGTTCGAG CTCACCAAGCGCCTGGAGCACGACTTT GGCAAGGTCACCAAGCAGGAAGTCAA AGACTTTTTCCGGTGGGCGTCAGATCA CGTGACCGAGGTGACTCACGAGTTTTA CGTCAGAAAGGGTGGAGCTAGAAAGA GGCCCGCCCCCAATGACGCAGATATAA GTGAGCCCAAGCGGGCCTGTCCGTCAG TTGCGCAGCCATCGACGTCAGACGCGG AAGCTCCGGTGGACTACGCGGACAGGT ACCAAAACAAA | 80 |
| | | z | 1600-1872 | TGTTCTCGTCACGTGGGTATGAATCTG ATGCTTTTTCCCTGCCGGCAATGCGAG AGAATGAATCAGAATGTGGACATTTGC TTCACGCACGGGGTCATGGACTGTGCC GAGTGCTTCCCCGTGTCAGAATCTCAA CCCGTGTCTGTCGTCAGAAAGCGGACG TATCAGAAACTGTGTCCGATTCATCAC ATCATGGGGAGGGCGCCCGAGGTGGC CTGCTCGGCCTGCGAACTGGCCAATGT GGACTTGGATGACTGTGACATGGAACA ATAA | 81 |
| | PRT | n | 1-102 | TPGFYEIVLKVPSDLDEHLPGISDSFVSW VAEKEWELPPDSDMDLNLIEQAPLTVAE KLQREFLVEWRRVSKAPEALFFVQFEKG DSYFHLHILVETVGVKS | 82 |
| | | d | 103-242 | MVVGRYVSQIKEKLVTRIYRGVEPQLPN WFAVTKTRNGAGGGNKVVDDCYIPNYL LPKTQPELQWAWTNMDQYISACLNLAE RKRLVAQHLTHVSQTQEQNKENQNPNS DAPVIRSKTSARYMELVGWLVDRGITSE KQW | 83 |
| | | h | 243-369 | IQEDQASYISFNAASNSRSQIKAALDNAS KIMSLTKTAPDYLVGQNPPEDISSNRIYRI LEMNGYDPQYAASVFLGWAQKKFGKR NTIWLFGPATTGKTNIAEAIAHAVPFYGC VNWTNENFPFNDC | 84 |
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT KRLEHDFGKVTKQEVKDFFRWASDHVT EVTHEFYVRKGGARKRPAPNDADISEPK RACPSVAQPSTSDAEAPVDYADRYQNK CSRHVGMNLMLFPCRQCERMNQNVDIC FTHGVMDCAECFPVSESQPVSVVRKRTY QKLCPIHHIMGRAPEVACSACELANVDL DDCDMEQ | 85 |
| | | y | 370-533 | VDKMVIWWEEGKMTAKVVESAKAILG GSKVRVDQKCKSSAQIDPTPVIVTSNTN MCAVIDGNSTTFEHQQPLQDRMFKFELT KRLEHDFGKVTKQEVKDFFRWASDHVT EVTHEFYVRKGGARKRPAPNDADISEPK RACPSVAQPSTSDAEAPVDYADRYQNK | 86 |
| | | z | 534-623 | CSRHVGMNLMLFPCRQCERMNQNVDIC FTHGVMDCAECFPVSESQPVSVVRKRTY QKLCPIHHIMGRAPEVACSACELANVDL DDCDMEQ | 87 |
| AAV5 | DNA | n | 1-306 | ATGGCTACCTTCTATGAAGTCATTGTTC GCGTCCCATTTGACGTGGAGGAACATC TGCCTGGAATTTCTGACAGCTTTGTGG | 88 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | ACTGGGTAACTGGTCAAATTTGGGAGC TGCCTCCAGAGTCAGATTTAAATTTGA CTCTGGTTGAACAGCCTCAGTTGACGG TGGCTGATAGAATTCGCCGCGTGTTCC TGTACGAGTGGAACAAATTTTCCAAGC AGGAGTCCAAATTCTTTGTGCAGTTTG AAAAGGGATCTGAATATTTTCATCTGC ACACGCTTGTGGAGACCTCCGGCATCT CTTCC | |
| | | d | 307-714 | ATGGTCCTCGGCCGCTACGTGAGTCAG ATTCGCGCCCAGCTGGTGAAAGTGGTC TTCCAGGGAATTGAACCCCAGATCAAC GACTGGGTCGCCATCACCAAGGTAAAG AAGGGCGGAGCCAATAAGGTGGTGGA TTCTGGGTATATTCCCGCCTACCTGCTG CCGAAGGTCCAACCGGAGCTTCAGTGG GCGTGGACAAACCTGGACGAGTATAA ATTGGCCGCCCTGAATCTGGAGGAGCG CAAACGGCTCGTCGCGCAGTTTCTGGC AGAATCCTCGCAGCGCTCGCAGGAGGC GGCTTCGCAGCGTGAGTTCTCGGCTGA CCCGGTCATCAAAAGCAAGACTTCCCA GAAATACATGGCGCTCGTCAACTGGCT CGTGGAGCACGGCATCACTTCCGAGAA GCAGTGG | 89 |
| | | h | 715-1095 | ATCCAGGAAAATCAGGAGAGCTACCTC TCCTTCAACTCCACCGGCAACTCTCGG AGCCAGATCAAGGCCGCGCTCGACAA CGCGACCAAAATTATGAGTCTGACAAA AAGCGCGGTGGACTACCTCGTGGGGA GCTCCGTTCCCGAGGACATTTCAAAAA ACAGAATCTGGCAAATTTTTGAGATGA ATGGCTACGACCCGGCCTACGCGGGAT CCATCCTCTACGGCTGGTGTCAGCGCT CCTTCAACAAGAGGAACACCGTCTGGC TCTACGGACCCGCCACGACCGGCAAGA CCAACATCGCGGAGGCCATCGCCCACA CTGTGCCCTTTTACGGCTGCGTGAACT GGACCAATGAAAACTTTCCCTTTAATG ACTGT | 90 |
| | | c | 1096-1833 | GTGGACAAAATGCTCATTTGGTGGGAG GAGGGAAAGATGACCAACAAGGTGGT TGAATCCGCCAAGGCCATCCTGGGGGG CTCAAAGGTGCGGGTCGATCAGAAATG TAAATCCTCTGTTCAAATTGATTCTACC CCTGTCATTGTAACTTCCAATACAAAC ATGTGTGTGGTGGTGGATGGGAATTCC ACGACCTTTGAACACCAGCAGCCGCTG GAGGACCGCATGTTCAAATTTGAACTG ACTAAGCGGCTCCCGCCAGATTTTGGC AAGATTACTAAGCAGGAAGTCAAGGA CTTTTTTGCTTGGGCAAAGGTCAATCA GGTGCCGGTGACTCACGAGTTTAAAGT TCCCAGGGAATTGGCGGGAACTAAAG GGGCGGAGAAATCTCTAAAACGCCCA CTGGGTGACGTCACCAATACTAGCTAT AAAAGTCTGGAGAAGCGGGCCAGGCT CTCATTTGTTCCCGAGACGCCTCGCAG TTCAGACGTGACTGTTGATCCCGCTCC TCTGCGACCGCTCAATTGGAATTCAAG GTATGATTGCAAATGTGACTATCATGC TCAATTTGACAACATTTCTAACAAATG TGATGAATGTGAATATTTGAATCGGGG CAAAAATGGATGTATCTGTCACAATGT AACTCACTGTCAAATTTGTCATGGGAT TCCCCCCTGGGAAAAGGAAAACTTGTC AGATTTGGGGATTTTGACGATGCCAA TAAAGAACAGTAA | 91 |
| | | y | 1096-1644 | GTGGACAAAATGCTCATTTGGTGGGAG GAGGGAAAGATGACCAACAAGGTGGT TGAATCCGCCAAGGCCATCCTGGGGGG | 92 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | CTCAAAGGTGCGGGTCGATCAGAAATG TAAATCCTCTGTTCAAATTGATTCTACC CCTGTCATTGTAACTTCCAATACAAAC ATGTGTGGTGGTGGATGGGAATTCC ACGACCTTTGAACACCAGCAGCCGCTG GAGGACCGCATGTTCAAATTTGAACTG ACTAAGCGGCTCCCGCCAGATTTTGGC AAGATTACTAAGCAGGAAGTCAAGGA CTTTTTTGCTTGGGCAAAGGTCAATCA GGTGCCGGTGACTCACGAGTTTAAAGT TCCCAGGGAATTGGCGGGAACTAAAG GGGCGGAGAAATCTCTAAAACGCCCA CTGGGTGACGTCACCAATACTAGCTAT AAAAGTCTGGAGAAGCGGGCCAGGCT CTCATTTGTTCCCGAGACGCCTCGCAG TTCAGACGTGACTGTTGATCCCGCTCC TCTGCGACCGCTCAATTGGAATTCAAG GTATGATTGCAAA | |
| | | z | 1645-1833 | TGTGACTATCATGCTCAATTTGACAAC ATTTCTAACAAATGTGATGAATGTGAA TATTTGAATCGGGGCAAAAATGGATGT ATCTGTCACAATGTAACTCACTGTCAA ATTTGTCATGGGATTCCCCCCTGGGAA AAGGAAAACTTGTCAGATTTTGGGGAT TTTGACGATGCCAATAAAGAACAGTAA | 93 |
| | PRT | n | 1-101 | MATFYEVIVRVPFDVEEHLPGISDSFVD WVTGQIWELPPESDLNLTLVEQPQLTVA DRIRRVFLYEWNKFSKQESKFFVQFEKG SEYFHLHTLVETSGISS | 94 |
| | | d | 102-238 | MVLGRYVSQIRAQLVKVVFQGIEPQIND WVAITKVKKGGANKVVDSGYIPAYLLP KVQPELQWAWTNLDEYKLAALNLEERK RLVAQFLAESSQRSQEAASQREFSADPVI KSKTSQKYMALVNWLVEHGITSEKQW | 95 |
| | | h | 239-365 | IQENQESYLSFNSTGNSRSQIKAALDNAT KIMSLTKSAVDYLVGSSVPEDISKNRIWQ IFEMNGYDPAYAGSILYGWCQRSFNKRN TVWLYGPATTGKTNIAEAIAHTVPFYGC VNWTNENFPFNDC | 96 |
| | | c | 366-610 | VDKMLIWWEEGKMTNKVVESAKAILGG SKVRVDQKCKSSVQIDSTPVIVTSNTNM CVVVDGNSTTFEHQQPLEDRMFKFELTK RLPPDFGKITKQEVKDFFAWAKVNQVPV THEFKVPRELAGTKGAEKSLKRPLGDVT NTSYKSLEKRARLSFVPETPRSSDVTVDP APLRPLNWNSRYDCKCDYHAQFDNISN KCDECEYLNRGKNGCICHNVTHCQICHG IPPWEKENLSDFGDFDDANKEQ | 97 |
| | | y | 366-548 | VDKMLIWWEEGKMTNKVVESAKAILGG SKVRVDQKCKSSVQIDSTPVIVTSNTNM CVVVDGNSTTFEHQQPLEDRMFKFELTK RLPPDFGKITKQEVKDFFAWAKVNQVPV THEFKVPRELAGTKGAEKSLKRPLGDVT NTSYKSLEKRARLSFVPETPRSSDVTVDP APLRPLNWNSRYDCK | 98 |
| | | z | 549-610 | CDYHAQFDNISNKCDECEYLNRGKNGCI CHNVTHCQICHGIPPWEKENLSDFGDFD DANKEQ | 99 |
| AAV6 | DNA | n | 1-306 | ATGCCGGGGTTTTACGAGATTGTGATT AAGGTCCCCAGCGACCTTGACGAGCAT CTGCCCGGCATTTCTGACAGCTTTGTG AACTGGGTGGCCGAGAAGGAATGGGA GTTGCCGCCAGATTCTGACATGGATCT GAATCTGATTGAGCAGGCACCCCTGAC CGTGGCCGAGAAGCTGCAGCGCGACTT CCTGGTCCAGTGGCGCCGCGTGAGTAA GGCCCCGGAGGCCCTCTTCTTTGTTCA GTTCGAGAAGGGCGAGTCCTACTTCCA CCTCCATATTCTGGTGGAGACCACGGG GGTCAAATCC | 100 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | d | 307-726 | ATGGTGCTGGGCCGCTTCCTGAGTCAG ATTAGGGACAAGCTGGTGCAGACCATC TACCGCGGGATCGAGCCGACCCTGCCC AACTGGTTCGCGGTGACCAAGACGCGT AATGGCGCCGGAGGGGGGAACAAGGT GGTGGACGAGTGCTACATCCCCAACTA CCTCCTGCCCAAGACTCAGCCCGAGCT GCAGTGGGCGTGGACTAACATGGAGG AGTATATAAGCGCGTGTTTAAACCTGG CCGAGCGCAAACGGCTCGTGGCGCAC GACCTGACCCACGTCAGCCAGACCCAG GAGCAGAACAAGGAGAATCTGAACCC CAATTCTGACGCGCCTGTCATCCGGTC AAAAACCTCCGCACGCTACATGGAGCT GGTCGGGTGGCTGGTGGACCGGGGCAT CACCTCCGAGAAGCAGTGG | 101 |
| | | h | 727-1107 | ATCCAGGAGGACCAGGCCTCGTACATC TCCTTCAACGCCGCCTCCAACTCGCGG TCCCAGATCAAGGCCGCTCTGGACAAT GCCGGCAAGATCATGGCGCTGACCAA ATCCGCGCCCGACTACCTGGTAGGCCC CGCTCCGCCCGCCGACATTAAAACCAA CCGCATTTACCGCATCCTGGAGCTGAA CGGCTACGACCCTGCCTACGCCGGCTC CGTCTTTCTCGGCTGGGCCCAGAAAAG GTTCGGAAAACGCAACACCATCTGGCT GTTTGGGCCGGCCACCACGGGCAAGAC CAACATCGCGGAAGCCATCGCCCACGC CGTGCCCTTCTACGGCTGCGTCAACTG GACCAATGAGAACTTTCCCTTCAACGA TTGC | 102 |
| | | c | 1108-1872 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGATCCCA CCCCCGTGATCGTCACCTCCAACACCA ACATGTGCGCCGTGATTGACGGGAACA GCACCACCTTCGAGCACCAGCAGCCGT TGCAGGACCGGATGTTCAAATTTGAAC TCACCCGCCGTCTGGAGCATGACTTTG GCAAGGTGACAAAGCAGGAAGTCAAA GAGTTCTTCCGCTGGGCGCAGGATCAC GTGACCGAGGTGGCGCATGAGTTCTAC GTCAGAAAGGGTGGAGCCAACAAGAG ACCCGCCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAATGTTCTCGTCACG CGGGCATGCTTCAGATGCTGTTTCCCT GCAAAACATGCGAGAGAATGAATCAG AATTTCAACATTTGCTTCACGCACGGG ACCAGAGACTGTTCAGAATGTTTCCCC GGCGTGTCAGAATCTCAACCGGTCGTC AGAAAGAGGACGTATCGGAAACTCTG TGCCATTCATCATCTGCTGGGGCGGGC TCCCGAGATTGCTTGCTCGGCCTGCGA TCTGGTCAACGTGGATCTGGATGACTG TGTTTCTGAGCAATAA | 103 |
| | | y | 1108-1602 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGATCCCA CCCCCGTGATCGTCACCTCCAACACCA ACATGTGCGCCGTGATTGACGGGAACA GCACCACCTTCGAGCACCAGCAGCCGT TGCAGGACCGGATGTTCAAATTTGAAC TCACCCGCCGTCTGGAGCATGACTTTG GCAAGGTGACAAAGCAGGAAGTCAAA | 104 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | GAGTTCTTCCGCTGGGCGCAGGATCAC GTGACCGAGGTGGCGCATGAGTTCTAC GTCAGAAAGGGTGGAGCCAACAAGAG ACCCGCCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAA | |
| | | z | 1603-1872 | TGTTCTCGTCACGCGGGCATGCTTCAG ATGCTGTTTCCCTGCAAAACATGCGAG AGAATGAATCAGAATTTCAACATTTGC TTCACGCACGGGACCAGAGACTGTTCA GAATGTTTCCCCGGCGTGTCAGAATCT CAACCGGTCGTCAGAAAGAGGACGTA TCGGAAACTCTGTGCCATTCATCATCT GCTGGGGCGGGCTCCCGAGATTGCTTG CTCGGCCTGCGATCTGGTCAACGTGGA TCTGGATGACTGTGTTTCTGAGCAATA A | 105 |
| | PRT | n | 1-102 | MPGFYEIVIKVPSDLDEHLPGISDSFVNW VAEKEWELPPDSDMDLNLIEQAPLTVAE KLQRDFLVQWRRVSKAPEALFFVQFEK GESYPHLHILVETTGVKS | 106 |
| | | d | 103-242 | MVLGRFLSQIRDKLVQTIYRGIEPTLPNW FAVTKTRNGAGGGNKVVDECYIPNYLLP KTQPELQWAWTNMEEYISACLNLAERK RLVAHDLTHVSQTEQNKENLNPNSDA PVIRSKTSARYMELVGWLVDRGITSEKQ W | 107 |
| | | h | 243-369 | IQEDQASYISFNAASNSRSQIKAALDNAG KIMALTKSAPDYLVGPAPPADIKTNRIYR ILELNGYDPAYAGSVFLGWAQKRFGKR NTIWLFGPATTGKTNIAEAIAHAVPFYGC VNWTNENFPFNDC | 108 |
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGANKRPAPDDADKSEP KRACPSVADPSTSDAEGAPVDFADRYQN KCSRHAGMLQMLFPCKTCERMNQNFNI CFTHGTRDCSECFPGVSESQPVVRKRTY RKLCAIHHLLGRAPEIACSACDLVNVDL DDCVSEQ | 109 |
| | | y | 370-534 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGANKRPAPDDADKSEP KRACPSVADPSTSDAEGAPVDFADRYQN K | 110 |
| | | z | 535-623 | CSRHAGMLQMLFPCKTCERMNQNFNIC FTHGTRDCSECFPGVSESQPVVRKRTYR KLCAIHHLLGRAPEIACSACDLVNVDLD DCVSEQ | 111 |
| AAV7 | DNA | n | 1-306 | ACGCCGGGTTTCTACGAGATCGTGATC AAGGTGCCGAGCGACCTGGACGAGCA CCTGCCGGGCATTTCTGACTCGTTTGTG AACTGGGTGGCCGAGAAGGAATGGGA GCTGCCCCCGGATTCTGACATGGATCT GAATCTGATCGAGCAGGCACCCCTGAC CGTGGCCGAGAAGCTGCAGCGCGACTT CCTGGTCCAATGGCGCCGCGTGAGTAA GGCCCCGGAGGCCCTGTTCTTTGTTCA GTTCGAGAAGGGCGAGTACTTCCA CCTTCACGTTCTGGTGGAGACCACGGG GGTCAAGTCC | 112 |
| | | d | 307-726 | ATGGTGCTAGGCCGCTTCCTGAGTCAG ATTCGGGAGAAGCTGGTCCAGACCATC TACCGCGGGGTCGAGCCCACGCTGCCC | 113 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | AACTGGTTCGCGGTGACCAAGACGCGT AATGGCGCCGGCGGGGGGAACAAGGT GGTGGACGAGTGCTACATCCCCAACTA CCTCCTGCCCAAGACCCAGCCCGAGCT GCAGTGGGCGTGGACTAACATGGAGG AGTATATAAGCGCGTGTTTGAACCTGG CCGAACGCAAACGGCTCGTGGCGCAG CACCTGACCCACGTCAGCCAGACGCAG GAGCAGAACAAGGAGAATCTGAACCC CAATTCTGACGCGCCCGTGATCAGGTC AAAAACCTCCGCGCGCTACATGGAGCT GGTCGGGTGGCTGGTGGACCGGGGCAT CACCTCCGAGAAGCAGTGG | |
| | | h | 727-1107 | ATCCAGGAGGACCAGGCCTCGTACATC TCCTTCAACGCCGCCTCCAACTCGCGG TCCCAGATCAAGGCCCGCGCTGGACAAT GCCGGCAAGATCATGGCGCTGACCAA ATCCGCGCCCGACTACCTGGTGGGGCC CTCGCTGCCCGCGGACATTAAAACCAA CCGCATCTACCGCATCCTGGAGCTGAA CGGGTACGATCCTGCCTACGCCGGCTC CGTCTTTCTCGGCTGGGCCCAGAAAAA GTTCGGGAAGCGCAACACCATCTGGCT GTTTGGGCCCGCCACCACCGGCAAGAC CAACATTGCGGAAGCCATCGCCCACGC CGTGCCCTTCTACGGCTGCGTCAACTG GACCAATGAGAACTTTCCCTTCAACGA TTGC | 114 |
| | | c | 1108-1872 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA ACATGTGCGCCGTGATTGACGGGAACA GCACCACCTTCGAGCACCAGCAGCCGT TGCAGGACCGGATGTTCAAATTTGAAC TCACCCGCCGTCTGGAGCACGACTTTG GCAAGGTGACGAAGCAGGAAGTCAAA GAGTTCTTCCGCTGGGCCAGTGATCAC GTGACCGAGGTGGCGCATGAGTTCTAC GTCAGAAAGGGCGGAGCCAGCAAAAG ACCCGCCCCCGATGACGCGGATATAAG CGAGCCCAAGCGGGCCTGCCCCTCAGT CGCGGATCCATCGACGTCAGACGCGGA AGGAGCTCCGGTGGACTTTGCCGACAG GTACCAAAACAAATGTTCTCGTCACGC GGGCATGATTCAGATGCTGTTTCCCTG CAAAACGTGCGAGAGAATGAATCAGA ATTTCAACATTTGCTTCACACACGGGG TCAGAGACTGTTTAGAGTGTTTCCCCG GCGTGTCAGAATCTCAACCGGTCGTCA GAAAAAAGACGTATCGGAAACTCTGC GCGATTCATCATCTGCTGGGGCGGGCG CCCGAGATTGCTTGCTCGGCCTGCGAC CTGGTCAACGTGGACCTGGACGACTGC GTTTCTGAGCAATAA | 115 |
| | | y | 1108-1602 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA ACATGTGCGCCGTGATTGACGGGAACA GCACCACCTTCGAGCACCAGCAGCCGT TGCAGGACCGGATGTTCAAATTTGAAC TCACCCGCCGTCTGGAGCACGACTTTG GCAAGGTGACGAAGCAGGAAGTCAAA GAGTTCTTCCGCTGGGCCAGTGATCAC GTGACCGAGGTGGCGCATGAGTTCTAC GTCAGAAAGGGCGGAGCCAGCAAAAG | 116 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | ACCCGCCCCCGATGACGCGGATATAAG CGAGCCCAAGCGGGCCTGCCCCTCAGT CGCGGATCCATCGACGTCAGACGCGGA AGGAGCTCCGGTGGACTTTGCCGACAG GTACCAAAACAAA | |
| | | z | 1603-1872 | TGTTCTCGTCACGCGGGCATGATTCAG ATGCTGTTTCCCTGCAAAACGTGCGAG AGAATGAATCAGAATTTCAACATTTGC TTCACACACGGGGTCAGAGACTGTTTA GAGTGTTTCCCCGGCGTGTCAGAATCT CAACCGGTCGTCAGAAAAAAGACGTA TCGGAAACTCTGCGCGATTCATCATCT GCTGGGGCGGGCGCCCGAGATTGCTTG CTCGGCCTGCGACCTGGTCAACGTGGA CCTGGACGACTGCGTTTCTGAGCAATA A | 117 |
| | PRT | n | 1-102 | TPGFYEIVIKVPSDLDEHLPGISDSFVNW VAEKEWELPPDSDMDLNLIEQAPLTVAE KLQRDFLVQWRRVSKAPEALFFVQFEK GESYFHLHVLVETTGVKS | 118 |
| | | d | 103-242 | MVLGRFLSQIREKLVQTIYRGVEPTLPN WFAVTKTRNGAGGGNKVVDECYIPNYL LPKTQPELQWAWTNMEEYISACLNLAE RKRLVAQHLTHVSQTQEQNKENLNPNS DAPVIRSKTSARYMELVGWLVDRGITSE KQW | 119 |
| | | h | 243-369 | IQEDQASYISFNAASNSRSQIKAALDNAG KIMALTKSAPDYLVGPSLPADIKTNRIYR ILELNGYDPAYAGSVFLGWAQKKFGKR NTIWLFGPATTGKTNIAEAIAHAVPFYGC VNWTNENFPFNDC | 120 |
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWASDHVT EVAHEFYVRKGGASKRPAPDDADISEPK RACPSVADPSTSDAEGAPVDFADRYQNK CSRHAGMIQMLFPCKTCERMNQNFNICF THGVRDCLECFPGVSESQPVVRKKTYRK LCAIHHLLGRAPEIACSACDLVNVDLDD CVSEQ | 121 |
| | | y | 370-534 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWASDHVT EVAHEFYVRKGGASKRPAPDDADISEPK RACPSVADPSTSDAEGAPVDFADRYQNK | 122 |
| | | z | 535-623 | CSRHAGMIQMLFPCKTCERMNQNFNICF THGVRDCLECFPGVSESQPVVRKKTYRK LCAIHHLLGRAPEIACSACDLVNVDLDD CVSEQ | 123 |
| AAV8 | DNA | n | 1-306 | ATGCCGGGCTTCTACGAGATCGTGATC AAGGTGCCGAGCGACCTGGACGAGCA CCTGCCGGGCATTTCTGACTCGTTTGTG AACTGGGTGGCCGAGAAGGAATGGGA GCTGCCCCCGGATTCTGACATGGATCG GAATCTGATCGAGCAGGCACCCCTGAC CGTGGCCGAGAAGCTGCAGCGCGACTT CCTGGTCCAATGGCGCCGCGTGAGTAA GGCCCCGGAGGCCCTCTTCTTTGTTCA GTTCGAGAAGGGCGAGAGCTACTTTCA CCTGCACGTTCTGGTCGAGACCACGGG GGTCAAGTCC | 124 |
| | | d | | ATGGTGCTAGGCCGCTTCCTGAGTCAG ATTCGGGAAAAGCTTGTCCAGACCAT CTACCCGCGGGGTCGAGCCCCACCTTG CCCAACTGGTTCGCGGTGACCAAAGAC GCGGTAATGGCGCCGGCGGGGGGGAA CAAGGTGGTGGACGAGTGCTACATCCC CAACTACCTCCTGCCCAAGACTCAGCC | 125 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | CGAGCTGCAGTGGGCGTGGACTAACAT GGAGGAGTATATAAGCGCGTGCTTGAA CCTGGCCGAGCGCAAACGGCTCGTGGC GCAGCACCTGACCCACGTCAGCCAGAC GCAGGAGCAGAACAAGGAGAATCTGA ACCCCAATTCTGACGCGCCCGTGATCA GGTCAAAAACCTCCGCGCGCTATATGG AGCTGGTCGGGTGGCTGGTGGACCGGG GCATCACCTCCGAGAAGCAGTGG | |
| | d | 307-726 | ATGGTGCTAGGCCGCTTCCTGAGTCAG ATTCGGGAAAAGCTGGTCCAGACCATC TACCGCGGGGTCGAGCCCACCTTGCCC AACTGGTTCGCGGTGACCAAGACGCGT AATGGCGCCGGGGGGGGAACAAGGT GGTGGACGAGTGCTACATCCCCAACTA CCTCCTGCCCAAGACTCAGCCCGAGCT GCAGTGGGCGTGGACTAACATGGAGG AGTATATAAGCGCGTGCTTGAACCTGG CCGAGCGCAAACGGCTCGTGGCGCAG CACCTGACCCACGTCAGCCAGACGCAG GAGCAGAACAAGGAGAATCTGAACCC CAATTCTGACGCGCCCGTGATCAGGTC AAAAACCTCCGCGCGCTATATGGAGCT GGTCGGGTGGCTGGTGGACCGGGGCAT CACCTCCGAGAAGCAGTGG | 126 |
| | h | 727-1107 | ATCCAGGAGGACCAGGCCTCGTACATC TCCTTCAACGCCGCCTCCAACTCGCGG TCCCAGATCAAGGCCGCGCTGGACAAT GCCGGCAAGATCATGGCGCTGACCAA ATCCGCGCCCGACTACCTGGTGGGGCC CTCGCTGCCCGCGGACATTACCCAGAA CCGCATCTACCGCATCCTCGCTCTCAA CGGCTACGACCCTGCCTACGCCGGCTC CGTCTTTCTCGGCTGGGCTCAGAAAAA GTTCGGGAAACGCAACACCATCTGGCT GTTTGGACCCGCCACCACCGGCAAGAC CAACATTGCGGAAGCCATCGCCCACGC CGTGCCCTTCTACGGCTGCGTCAACTG GACCAATGAGAACTTTCCCTTCAATGA TTGC | 127 |
| | c | 1108-1872 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA ACATGTGCGCCGTGATTGACGGGAACA GCACCACCTTCGAGCACCAGCAGCCTC TCCAGGACCGGATGTTTAAGTTCGAAC TCACCCGCCGTCTGGAGCACGACTTTG GCAAGGTGACAAAGCAGGAAGTCAAA GAGTTCTTCCGCTGGGCCAGTGATCAC GTGACCGAGGTGGCGCATGAGTTTTAC GTCAGAAAGGGCGGAGCCAGCAAAAG ACCCGCCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAATGTTCTCGTCACG CGGGCATGCTTCAGATGCTGTTTCCCT GCAAAACGTGCGAGAGAATGAATCAG AATTTCAACATTTGCTTCACACACGGG GTCAGAGACTGCTCAGAGTGTTTCCCC GGCGTGTCAGAATCTCAACCGGTCGTC AGAAAGAGGACGTATCGGAAACTCTG TGCGATTCATCATCTGCTGGGGCGGGC TCCCGAGATTGCTTGCTCGGCCTGCGA TCTGGTCAACGTGGACCTGGATGACTG TGTTTCTGAGCAATAA | 128 |
| | y | 1108-1602 | GTCGACAAGATGGTGATCTGGTGGGAG GAGGGCAAGATGACGGCCAAGGTCGT | 129 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA ACATGTGCGCCGTGATTGACGGGAACA GCACCACCTTCGAGCACCAGCAGCCTC TCCAGGACCGGATGTTTAAGTTCGAAC TCACCCGCCGTCTGGAGCACGACTTTG GCAAGGTGACAAAGCAGGAAGTCAAA GAGTTCTTCCGCTGGGCCAGTGATCAC GTGACCGAGGTGGCGCATGAGTTTTAC GTCAGAAAGGGCGGAGCCAGCAAAAG ACCCGCCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAA | |
| | | z | 1603-1872 | TGTTCTCGTCACGCGGGCATGCTTCAG ATGCTGTTTCCCTGCAAAACGTGCGAG AGAATGAATCAGAATTTCAACATTTGC TTCACACACGGGGTCAGAGACTGCTCA GAGTGTTTCCCCGGCGTGTCAGAATCT CAACCGGTCGTCAGAAAGAGGACGTA TCGGAAACTCTGTGCGATTCATCATCT GCTGGGGCGGGCTCCCGAGATTGCTTG CTCGGCCTGCGATCTGGTCAACGTGGA CCTGGATGACTGTGTTTCTGAGCAATA A | 130 |
| | PRT | n | 1-102 | MPGFYEIVIKVPSDLDEHLPGISDSFVNW VAEKEWELPPDSDMDRNLIEQAPLTVAE KLQRDFLVQWRRVSKAPEALFFVQFEK GESYFHLVLVETTGVKS | 131 |
| | | d | | MVLGRFLSQIREKLGPDHLPAGSSPTLPN WFAVTKDAVMAPAGGNKVVDECYIPN YLLPKTQPELQWAWTNMEEYISACLNL AERKRLVAQHLTHVSQTQEQNKENLNP NSDAPVIRSKTSARYMELVGWLVDRGIT SEKQW | 132 |
| | | d (p1/2) | 103-224 | MVLGRFLSQIREKLVQTIYRGVEPTLPN WFAVTKTRNGAGGGNKVVDECYIPNYL LPKTQPELQWAWTNMEEYISACLNLAE RKRLVAQHLTHVSQTQEQNKENLNPNS DAPVIRSKTSA | 133 |
| | | h | 225-369 | RYMELVGWLVDRGITSEKQWIQEDQAS YISFNAASNSRSQIKAALDNAGKIMALT KSAPDYLVGPSLPADITQNRIYRILALNG YDPAYAGSVFLGWAQKKFGKRNTIWLF GPATTGKTNIAEAIAHAVPFYGCVNWTN ENFPFNDC | 134 |
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWASDHVT EVAHEFYVRKGGASKRPAPDDADKSEP KRACPSVADPSTSDAEGAPVDFADRYQN KCSRHAGMLQMLFPCKTCERMNQNFNI CFTHGVRDCSECFPGVSESQPVVRKRTY RKLCAIHHLLGRAPEIACSACDLVNVDL DDCVSEQ | 135 |
| | | y | 370-536 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWASDHVT EVAHEFYVRKGGASKRPAPDDADKSEP KRACPSVADPSTSDAEGAPVDFADRYQN K | 136 |
| | | z | 537-623 | CSRHAGMLQMLFPCKTCERMNQNFNIC FTHGVRDCSECFPGVSESQPVVRKRTYR KLCAIHHLLGRAPEIACSACDLVNVDLD DCVSEQ | 137 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
| --- | --- | --- | --- | --- | --- |
| AAV10 | DNA | n | 1-306 | ATGCCGGGCTTCTACGAGATCGTGATC AAGGTGCCGAGCGACCTGGACGAGCA CCTGCCGGGCATTTCTGACTCGTTTGTG AACTGGGTGGCCGAGAAGGAATGGGA GCTGCCCCCGGATTCTGACATGGATCG GAATCTGATCGAGCAGGCACCCCTGAC CGTGGCCGAGAAGCTGCAGCGCGACTT CCTGGTCCACTGGCGCCGCGTGAGTAA GGCCCCGGAGGCCCTCTTCTTTGTTCA GTTCGAGAAGGGCGAGTCCTACTTTCA CCTGCACGTTCTGGTCGAGACCACGGG GGTCAAGTCC | 138 |
| | | d | 307-726 | ATGGTCCTGGGCCGCTTCCTGAGTCAG ATCAGAGACAGGCTGGTGCAGACCATC TACCGCGGGGTAGAGCCCACGCTGCCC AACTGGTTCGCGGTGACCAAGACGCGA AATGGCGCCGGCGGGGGGAACAAGGT GGTGGACGAGTGCTACATCCCCAACTA CCTCCTGCCCAAGACGCAGCCCGAGCT GCAGTGGGCGTGGACTAACATGGAGG AGTATATAAGCGCGTGTCTGAACCTCG CGGAGCGTAAACGGCTCGTGGCGCAG CACCTGACCCACGTCAGCCAGACGCAG GAGCAGAACAAGGAGAATCTGAACCC GAATTCTGACGCGCCCGTGATCAGGTC AAAAACCTCCGCGCGCTACATGGAGCT GGTCGGGTGGCTGGTGGACCGGGGCAT CACCTCCGAGAAGCAGTGG | 139 |
| | | h | 727-1107 | ATCCAGGAGGACCAGGCCTCGTACATC TCCTTCAACGCCGCCTCCAACTCGCGG TCCCAGATCAAGGCCGCGCTGGACAAT GCCGGAAAGATCATGGCGCTGACCAA ATCCGCGCCCGACTACCTGGTAGGCCC GTCCTTACCCGCGGACATTAAGGCCAA CCGCATCTACCGCATCCTGGAGCTCAA CGGCTACGACCCCGCCTACGCCGGCTC CGTCTTCCTGGGCTGGGCGCAGAAAAA GTTCGGTAAAAGGAATACAATTTGGCT GTTCGGGCCCGCCACCACCGGCAAGAC CAACATCGCGGAAGCCATCGCCCACGC CGTGCCCTTCTACGGCTGCGTCAACTG GACCAATGAGAACTTTCCCTTCAACGA TTGC | 140 |
| | | c | 1108-1869 | GTCGACAAGATGGTGATCTGGTGGGAG GAGGGCAAGATGACCGCCAAGGTCGT GGAGTCCGCCAAGGCCATTCTGGGCGG AAGCAAGGTGCGCGTCGACCAAAAGT GCAAGTCCTCGGCCCAGATCGACCCCA CGCCCGTGATCGTCACCTCCAACACCA ACATGTGCGCCGTGATCGACGGGAACA GCACCACCTTCGAGCACCAGCAGCCCC TGCAGGACCGCATGTTCAAGTTCGAGC TCACCCGCCGTCTGGAGCACGACTTTG GCAAGGTGACCAAGCAGGAAGTCAAA GAGTTCTTCCGCTGGGCTCAGGATCAC GTGACTGAGGTGACGCATGAGTTCTAC GTCAGAAAGGGCGGAGCCACCAAAAG ACCCGCCCCAGTGACGCGGATATAAG CGAGCCCAAGCGGGCCTGCCCCTCAGT TGCGGAGCCATCGACGTCAGACGCGG AAGCACCGGTGGACTTTGCGGACAGGT ACCAAAACAAATGTTCTCGTCACGCGG GCATGCTTCAGATGCTGTTTCCCTGCA AGACATGCGAGAGAATGAATCAGAAT TTCAACGTCTGCTTCACGCACGGGGTC AGAGACTGCTCAGAGTGCTTCCCCGGC GCGTCAGAATCTCAACCTGTCGTCAGA AAAAAGACGTATCAGAAACTGTGCGC | 141 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | GATTCATCATCTGCTGGGGCGGGCACC CGAGATTGCGTGTTCGGCCTGCGATCT CGTCAACGTGGACTTGGATGACTGTGT TTCTGAGCAATAA | |
| | | y | 1108-1599 | GTCGACAAGATGGTGATCTGGTGGGAG GAGGGCAAGATGACCGCCAAGGTCGT GGAGTCCGCCAAGGCCATTCTGGGCGG AAGCAAGGTGCGCGTCGACCAAAAGT GCAAGTCCTCGGCCCAGATCGACCCCA CGCCCGTGATCGTCACCTCCAACACCA ACATGTGCGCCGTGATCGACGGGAACA GCACCACCTTCGAGCACCAGCAGCCCC TGCAGGACCGCATGTTCAAGTTCGAGC TCACCCGCCGTCTGGAGCACGACTTTG GCAAGGTGACCAAGCAGGAAGTCAAA GAGTTCTTCCGCTGGGCTCAGGATCAC GTGACTGAGGTGACGCATGAGTTCTAC GTCAGAAAGGGCGGAGCCACCAAAAG ACCCGCCCCCAGTGACGCGGATATAAG CGAGCCCAAGCGGGCCTGCCCCTCAGT TGCGGAGCCATCGACGTCAGACGCGG AAGCACCGGTGGACTTTGCGGACAGGT ACCAAAACAAA | 142 |
| | | z | 1600-1869 | TGTTCTCGTCACGCGGGCATGCTTCAG ATGCTGTTTCCCTGCAAGACATGCGAG AGAATGAATCAGAATTTCAACGTCTGC TTCACGCACGGGGTCAGAGACTGCTCA GAGTGCTTCCCCGGCGCGTCAGAATCT CAACCTGTCGTCAGAAAAAAGACGTAT CAGAAACTGTGCGCGATTCATCATCTG CTGGGGCGGGCACCCGAGATTGCGTGT TCGGCCTGCGATCTCGTCAACGTGGAC TTGGATGACTGTGTTTCTGAGCAATAA | 143 |
| | PRT | n | 1-102 | MPGFYEIVIKVPSDLDEHLPGISDSFVNW VAEKEWELPPDSDMDRNLIEQAPLTVAE KLQRDFLVHWRRVSKAPEALFFVQFEK GESYFHLHVLVETTGVKS | 144 |
| | | d | 103-242 | MVLGRFLSQIRDRLVQTIYRGVEPTLPN WFAVTKTRNGAGGGNKVVDECYIPNYL LPKTQPELQWAWTNMEEYISACLNLAE RKRLVAQHLTHVSQTQEQNKENLNPNS DAPVIRSKTSARYMELVGWLVDRGITSE KQW | 145 |
| | | h | 243-369 | IQEDQASYISFNAASNSRSQIKAALDNAG KIMALTKSAPDYLVGPSLPADIKANRIYR ILELNGYDPAYAGSVFLGWAQKKFGKR NTIWLFGPATTGKTNIAEAIAHAVPFYGC VNWTNENFPFNDC | 146 |
| | | c | 370-622 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVTHEFYVRKGGATKRPAPSDADISEPK RACPSVAEPSTSDAEAPVDFADRYQNKC SRHAGMLQMLFPCKTCERMNQNFNVCF THGVRDCSECFPGASESQPVVRKKTYQK LCAIHHLLGRAPEIACSACDLVNVDLDD CVSEQ | 147 |
| | | y | 370-533 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVTHEFYVRKGGATKRPAPSDADISEPK RACPSVAEPSTSDAEAPVDFADRYQNK | 148 |
| | | z | 534-622 | CSRHAGMLQMLFPCKTCERMNQNFNVC FTHGVRDCSECFPGASESQPVVRKKTYQ KLCAIHHLLGRAPEIACSACDLVNVDLD DCVSEQ | 149 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| AAV11 | DNA | n | 1-306 | ATGCCGGGCTTCTACGAGATCGTGATC AAGGTGCCGAGCGACCTGGACGAGCA CCTGCCGGGCATTTCTGACTCGTTTGTG AACTGGGTGGCCGAGAAGGAATGGGA GCTGCCCCCGGATTCTGACATGGATCG GAATCTGATCGAGCAGGCACCCCTGAC CGTGGCCGAGAAGCTGCAGCGCGACTT CCTGGTCCACTGGCGCCGCGTGAGTAA GGCCCCGGAGGCCCTCTTCTTTGTTCA GTTCGAGAAGGGCGAGTCCTACTTCCA CCTCCACGTTCTCGTCGAGACCACGGG GGTCAAGTCC | 150 |
| | | d | 307-726 | ATGGTCCTGGGCCGCTTCCTGAGTCAG ATCAGAGACAGGCTGGTGCAGACCATC TACCGCGGGGTCGAGCCCACGCTGCCC AACTGGTTCGCGGTGACCAAGACGCGA AATGGCGCCGGCGGGGGGAACAAGGT GGTGGACGAGTGCTACATCCCCAACTA CCTCCTGCCCAAGACCCAGCCCGAGCT GCAGTGGGCGTGGACTAACATGGAGG AGTATATAAGCGCGTGTCTAAACCTCG CGGAGCGTAAACGGCTCGTGGCGCAG CACCTGACCCACGTCAGCCAGACGCAG GAGCAGAACAAGGAGAATCTGAACCC GAATTCTGACGCGCCCGTGATCAGGTC AAAAACCTCCGCGCTACATGGAGCT GGTCGGGTGGCTGGTGGACCGGGGCAT CACCTCCGAGAAGCAGTGG | 151 |
| | | h | 727-1107 | ATCCAGGAGGACCAGGCCTCGTACATC TCCTTCAACGCCGCCTCCAACTCGCGG TCCCAGATCAAGGCCGCGCTGGACAAT GCCGGAAAGATCATGGCGCTGACCAA ATCCGCGCCCGACTACCTGGTAGGCCC GTCCTTACCCGCGGACATTAAGGCCAA CCGCATCTACCGCATCCTGGAGCTCAA CGGCTACGACCCCGCCTACGCCGGCTC CGTCTTCCTGGGCTGGGCGCAGAAAAA GTTCGGTAAACGCAACACCATCTGGCT GTTTGGGCCCGCCACCACCGGCAAGAC CAACATCGCGGAAGCCATAGCCCACGC CGTGCCCTTCTACGGCTGCGTGAACTG GACCAATGAGAACTTTCCCTTCAACGA TTGC | 152 |
| | | c | 1108-1869 | GTCGACAAGATGGTGATCTGGTGGGAG GAGGGCAAGATGACCGCCAAGGTCGT GGAGTCCGCCAAGGCCATTCTGGGCGG AAGCAAGGTGCGCGTGGACCAAAAGT GCAAGTCCTCGGCCCAGATCGACCCCA CGCCCGTGATCGTCACCTCCAACACCA ACATGTGCGCCGTGATCGACGGGAACA GCACCACCTTCGAGCACCAGCAGCCGC TGCAGGACCGCATGTTCAAGTTCGAGC TCACCCGCCGTCTGGAGCACGACTTTG GCAAGGTGACCAAGCAGGAAGTCAAA GAGTTCTTCCGCTGGGCTCAGGATCAC GTGACTGAGGTGGCGCATGAGTTCTAC GTCAGAAAGGGCGGAGCCACCAAAAG ACCCGCCCCAGTGACGCGGATATAAG CGAGCCCAAGCGGGCCTGCCCCTCAGT TCCGGAGCCATCGACGTCAGACGCGGA AGCACCGGTGGACTTTGCGGACAGGTA CCAAAACAAATGTTCTCGTCACGCGGG CATGCTTCAGATGCTGTTTCCCTGCAA GACATGCGAGAGAATGAATCAGAATTT CAACGTCTGCTTCACGCACGGGGTCAG AGACTGCTCAGAGTGCTTCCCCGGCGC GTCAGAATCTCAACCCGTCGTCAGAAA AAAGACGTATCAGAAACTGTGCGCGAT TCATCATCTGCTGGGGCGGGCACCCGA GATTGCGTGTTCGGCCTGCGATCTCGT | 153 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | CAACGTGGACTTGGATGACTGTGTTTC TGAGCAATAA | |
| | | y | 1108-1599 | GTCGACAAGATGGTGATCTGGTGGGAG GAGGGCAAGATGACCGCCAAGGTCGT GGAGTCCGCCAAGGCCATTCTGGGCGG AAGCAAGGTGCGCGTGGACCAAAAGT GCAAGTCCTCGGCCCAGATCGACCCCA CGCCCGTGATCGTCACCTCCAACACCA ACATGTGCGCCGTGATCGACGGGAACA GCACCACCTTCGAGCACCAGCAGCCGC TGCAGGACCGCATGTTCAAGTTCGAGC TCACCCGCCGTCTGGAGCACGACTTTG GCAAGGTGACCAAGCAGGAAGTCAAA GAGTTCTTCCGCTGGGCTCAGGATCAC GTGACTGAGGTGGCGCATGAGTTCTAC GTCAGAAAGGGCGGAGCCACCAAAAG ACCCGCCCCAGTGACGCGGATATAAG CGAGCCCAAGCGGGCCTGCCCCTCAGT TCCGGAGCCATCGACGTCAGACGCGGA AGCACCGGTGGACTTTGCGGACAGGTA CCAAAACAAA | 154 |
| | | z | 1600-1869 | TGTTCTCGTCACGCGGGCATGCTTCAG ATGCTGTTTCCTGCAAGACATGCGAG AGAATGAATCAGAATTTCAACGTCTGC TTCACGCACGGGGTCAGAGACTGCTCA GAGTGCTTCCCCGGCGCGTCAGAATCT CAACCCGTCGTCAGAAAAAAGACGTAT CAGAAACTGTGCGCGATTCATCATCTG CTGGGGCGGGCACCCGAGATTGCGTGT TCGGCCTGCGATCTCGTCAACGTGGAC TTGGATGACTGTGTTTCTGAGCAATAA | 155 |
| | PRT | n | 1-102 | MPGFYEIVIKVPSDLDEHLPGISDSFVNW VAEKEWELPPDSDMDRNLIEQAPLTVAE KLQRDFLVHWRRVSKAPEALFFVQFEK GESYFHLHVLVETTGVKS | 156 |
| | | d | 103-242 | MVLGRFLSQIRDRLVQTIYRGVEPTLPN WFAVTKTRNGAGGGNKVVDECYIPNYL LPKTQPELQWAWTNMEEYISACLNLAE RKRLVAQHLTHVSQTQEQNKENLNPNS DAPVIRSKTSARYMELVGWLVDRGITSE KQW | 157 |
| | | h | 243-369 | IQEDQASYISFNAASNSRSQIKAALDNAG KIMALTKSAPDYLVGPSLPADIKANRIYR ILELNGYDPAYAGSVFLGWAQKKFGKR NTIWLFGPATTGKTNIAEAIAHAVPFYGC VNWTNENFPFNDC | 158 |
| | | c | 370-622 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGATKRPAPSDADISEPK RACPSVPEPSTSDAEAPVDFADRYQNKC SRHAGMLQMLFPCKTCERMNQNFNVCF THGVRDCSECFPGASESQPVVRKKTYQK LCAIHHLLGRAPEIACSACDLVNVDLDD CVSEQ | 159 |
| | | y | 370-533 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGATKRPAPSDADISEPK RACPSVPEPSTSDAEAPVDFADRYQNK | 160 |
| | | z | 534-622 | CSRHAGMLQMLFPCKTCERMNQNFNVC FTHGVRDCSECFPGASESQPVVRKKTYQ KLCAIHHLLGRAPEIACSACDLVNVDLD DCVSEQ | 161 |
| AAV12 | DNA | n | 1-306 | ATGCCGGGGTTCTACGAGGTGGTGATC AAGGTGCCCAGCGACCTGGACGAGCA CCTGCCCGGCATTTCTGACTCCTTTGTG AACTGGGTGGCCGAGAAGGAATGGGA | 162 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | GTTGCCCCGGATTCTGACATGGATCA GAATCTGATTGAGCAGGCACCCCTGAC CGTGGCCGAGAAGCTGCAGCGCGAGTT CCTGGTGGAATGGCGCCGAGTGAGTAA ATTTCTGGAGGCCAAGTTTTTTGTGCA GTTTGAAAAGGGGGACTCGTACTTTCA TTTGCATATTCTGATTGAAATTACCGG CGTGAAATCC | |
| | | d | 307-726 | ATGGTGGTGGGCCGCTACGTGAGTCAG ATTAGGGATAAACTGATCCAGCGCATC TACCGCGGGGTCGAGCCCCAGCTGCCC AACTGGTTCGCGGTCACAAAGACCCGA AATGGCGCCGGAGGCGGGAACAAGGT GGTGGACGAGTGCTACATCCCCAACTA CCTGCTCCCCAAGGTCCAGCCCGAGCT TCAGTGGGCGTGGACTAACATGGAGG AGTATATAAGCGCCTGTTTGAACCTCG CGGAGCGTAAACGGCTCGTGGCGCAG CACCTGACGCACGTCTCCCAGACCCAG GAGGGCGACAAGGAGAATCTGAACCC GAATTCTGACGCGCCGGTGATCCGGTC AAAAACCTCCGCCAGGTACATGGAGCT GGTCGGGTGGCTGGTGGACAAGGGCA TCACGTCCGAGAAGCAGTGG | 163 |
| | | h | 727-1107 | ATCCAGGAGGACCAGGCCTCGTACATC TCCTTCAACGCGGCCTCCAACTCCCGG TCGCAGATCAAGGCGGCCCTGGACAAT GCCTCCAAAATCATGAGCCTCACCAAA ACGGCTCCGGACTATCTCATCGGGCAG CAGCCCGTGGGGGACATTACCACCAAC CGGATCTACAAAATCCTGGAACTGAAC GGGTACGACCCCCAGTACGCCGCCTCC GTCTTTCTCGGCTGGGCCCAGAAAAAG TTTGGAAAGCGCAACACCATCTGGCTG TTTGGGCCCGCCACCACCGGCAAGACC AACATCGCGGAAGCCATCGCCCACGCG GTCCCCTTCTACGGCTGCGTCAACTGG ACCAATGAGAACTTTCCCTTCAACGAC TGC | 164 |
| | | c | 1108-1866 | GTCGACAAAATGGTGATTTGGTGGGAG GAGGGCAAGATGACCGCCAAGGTCGT AGAGTCCGCCAAGGCCATTCTGGGCGG CAGCAAGGTGCGCGTGGACCAAAAAT GCAAGGCCTCTGCGCAGATCGACCCCA CCCCCGTGATCGTCACCTCCAACACCA ACATGTGCGCCGTGATTGACGGGAACA GCACCACCTTCGAGCACCAGCAGCCCC TGCAGGACCGGATGTTCAAGTTTGAAC TCACCCGCCGCCTCGACCACGACTTTG GCAAGGTCACCAAGCAGGAAGTCAAG GACTTTTTCCGGTGGGCGGCTGATCAC GTGACTGACGTGGCTCATGAGTTTTAC GTCACAAAGGGTGGAGCTAAGAAAAG GCCCGCCCCTCTGACGAGGATATAAG CGAGCCCAAGCGGCCGCGCGTGTCATT TGCGCAGCCGGAGACGTCAGACGCGG AAGCTCCCGGAGACTTCGCCGACAGGT ACCAAAACAAATGTTCTCGTCACGCGG GTATGCTGCAGATGCTCTTTCCCTGCA AGACGTGCGAGAGAATGAATCAGAAT TCCAACGTCTGCTTCACGCACGGTCAG AAAGATTGCGGGAGTGCTTTCCCGGG TCAGAATCTCAACCGGTTTCTGTCGTC AGAAAAACGTATCAGAAACTGTGCATC CTTCATCAGCTCCGGGGGGCACCCGAG ATCGCCTGCTCTGCTTGCGACCAACTC AACCCCGATTTGGACGATTGCCAATTT GAGCAATAA | 165 |
| | | y | 1108-1599 | GTCGACAAAATGGTGATTTGGTGGGAG GAGGGCAAGATGACCGCCAAGGTCGT AGAGTCCGCCAAGGCCATTCTGGGCGG | 166 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | CAGCAAGGTGCGCGTGGACCAAAAAT GCAAGGCCTCTGCGCAGATCGACCCCA CCCCCGTGATCGTCACCTCCAACACCA ACATGTGCGCCGTGATTGACGGGAACA GCACCACCTTCGAGCACCAGCAGCCCC TGCAGGACCGGATGTTCAAGTTTGAAC TCACCCGCCGCCTCGACCACGACTTTG GCAAGGTCACCAAGCAGGAAGTCAAG GACTTTTTCCGGTGGGCGGCTGATCAC GTGACTGACGTGGCTCATGAGTTTTAC GTCACAAAGGGTGGAGCTAAGAAAAG GCCCGCCCCTCTGACGAGGATATAAG CGAGCCCAAGCGGCCGCGCGTGTCATT TGCGCAGCCGGAGACGTCAGACGCGG AAGCTCCCGGAGACTTCGCCGACAGGT ACCAAAACAAA | |
| | | z | 1600-1866 | TGTTCTCGTCACGCGGGTATGCTGCAG ATGCTCTTTCCCTGCAAGACGTGCGAG AGAATGAATCAGAATTCCAACGTCTGC TTCACGCACGGTCAGAAAGATTGCGGG GAGTGCTTTCCCGGGTCAGAATCTCAA CCGGTTTCTGTCGTCAGAAAAACGTAT CAGAAACTGTGCATCCTTCATCAGCTC CGGGGGGCACCCGAGATCGCCTGCTCT GCTTGCGACCAACTCAACCCCGATTTG GACGATTGCCAATTTGAGCAATAA | 167 |
| | PRT | n | 1-102 | MPGFYEVVIKVPSDLDEHLPGISDSFVN WVAEKEWELPPDSDMDQNLIEQAPLTV AEKLQREFLVEWRRVSKFLEAKFFVQFE KGDSYFHLHILIEITGVKS | 168 |
| | | d | 103-242 | MVVGRYVSQIRDKLIQRIYRGVEPQLPN WFAVTKTRNGAGGGNKVVDECYIPNYL LPKVQPELQWAWTNMEEYISACLNLAE RKRLVAQHLTHVSQTQEGDKENLNPNS DAPVIRSKTSARYMELVGWLVDKGITSE KQW | 169 |
| | | h | 243-369 | IQEDQASYISFNAASNSRSQIKAALDNAS KIMSLTKTAPDYLIGQQPVGDITTNRIYKI LELNGYDPQYAASVFLGWAQKKFGKRN TIWLFGPATTGKTNIAEAIAHAVPFYGCV NWTNENFPFNDC | 170 |
| | | c | 370-621 | VDKMVIWWEEGKMTAKVVESAKAILG GSKVRVDQKCKASAQIDPTPVIVTSNTN MCAVIDGNSTTFEHQQPLQDRMFKFELT RRLDHDFGKVTKQEVKDFFRWAADHVT DVAHEFYVTKGGAKKRPAPSDEDISEPK RPRVSFAQPETSDAEAPGDFADRYQNKC SRHAGMLQMLFPCKTCERMNQNSNVCF THGQKDCGECFPGSESQPVSVVRKTYQK LCILHQLRGAPEIACSACDQLNPDLDDC QFEQ | 171 |
| | | y | 370-533 | VDKMVIWWEEGKMTAKVVESAKAILG GSKVRVDQKCKASAQIDPTPVIVTSNTN MCAVIDGNSTTFEHQQPLQDRMFKFELT RRLDHDFGKVTKQEVKDFFRWAADHVT DVAHEFYVTKGGAKKRPAPSDEDISEPK RPRVSFAQPETSDAEAPGDFADRYQNK | 172 |
| | | z | 534-621 | CSRHAGMLQMLFPCKTCERMNQNSNVC FTHGQKDCGECFPGSESQPVSVVRKTYQ KLCILHQLRGAPEIACSACDQLNPDLDD CQFEQ | 173 |
| AAV13 | DNA | n | 1-306 | ATGCCGGGATTCTACGAGATTGTCCTG AAGGTGCCCAGCGACCTGGACGAGCA CCTGCCTGGCATTTCTGACTCTTTTGTA AACTGGGTGGCGGAGAAGGAATGGGA GCTGCCGCCGGATTCTGACATGGATCT GAATCTGATTGAGCAGGCACCCCTAAC CGTGGCCGAAAAGCTGCAACGCGAATT CCTGGTCGAGTGGCGCCGCGTGAGTAA GGCCCCGGAGGCCCTCTTCTTTGTTCA | 174 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | GTTCGAGAAGGGGGACAGCTACTTCCA CCTACACATTCTGGTGGAGACCGTGGG CGTGAAATCC | |
| | | d | 307-726 | ATGGTGGTGGGCCGCTACGTGAGCCAG ATTAAAGAGAAGCTGGTGACCCGCATC TACCGCGGGGTCGAGCCGCAGCTTCCG AACTGGTTCGCGGTGACCAAGACGCGT AATGGCGCCGGAGGCGGGAACAAGGT GGTGGACGACTGCTACATCCCCAACTA CCTGCTCCCCAAGACCCAGCCCGAGCT CCAGTGGGCGTGGACTAATATGGACCA GTATTTAAGCGCCTGTTTGAATCTCGC GGAGCGTAAACGGCTGGTGGCGCAGC ATCTGACGCACGTGTCGCAGACGCAGG AGCAGAACAAAGAGAACCAGAATCCC AATTCTGACGCGCCGGTGATCAGATCA AAAACCTCCGCGAGGTACATGGAGCTG GTCGGGTGGCTGGTGGACCGCGGGATC ACGTCAGAAAAGCAATGG | 175 |
| | | h | 727-1107 | ATCCAGGAGGACCAGGCCTCTTACATC TCCTTCAACGCCGCCTCCAACTCGCGG TCACAAATCAAGGCCGCACTGGACAAT GCCTCCAAATTTATGAGCCTGACAAAA ACGGCTCCGGACTACCTGGTGGGAAAC AACCCGCCGGAGGACATTACCAGCAA CCGGATCTACAAAATCCTCGAGATGAA CGGGTACGATCCGCAGTACGCGGCCTC CGTCTTCCTGGGCTGGGCGCAAAAGAA GTTCGGGAAGAGGAACACCATCTGGCT CTTTGGGCCGGCCACGACGGGTAAAAC CAACATCGCTGAAGCTATCGCCCACGC CGTGCCCTTTTACGGCTGCGTGAACTG GACCAATGAGAACTTTCCGTTCAACGA TTGC | 176 |
| | | c | 1108-1872 | GTCGACAAGATGGTGATCTGGTGGGAG GAGGGCAAGATGACGGCCAAGGTCGT GGAGTCCGCCAAGGCCATTCTGGGCGG AAGCAAGGTGCGCGTGGACCAAAAGT GCAAGTCATCGGCCCAGATCGACCCAA CTCCCGTCATCGTCACCTCCAACACCA ACATGTGCGCGGTCATCGACGGAAATT CCACCACCTTCGAGCACCAACAACCAC TCCAAGACCGGATGTTCAAGTTCGAGC TCACCAAGCGCCTGGAGCACGACTTTG GCAAGGTCACCAAGCAGGAAGTCAAG GACTTTTTCCGGTGGGCGTCAGATCAC GTGACTGAGGTGTCTCACGAGTTTTAC GTCAGAAAGGGTGGAGCTAGAAAGAG GCCCGCCCCCAATGACGCAGATATAAG TGAGCCCAAGCGGGCCTGTCCGTCAGT TGCGCAGCCATCGACGTCAGACGCGGA AGCTCCGGTGGACTACGCGGACAGGTA CCAAAACAAATGTTCTCGTCACGTGGG CATGAATCTGATGCTTTTTCCCTGCCGG CAATGCGAGAGAATGAATCAGAATGT GGACATTTGCTTCACGCACGGGGTCAT GGACTGTGCCGAGTGCTTCCCCGTGTC AGAATCTCAACCCGTGTCTGTCGTCAG AAAGCGGACATATCAGAAACTGTGTCC GATTCATCACATCATGGGAGGGCGCC CGAGGTGGCTTGTTCGGCCTGCGATCT GGCCAATGTGGACTTGGATGACTGTGA CATGGAGCAATAA | 177 |
| | | y | 1108-1599 | GTCGACAAGATGGTGATCTGGTGGGAG GAGGGCAAGATGACGGCCAAGGTCGT GGAGTCCGCCAAGGCCATTCTGGGCGG AAGCAAGGTGCGCGTGGACCAAAAGT GCAAGTCATCGGCCCAGATCGACCCAA CTCCCGTCATCGTCACCTCCAACACCA ACATGTGCGCGGTCATCGACGGAAATT CCACCACCTTCGAGCACCAACAACCAC | 178 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | TCCAAGACCGGATGTTCAAGTTCGAGC TCACCAAGCGCCTGGAGCACGACTTTG GCAAGGTCACCAAGCAGGAAGTCAAG GACTTTTTCCGGTGGGCGTCAGATCAC GTGACTGAGGTGTCTCACGAGTTTTAC GTCAGAAAGGGTGGAGCTAGAAAGAG GCCCGCCCCCAATGACGCAGATATAAG TGAGCCCAAGCGGGCCTGTCCGTCAGT TGCGCAGCCATCGACGTCAGACGCGGA AGCTCCGGTGGACTACGCGGACAGGTA CCAAAACAAA | |
| | | z | 1600-1872 | TGTTCTCGTCACGTGGGCATGAATCTG ATGCTTTTTCCCTGCCGGCAATGCGAG AGAATGAATCAGAATGTGGACATTTGC TTCACGCACGGGGTCATGGACTGTGCC GAGTGCTTCCCCGTGTCAGAATCTCAA CCCGTGTCTGTCGTCAGAAAGCGGACA TATCAGAAACTGTGTCCGATTCATCAC ATCATGGGGAGGGCGCCCGAGGTGGC TTGTTCGGCCTGCGATCTGGCCAATGT GGACTTGGATGACTGTGACATGGAGCA ATAA | 179 |
| | PRT | n | 1-102 | MPGFYEIVLKVPSDLDEHLPGISDSFVNW VAEKEWELPPDSDMDLNLIEQAPLTVAE KLQREFLVEWRRVSKAPEALFFVQFEKG DSYFHLHILVETVGVKS | 180 |
| | | d | 103-242 | MVVGRYVSQIKEKLVTRIYRGVEPQLPN WFAVTKTRNGAGGGNKVVDDCYIPNYL LPKTQPELQWAWTNMDQYLSACLNLAE RKRLVAQHLTHVSQTQEQNKENQNPNS DAPVIRSKTSARYMELVGWLVDRGITSE KQW | 181 |
| | | h | 243-369 | IQEDQASYISFNAASNSRSQIKAALDNAS KFMSLTKTAPDYLVGNNPPEDITSNRIYK ILEMNGYDPQYAASVFLGWAQKKFGKR NTIWLFGPATTGKTNIAEAIAHAVPFYGC VNWTNENFPFNDC | 182 |
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT KRLEHDFGKVTKQEVKDFFRWASDHVT EVSHEFYVRKGGARKRPAPNDADISEPK RACPSVAQPSTSDAEAPVDYADRYQNK CSRHVGMNLMLFPCRQCERMNQNVDIC FTHGVMDCAECFPVSESQPVSVVRKRTY QKLCPIHHIMGRAPEVACSACDLANVDL DDCDMEQ | 183 |
| | | y | 370-533 | VDKMVIWWEEGKMTAKVVESAKAILG GSKVRVDQKCKSSAQIDPTPVIVTSNTN MCAVIDGNSTTFEHQQPLQDRMFKFELT KRLEHDFGKVTKQEVKDFFRWASDHVT EVSHEFYVRKGGARKRPAPNDADISEPK RACPSVAQPSTSDAEAPVDYADRYQNK | 184 |
| | | z | 534-623 | CSRHVGMNLMLFPCRQCERMNQNVDIC FTHGVMDCAECFPVSESQPVSVVRKRTY QKLCPIHHIMGRAPEVACSACDLANVDL DDCDMEQ | 185 |

In some embodiments, disclosed herein is a chimeric rep gene. In some embodiments, a chimeric rep gene has at least one domain (e.g., n, d, h, y, or z) or at least one terminus (e.g., N terminus or C terminus) that is of a serotype that is different than the serotype of majority of the rep gene, or the serotypes of the other domains or terminus. In some embodiments, the N terminus is of serotype (e.g., 1, 2, 3, 4, 5, 6, 7, 8, 9, 10, 11, 12, or 13) different than the serotype of the C terminus (e.g., 1, 2, 3, 4, 5, 6, 7, 8, 9, 10, 11, 12, or 13). In some embodiments, the N terminus is of one serotype and the C-terminus is of a second serotype (e.g., 1, 2, 3, 4, 5, 6, 7, 8, 9, 10, 11, 12, or 13).

In some embodiments, the n domain is of AAV serotype 1, and each of the d, h, y, and z are of a serotype other than AAV1 (e.g., 2, 3, 4, 5, 6, 7, 8, 9, 10, 11, 12, or 13). For example, each of the d, h, y, and z domains may be of the same serotype (e.g., 2, 3, 4, 5, 6, 7, 8, 9, 10, 11, 12, or 13). In some embodiments, each of the d, h, y, and z domains may be of different serotypes relative to each other, e.g., d, h, and y may be of AAV2 serotype, while z may be of AAV3 serotype. In some embodiments, the n domain is of AAV serotype 2, and each of the d, h, y, and z domains are of a serotype other than AAV2 (e.g., 1, 3, 4, 5, 6, 7, 8, 9, 10, 11, 12, or 13). The serotypes of each of the d, h, y, and z domains may be the same, or may be different from each other. In some embodiments, the n domain is of AAV serotype 3, and each of the d, h, y, and z domains are of a serotype other than AAV3 (e.g., 1, 2, 4, 5, 6, 7, 8, 9, 10, 11, 12, or 13). The serotypes of each of the d, h, y, and z domains may be the same, or may be different from each other. In some embodiments, the n domain is of AAV serotype 4, and each of the d, h, y, and z domains are of a serotype other than AAV4 (e.g., 1, 2, 4, 5, 6, 7, 8, 9, 10, 11, 12, or 13). The serotypes of each of the d, h, y, and z domains may be the same, or may be different from each other. In some embodiments, the n domain is of AAV serotype 5, and each of the d, h, y, and z domains are of a serotype other than AAV5 (e.g., 1, 2, 3, 4, 6, 7, 8, 9, 10, 11, 12, or 13). The serotypes of each of the d, h, y, and z domains may be the same, or may be different from each other. In some embodiments, the n domain is of AAV serotype 6, and each of the d, h, y, and z domains are of a serotype other than AAV6 (e.g., 1, 2, 3, 4, 5, 7, 8, 9, 10, 11, 12, or 13). The serotypes of each of the d, h, y, and z domains may be the same, or may be different from each other. In some embodiments, the n domain is of AAV serotype 7, and each of the d, h, y, and z domains are of a serotype other than AAV7 (e.g., 1, 2, 3, 4, 5, 6, 8, 9, 10, 11, 12, or 13). The serotypes of each of the d, h, y, and z domains may be the same, or may be different from each other. In some embodiments, the n domain is of AAV serotype 8, and each of the d, h, y, and z domains are of a serotype other than AAV8 (e.g., 1, 2, 3, 4, 5, 6, 7, 9, 10, 11, 12, or 13). The serotypes of each of the d, h, y, and z domains may be the same, or may be different from each other. In some embodiments, the n domain is of AAV serotype 9, and each of the d, h, y, and z domains are of a serotype other than AAV9 (e.g., 1, 2, 3, 4, 5, 6, 7, 8, 10, 11, 12, or 13). The serotypes of each of the d, h, y, and z domains may be the same, or may be different from each other. In some embodiments, the n domain is of AAV serotype 10, and each of the d, h, y, and z domains are of a serotype other than AAV10 (e.g., 1, 2, 3, 4, 5, 6, 7, 8, 9, 11, 12, or 13). The serotypes of each of the d, h, y, and z domains may be the same, or may be different from each other. In some embodiments, the n domain is of AAV serotype 11, and each of the d, h, y, and z domains are of a serotype other than AAV11 (e.g., 1, 2, 3, 4, 5, 6, 7, 8, 9, 10, 12, or 13). The serotypes of each of the d, h, y, and z domains may be the same, or may be different from each other. In some embodiments, the n domain is of AAV serotype 12, and each of the d, h, y, and z domains are of a serotype other than AAV12 (e.g., 1, 2, 3, 4, 5, 6, 7, 8, 9, 10, 11, or 13). The serotypes of each of the d, h, y, and z domains may be the same, or may be different from each other. In some embodiments, then domain is of AAV serotype 13, and each of the d, h, y, and z domains are of a serotype other than AAV13 (e.g., 1, 2, 3, 4, 5, 6, 7, 8, 9, 10, 11, or 12). The serotypes of each of the d, h, y, and z domains may be the same, or may be different from each other.

In some embodiments, the d domain is of AAV serotype 1, and each of the n, h, y, and z are of a serotype other than AAV1 (e.g., 2, 3, 4, 5, 6, 7, 8, 9, 10, 11, 12, or 13). For example, each of the n, h, y, and z domains may be of the same serotype (e.g., 2, 3, 4, 5, 6, 7, 8, 9, 10, 11, 12, or 13). In some embodiments, each of the n, h, y, and z domains may be of different serotypes relative to each other, e.g., n, h, and y may be of AAV2 serotype, while z may be of AAV3 serotype. In some embodiments, the d domain is of AAV serotype 2, and each of the n, h, y, and z domains are of a serotype other than AAV2 (e.g., 1, 3, 4, 5, 6, 7, 8, 9, 10, 11, 12, or 13). The serotypes of each of the n, h, y, and z domains may be the same, or may be different from each other. In some embodiments, the d domain is of AAV serotype 3, and each of the n, h, y, and z domains are of a serotype other than AAV3 (e.g., 1, 2, 4, 5, 6, 7, 8, 9, 10, 11, 12, or 13). The serotypes of each of the n, h, y, and z domains may be the same, or may be different from each other. In some embodiments, the d domain is of AAV serotype 4, and each of the n, h, y, and z domains are of a serotype other than AAV4 (e.g., 1, 2, 4, 5, 6, 7, 8, 9, 10, 11, 12, or 13). The serotypes of each of the n, h, y, and z domains may be the same, or may be different from each other. In some embodiments, the d domain is of AAV serotype 5, and each of the n, h, y, and z domains are of a serotype other than AAV5 (e.g., 1, 2, 3, 4, 6, 7, 8, 9, 10, 11, 12, or 13). The serotypes of each of the n, h, y, and z domains may be the same, or may be different from each other. In some embodiments, the n domain is of AAV serotype 6, and each of the n, h, y, and z domains are of a serotype other than AAV6 (e.g., 1, 2, 3, 4, 5, 7, 8, 9, 10, 11, 12, or 13). The serotypes of each of the n, h, y, and z domains may be the same, or may be different from each other. In some embodiments, the d domain is of AAV serotype 7, and each of the n, h, y, and z domains are of a serotype other than AAV7 (e.g., 1, 2, 3, 4, 5, 6, 8, 9, 10, 11, 12, or 13). The serotypes of each of the n, h, y, and z domains may be the same, or may be different from each other. In some embodiments, the n domain is of AAV serotype 8, and each of the n, h, y, and z domains are of a serotype other than AAV8 (e.g., 1, 2, 3, 4, 5, 6, 7, 9, 10, 11, 12, or 13). The serotypes of each of the n, h, y, and z domains may be the same, or may be different from each other. In some embodiments, the d domain is of AAV serotype 9, and each of the n, h, y, and z domains are of a serotype other than AAV9 (e.g., 1, 2, 3, 4, 5, 6, 7, 8, 10, 11, 12, or 13). The serotypes of each of the n, h, y, and z domains may be the same, or may be different from each other. In some embodiments, the d domain is of AAV serotype 10, and each of the n, h, y, and z domains are of a serotype other than AAV10 (e.g., 1, 2, 3, 4, 5, 6, 7, 8, 9, 11, 12, or 13). The serotypes of each of the n, h, y, and z domains may be the same, or may be different from each other. In some embodiments, the d domain is of AAV serotype 11, and each of the n, h, y, and z domains are of a serotype other than AAV11 (e.g., 1, 2, 3, 4, 5, 6, 7, 8, 9, 10, 12, or 13). The serotypes of each of the n, h, y, and z domains may be the same, or may be different from each other. In some embodiments, the d domain is of AAV serotype 12, and each of the n, h, y, and z domains are of a serotype other than AAV12 (e.g., 1, 2, 3, 4, 5, 6, 7, 8, 9, 10, 11, or 13). The serotypes of each of the n, h, y, and z domains may be the same, or may be different from each other. In some embodiments, the d domain is of AAV serotype 13, and each of the n, h, y, and z domains are of a serotype other than AAV13 (e.g., 1, 2, 3, 4, 5, 6, 7, 8, 9, 10, 11, or 12). The serotypes of each of the n, h, y, and z domains may be the same, or may be different from each other.

In some embodiments, the h domain is of AAV serotype 1, and each of the d, n, y, and z are of a serotype other than AAV1 (e.g., 2, 3, 4, 5, 6, 7, 8, 9, 10, 11, 12, or 13). For example, each of the d, n, y, and z domains may be of the same serotype (e.g., 2, 3, 4, 5, 6, 7, 8, 9, 10, 11, 12, or 13). In some embodiments, each of the d, n, y, and z domains may be of different serotypes relative to each other, e.g., d, n, and y may be of AAV2 serotype, while z may be of AAV3 serotype. In some embodiments, the h domain is of AAV serotype 2, and each of the d, n, y, and z domains are of a serotype other than AAV2 (e.g., 1, 3, 4, 5, 6, 7, 8, 9, 10, 11, 12, or 13). The serotypes of each of the d, n, y, and z domains may be the same, or may be different from each other. In some embodiments, the h domain is of AAV serotype 3, and each of the d, n, y, and z domains are of a serotype other than AAV3 (e.g., 1, 2, 4, 5, 6, 7, 8, 9, 10, 11, 12, or 13). The serotypes of each of the d, n, y, and z domains may be the same, or may be different from each other. In some embodiments, the h domain is of AAV serotype 4, and each of the d, n, y, and z domains are of a serotype other than AAV4 (e.g., 1, 2, 4, 5, 6, 7, 8, 9, 10, 11, 12, or 13). The serotypes of each of the d, n, y, and z domains may be the same, or may be different from each other. In some embodiments, the h domain is of AAV serotype 5, and each of the d, n, y, and z domains are of a serotype other than AAV5 (e.g., 1, 2, 3, 4, 6, 7, 8, 9, 10, 11, 12, or 13). The serotypes of each of the d, n, y, and z domains may be the same, or may be different from each other. In some embodiments, the h domain is of AAV serotype 6, and each of the d, n, y, and z domains are of a serotype other than AAV6 (e.g., 1, 2, 3, 4, 5, 7, 8, 9, 10, 11, 12, or 13). The serotypes of each of the d, n, y, and z domains may be the same, or may be different from each other. In some embodiments, the h domain is of AAV serotype 7, and each of the d, n, y, and z domains are of a serotype other than AAV7 (e.g., 1, 2, 3, 4, 5, 6, 8, 9, 10, 11, 12, or 13). The serotypes of each of the d, n, y, and z domains may be the same, or may be different from each other. In some embodiments, the h domain is of AAV serotype 8, and each of the d, n, y, and z domains are of a serotype other than AAV8 (e.g., 1, 2, 3, 4, 5, 6, 7, 9, 10, 11, 12, or 13). The serotypes of each of the d, n, y, and z domains may be the same, or may be different from each other. In some embodiments, the h domain is of AAV serotype 9, and each of the d, n, y, and z domains are of a serotype other than AAV9 (e.g., 1, 2, 3, 4, 5, 6, 7, 8, 10, 11, 12, or 13). The serotypes of each of the d, n, y, and z domains may be the same, or may be different from each other. In some embodiments, the h domain is of AAV serotype 10, and each of the d, n, y, and z domains are of a serotype other than AAV10 (e.g., 1, 2, 3, 4, 5, 6, 7, 8, 9, 11, 12, or 13). The serotypes of each of the d, n, y, and z domains may be the same, or may be different from each other. In some embodiments, the h domain is of AAV serotype 11, and each of the d, n, y, and z domains are of a serotype other than AAV11 (e.g., 1, 2, 3, 4, 5, 6, 7, 8, 9, 10, 12, or 13). The serotypes of each of the d, n, y, and z domains may be the same, or may be different from each other. In some embodiments, the h domain is of AAV serotype 12, and each of the d, n, y, and z domains are of a serotype other than AAV12 (e.g., 1, 2, 3, 4, 5, 6, 7, 8, 9, 10, 11, or 13). The serotypes of each of the d, n, y, and z domains may be the same, or may be different from each other. In some embodiments, the h domain is of AAV serotype 13, and each of the d, n, y, and z domains are of a serotype other than AAV13 (e.g., 1, 2, 3, 4, 5, 6, 7, 8, 9, 10, 11, or 12). The serotypes of each of the d, n, y, and z domains may be the same, or may be different from each other.

In some embodiments, the y domain is of AAV serotype 1, and each of the n, d, h, and z are of a serotype other than AAV1 (e.g., 2, 3, 4, 5, 6, 7, 8, 9, 10, 11, 12, or 13). For example, each of the n, d, h, and z domains may be of the same serotype (e.g., 2, 3, 4, 5, 6, 7, 8, 9, 10, 11, 12, or 13). In some embodiments, each of the n, d, h, and z domains may be of different serotypes relative to each other, e.g., d, h may be of AAV2 serotype, while z may be of AAV3 serotype. In some embodiments, the y domain is of AAV serotype 2, and each of the n, d, h, and z domains are of a serotype other than AAV2 (e.g., 1, 3, 4, 5, 6, 7, 8, 9, 10, 11, 12, or 13). The serotypes of each of the n, d, h, and z domains may be the same, or may be different from each other. In some embodiments, the y domain is of AAV serotype 3, and each of the n, d, h, and z domains are of a serotype other than AAV3 (e.g., 1, 2, 4, 5, 6, 7, 8, 9, 10, 11, 12, or 13). The serotypes of each of the n, d, h, and z domains may be the same, or may be different from each other. In some embodiments, the y domain is of AAV serotype 4, and each of the n, d, h, and z domains are of a serotype other than AAV4 (e.g., 1, 2, 4, 5, 6, 7, 8, 9, 10, 11, 12, or 13). The serotypes of each of the n, d, h, and z domains may be the same, or may be different from each other. In some embodiments, the y domain is of AAV serotype 5, and each of the n, d, h, and z domains are of a serotype other than AAV5 (e.g., 1, 2, 3, 4, 6, 7, 8, 9, 10, 11, 12, or 13). The serotypes of each of the n, d, h, and z domains may be the same, or may be different from each other. In some embodiments, the y domain is of AAV serotype 6, and each of the n, d, h, and z domains are of a serotype other than AAV6 (e.g., 1, 2, 3, 4, 5, 7, 8, 9, 10, 11, 12, or 13). The serotypes of each of the n, d, h, and z domains may be the same, or may be different from each other. In some embodiments, the y domain is of AAV serotype 7, and each of the n, d, h, and z domains are of a serotype other than AAV7 (e.g., 1, 2, 3, 4, 5, 6, 8, 9, 10, 11, 12, or 13). The serotypes of each of the n, d, h, and z domains may be the same, or may be different from each other. In some embodiments, the y domain is of AAV serotype 8, and each of the n, d, h, and z domains are of a serotype other than AAV8 (e.g., 1, 2, 3, 4, 5, 6, 7, 9, 10, 11, 12, or 13). The serotypes of each of the n, d, h, and z domains may be the same, or may be different from each other. In some embodiments, the y domain is of AAV serotype 9, and each of the n, d, h, and z domains are of a serotype other than AAV9 (e.g., 1, 2, 3, 4, 5, 6, 7, 8, 10, 11, 12, or 13). The serotypes of each of the n, d, h, and z domains may be the same, or may be different from each other. In some embodiments, the y domain is of AAV serotype 10, and each of the n, d, h, and z domains are of a serotype other than AAV10 (e.g., 1, 2, 3, 4, 5, 6, 7, 8, 9, 11, 12, or 13). The serotypes of each of the n, d, h, and z domains may be the same, or may be different from each other. In some embodiments, the y domain is of AAV serotype 11, and each of the n, d, h, and z domains are of a serotype other than AAV11 (e.g., 1, 2, 3, 4, 5, 6, 7, 8, 9, 10, 12, or 13). The serotypes of each of the n, d, h, and z domains may be the same, or may be different from each other. In some embodiments, the y domain is of AAV serotype 12, and each of the n, d, h, and z domains are of a serotype other than AAV12 (e.g., 1, 2, 3, 4, 5, 6, 7, 8, 9, 10, 11, or 13). The serotypes of each of the n, d, h, and z domains may be the same, or may be different from each other. In some embodiments, the y domain is of AAV serotype 13, and each of the n, d, h, and z domains are of a serotype other than AAV13 (e.g., 1, 2, 3, 4, 5, 6, 7, 8, 9, 10, 11, or 12). The serotypes of each of the n, d, h, and z domains may be the same, or may be different from each other.

In some embodiments, the z domain is of AAV serotype 1, and each of the n, d, h, and y are of a serotype other than AAV1 (e.g., 2, 3, 4, 5, 6, 7, 8, 9, 10, 11, 12, or 13). For example, each of the n, d, h, and y domains may be of the same serotype (e.g., 2, 3, 4, 5, 6, 7, 8, 9, 10, 11, 12, or 13). In some embodiments, each of the n, d, h, and y domains may be of different serotypes relative to each other, e.g., d, h may be of AAV2 serotype, while z may be of AAV3 serotype. In some embodiments, the z domain is of AAV serotype 2, and each of the n, d, h, and y domains are of a serotype other than AAV2 (e.g., 1, 3, 4, 5, 6, 7, 8, 9, 10, 11, 12, or 13). The serotypes of each of the n, d, h, and y domains may be the same, or may be different from each other. In some embodiments, the z domain is of AAV serotype 3, and each of the n, d, h, and y domains are of a serotype other than AAV3 (e.g., 1, 2, 4, 5, 6, 7, 8, 9, 10, 11, 12, or 13). The serotypes of each of the n, d, h, and y domains may be the same, or may be different from each other. In some embodiments, the z domain is of AAV serotype 4, and each of the n, d, h, and y domains are of a serotype other than AAV4 (e.g., 1, 2, 4, 5, 6, 7, 8, 9, 10, 11, 12, or 13). The serotypes of each of the n, d, h, and y domains may be the same, or may be different from each other. In some embodiments, the z domain is of AAV serotype 5, and each of the n, d, h, and y domains are of a serotype other than AAV5 (e.g., 1, 2, 3, 4, 6, 7, 8, 9, 10, 11, 12, or 13). The serotypes of each of the n, d, h, and y domains may be the same, or may be different from each other. In some embodiments, the z domain is of AAV serotype 6, and each of the n, d, h, and y domains are of a serotype other than AAV6 (e.g., 1, 2, 3, 4, 5, 7, 8, 9, 10, 11, 12, or 13). The serotypes of each of the n, d, h, and y domains may be the same, or may be different from each other. In some embodiments, the z domain is of AAV serotype 7, and each of the n, d, h, and y domains are of a serotype other than AAV7 (e.g., 1, 2, 3, 4, 5, 6, 8, 9, 10, 11, 12, or 13). The serotypes of each of the n, d, h, and y domains may be the same, or may be different from each other. In some embodiments, the z domain is of AAV serotype 8, and each of the n, d, h, and y domains are of a serotype other than AAV8 (e.g., 1, 2, 3, 4, 5, 6, 7, 9, 10, 11, 12, or 13). The serotypes of each of the n, d, h, and y domains may be the same, or may be different from each other. In some embodiments, the z domain is of AAV serotype 9, and each of the n, d, h, and y domains are of a serotype other than AAV9 (e.g., 1, 2, 3, 4, 5, 6, 7, 8, 10, 11, 12, or 13). The serotypes of each of the n, d, h, and y domains may be the same, or may be different from each other. In some embodiments, the z domain is of AAV serotype 10, and each of the n, d, h, and y domains are of a serotype other than AAV10 (e.g., 1, 2, 3, 4, 5, 6, 7, 8, 9, 11, 12, or 13). The serotypes of each of the n, d, h, and y domains may be the same, or may be different from each other. In some embodiments, the z domain is of AAV serotype 11, and each of the n, d, h, and y domains are of a serotype other than AAV11 (e.g., 1, 2, 3, 4, 5, 6, 7, 8, 9, 10, 12, or 13). The serotypes of each of the n, d, h, and y domains may be the same, or may be different from each other. In some embodiments, the z domain is of AAV serotype 12, and each of the n, d, h, and y domains are of a serotype other than AAV12 (e.g., 1, 2, 3, 4, 5, 6, 7, 8, 9, 10, 11, or 13). The serotypes of each of the n, d, h, and y domains may be the same, or may be different from each other. In some embodiments, the z domain is of AAV serotype 13, and each of the n, d, h, and y domains are of a serotype other than AAV13 (e.g., 1, 2, 3, 4, 5, 6, 7, 8, 9, 10, 11, or 12). The serotypes of each of the n, d, h, and y domains may be the same, or may be different from each other.

FIGS. 7-16 provide examples of chimeric rep genes. It is to be understood that any combination of domains may be of a serotype that is different from the serotypes of the other domains. For example, only one domain may have a serotype that is different from the serotypes of the other domain. In some embodiments, all five domains have different serotypes. In some embodiments, the domains of a chimeric rep gene is of two different serotypes (e.g., R1h2, i.e., an h domain of AAV2 and other domains of AAV1). In some embodiments, the domains of a chimeric rep gene is of three different serotypes (e.g., R1c3h4, i.e, a C terminus of AAV3, a h domain of AAV4 and n and d domains of AA1). In some embodiments, the domains of a chimeric rep gene is of four different serotypes (e.g., R1h2d3y4, i.e., an h domain of AA2, d domain of AAV3, y domain of AAV3 and n and y domains of AAV1). In some embodiments, the domains of a chimeric rep gene is of five different serotypes (e.g., R1n2d3h4y8).

In some embodiments, a domain is truncated. In some embodiments a domain of a chimeric rep gene is truncated on the N terminal end of the domain. In some embodiments, a chimeric rep gene is truncated on the C terminal end of the domain. In some embodiments, a domain is modified such that non-contiguous nucleotides are deleted. In some embodiments, a domain is truncated by 1-18 nucleotides (e.g., 1, 2, 3, 4, 5, 6, 7, 8, 9, 10, 11, 12, 13, 14, 15, 16, 17, or 18 nucleotides). For example, a d domain may be truncated by 6 nucleotides on either the N terminal end or the C terminal end.

In some embodiments, any of the rep genes described herein comprises a start codon with the sequence ACG. In some embodiments, any of the rep genes described herein comprises a start codon with the sequence other than or different from ACG. In some embodiments, a start codon that has a sequence that is different from ACG is ATG.

It is also to be understood that the present disclosure also provides any chimeric Rep proteins that are encoded by any one of the chimeric rep genes disclosed herein, as well as any chimeric rep genes that may encode any one of the chimeric Rep proteins as disclosed herein.

In some embodiments of the present application, a Rep protein is chimeric in that it comprises amino acid sequences from more than one AAV serotype. In some embodiments, a chimeric Rep protein may comprise an N terminus comprising amino acids from one AAV serotype (e.g., AAV1, 2, 3, 4, 5, 6, 7, 8, 9, 10, 11, 12, or 13) and a C terminus comprising amino acids from another AAV serotype (e.g., AAV1, 2, 3, 4, 5, 6, 7, 8, 9, 10, 11, 12, or 13). For example, a Rep protein may comprise an N terminus comprising corresponding amino acids of AAV1 Rep protein, and a C terminus comprising corresponding amino acids of AAV2 Rep protein (e.g., SEQ ID NO: 34 for Rep78 comprising an N term of AAV1 and a C term of AAV2). A Rep protein may comprise an N terminus comprising corresponding amino acids of AAV2 Rep protein, and a C terminus comprising corresponding amino acids of AAV1 Rep protein (e.g., SEQ ID NO: 35 for Rep78 comprising an N term of AAV2 and a C term of AAV1). In another non-limiting example, a Rep protein comprises an N terminus comprising corresponding amino acids of AAV2 Rep protein, and a C terminus comprising corresponding amino acids of AAV5 Rep protein (e.g., SEQ ID NO: 36 for Rep78 comprising an N term of AAV2 and a C term of AAV5). In another non-limiting example, a Rep protein comprises an N terminus comprising corresponding amino acids of AAV5 Rep protein, and a C terminus comprising corresponding amino acids of AAV2 Rep protein (e.g., SEQ ID NO: 37 for Rep78 comprising an N term of AAV5 and a C term of AAV2). In some embodiments, a Rep protein comprises corresponding amino acids of more than two AAV serotypes (e.g., three, four, or five AAV serotypes). A non-limiting example of a Rep protein comprising corresponding amino acids of three AAV serotypes is Rep protein with corresponding amino acids from AAV1, AAV2 and AAV5. The term "corresponding amino acids" as used herein means amino acids in positions that align with each other in amino acid sequences of different AAV serotypes. In some embodiments, the corresponding amino acids between two AAV serotypes have the same positions. In some embodiments, corresponding amino acids between two AAV serotypes are in positions that are 1-5 amino acids shifted from each other. Methods of aligning amino acid sequences are known in the art, and algorithms to perform such alignments are also readily available. See e.g., Michael S. Rosenberg, Sequence Alignment: Methods, Models, Concepts, and Strategies, 2009, http://www.jstor.org/stable/10.1525/j.calpps7t. For example, alignment of AAV ITRs and/or Rep proteins can be performed using Protein BLAST, https://blast.ncbi.nlm.nih.g_ov/Blast.cgi?PROGRAM=blastp&PAGE TYPE=BlastSearch&BLAS T_SPEC=blast2seq&LINK LOC=blasttab.

```
Example of Rep78 amino acid sequence with an AAV1 N term
and an AAV2 C term:
                                              (SEQ ID NO: 34)
MPGFYEIVIKVPSDLDEHLPGISDSFVSWVAEKEWELPPDSDMDLNLIEQAPLTVAEK

LQRDFLVQWRRVSKAPEALFFVQFEKGESYFHLHILVETTGVKSMVLGRFLSQIRDK

LVQTIYRGIEPTLPNWFAVTKTRNGAGGGNKVVDECYIPNYLLPKTQPELQWAWTN

MEEYISACLNLAERKRLVAQHLTHVSQTQEQNKENLNPNSDAPVIRSKTSARYMELV

GWLVDKGITSEKQWIQEDQASYISFNAASNSRSQIKAALDNAGKIMSLTKTAPDYLV

GQQPVEDISSNRIYKILELNGYDPQYAASVFLGWATKKFGKRNTIWLFGPATTGKTNI

AEAIAHTVPFYGCVNWTNENFPFNDCVDKMVIWWEEGKMTAKVVESAKAILGGSK

VRVDQKCKSSAQIDPTPVIVTSNTNMCAVIDGNSTTFEHQQPLQDRMFKFELTRRLD

HDFGKVTKQEVKDFFRWAKDHVVEVEHEFYVKKGGAKKRPAPSDADISEPKRVRE

SVAQPSTSDAEASINYADRYQNKCSRHVGMNLMLFPCRQCERMNQNSNICFTHGQKDCLECF

PVSESQPVSVVKKAYQKLCYIHHIMGKVPDACTACDLVNVDLDDCIFEQ

Example of Rep78 amino acid sequence with an AAV2 N term
and an AAV1 C term:
                                              (SEQ ID NO: 35)
MPGFYEIVIKVPSDLDGHLPGISDSFVNWVAEKEWELPPDSDMDLNLIEQAPLTVAE

KLQRDFLTEWRRVSKAPEALFFVQFEKGESYFHMHVLVETTGVKSMVLGRFLSQIRE

KLIQRIYRGIEPTLPNWFAVTKTRNGAGGGNKVVDECYIPNYLLPKTQPELQWAWTN

MEQYLSACLNLTERKRLVAQHLTHVSQTQEQNKENQNPNSDAPVIRSKTSARYMEL

VGWLVDRGITSEKQWIQEDQASYISFNAASNSRSQIKAALDNAGKIMALTKSAPDYL

VGPAPPADIKTNRIYRILELNGYEPAYAGSVFLGWAQKRFGKRNTIWLFGPATTGKT

NIAEAIAHAVPFYGCVNWTNENFPFNDCVDKMVIWWEEGKMTAKVVESAKAILGG

SKVRVDQKCKSSAQIDPTPVIVTSNTNMCAVIDGNSTTFEHQQPLQDRMFKFELTRR

LEHDFGKVTKQEVKEFFRWAQDHVTEVAHEFYVRKGGANKRPAPDDADKSEPKRA

CPSVADPSTSDAEGAPVDFADRYQNKCSRHAGMLQMLFPCKTCERMNQNFNICFTHGTRDCS

ECFPGVSESQPVVRKRTYRKLCAIHHLLGRAPEIACSACDLVNVDLDDCVSEQ

Example of Rep78 amino acid sequence with an AAV2 N term
and an AAV5 C term:
                                              (SEQ ID NO: 36)
MPGFYEIVIKVPSDLDGHLPGISDSFVNWVAEKEWELPPDSDMDLNLIEQAPLTVAE

KLQRDFLTEWRRVSKAPEALFFVQFEKGESYFHMHVLVETTGVKSMVLGRFLSQIRE

KLIQRIYRGIEPTLPNWFAVTKTRNGAGGGNKVVDECYIPNYLLPKTQPELQWAWTN

MEQYLSACLNLTERKRLVAQHLTHVSQTQEQNKENQNPNSDAPVIRSKTSARYMAL

VNWLVEHGITSEKQWIQENQESYLSFNSTGNSRSQIKAALDNATKIMSLTKSAVDYL

VGSSVPEDISKNRIWQIFEMNGYDPAYAGSILYGWCQRSFNKRNTVWLYGPATTGK

TNIAEAIAHTVPFYGCVNWTNENFPFNDCVDKMLIWWEEGKMTNKVVESAKAILGG

SKVRVDQKCKSSVQIDSTPVIVTSNTNMCVVVDGNSTTFEHQQPLEDRMFKFELTKR
```

-continued

```
LPPDFGKITKQEVKDFFAWAKVNQVPVTHEFKVPRELAGTKGAEKSLKRPLGDVTN

TSYKSLEKRARLSFVPETPRSSDVTVDPAPLRPLNWNSRYDCKCDYHAQFDNISNKCDECEY

LNRGKNGCICHNVTHCQICHGIPPWEKENLSDFGDFDDANKEQ
```

Example of Rep78 amino acid sequence with an AAV5 N term
and an AAV2 C term:
(SEQ ID NO: 37)
```
MATFYEVIVRVPFDVEEHLPGISDSFVDWVTGQIWELPPESDLNLTLVEQPQLTVADR

IRRVFLYEWNKFSKQESKFFVQFEKGSEYFHLHTLVETSGISSMVLGRYVSQIRAQLV

KVVFQGIEPQINDWVAITKVKKGGANKVVDSGYIPAYLLPKVQPELQWAWTNLDEY

KLAALNLEERKRLVAQFLAESSQRSQEAASQREFSADPVIKSKTSQKYMELVGWLV

DKGITSEKQWIQEDQASYISFNAASNSRSQIKAALDNAGKIMSLTKTAPDYLVGQQP

VEDISSNRIYKILELNGYDPQYAASVFLGWATKKFGKRNTIWLFGPATTGKTNIAEAI

AHTVPFYGCVNWTNENFPFNDCVDKMVIWWEEGKMTAKVVESAKAILGGSKVRV

DQKCKSSAQIDPTPVIVTSNTNMCAVIDGNSTTFEHQQPLQDRMFKFELTRRLDHDF

GKVTKQEVKDFFRWAKDHVVEVEHEFYVKKGGAKKRPAPSDADISEPKRVRESVA

QPSTSDAEASINYADRYQNKCSRHVGMNLMLFPCRQCERMNQNSNICFTHGQKDCLECFPVS

ESQPVSVVKKAYQKLCYIHHIMGKVPDACTACDLVNVDLDDCIFEQ
```

Examples of non-limiting chimeric Rep proteins and nucleic
acid sequences encoding them:
R1c2 amino acid sequence:
(SEQ ID NO: 188)
```
MPGFYEIVIKVPSDLDEHLPGISDSFVSWVAEKEWELPPDSDMDLNLIEQAPLTVAEK

LQRDFLVQWRRVSKAPEALFFVQFEKGESYFHLHILVETTGVKSMVLGRFLSQIRDK

LVQTIYRGIEPTLPNWFAVTKTRNGAGGGNKVVDECYIPNYLLPKTQPELQWAWTN

MEEYISACLNLAERKRLVAQHLTHVSQTQEQNKENLNPNSDAPVIRSKTSARYMELV

GWLVDRGITSEKQWIQEDQASYISFNAASNSRSQIKAALDNAGKIMALTKSAPDYLV

GPAPPADIKTNRIYRILELNGYEPAYAGSVFLGWAQKRFGKRNTIWLFGPATTGKTNI

AEAIAHAVPFYGCVNWTNENFPFNDCVDKMVIWWEEGKMTAKVVESAKAILGGSK

VRVDQKCKSSAQIDPTPVIVTSNTNMCAVIDGNSTTFEHQQPLQDRMFKFELTRRLD

HDFGKVTKQEVKDFFRWAKDHVVEVEHEFYVKKGGAKKRPAPSDADISEPKRVRE

SVAQPSTSDAEASINYADRYQNKCSRHVGMNLMLFPCRQCERMNQNSNICFTHGQKDCLEC

FPVSESQPVSVVKKAYQKLCYIHHIMGKVPDACTACDLVNVDLDDCIFEQ
```

R1hc2 amino acid:
(SEQ ID NO: 189)
```
MPGFYEIVIKVPSDLDEHLPGISDSFVSWVAEKEWELPPDSDMDLNLIEQAPLTVAEK

LQRDFLVQWRRVSKAPEALFFVQFEKGESYFHLHILVETTGVKSMVLGRFLSQIRDK

LVQTIYRGIEPTLPNWFAVTKTRNGAGGGNKVVDECYIPNYLLPKTQPELQWAWTN

MEEYISACLNLAERKRLVAQHLTHVSQTQEQNKENLNPNSDAPVIRSKTSARYMELV

GWLVDRGITSEKQWIQEDQASYISFNAASNSRSQIKAALDNAGKIMSLTKTAPDYLV

GQQPVEDISSNRIYKILELNGYDPQYAASVFLGWATKKFGKRNTIWLFGPATTGKTNI

AEAIAHTVPFYGCVNWTNENFPFNDCVDKMVIWWEEGKMTAKVVESAKAILGGSK

VRVDQKCKSSAQIDPTPVIVTSNTNMCAVIDGNSTTFEHQQPLQDRMFKFELTRRLD

HDFGKVTKQEVKDFFRWAKDHVVEVEHEFYVKKGGAKKRPAPSDADISEPKRVRE

SVAQPSTSDAEASINYADRYQNKCSRHVGMNLMLFPCRQCERMNQNSNICFTHGQKDCLEC

FPVSESQPVSVVKKAYQKLCYIHHIMGKVPDACTACDLVNVDLDDCIFEQ
```

-continued

R2d1 amino acid:
(SEQ ID NO: 190)
TPGFYEIVIKVPSDLDEHLPGISDSFVNWVAEKEWELPPDSDMDLNLIEQAPLTVAEK
LQRDFLTEWRRVSKAPEALFFVQFEKGESYFHMHVLVETTGVKSMVLGRFLSQIRD
KLVQTIYRGIEPTLPNWFAVTKTRNGAGGGNKVVDECYIPNYLLPKTQPELQWAWT
NMEEYISACLNLAERKRLVAQHLTHVSQTQEQNKENLNPNSDAPVIRSKTSARYMEL
VGWLVDRGITSEKQWIQEDQASYISFNAASNSRSQIKAALDNAGKIMSLTKTAPDYL
VGQQPVEDISSNRIYKILELNGYDPQYAASVFLGWATKKFGKRNTIWLFGPATTGKT
NIAEAIAHTVPFYGCVNWTNENFPFNDCVDKMVIWWEEGKMTAKVVESAKAILGGS
KVRVDQKCKSSAQIDPTPVIVTSNTNMCAVIDGNSTTFEHQQPLQDRMFKFELTRRL
DHDFGKVTKQEVKDFFRWAKDHVVEVEHEFYVKKGGAKKRPAPSDADISEPKRVR
ESVAQPSTSDAEASINYADRYQNKCSRHVGMNLMLFPCRQCERMNQNSNICFTHGQKDCLEC
FPVSEDNASQPVSVVKKAYQKLCYIHHIMGKVPDACTACDLVNVDLDDCI
FEQ R2h1 amino acid:
(SEQ ID NO: 191)
TPGFYEIVIKVPSDLDEHLPGISDSFVNWVAEKEWELPPDSDMDLNLIEQAPLTVAEK
LQRDFLTEWRRVSKAPEALFFVQFEKGESYFHMHVLVETTGVKSMVLGRFLSQIREK
LIQRIYRGIEPTLPNWFAVTKTRNGAGGGNKVVDECYIPNYLLPKTQPELQWAWTN
MEQYLSACLNLTERKRLVAQHLTHVSQTQEQNKENQNPNSDAPVIRSKTSARYMEL
VGWLVDKGITSEKQWIQEDQASYISFNAASNSRSQIKAALDNAGKIMALTKSAPDYL
VGPAPPADIKTNRIYRILELNGYEPAYAGSVFLGWAQKRFGKRNTIWLFGPATTGKT
NIAEAIAHAVPFYGCVNWTNENFPFNDCVDKMVIWWEEGKMTAKVVESAKAILGG
SKVRVDQKCKSSAQIDPTPVIVTSNTNMCAVIDGNSTTFEHQQPLQDRMFKFELTRR
LDHDFGKVTKQEVKDFFRWAKDHVVEVEHEFYVKKGGAKKRPAPSDADISEPKRV
RESVAQPSTSDAEASINYADRYQNKCSRHVGMNLMLFPCRQCERMNQNSNICFTHGQKDCL
ECFPVSESQPVSVVKKAYQKLCYIHHIMGKVPDACTACDLVNVDLDDCIFEQ R8d1c2 amino acid:
(SEQ ID NO: 192)
MPGFYEIVIKVPSDLDEHLPGISDSFVNWVAEKEWELPPDSDMDRNLIEQAPLTVAEK
LQRDFLVQWRRVSKAPEALFFVQFEKGESYFHLHVLVETTGVKSMVLGRFLSQIRD
KLVQTIYRGIEPTLPNWFAVTKTRNGAGGGNKVVDECYIPNYLLPKTQPELQWAWT
NMEEYISACLNLAERKRLVAQHLTHVSQTQEQNKENLNPNSDAPVIRSKTSARYMEL
VGWLVDRGITSEKQWIQEDQASYISFNAASNSRSQIKAALDNAGKIMALTKSAPDYL
VGPSLPADITQNRIYRILALNGYDPAYAGSVFLGWAQKKFGKRNTIWLFGPATTGKT
NIAEAIAHAVPFYGCVNWTNENFPFNDCVDKMVIWWEEGKMTAKVVESAKAILGG
SKVRVDQKCKSSAQIDPTPVIVTSNTNMCAVIDGNSTTFEHQQPLQDRMFKFELTRR
LDHDFGKVTKQEVKDFFRWAKDHVVEVEHEFYVKKGGAKKRPAPSDADISEPKRV
RESVAQPSTSDAEASINYADRYQNKCSRHVGMNLMLFPCRQCERMNQNSNICFTHGQKDCLE
CFPVSESQPVSVVKKAYQKLCYIHHIMGKVPDACTACDLVNVDLDDCIFEQ R8p1/2c2 amino acid:
(SEQ ID NO: 193)
MPGFYEIVIKVPSDLDEHLPGISDSFVNWVAEKEWELPPDSDMDRNLIEQAPLTVAEK
LQRDFLVQWRRVSKAPEALFFVQFEKGESYFHLHVLVETTGVKSMVLGRFLSQIREK
LVQTIYRGVEPTLPNWFAVTKTRNGAGGGNKVVDECYIPNYLLPKTQPELQWAWTN -continued MEEYISACLNLAERKRLVAQHLTHVSQTQEQNKENLNPNSDAPVIRSKTSARYMELV
GWLVDRGITSEKQWIQEDQASYISFNAASNSRSQIKAALDNAGKIMALTKSAPDYLV
GPSLPADITQNRIYRILALNGYDPAYAGSVFLGWAQKKFGKRNTIWLFGPATTGKTNI
AEAIAHAVPFYGCVNWTNENFPFNDCVDKMVIWWEEGKMTAKVVESAKAILGGSK
VRVDQKCKSSAQIDPTPVIVTSNTNMCAVIDGNSTTFEHQQPLQDRMFKFELTRRLD
HDFGKVTKQEVKDFFRWAKDHVVEVEHEFYVKKGGAKKRPAPSDADISEPKRVRE
SVAQPSTSDAEASINYADRYQNKCSRHVGMNLMLFPCRQCERMNQNSNICFTHGQKDCLEC
FPVSESQPVSVVKKAYQKLCYIHHIMGKVPDACTACDLVNVDLDDCIFEQ R1c2 gene sequence:

(SEQ ID NO: 194)
ATGCCGGGCTTCTACGAGATCGTGATCAAGGTGCCGAGCGACCTGGACGAGCAC
CTGCCGGGCATTTCTGACTCGTTTGTGAGCTGGGTGGCCGAGAAGGAATGGGAG
CTGCCCCCGGATTCTGACATGGATCTGAATCTGATTGAGCAGGCACCCCTGACCG
TGGCCGAGAAGCTGCAGCGCGACTTCCTGGTCCAATGGCGCCGCGTGAGTAAGG
CCCCGGAGGCCCTCTTCTTTGTTCAGTTCGAGAAGGGCGAGTCCTACTTCCACCT
CCATATTCTGGTGGAGACCACGGGGGTCAAATCCATGGTGCTGGGCCGCTTCCTG
AGTCAGATTAGGGACAAGCTGGTGCAGACCATCTACCGCGGGATCGAGCCGACC
CTGCCCAACTGGTTCGCGGTGACCAAGACGCGTAATGGCGCCGGAGGGGGAAC
AAGGTGGTGGACGAGTGCTACATCCCCAACTACCTCCTGCCCAAGACTCAGCCC
GAGCTGCAGTGGGCGTGGACTAACATGGAGGAGTATATAAGCGCCTGTTTGAAC
CTGGCCGAGCGCAAACGGCTCGTGGCGCAGCACCTGACCCACGTCAGCCAGACC
CAGGAGCAGAACAAGGAGAATCTGAACCCCAATTCTGACGCGCCTGTCATCCGG
TCAAAAACCTCCGCGCGCTACATGGAGCTGGTCGGGTGGCTGGTGGACCGGGGC
ATCACCTCCGAGAAGCAGTGGATCCAGGAGGACCAGGCCTCGTACATCTCCTTC
AACGCCGCTTCCAACTCGCGGTCCCAGATCAAGGCCGCTCTGGACAATGCCGGC
AAGATCATGGCGCTGACCAAATCCGCGCCCGACTACCTGGTAGGCCCCGCTCCG
CCCGCGGACATTAAAACCAACCGCATCTACCGCATCCTGGAGCTGAACGGCTAC
GAACCTGCCTACGCCGGCTCCGTCTTTCTCGGCTGGGCCCAGAAAAGGTTCGGGA
AGCGCAACACCATCTGGCTGTTTGGGCCGGCCACCACGGGCAAGACCAACATCG
CGGAAGCCATCGCCCACGCCGTGCCCTTCTACGGCTGCGTCAACTGGACCAATGA
GAACTTTCCCTTCAATGATTGCGTCGACAAGATGGTGATCTGGTGGGAGGAGGG
GAAGATGACCGCCAAGGTCGTGGAGTCGGCCAAAGCCATTCTCGGAGGAAGCAA
GGTGCGCGTGGACCAGAAATGCAAGTCCTCGGCCCAGATAGACCCGACTCCCGT
GATCGTCACCTCCAACACCAACATGTGCGCCGTGATTGACGGGAACTCAACGAC
CTTCGAACACCAGCAGCCGTTGCAAGACCGGATGTTCAAATTTGAACTCACCCGC
CGTCTGGATCATGACTTTGGGAAGGTCACCAAGCAGGAAGTCAAAGACTTTTTCC
GGTGGGCAAAGGATCACGTGGTTGAGGTGGAGCATGAATTCTACGTCAAAAAGG
GTGGAGCCAAGAAAAGACCCGCCCCCAGTGACGCAGATATAAGTGAGCCCAAAC
GGGTGCGCGAGTCAGTTGCGCAGCCATCGACGTCAGACGCGGAAGCTTCGATCA
ACTACGCAGACAGGTACCAAAACAAATGTTCTCGTCACGTGGGCATGAATCTGA
TGCTGTTTCCCTGCAGACAATGCGAGAGAATGAATCAGAATTCAAATATCTGCTT

-continued
CACTCACGGACAGAAAGACTGTTTAGAGTGCTTTCCCGTGTCAGAATCTCAACCC

GTTTCTGTCGTCAAAAAGGCGTATCAGAAACTGTGCTACATTCATCATATCATGG

GAAAGGTGCCAGACGCTTGCACTGCCTGCGATCTGGTCAATGTGGATTTGGATGACTGCAT

CTTTGAACAATAA

Rlhc2 gene sequence:

(SEQ ID NO: 195)
ATGCCGGGCTTCTACGAGATCGTGATCAAGGTGCCGAGCGACCTGGACGAGCAC

CTGCCGGGCATTTCTGACTCGTTTGTGAGCTGGGTGGCCGAGAAGGAATGGGAG

CTGCCCCCGGATTCTGACATGGATCTGAATCTGATTGAGCAGGCACCCCTGACCG

TGGCCGAGAAGCTGCAGCGCGACTTCCTGGTCCAATGGCGCCGCGTGAGTAAGG

CCCCGGAGGCCCTCTTCTTTGTTCAGTTCGAGAAGGGCGAGTCCTACTTCCACCT

CCATATTCTGGTGGAGACCACGGGGGTCAAATCCATGGTGCTGGGCCGCTTCCTG

AGTCAGATTAGGGACAAGCTGGTGCAGACCATCTACCGCGGGATCGAGCCGACC

CTGCCCAACTGGTTCGCGGTGACCAAGACGCGTAATGGCGCCGGAGGGGGGAAC

AAGGTGGTGGACGAGTGCTACATCCCCAACTACCTCCTGCCCAAGACTCAGCCC

GAGCTGCAGTGGGCGTGGACTAACATGGAGGAGTATATAAGCGCCTGTTTGAAC

CTGGCCGAGCGCAAACGGCTCGTGGCGCAGCACCTGACCCACGTCAGCCAGACC

CAGGAGCAGAACAAGGAGAATCTGAACCCCAATTCTGACGCGCCTGTCATCCGG

TCAAAAACCTCCGCGCGCTACATGGAGCTGGTCGGGTGGCTGGTGGACCGGGGC

ATCACCTCCGAGAAGCAGTGGATCCAGGAGGACCAGGCCTCATACATCTCCTTC

AATGCGGCCTCCAACTCGCGGTCCCAAATCAAGGCTGCCTTGGACAATGCGGGA

AAGATTATGAGCCTGACTAAAACCGCCCCCGACTACCTGGTGGGCCAGCAGCCC

GTGGAGGACATTTCCAGCAATCGGATTTATAAAATTTTGGAACTAAACGGGTACG

ATCCCCAATATGCGGCTTCCGTCTTTCTGGGATGGGCCACGAAAAAGTTCGGCAA

GAGGAACACCATCTGGCTGTTTGGGCCTGCAACTACCGGGAAGACCAACATCGC

GGAGGCCATAGCCCACACTGTGCCCTTCTACGGGTGCGTAAACTGGACCAATGA

GAACTTTCCCTTCAACGACTGTGTCGACAAGATGGTGATCTGGTGGGAGGAGGG

GAAGATGACCGCCAAGGTCGTGGAGTCGGCCAAAGCCATTCTCGGAGGAAGCAA

GGTGCGCGTGGACCAGAAATGCAAGTCCTCGGCCCAGATAGACCCGACTCCCGT

GATCGTCACCTCCAACACCAACATGTGCGCCGTGATTGACGGGAACTCAACGAC

CTTCGAACACCAGCAGCCGTTGCAAGACCGGATGTTCAAATTTGAACTCACCCGC

CGTCTGGATCATGACTTTGGGAAGGTCACCAAGCAGGAAGTCAAAGACTTTTTCC

GGTGGGCAAAGGATCACGTGGTTGAGGTGGAGCATGAATTCTACGTCAAAAAGG

GTGGAGCCAAGAAAAGACCCGCCCCCAGTGACGCAGATATAAGTGAGCCCAAAC

GGGTGCGCGAGTCAGTTGCGCAGCCATCGACGTCAGACGCGGAAGCTTCGATCA

ACTACGCAGACAGGTACCAAAACAAATGTTCTCGTCACGTGGGCATGAATCTGA

TGCTGTTTCCCTGCAGACAATGCGAGAGAATGAATCAGAATTCAAATATCTGCTT

CACTCACGGACAGAAAGACTGTTTAGAGTGCTTTCCCGTGTCAGAATCTCAACCC

GTTTCTGTCGTCAAAAAGGCGTATCAGAAACTGTGCTACATTCATCATATCATGG

GAAAGGTGCCAGACGCTTGCACTGCCTGCGATCTGGTCAATGTGGATTTGGATGACTGCAT

CTTTGAACAATAA

R2d1 gene sequence:
(SEQ ID NO: 196)

ACGCCGGGGTTTTACGAGATTGTGATTAAGGTCCCCAGCGACCTTGACGAGCATC

TGCCCGGCATTTCTGACAGCTTTGTGAACTGGGTGGCCGAGAAGGAATGGGAGTT

GCCGCCAGATTCTGACATGGATCTGAATCTGATTGAGCAGGCACCCCTGACCGTG

GCCGAGAAGCTGCAGCGCGACTTTCTGACGGAATGGCGCCGTGTGAGTAAGGCC

CCGGAGGCCCTTTTCTTTGTGCAATTTGAGAAGGGAGAGAGCTACTTCCACATGC

ACGTGCTCGTGGAAACCACCGGGGTGAAATCCATGGTGCTGGGCCGCTTCCTGA

GTCAGATTAGGGACAAGCTGGTGCAGACCATCTACCGCGGGATCGAGCCGACCC

TGCCCAACTGGTTCGCGGTGACCAAGACGCGTAATGGCGCCGGAGGGGGAACA

AGGTGGTGGACGAGTGCTACATCCCCAACTACCTCCTGCCCAAGACTCAGCCCG

AGCTGCAGTGGGCGTGGACTAACATGGAGGAGTATATAAGCGCCTGTTTGAACC

TGGCCGAGCGCAAACGGCTCGTGGCGCAGCACCTGACCCACGTCAGCCAGACCC

AGGAGCAGAACAAGGAGAATCTGAACCCCAATTCTGACGCGCCTGTCATCCGGT

CAAAAACCTCCGCGCGCTACATGGAGCTGGTCGGGTGGCTGGTGGACCGGGGCA

TCACCTCCGAGAAGCAGTGGATCCAGGAGGACCAGGCCTCATACATCTCCTTCA

ATGCGGCCTCCAACTCGCGGTCCCAAATCAAGGCTGCCTTGGACAATGCGGGAA

AGATTATGAGCCTGACTAAAACCGCCCCCGACTACCTGGTGGGCCAGCAGCCCG

TGGAGGACATTTCCAGCAATCGGATTTATAAAATTTTGGAACTAAACGGGTACGA

TCCCCAATATGCGGCTTCCGTCTTTCTGGGATGGGCCACGAAAAAGTTCGGCAAG

AGGAACACCATCTGGCTGTTTGGGCCTGCAACTACCGGGAAGACCAACATCGCG

GAGGCCATAGCCCACACTGTGCCCTTCTACGGGTGCGTAAACTGGACCAATGAG

AACTTTCCCTTCAACGACTGTGTCGACAAGATGGTGATCTGGTGGAGGAGGGG

AAGATGACCGCCAAGGTCGTGGAGTCGGCCAAAGCCATTCTCGGAGGAAGCAAG

GTGCGCGTGGACCAGAAATGCAAGTCCTCGGCCCAGATAGACCCGACTCCCGTG

ATCGTCACCTCCAACACCAACATGTGCGCCGTGATTGACGGGAACTCAACGACCT

TCGAACACCAGCAGCCGTTGCAAGACCGGATGTTCAAATTTGAACTCACCCGCC

GTCTGGATCATGACTTTGGGAAGGTCACCAAGCAGGAAGTCAAAGACTTTTTCCG

GTGGGCAAAGGATCACGTGGTTGAGGTGGAGCATGAATTCTACGTCAAAAAGGG

TGGAGCCAAGAAAAGACCCGCCCCCAGTGACGCAGATATAAGTGAGCCCAAACG

GGTGCGCGAGTCAGTTGCGCAGCCATCGACGTCAGACGCGGAAGCTTCGATCAA

CTACGCAGACAGGTACCAAAACAAATGTTCTCGTCACGTGGGCATGAATCTGAT

GCTGTTTCCCTGCAGACAATGCGAGAGAATGAATCAGAATTCAAATATCTGCTTC

ACTCACGGACAGAAAGACTGTTTAGAGTGCTTTCCCGTGTCAGAATCTCAACCCG

TTTCTGTCGTCAAAAAGGCGTATCAGAAACTGTGCTACATTCATCATATCATGGG

AAAGGTGCCAGACGCTTGCACTGCCTGCGATCTGGTCAATGTGGATTTGGATGACTGCATC

TTTGAACAATAA

R2h1 gene sequence:
(SEQ ID NO: 197)

ACGCCGGGGTTTTACGAGATTGTGATTAAGGTCCCCAGCGACCTTGACGAGCATC

TGCCCGGCATTTCTGACAGCTTTGTGAACTGGGTGGCCGAGAAGGAATGGGAGTT

GCCGCCAGATTCTGACATGGATCTGAATCTGATTGAGCAGGCACCCCTGACCGTG

-continued

```
GCCGAGAAGCTGCAGCGCGACTTTCTGACGGAATGGCGCCGTGTGAGTAAGGCC

CCGGAGGCCCTTTTCTTTGTGCAATTTGAGAAGGGAGAGAGCTACTTCCACATGC

ACGTGCTCGTGGAAACCACCGGGGTGAAATCCATGGTTTTGGGACGTTTCCTGAG

TCAGATTCGCGAAAAACTGATTCAGAGAATTTACCGCGGGATCGAGCCGACTTTG

CCAAACTGGTTCGCGGTCACAAAGACCAGAAATGGCGCCGGAGGCGGGAACAA

GGTGGTGGATGAGTGCTACATCCCCAATTACTTGCTCCCCAAAACCCAGCCTGAG

CTCCAGTGGGCGTGGACTAATATGGAACAGTATTTAAGCGCCTGTTTGAATCTCA

CGGAGCGTAAACGGTTGGTGGCGCAGCATCTGACGCACGTGTCGCAGACGCAGG

AGCAGAACAAAGAGAATCAGAATCCCAATTCTGATGCGCCGGTGATCAGATCAA

AAACTTCAGCCAGGTACATGGAGCTGGTCGGGTGGCTCGTGGACAAGGGGATTA

CCTCGGAGAAGCAGTGGATCCAGGAGGACCAGGCCTCGTACATCTCCTTCAACG

CCGCTTCCAACTCGCGGTCCCAGATCAAGGCCGCTCTGGACAATGCCGGCAAGA

TCATGGCGCTGACCAAATCCGCGCCCGACTACCTGGTAGGCCCCGCTCCGCCCGC

GGACATTAAAACCAACCGCATCTACCGCATCCTGGAGCTGAACGGCTACGAACC

TGCCTACGCCGGCTCCGTCTTTCTCGGCTGGGCCCAGAAAAGGTTCGGGAAGCGC

AACACCATCTGGCTGTTTGGGCCGGCCACCACGGGCAAGACCAACATCGCGGAA

GCCATCGCCCACGCCGTGCCCTTCTACGGCTGCGTCAACTGGACCAATGAGAACT

TTCCCTTCAATGATTGCGTCGACAAGATGGTGATCTGGTGGGAGGAGGGGAAGA

TGACCGCCAAGGTCGTGGAGTCGGCCAAAGCCATTCTCGGAGGAAGCAAGGTGC

GCGTGGACCAGAAATGCAAGTCCTCGGCCCAGATAGACCCGACTCCCGTGATCG

TCACCTCCAACACCAACATGTGCGCCGTGATTGACGGGAACTCAACGACCTTCGA

ACACCAGCAGCCGTTGCAAGACCGGATGTTCAAATTTGAACTCACCCGCCGTCTG

GATCATGACTTTGGGAAGGTCACCAAGCAGGAAGTCAAAGACTTTTTCCGGTGG

GCAAAGGATCACGTGGTTGAGGTGGAGCATGAATTCTACGTCAAAAAGGGTGGA

GCCAAGAAAAGACCCGCCCCCAGTGACGCAGATATAAGTGAGCCCAAACGGGTG

CGCGAGTCAGTTGCGCAGCCATCGACGTCAGACGCGGAAGCTTCGATCAACTAC

GCAGACAGGTACCAAAACAAATGTTCTCGTCACGTGGGCATGAATCTGATGCTGT

TTCCCTGCAGACAATGCGAGAGAATGAATCAGAATTCAAATATCTGCTTCACTCA

CGGACAGAAAGACTGTTTAGAGTGCTTTCCCGTGTCAGAATCTCAACCCGTTTCT

GTCGTCAAAAAGGCGTATCAGAAACTGTGCTACATTCATCATATCATGGGAAAG

GTGCCAGACGCTTGCACTGCCTGCGATCTGGTCAATGTGGATTTGGATGACTGCATCTTT

GAACAATAA
```

R8d1c2 gene sequence:

(SEQ ID NO: 198)

```
ATGCCGGGCTTCTACGAGATCGTGATCAAGGTGCCGAGCGACCTGGACGAGCAC

CTGCCGGGCATTTCTGACTCGTTTGTGAACTGGGTGGCCGAGAAGGAATGGGAG

CTGCCCCCGGATTCTGACATGGATCGGAATCTGATCGAGCAGGCACCCCTGACCG

TGGCCGAGAAGCTGCAGCGCGACTTCCTGGTCCAATGGCGCCGCGTGAGTAAGG

CCCCGGAGGCCCTCTTCTTTGTTCAGTTCGAGAAGGGCGAGAGCTACTTTCACCT

GCACGTTCTGGTCGAGACCACGGGGGTCAAGTCCATGGTGCTGGGCCGCTTCCTG

AGTCAGATTAGGGACAAGCTGGTGCAGACCATCTACCGCGGGATCGAGCCGACC

CTGCCCAACTGGTTCGCGGTGACCAAGACGCGTAATGGCGCCGGAGGGGGGAAC
```

-continued

AAGGTGGTGGACGAGTGCTACATCCCCAACTACCTCCTGCCCAAGACTCAGCCC

GAGCTGCAGTGGGCGTGGACTAACATGGAGGAGTATATAAGCGCCTGTTTGAAC

CTGGCCGAGCGCAAACGGCTCGTGGCGCAGCACCTGACCCACGTCAGCCAGACC

CAGGAGCAGAACAAGGAGAATCTGAACCCCAATTCTGACGCGCCTGTCATCCGG

TCAAAAACCTCCGCGCGCTATATGGAGCTGGTCGGGTGGCTGGTGGACCGGGGC

ATCACCTCCGAGAAGCAGTGGATCCAGGAGGACCAGGCCTCGTACATCTCCTTC

AACGCCGCCTCCAACTCGCGGTCCCAGATCAAGGCCGCGCTGGACAATGCCGGC

AAGATCATGGCGCTGACCAAATCCGCGCCCGACTACCTGGTGGGGCCCTCGCTG

CCCGCGGACATTACCCAGAACCGCATCTACCGCATCCTCGCTCTCAACGGCTACG

ACCCTGCCTACGCCGGCTCCGTCTTTCTCGGCTGGGCTCAGAAAAAGTTCGGGAA

ACGCAACACCATCTGGCTGTTTGGACCCGCCACCACCGGCAAGACCAACATTGC

GGAAGCCATCGCCCACGCCGTGCCCTTCTACGGCTGCGTCAACTGGACCAATGA

GAACTTTCCCTTCAATGATTGCGTCGACAAGATGGTGATCTGGTGGGAGGAGGG

GAAGATGACCGCCAAGGTCGTGGAGTCGGCCAAAGCCATTCTCGGAGGAAGCAA

GGTGCGCGTGGACCAGAAATGCAAGTCCTCGGCCCAGATAGACCCGACTCCCGT

GATCGTCACCTCCAACACCAACATGTGCGCCGTGATTGACGGGAACTCAACGAC

CTTCGAACACCAGCAGCCGTTGCAAGACCGGATGTTCAAATTTGAACTCACCCGC

CGTCTGGATCATGACTTTGGGAAGGTCACCAAGCAGGAAGTCAAAGACTTTTTCC

GGTGGGCAAAGGATCACGTGGTTGAGGTGGAGCATGAATTCTACGTCAAAAAGG

GTGGAGCCAAGAAAAGACCCGCCCCCAGTGACGCAGATATAAGTGAGCCCAAAC

GGGTGCGCGAGTCAGTTGCGCAGCCATCGACGTCAGACGCGGAAGCTTCGATCA

ACTACGCAGACAGGTACCAAAACAAATGTTCTCGTCACGTGGGCATGAATCTGA

TGCTGTTTCCCTGCAGACAATGCGAGAGAATGAATCAGAATTCAAATATCTGCTT

CACTCACGGACAGAAAGACTGTTTAGAGTGCTTTCCCGTGTCAGAATCTCAACCC

GTTTCTGTCGTCAAAAAGGCGTATCAGAAACTGTGCTACATTCATCATATCATGG

GAAAGGTGCCAGACGCTTGCACTGCCTGCGATCTGGTCAATGTGGATTTGGATGACTGCAT

CTTTGAACAATAA

R8p1/2c2 gene sequence:
(SEQ ID NO: 199)
ATGCCGGGCTTCTACGAGATCGTGATCAAGGTGCCGAGCGACCTGGACGAGCAC

CTGCCGGGCATTTCTGACTCGTTTGTGAACTGGGTGGCCGAGAAGGAATGGGAG

CTGCCCCCGGATTCTGACATGGATCGGAATCTGATCGAGCAGGCACCCCTGACCG

TGGCCGAGAAGCTGCAGCGCGACTTCCTGGTCCAATGGCGCCGCGTGAGTAAGG

CCCCGGAGGCCCTCTTCTTTGTTCAGTTCGAGAAGGGCGAGAGCTACTTTCACCT

GCACGTTCTGGTCGAGACCACGGGGGTCAAGTCCATGGTGCTAGGCCGCTTCCTG

AGTCAGATTCGGGAAAAGCTGGTCCAGACCATCTACCGCGGGGTCGAGCCCACC

TTGCCCAACTGGTTCGCGGTGACCAAGACGCGTAATGGCGCCGGGGGGGGAAC

AAGGTGGTGGACGAGTGCTACATCCCCAACTACCTCCTGCCCAAGACTCAGCCC

GAGCTGCAGTGGGCGTGGACTAACATGGAGGAGTATATAAGCGCGTGCTTGAAC

CTGGCCGAGCGCAAACGGCTCGTGGCGCAGCACCTGACCCACGTCAGCCAGACG

CAGGAGCAGAACAAGGAGAATCTGAACCCCAATTCTGACGCGCCCGTGATCAGG

```
-continued
TCAAAAACCTCCGCGCGCTATATGGAGCTGGTCGGGTGGCTGGTGGACCGGGGC

ATCACCTCCGAGAAGCAGTGGATCCAGGAGGACCAGGCCTCGTACATCTCCTTC

AACGCCGCCTCCAACTCGCGGTCCCAGATCAAGGCCGCGCTGGACAATGCCGGC

AAGATCATGGCGCTGACCAAATCCGCGCCCGACTACCTGGTGGGGCCCTCGCTG

CCCGCGGACATTACCCAGAACCGCATCTACCGCATCCTCGCTCTCAACGGCTACG

ACCCTGCCTACGCCGGCTCCGTCTTTCTCGGCTGGGCTCAGAAAAAGTTCGGGAA

ACGCAACACCATCTGGCTGTTTGGACCCGCCACCACCGGCAAGACCAACATTGC

GGAAGCCATCGCCCACGCCGTGCCCTTCTACGGCTGCGTCAACTGGACCAATGA

GAACTTTCCCTTCAATGATTGCGTCGACAAGATGGTGATCTGGTGGGAGGAGGG

GAAGATGACCGCCAAGGTCGTGGAGTCGGCCAAAGCCATTCTCGGAGGAAGCAA

GGTGCGCGTGGACCAGAAATGCAAGTCCTCGGCCCAGATAGACCCGACTCCCGT

GATCGTCACCTCCAACACCAACATGTGCGCCGTGATTGACGGGAACTCAACGAC

CTTCGAACACCAGCAGCCGTTGCAAGACCGGATGTTCAAATTTGAACTCACCCGC

CGTCTGGATCATGACTTTGGGAAGGTCACCAAGCAGGAAGTCAAAGACTTTTTCC

GGTGGGCAAAGGATCACGTGGTTGAGGTGGAGCATGAATTCTACGTCAAAAAGG

GTGGAGCCAAGAAAAGACCCGCCCCCAGTGACGCAGATATAAGTGAGCCCAAAC

GGGTGCGCGAGTCAGTTGCGCAGCCATCGACGTCAGACGCGGAAGCTTCGATCA

ACTACGCAGACAGGTACCAAAACAAATGTTCTCGTCACGTGGGCATGAATCTGA

TGCTGTTTCCCTGCAGACAATGCGAGAGAATGAATCAGAATTCAAATATCTGCTT

CACTCACGGACAGAAAGACTGTTTAGAGTGCTTTCCCGTGTCAGAATCTCAACCC

GTTTCTGTCGTCAAAAAGGCGTATCAGAAACTGTGCTACATTCATCATATCATGG

GAAAGGTGCCAGACGCTTGCACTGCCTGCGATCTGGTCAATGTGGATTTGGATGACTGCAT

CTTTGAACAATAA
```

Methods of Packaging Particles

Methods of producing rAAV particles are known in the art and reagents are commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.).

Generally, rAAV production involves culturing cells, introducing AAV genes and any genes of interest (e.g., flanked by ITRs) desired to be packaged to the cells, and allowing the cells to produce or package rAAV. The last step is followed by harvesting rAAV particles and subsequent purification steps. AAV genes and any genes desired to be packaged into rAAV particles may be introduced to cells by either transfection methods (e.g., using plasmid vectors and a transfection agent) or infection methods (e.g., using a viral vector).

In some embodiments, one or more genes of interest, rep gene (e.g., encoding a wild-type or recombinant, for example chimeric, Rep protein as described in this application), cap gene and helper genes (e.g., E1a gene, a E1b gene, a E4 gene, a E2a gene, and a VA gene) are introduced to a cell wherein the genes are comprised in one or more vectors (e.g., plasmids) such that the cell gets transfected or infected by the vectors. For clarity, helper genes are genes that encode helper proteins E1a, E1b, E4, E2a, and VA. In some embodiments, only one or more genes of interest and the control elements to which they are operably linked are comprised in one vector, while one or more of the rep, cap and helper genes are comprised in comprised in one or more of separate vectors. For example, a first vector may comprise one more genes of interest, while a second vector may comprise rep, cap and helper genes. In some embodiments, a first vector may comprise one more genes of interest, while a second vector may comprise rep, and a third vector may comprise helper genes and cap. In some embodiments, a first vector may comprise one more genes of interest, while a second vector may comprise rep, and a third vector may comprise helper genes, and a forth vector may comprise cap.

In some embodiments, a nucleic acid vector used to deliver a gene of interest or AAV gene to a producer cell is circular. In some embodiments, a nucleic acid vector is single-stranded. In some embodiments, a nucleic acid vector is double-stranded. In some embodiments, a double-stranded nucleic acid vector may be, for example, a self-complimentary vector that contains a region of the nucleic acid vector that is complementary to another region of the nucleic acid vector, initiating the formation of the double-strandedness of the nucleic acid vector.

In some embodiments of any one of the methods disclosed herein, the regions of nucleic acid (e.g., heterologous nucleic acid regions) that is flanked by ITRs comprises one or more genes of interest. Regions of nucleic acid flanked by ITRs may also comprise control elements that are operably linked to one or more genes of interest. In some embodiments either a rep gene or a cap gene or both the rep and cap genes are flanked by ITRs.

In some embodiments, a cell to which one or more genes of interest are introduced already comprise one or more of one rep gene, cap gene, and/or helper genes useful to package rAAV particles. As a non-limiting example, a cell may already comprise rep and express Rep proteins Rep78, Rep68, Rep52, and Rep40. Such a cell that expresses Rep proteins can be introduced to vectors comprising ITR-flanked genes of interest, and vectors that express cap and helper genes. In some embodiments, a cell may already comprise rep and helper genes.

Methods of transfecting a cell are known in the art. Non-limiting methods of transfecting cells are CaPO4-mediated transfection, transfection using lipids or polymeric molecules such as Polyethylenimine (PEI), and electroporation. Cells can also be introduced to nucleic acid using using viral vectors (e.g., HSV vectors or baculovirus).

After introducing one or more of one or more genes of interest, rep gene, cap gene, and helper genes to a cell in a manner that they enter the cell by transfection or infection, the cell is incubated under conditions in which rAAV particles will be produced in the cell and escape from the cell. The rAAV particles can then be purified using any method known the art or described herein, e.g., by iodixanol step gradient, CsCl gradient, chromatography, or polyethylene glycol (PEG) precipitation.

Improving Packaging of AAV Particles Using Combinations of ITRs and Rep of Different Serotypes, and or Chimeric Rep Genes Disclosed here are combinations of rep and ITRs of different serotypes such that their use in any method to produce or package rAAV particles results in greater packaging or production efficiency compared to similar conditions in which ITRs and rep gene of the same serotype are used. Accordingly, disclosed herein is also a method of packaging a rAAV particle comprising contacting a cell that expresses a rep gene of a first serotype with a recombinant nucleic acid comprising a pair of ITRs of a second serotype. In some embodiments, the first serotype and the second serotype are the same. In some embodiments, the first and second serotypes are different.

In some embodiments on any one of the rAAV particle producing methods disclosed herein, the rep gene is expressed in any one of the producer cells disclosed herein by transfected or infecting the cells with a nucleic acid encoding the rep gene.

In some embodiments, a first serotype of rep gene is any one of serotypes 1, 2, 3, 4, 5, 6, 7, 8, 9, 10, 11, 12, and 13. In some embodiments, a second serotype of AAV ITRs is any one of serotypes 1, 2, 3, 4, 5, 6, 7, 8, 9, 10, 11, 12, and 13. In some embodiments, any one of the first serotype for rep is used with any serotype for ITRs. For example, rep of serotype 1 can be used with ITRs of any one of serotypes 1, 2, 3, 4, 5, 6, 7, 8, 9, 10, 11, 12, and 13. As another example, rep of serotype 2 can be used with ITRs of any one of serotypes 1, 2, 3, 4, 5, 6, 7, 8, 9, 10, 11, 12, and 13, and so on.

In some embodiments, rep of serotype 1 is used with ITRs or serotype 1, 2, 3, 4, or 7.

In some embodiments, ITRs of serotype 6 are used with rep of serotype 2, 3, 4, 6, 12, or 13. In some embodiments, ITRs of serotype 1 are used with rep of serotype 2, 3, 4, 12, or 13.

In some embodiments, a rep gene is chimeric. A chimeric AAV gene is one which comprises amino acids of more than one serotype. SEQ ID NOs 34-37 provide examples of chimeric Rep78 proteins. In some embodiments, ITRs of serotype 6 are used with chimeric rep of serotype 1 and 2. In some embodiments, ITRs of serotype 1 are used with chimeric rep of serotype 1 and 2. In some embodiments, ITRs of serotype 2 are used with chimeric rep of serotype 2 and 5. In some embodiments, ITRs of serotype 5 are used with chimeric rep of serotype 2 and 5.

Chimeric rep genes and Rep proteins are described above and may be used in any one of the methods of packaging rAAV particles as described herein.

In some embodiments, chimeric Rep proteins may comprise corresponding amino acids of a first serotype in the N terminus and corresponding amino acids of a second serotype in the C terminus. For example, a Rep protein may comprise amino acids of serotype 1 in the N terminus and amino acids of serotype 2 in the C terminus. In some embodiments, a Rep protein may comprise amino acids of serotype 2 in the N terminus and amino acids of serotype 1 in the C terminus. In some embodiments, a Rep protein may comprise amino acids of serotype 2 in the N terminus and amino acids of serotype 5 in the C terminus. In some embodiments, a Rep protein may comprise amino acids of serotype 5 in the N terminus and amino acids of serotype 2 in the C terminus. It is to be understood that a chimeric rep gene may be used in combination with ITRs of any serotype for producing rAAV particles or any serotype or pseudo-serotype. Table 2 provides examples of combinations of rep serotypes that can be used with ITRs of different serotypes to improve rAAV particle production. It is to be understood that, in addition the combinations of ITRs and rep genes provided in Table 2, any one chimeric rep genes or chimeric Rep proteins can be used in combination with any one of the ITRs as described herein, which in turn can be used with any one of the cap genes and capsid proteins described herein for producing rAAV particles.

Table 2. Examples of ITR and Rep combinations (including examples of chimeras) to be generated and tested

TABLE 2

| | Examples of ITR and Rep combinations (including examples of chimeras) to be generated and tested |
|---|---|
| 1. | AAV1_ITR+AAV1_Rep |
| 2. | AAV2_ITR+AAV1_Rep |
| 3. | AAV3_ITR+AAV1_Rep |
| 4. | AAV4_ITR+AAV1_Rep |
| 5. | AAV7_ITR+AAV1_Rep |
| 6. | AAV6_ITR+AAV2_Rep |
| 7. | AAV6_ITR+AAV3_Rep |
| 8. | AAV6_ITR+AAV4_Rep |
| 9. | AAV6_ITR+AAV6_Rep |
| 10. | AAV6_ITR+AAV12_Rep |
| 11. | AAV6_ITR+AAV13_Rep |
| 12. | AAV1_ITR+AAV2_Rep |
| 13. | AAV1_ITR+AAV3_Rep |
| 14. | AAV1_ITR+AAV4_Rep |
| 15. | AAV1_ITR+AAV12_Rep |
| 16. | AAV1_ITR+AAV13_Rep |
| 17. | AAV6_ITR+AAV1N/2C_chimeric_Rep |
| 18. | AAV1_ITR+AAV1N/2C_chimeric_Rep |
| 19. | AAV6_ITR+AAV2N/1C_chimeric_Rep |
| 20. | AAV1_ITR+AAV2N/1C_chimeric_Rep |
| 21. | AAV2_ITR+AAV2N/5C_chimeric_Rep |
| 22. | AAV5_ITR+AAV5N/2C_chimeric_Rep |

Producer Cells

Provided herein are cells used to produce rAAV particles using the combinations of ITRs, cap and/or rep of different serotypes as disclosed herein. Accordingly, in some embodiments, a producer cell as disclosed herein comprises rep of a first AAV serotype and ITRs of a second AAV serotype. In some embodiments, a producer cell as disclosed herein comprises a combination of rep and ITRs, wherein the serotypes of the rep and ITRs are any one of the combinations disclosed herein.

In some embodiments, the packaging is performed in a helper cell or producer cell, such as a mammalian cell or an insect cell. Exemplary mammalian cells include, but are not limited to, HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). Exemplary insect cells include, but are not limited to Sf9 cells (see, e.g., ATCC® CRL-1711™). The helper cell may comprises rep and/or cap genes that encode the Rep protein and/or Cap proteins for use in a method described herein. In some embodiments, the packaging is performed in vitro.

Improvement in rAAV Particle Yield

Recombinant AAV particle yields may improve by using any one of the methods described herein compared to rAAV production processes that are the same with the exception of the particular combination of serotypes of ITR and Rep proteins. In some embodiments, particle yields are defined by the amount of rAAV particles produced. In some embodiments, particle yields are defined by the amount of full rAAV particles (i.e., those that contain nucleic acid or genomes) produced. In some embodiments, yields of rAAV particles are increased relative to when ITRs of serotype 2 are used for packaging rAAV. In some embodiments, the yield of rAAV production involving any one of the particular combination of serotypes of ITR and Rep protein may increase by 2-20% (e.g., 2-4%. 2-10%, 5-10%, 5-20%, 15-20% or 10-20%), or even by up to 5-10 fold or 100-fold or more (e.g., up to 2-fold, up to 3-fold, up to 5-fold, up to 10-fold, up to 20-fold, up to 50-fold, or up to 100-fold or more) compared to rAAV production processes wherein an ITR of serotype 2 is used.

Recombinant AAV particle yields may improve by using any one of the chimeric rep genes described herein compared to rAAV particles produced using production processes that use rep genes of serotype that is a wild-type serotype closest to the majority of the nucleotides in the chimeric gene. For example, the packaging or particle yields for particles produced using ITRs of AAV2, cap of AAV3, and a chimeric rep of serotype 2 except for having a h domain of serotype 8 (R2h8) may be compared to packaging yields for particles produced using ITRs of AAV2, cap of AAV3 and rep of AAV2. In some embodiments, packaging yields as described herein are compared to that of particles of the same serotype made with ITRs of AAV2 and rep of AAV2. In some embodiments, particle yields achieved by using any one of the chimeric rep genes as described herein is improved by at least 1.5-fold (e.g., at least 1.5-fold, at least 2-fold, at least 3-fold, at least 4-fold, at least 5-fold, at least 6-fold, at least 7-fold, at least 8-fold, at least 9-fold, or at least 10-fold).

Methods of measuring packaging of rAAV particles is known in the art. For example, the quantity of genome can be measured using methods such as PCR (e.g., quantitative PCR). Quantities of capsids or particles can be measured using protein-based assays such as ELISA. In some embodiments, electron microscopy (e.g., cryo-electron microscopy) can be used to differentiate visually empty capsids from full capsids (i.e. those that comprise nucleic acid or genomes).

Cap Genes and Capsid Proteins

A rAAV particle or particle within an rAAV preparation may be of any AAV serotype, including any derivative or pseudotype (e.g., 1, 2, 3, 4, 5, 6, 7, 8, 9, 10, 11, 12, 13, 2/1, 2/5, 2/8, 2/9, 3/1, 3/5, 3/8, or 3/9). A cap gene may be used to package the rAAV genome or any gene of interest flanked by any one of the ITRs as described herein. As a result, a rAAV particle produced from any one of the methods described herein can be of any serotype or pseudotype, which in turn may use any one of the chimeric rep genes described herein. A rAAV particle produced using any one of the methods disclosed herein (e.g., with any one of the rep genes, any one of the cap genes, and/or any one of the ITRs described here) can be used to deliver a gene of interest to a cell (e.g., a cell in a subject's body, or an in vitro cell), or to treat a condition or disease in a subject.

The serotype of an rAAV viral particle refers to the serotype of the capsid proteins of the recombinant virus. Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6 (Y445F/Y731F), AAV2.5T, AAV-HAE1/2, AAV clone 32/83, AAVShH10, AAV2 (Y->F), AAV8 (Y733F), AAV2.15, AAV2.4, AAVM41, and AAVr3.45. In some embodiments, cap proteins have one or more amino acid substitutions. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.). In some embodiments, the rAAV particle is a pseudotyped rAAV particle, which comprises (a) a nucleic acid vector comprising ITRs from one serotype (e.g., AAV2, AAV3) and (b) a capsid comprised of capsid proteins derived from another serotype (e.g., AAV1, AAV2, AAV3, AAV4, AAV5, AAV6, AAV7, AAV8, AAV9, or AAV10). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Helper Genes and Vectors

In some embodiments, the one or more helper vectors (e.g., plasmids) include a first helper plasmid comprising a rep gene and/or a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. In some embodiments, the cap gene is modified such that one or more of the proteins VP1, VP2, and VP3 do not get expressed. In some embodiments, the cap gene is modified such that VP2 does not get expressed. Methods for making such modifications are known in the art (Lux et al. (2005), J Virology, 79: 11776-87)

Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG (R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Ca; and Addgene, Cambridge, Mass.; pxx6; Grimm et al. (1998), Novel Tools for Production and Purification of Recombinant Adeno associated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188). Plasmids that encode wild-type AAV coding regions for specific serotypes are also know and available. For example pSub201 is a plasmid that comprises the coding regions of the wild-type AAV2 genome (Samulski et al. (1987), J Virology, 6:3096-3101).

Gene of Interest and Control Elements

A gene of interest is a gene that encodes a protein of interest. A protein of interest may be a detectable marker or a therapeutic protein. A detectable marker is a molecule that can be visualized (e.g., using a naked eye or under a microscope). In some embodiments, the detectable marker is a fluorescent molecule, a bioluminescent molecule, or a molecule that provides color (e.g., β-galactosidase, β-lactamases, β-glucuronidase, and spheriodenone). In some embodiments, a detectable marker is a fluorescent protein or functional peptide or functional polypeptide thereof.

In some embodiments, a gene of interest encodes a therapeutic protein. In some embodiments, a therapeutic gene encodes an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic proteins, a nuclease or other protein used for gene editing, an Fc-fusion protein, an anticoagulant, a nuclease, guide RNA or other nucleic acid, or protein for gene editing.

In some embodiments, the nucleic acid vector comprises one or more regions comprising a sequence that facilitates expression of the nucleic acid (e.g., the heterologous nucleic acid), e.g., expression control sequences operatively linked to the nucleic acid. Such control elements can be delivered to a producer cell such that it aids in expression of one or more proteins in the producer cells. In some embodiments, a control element is delivered to a producer cells such that it gets packaged with the one or more genes of interest so that the packaged rAAV particle, when used to infect a target cell, tissue, or organ, aids in the expression of the product of the gene of interest in the target cell, tissue, or organ.

Numerous control elements are known in the art. Non-limiting examples of control elements include promoters, insulators, silencers, response elements, introns, enhancers, initiation sites, termination signals, and poly(A) tails. Any combination of such control elements is contemplated herein (e.g., a promoter and an enhancer). To achieve appropriate expression levels of the protein or polypeptide of interest, any of a number of promoters suitable for use in the selected host cell may be employed. The promoter may be, for example, a constitutive promoter, tissue-specific promoter, inducible promoter, or a synthetic promoter. For example, constitutive promoters of different strengths can be used. A nucleic acid vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A, and cytomegalovirus (CMV) promoters. Non-limiting examples of constitutive mammalian promoters include various housekeeping gene promoters, as exemplified by the β-actin promoter (e.g., chicken β-actin promoter) and human elongation factor-1 α (EF-1α) promoter. Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline. Tissue-specific promoters and/or regulatory elements are also contemplated herein. Non-limiting examples of such promoters that may be used include airway epithelial cell-specific promoters. Synthetic promoters are also contemplated herein. A synthetic promoter may comprise, for example, regions of known promoters, regulatory elements, transcription factor binding sites, enhancer elements, repressor elements, and the like.

In some embodiments, a gene of interest, optionally including one or more control elements, is flanked by ITRs. In some embodiments, a nucleic acid vector comprising the gene of interest flanked by ITRs is an RNA, a DNA, a ssDNA, or a self-complementary DNA molecule. In some embodiments, the nucleic acid vector is packaged into a viral particle using one or more techniques described in this application (e.g., by introducing the nucleic acid vector, for example via transfection, into a producer cell that expresses a chimeric rep gene or a gene that is of a different serotype than the ITRs flanking the gene of interest, wherein the producer cell further optionally expresses one or more cap genes and/or helper genes).

Without further elaboration, it is believed that one skilled in the art can, based on the above description, utilize the present application to its fullest extent. The following specific embodiments are, therefore, to be construed as merely illustrative, and not limitative of the remainder of the application in any way whatsoever. All publications cited herein are incorporated by reference for the purposes or subject matter referenced herein.

Use of rAAV Particles as Produced by Methods Described Herein

A rAAV particle produced using any one of the methods disclosed herein (e.g., with any one of the rep genes, any one of the cap genes, and/or any one of the ITRs described here) can be used to deliver a gene of interest to a cell (e.g., a cell in a subject's body, or an in vitro cell), or to treat a condition or disease in a subject. In some embodiments, a subject is a mammal (e.g., a human). In some embodiments, a subject is in need of treatment with a gene of interest as described above.

In some embodiments, "administering" or "administration" means providing a material to a subject in a manner that is pharmacologically useful. In some embodiments, a rAAV particle is administered to a subject enterally. In some embodiments, an enteral administration of the essential metal element's is oral. In some embodiments, a rAAV particle is administered to the subject parenterally. In some embodiments, a rAAV particle is administered to a subject subcutaneously, intraocularly, intravitreally, subretinally, intravenously (IV), intracerebro-ventricularly, intramuscularly, intrathecally (IT), intracisternally, intraperitoneally, via inhalation, topically, or by direct injection to one or more cells, tissues, or organs. In some embodiments, a rAAV particle is administered to the subject by injection into the hepatic artery or portal vein.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host organ, tissue, or cell. A therapeutically acceptable amount may be an amount that is capable of treating a disease, e.g., Friedreich's ataxia. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

In some embodiments, the composition comprises a pharmaceutically acceptable carrier. The term "carrier" refers to a diluent, adjuvant, excipient, or vehicle with which the rAAV particle is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

EXAMPLES

Example 1: Comparison of AAV ITRs and Rep Proteins of Different Serotypes

To begin to explore the impact of using AAV Rep protein and/or AAV ITRs of different serotypes on the genome packaging efficiency, the Rep and available ITR sequences of AAV1 to AAV13 were compared (FIG. 1). The ITR sequences are only available for AAV1-AAV7. AAV1 and AAV6 share high sequence identity in both Rep (99.4%) and Cap (99.2%) proteins. In contrast, their ITR sequences show divergence (81.6%). The AAV6 ITR is identical to that of AAV2 ITR while the Rep and Cap protein sequences are more diverse at 87.3% and 83.4%, respectively. This is consistent with AAV6 being a chimera between AAV1 and AAV2. The AAV1 and AAV6 Rep share high sequence homology (>95.0%) to AAV7, AAV8, AAV9, AAV10, and AAV11, although their Cap protein sequences are more diverse (FIG. 1). Significantly, AAV5 is consistently diverse in its ITR sequence, Rep protein, and Cap proteins compared to the other AAVs (FIG. 1).

Figure 3:
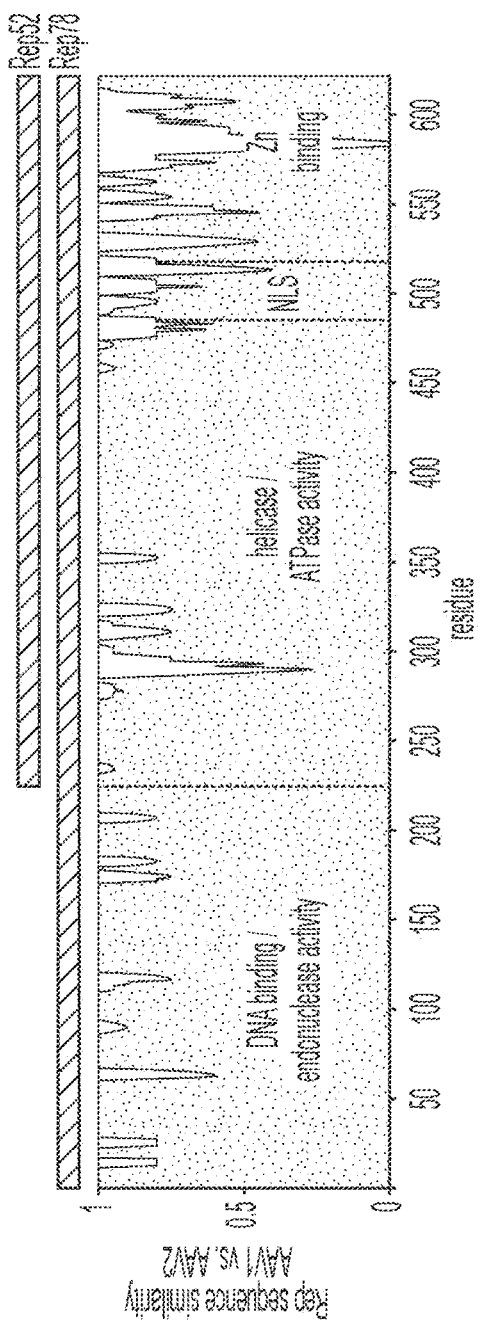
FIG. 3 shows a graphical representation of AAV1 versus AAV2 Rep protein sequence identity.

An analysis of the locations of the sequence variations within the ITRs shows minor variations in the A-region but higher variation in the D-sequence and the hairpin (B- and C-region) (FIG. 2). The D-sequence is reportedly important for AAV packaging while the sequence in the hairpin is exchangeable as long as the secondary structure is maintained. A graphical representation of the comparison of the AAV1 and AAV2, as an example, shows that variation exists in both the DNA binding and helicase domains (FIG. 3). These observations indicate a level of complexity in these essential viral elements that may relate to their function.

Example 2: Effect of Using Combination of ITRs and Rep Proteins of Different Serotypes on rAAV Particle Packaging First, a comparison between the packaging of AAV6 capsids with Rep proteins of all AAV serotypes is carried out. Vector constructs having a genome flanked by ITRs of AAV1 to AAV6 are used. Existing Rep2 (of AAV2)-cap6 (of AAV6) helper plasmids containing the AAV2 rep gene is substituted by rep genes from other AAV serotypes. These constructs are used to transfect HEK293 cells to generate rAAV6 (rAAVX/6) vectors. AAV vector genomes flanked by ITRs from alternative AAV serotypes are used for AAV6 vector production, starting with matching pairs of ITR and Rep proteins (e.g., AAV1 ITR plus AAV1 rep, or AAV3 ITR plus AAV3 rep, etc.). The resulting vectors are purified by AVB sepharose, which purifies genome-containing as well as empty (no DNA) AAV particles. The full and empty capsids are separated either by a density gradient (e.g., Iodixanol) or a sedimentation gradient (e.g., Sucrose gradient), and for each sample, a capsid ELISA (with the ADK1a antibody) is used to quantify the capsid titer. The individual vector preparations are subsequently analyzed and compared for their empty:full ratio, overall production yield, and gene expression efficiency.

If significant differences in the packaging efficiencies of the same transgenes are observed, a finer analysis of the residue differences in the two Rep domains is carried out along with mutation of certain residues to identify residues important for the differences.

Then, Rep sequences of AAV1 to AAV13 were compared to determine where differences between them are located. Their role in packaging is then examined. It is known that AAV5 ITRs can only be packaged with the AAV5 Rep proteins, thus chimeras will test both the DNA binding and helicase domains to pinpoint the determinant of this requirement. If significant differences in packaging efficiency or vector productivity are found to be dictated by serotype Rep or ITR, domains are swapped between the viruses (e.g., utilization of the AAV1 DNA binding domain and/or helicase/ATPase or the utilization of the D-sequence from AAV1) and tested for their effect on rAAV particle packaging.

Figure 4:
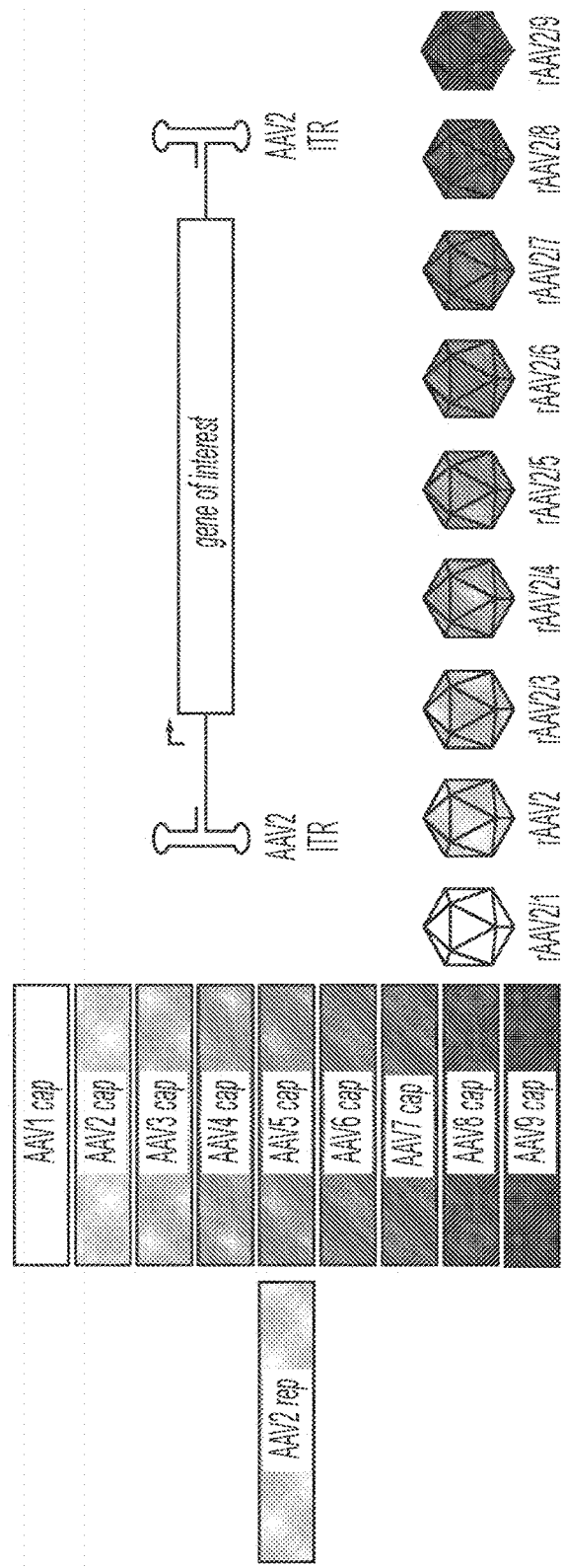
FIG. 4 is a schematic showing the standard AAV vector production system.

Example 3: Effect of Using Chimeric Rep Gene to Produce rAAV Particles of Various Serotypes FIG. 4 shows a schematic of the standard AAV productions system used to produce rAAV particles. A cell, also called a helper or producer cell, is transfected with one or more plasmids comprising genes encoding Rep and capsid proteins, and optionally, a gene of interest between ITRs so that it can be packaged within rAAV particle. The standard technique utilizes various chimeric and modified cap genes but usually rep and ITRs of serotype 2. The following describes experiments and data therefrom in which the rep gene is modified and used with ITRs having sequence of AAV2 to produce capsids of different serotypes. The modified rep genes that were tested are chimeric rep genes having domains that are substituted with domains or other serotypes.

An analysis of the DNA sequence identity for ITR AAV1-7 and Rep78 AAV1-8 was performed (FIG. 5). Sequences for AAV8 ITR, AAV9 ITR, and AAV9 Rep are not available.

Figure 6:
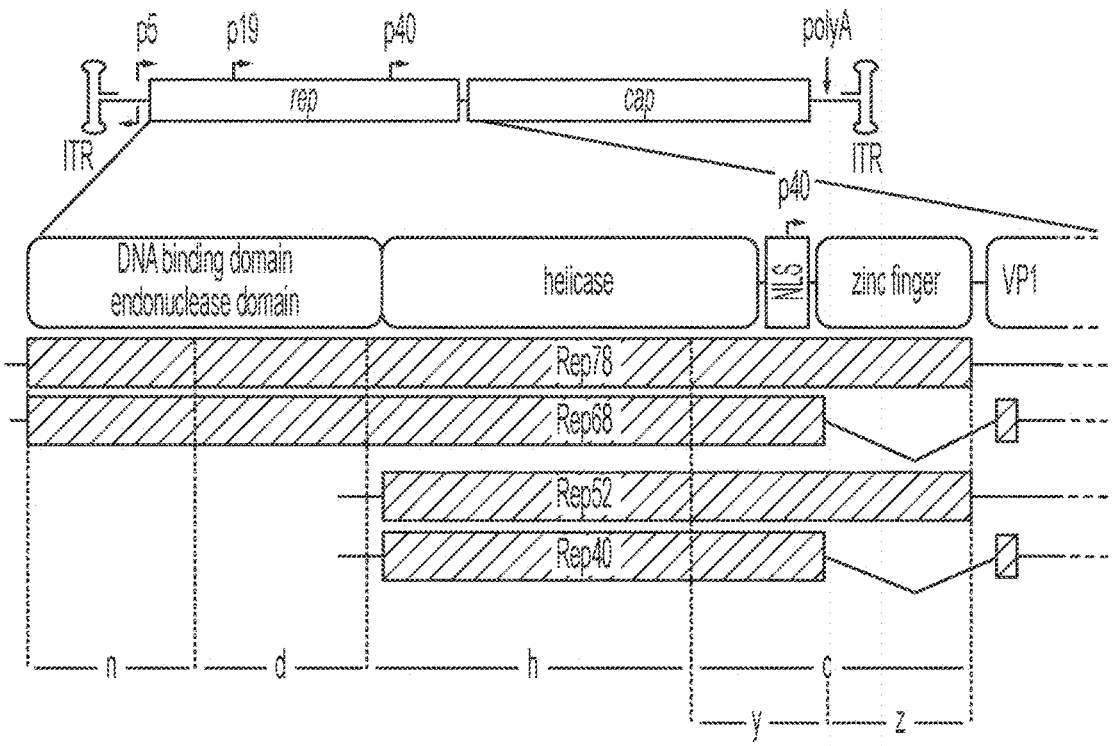
FIG. 6 shows an overview of an AAV genome is shown with its two open reading frames flanked by inverted terminal repeats (ITRs). The zoom-in shows an illustration of the domains of the Rep proteins and the transcripts leading to the expression of Rep78/68/52/40. Regions of the rep gene used for the generations of hybrids are indicated as lower case letter: n=N-terminus, d=DNA binding domain, h=helicase, c=C-terminus, y=nuclear localization signal (NLS)/p40 promoter, z=Zinc finger domain.

FIG. 5 shows percent sequence identity analysis for AAV ITR and Rep78 for AAV serotypes 1-9. FIG. 6 provides a schematic showing the arrangement of rep and cap genes in an AAV genome and various domains of AAV Rep proteins expressed from the rep gene. A schematic of AAV genome is shown with its two open reading frames flanked by inverted terminal repeats (ITRs). The zoom-in shows an illustration of the domains of the Rep proteins and the transcripts leading to the expression of Rep78/68/52/40. The specific domains of the rep gene used for the generations of hybrids are indicated by follows:

n=N-terminus domain,
d=DNA binding domain,
h=helicase domain,
y=NLS/p40 promoter domain, and
z=Zinc finger domain;

wherein the N-terminus as defined herein consists of domains n, d, and h; and the C-terminus (c) consists of domains y and z.

Figure 7A:
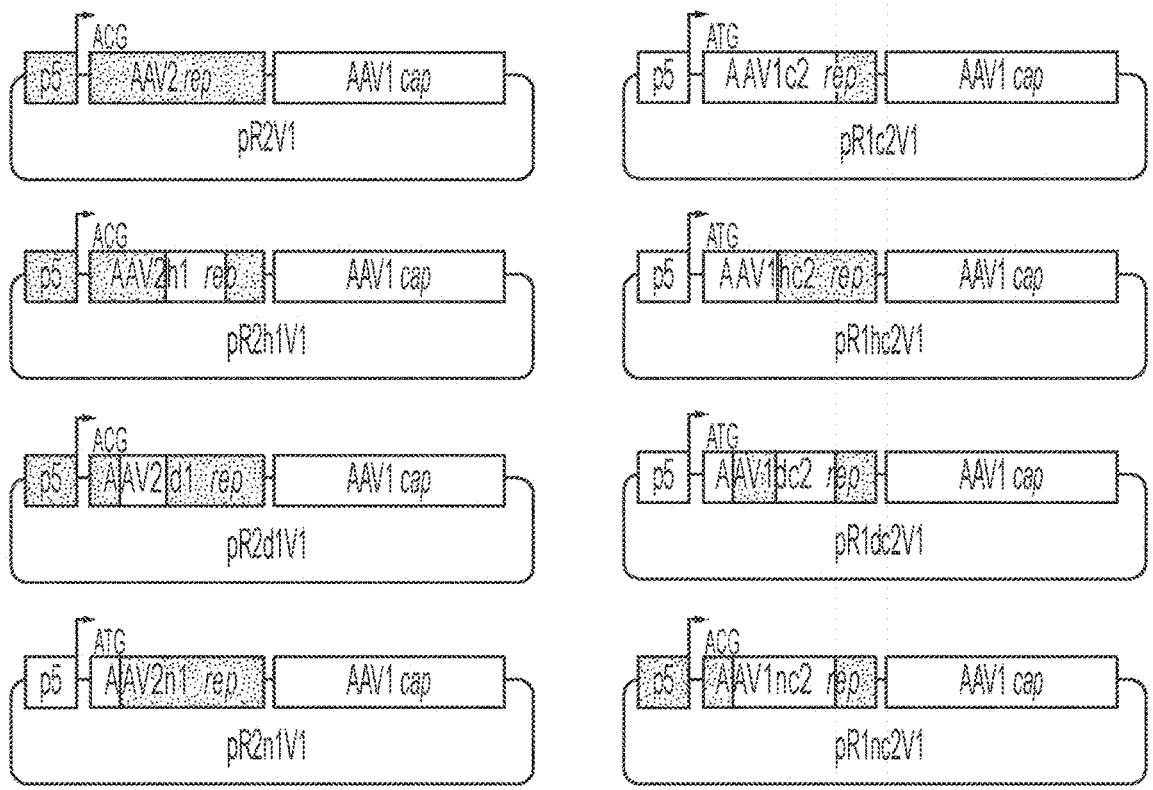
Figure 9A:
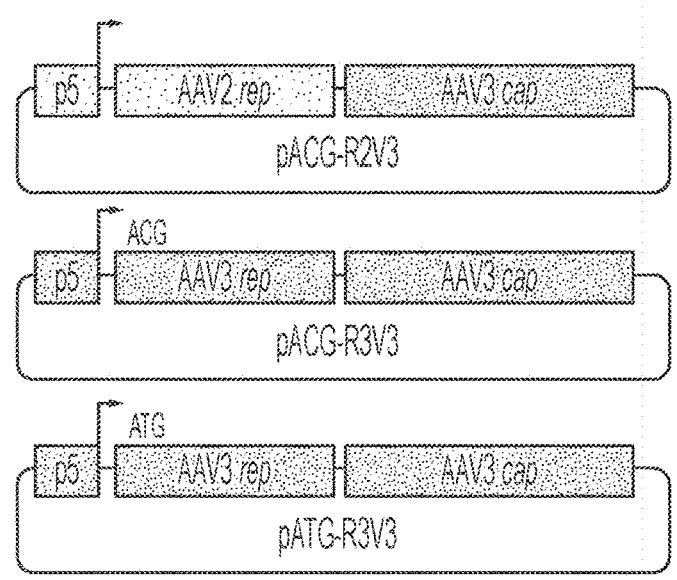
Figure 9B:
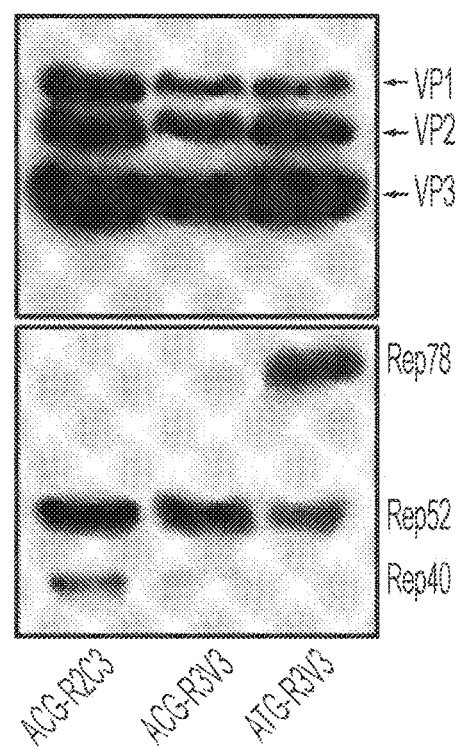
Figure 10A:
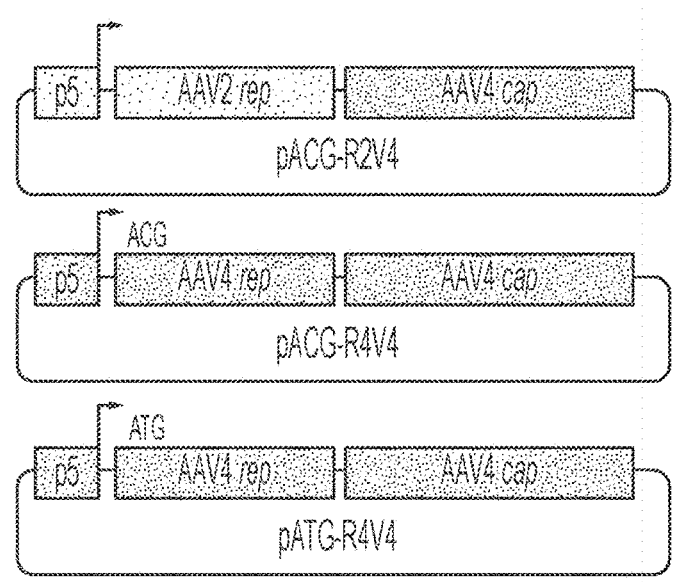
Figure 10B:
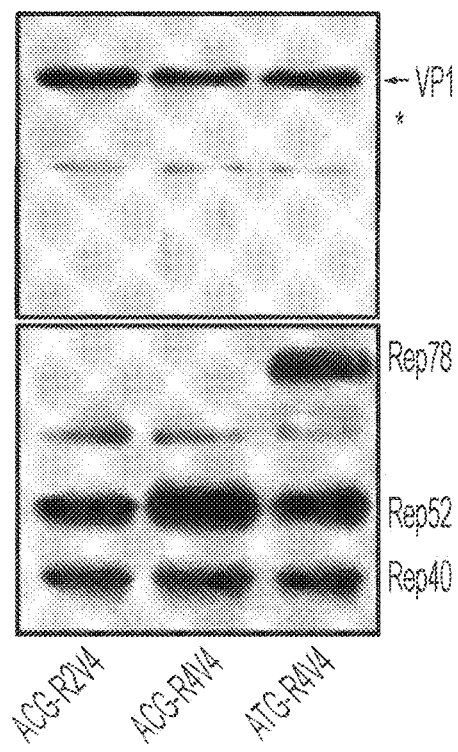
Figure 11A:
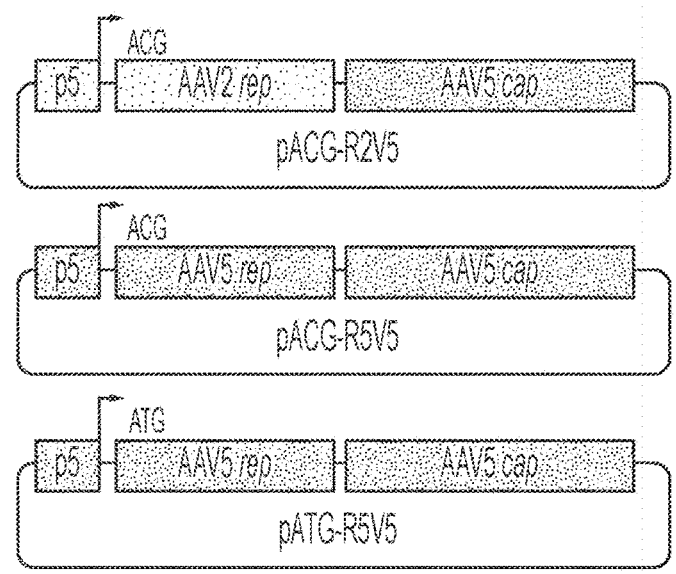
Figure 11B:
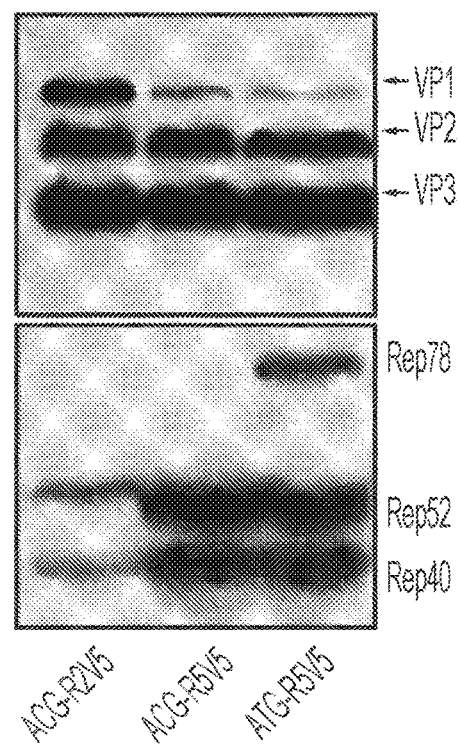

The characterization and optimization of the rep gene for AAV1 vector production is shown in FIGS. 7A-7B. Swaps between the AAV1 and AAV2 rep gene were generated to identify the domain responsible for improved genome packaging. The DNA binding domain (DBD, d) plays an important role as the AAV2 DBD significantly affects packaging. The helicase domain (h) is also likely involved with the AAV2 helicase also showing improved packaging. Overall, the variants R1hc2V1 (i.e., denoting a plasmid with a cap gene of AAV1 sequence, and a rep gene of AAV1 sequence with the exception that the C terminus (c) and the helicase domain (h) are of AAV2 sequence) and R2d1V1 (denoting a plasmid with a cap gene of AAV1 sequence, and a rep gene of AAV2 sequence with the exception that the DNA binding domain (d) is of AAV1 sequence), which both have AAV1 DBD and AAV2 helicase, have the best vector genome packaging phenotypes in AAV1 capsids. Additional data for rep modifications for producing rAAV particles of AAV1 is provided in FIG. 8. For these variants the domains in rep gene are defined as follows: n=N-terminus: aa 1-102, d=DNA-binding domain: aa 103-242, h=helicase domain: aa 243-370, c=C-terminus: aa 371-621.

The AAV2 rep gene was substituted with the AAV3 rep gene for the production of AAV3 particles (FIGS. 9A-9D). For the standard production system, an ACG-start codon for AAV2 rep was used. Both ACG and ATG start codons were tested with the AAV3 rep gene. With the ATG start codon, AAV3 Rep78 was visible and it was not seen with the ACG start codon. The VP expression of the AAV3 rep constructs was slightly lower compared to the AAV2 rep gene construct. Nonetheless, the genome titer of ATG-R3V3 was comparable to that of ACG-R2V3. Thus, the packaging was slightly better with AAV3 Rep (FIGS. 9A-9D).

Next, the AAV2 rep gene was substituted with the AAV4 rep gene for the production of AAV4 particles (FIGS. 10A-10D). Both ACG and ATG start codons were tested with the AAV4 rep gene. With the ATG start codon AAV4 Rep78 was visible and it was not seen with ACG start codon. The VP1 expression with the AAV4 rep constructs was comparable to that of the AAV2 rep gene construct. Nonetheless, the genome titer of ACG-R4V4 was higher compared to ACG-R2V4. Thus, the packaging might be better with AAV4 Rep compared to AAV2 Rep.

The AAV2 rep gene was substituted with the AAV5 rep gene for the production of AAV5 particles (FIGS. 11A-11D). Both ACG and ATG start codons were tested with the AAV5 rep gene. With the ATG start codon, AAV5 Rep78 was visible and it was not seen with ACG start codon. The VP expression with the AAV5 rep constructs appeared to be slightly lower compared to the AAV2 rep gene construct. However, no packaged genomes had been detected with the AAV5. AAV5 Rep is known to be unable to interact with AAV2 ITRs (see e.g., Chiorini et al., J Virol. 1999 May; 73(5):4293-8).

Figure 12A:
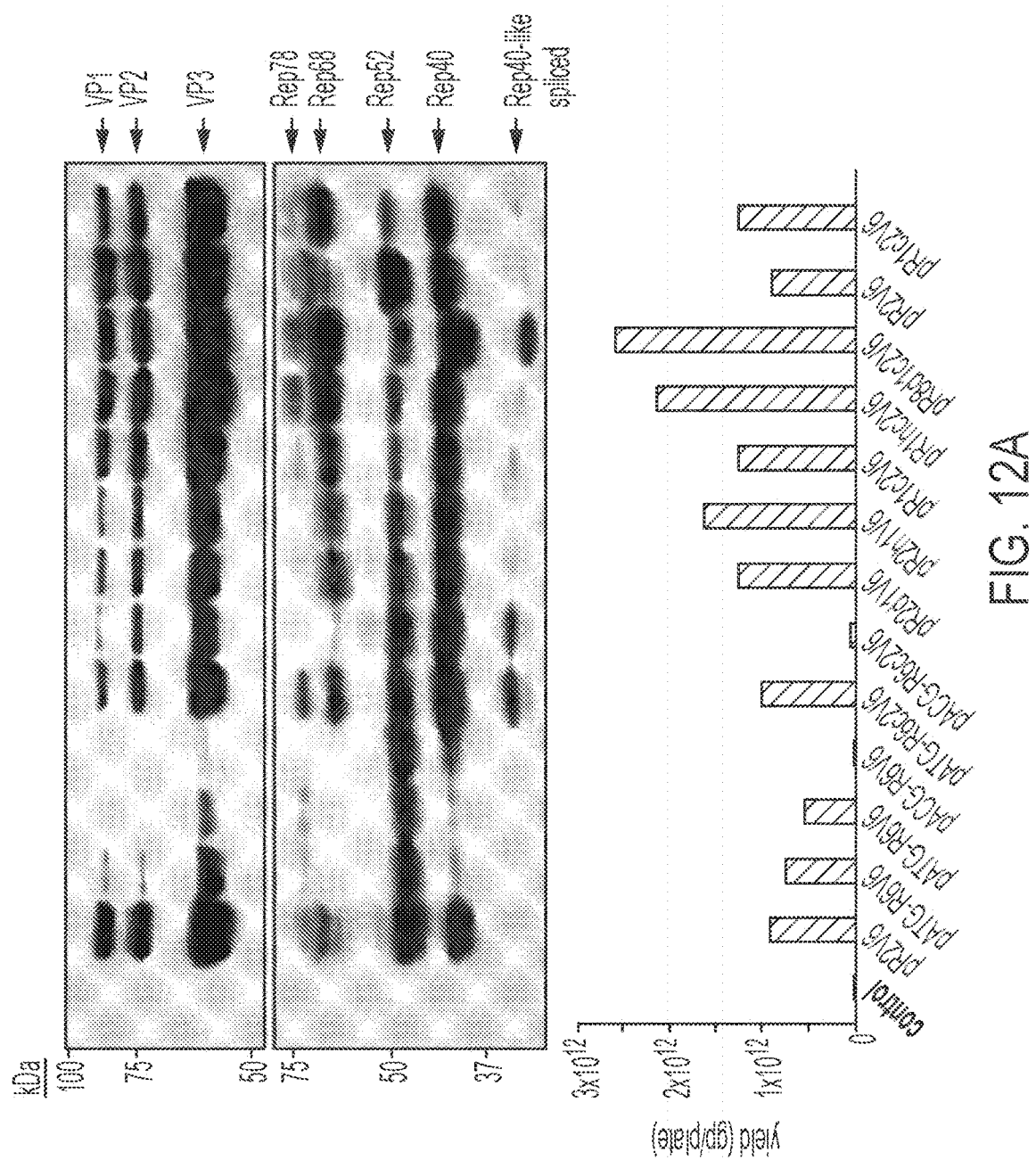
Figure 13A:
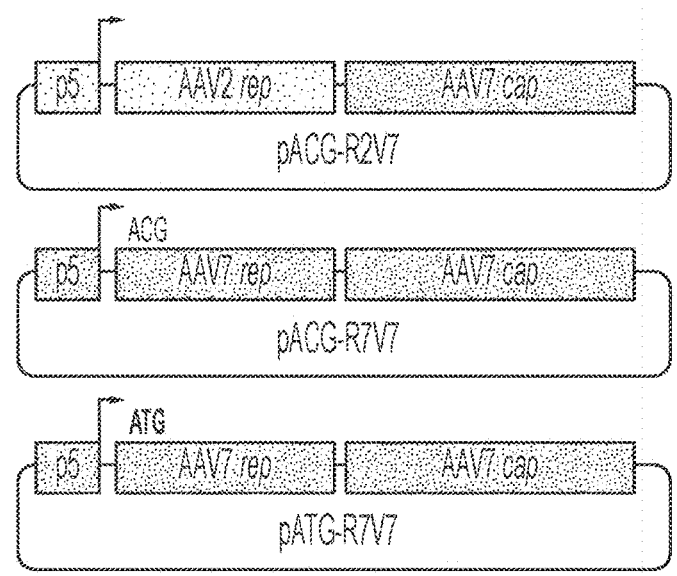
Figure 13B:
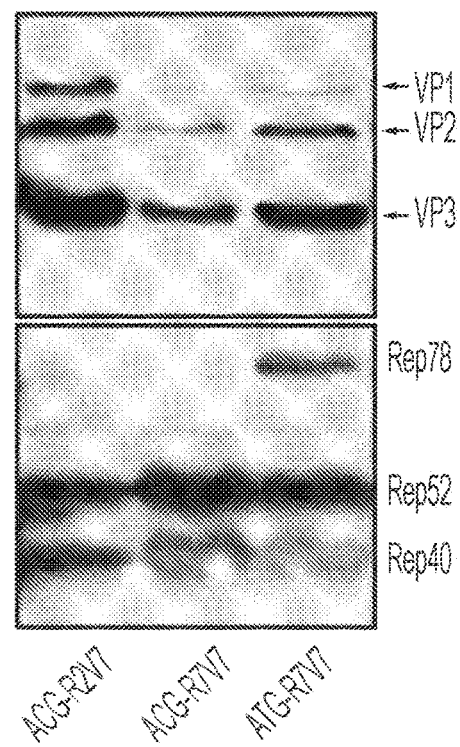

The AAV2 rep gene was substituted with the AAV6 rep gene for the production of AAV6 vectors (FIGS. 12A-12C). Both ACG and ATG start codons were tested with the AAV6 rep gene. Various Rep hybrids between the AAV serotypes AAV1, AAV2, AAV6 and AAV8 were also analyzed. The best vector genome packaging phenotypes were observed for the Rep variants plasmids R8d1c2V6 and R1hc2V6. However, both plasmids maintained high VP expression comparable to that of the reference plasmid pR2V6.

The AAV2 rep gene was substituted with the AAV7 rep gene for the production of AAV7 particles (FIGS. 13A-13D). Both ACG and ATG start codons were tested with the AAV7 rep gene. With the ATG start codon AAV7 Rep78 was visible and it was not seen with ACG start codon. The VP expression with the AAV7 rep constructs was lower compared to the AAV2 rep gene construct. Nonetheless, the genome titer of ACG-R7V7 was comparable to ACG-R2V7. Thus, the packaging was better with ACG-R7V7.

Figure 14A:
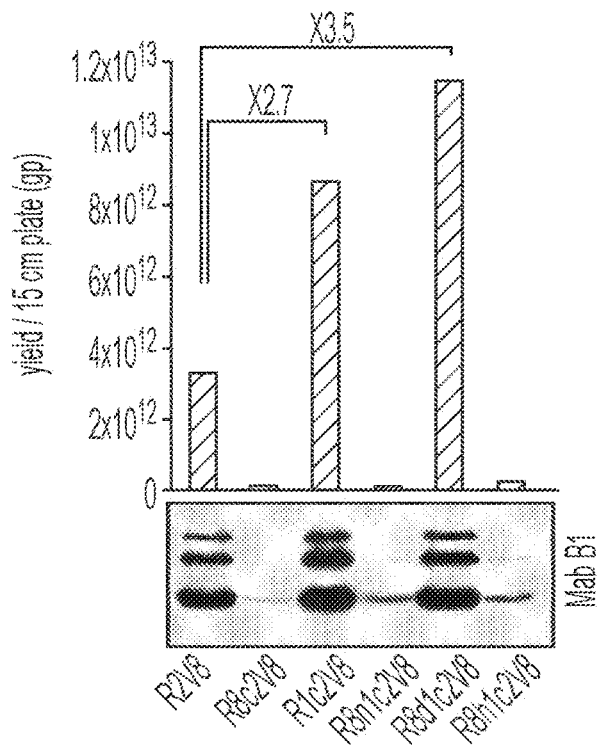
FIGS. 14A-14B provide characterization and optimization of the rep gene for AAV8 vector production.
Figure 14B:
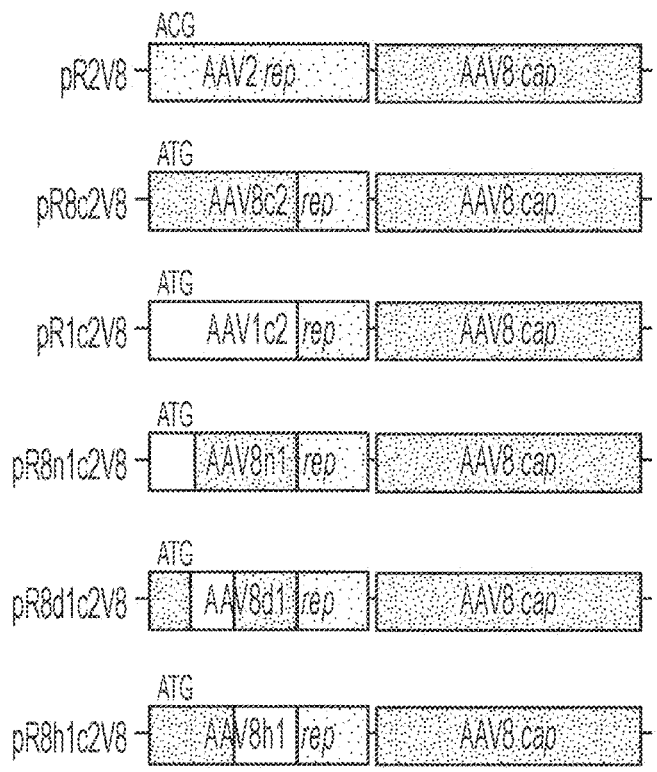

Swaps between the AAV1, AAV2, and AAV8 rep genes were generated to identify the domain responsible for improved genome packaging and to optimize the rep gene for AAV8 vector production (FIGS. 14A-14B). The DNA binding domain (DBD) appeared to play an important role for VP expression, as the substitution of the AAV8 DBD with the AAV1 DBD increased VP expression. The R1c2V8 and R8d1c2V8 hybrids/chimeras package vector genomes more efficiently into AAV8 capsids compared to the AAV2 rep gene. For these variants, the rep domains are defined as follows: n=N-terminus: aa 1-102, d=DNA-binding domain: aa 103-224, h=helicase domain: aa 225-372, c=C-terminus: aa 373-623.

Figure 15A:
FIGS. 15A-15B show an example of the ratio of genome-containing AAV8 particles for 'standard' AAV vector production compared to the vector production using rep chimeras as described herein.
Figure 15B:
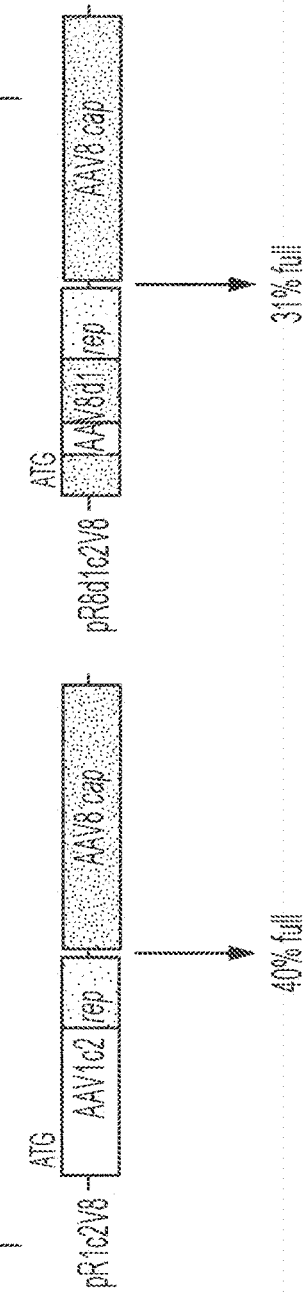

The improvement in genome packaging of AAV8 particles using rep chimeras is shown in FIGS. 15A-15B. The utilization of the new rep chimeras R1c2 and R8d1c2 lead to higher percentages (3- to 4-fold) of genome containing particles.

FIGS. 16A-16B provide data for more rep chimeras to package AAV8 particles. It can be seen that the genome packaging is improved when the listed rep chimeras are used over AAV2 rep.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present application, and without departing from the spirit and scope thereof, can make various changes and modifications of the application to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present application are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present application.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the application describes "a composition comprising A and B", the application also contemplates the alternative embodiments "a composition consisting of A and B" and "a composition consisting essentially of A and B".

What is claimed is:

1. A composition comprising: a nucleic acid sequence comprising a rep gene that encodes a chimeric rep protein, wherein the rep gene comprises at least one nucleic acid sequence from a rep gene of a first AAV serotype and at least one nucleic acid sequence from a rep gene of a second AAV serotype, wherein the first AAV serotype is AAV1 or AAV8, wherein the second AAV serotype is AAV2, and wherein the chimeric rep protein exhibits a higher rAAV nucleic acid packaging efficiency when introduced into a cell as compared to a nonchimeric rep protein of said first or second AAV serotype.

2. The composition of claim 1, wherein the at least one nucleic acid sequence from the rep gene of the first AAV serotype or the at least one nucleic acid sequence from the rep gene of the second AAV serotype encodes at least a portion of a domain selected from the group consisting of: a DNA binding domain, a helicase domain, a Nuclear Localization Signal/p40 promoter domain, and a zinc finger domain.

3. The composition of claim 1, wherein the at least one nucleic acid sequence from the rep gene of the first AAV serotype or the at least one nucleic acid sequence from the rep gene of the second AAV serotype encodes at least a portion of a DNA binding domain or a zinc finger domain.

4. The composition of claim 1, wherein the rep gene further comprises at least one nucleic acid sequence from a rep gene of a third AAV serotype, wherein the third AAV serotype is different from the first and the second AAV serotypes.

5. The composition of claim 1, wherein the nucleic acid sequence further comprises a cap gene from the first AAV serotype or the second AAV serotype.

* * * * *

SEQUENCE LISTING

<160> NUMBER OF SEQ ID NOS: 187

<210> SEQ ID NO 1

```
<211> LENGTH: 147
<212> TYPE: DNA
<213> ORGANISM: Artificial Sequence
<220> FEATURE:
<223> OTHER INFORMATION: Synthetic polynucleotide

<400> SEQUENCE: 1
ttgcccactc cctctctgcg cgctcgctcg ctcggtgggg cctgcggacc aaaggtccgc    60
agacggcaga gctctgctct gccggcccca ccgagcgagc gagcgcgcag agagggagtg   120
ggcaactcca tcactagggg taatcgc                                       147

<210> SEQ ID NO 2
<211> LENGTH: 145
<212> TYPE: DNA
<213> ORGANISM: Artificial Sequence
<220> FEATURE:
<223> OTHER INFORMATION: Synthetic polynucleotide

<400> SEQUENCE: 2
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcct                                         145

<210> SEQ ID NO 3
<211> LENGTH: 146
<212> TYPE: DNA
<213> ORGANISM: Artificial Sequence
<220> FEATURE:
<223> OTHER INFORMATION: Synthetic polynucleotide

<400> SEQUENCE: 3
tggccactcc ctctatgcgc actcgctcgc tcggtggggc ctggcgacca aaggtcgcca    60
gacggacgtg ctttgcacgt ccggccccac cgagcgagcg agtgcgcata gagggagtgg   120
ccaactccat cactagaggt atggca                                        146

<210> SEQ ID NO 4
<211> LENGTH: 148
<212> TYPE: DNA
<213> ORGANISM: Artificial Sequence
<220> FEATURE:
<223> OTHER INFORMATION: Synthetic polynucleotide

<400> SEQUENCE: 4
ttggccactc cctctatgcg cgctcgctca ctcactcggc cctggagacc aaaggtctcc    60
agactgccgg cctctggccg gcagggccga gtgagtgagc gagcgcgcat agagggagtg   120
gccaactcca tcatctaggt ttgcccac                                      148

<210> SEQ ID NO 5
<211> LENGTH: 176
<212> TYPE: DNA
<213> ORGANISM: Artificial Sequence
<220> FEATURE:
<223> OTHER INFORMATION: Synthetic polynucleotide

<400> SEQUENCE: 5
ctctcccccc tgtcgcgttc gctcgctcgc tggctcgttt gggggggtgg cagctcaaag    60
agctgccaga cgacggccct ctggccgtcg ccccccaaa cgagccagcg agcgagcgaa   120
cgcgacaggg gggagagtgc cacactctca agcaggggg ttttgtaagc agtgat       176
```

```
<210> SEQ ID NO 6
<211> LENGTH: 145
<212> TYPE: DNA
<213> ORGANISM: Artificial Sequence
<220> FEATURE:
<223> OTHER INFORMATION: Synthetic polynucleotide

<400> SEQUENCE: 6
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcct                                        145

<210> SEQ ID NO 7
<211> LENGTH: 146
<212> TYPE: DNA
<213> ORGANISM: Artificial Sequence
<220> FEATURE:
<223> OTHER INFORMATION: Synthetic polynucleotide

<400> SEQUENCE: 7
ttggccactc cctctatgcg cgctcgctcg ctcggtgggg cctgcggacc aaaggtccgc    60
agacggcaga gctctgctct gccggcccca ccgagcgagc gagcgcgcat agagggagtg   120
gccaactcca tcactagggg taccgc                                       146

<210> SEQ ID NO 8
<211> LENGTH: 1872
<212> TYPE: DNA
<213> ORGANISM: Artificial Sequence
<220> FEATURE:
<223> OTHER INFORMATION: Synthetic polynucleotide

<400> SEQUENCE: 8
atgccgggct tctacgagat cgtgatcaag gtgccgagcg acctggacga gcacctgccg    60
ggcatttctg actcgtttgt gagctgggtg gccgagaagg aatgggagct gccccccggat  120 tctgacatgg atctgaatct gattgagcag gcacccctga ccgtggccga gaagctgcag   180
cgcgacttcc tggtccaatg gcgccgcgtg agtaaggccc cggaggccct cttctttgtt   240
cagttcgaga agggcgagtc ctacttccac ctccatattc tggtggagac cacggggggtc  300 aaatccatgg tgctgggccg cttcctgagt cagattaggg acaagctggt gcagaccatc   360
taccgcggga tcgagccgac cctgcccaac tggttcgcgg tgaccaagac gcgtaatggc   420
gccggagggg ggaacaaggt ggtggacgag tgctacatcc ccaactacct cctgcccaag   480
actcagcccg agctgcagtg ggcgtggact aacatggagg agtatataag cgcctgtttg   540
aacctggccg agcgcaaacg gctcgtggcg cagcacctga cccacgtcag ccagacccag   600
gagcagaaca aggagaatct gaaccccaat tctgacgcgc tgtcatccg tcaaaaacc    660 tccgcgcgct acatggagct ggtcgggtgg ctggtggacc ggggcatcac ctccgagaag   720
cagtggatcc aggaggacca ggcctcgtac atctccttca cgccgcttc caactcgcgg   780 tcccagatca aggccgctct ggacaatgcc ggcaagatca tggcgctgac caaatccgcg   840
cccgactacc tggtaggccc cgctccgccc gcggacatta aaaccaaccg catctaccgc   900
atcctggagc tgaacggcta cgaacctgcc tacgccggct ccgtctttct cggctgggcc   960
cagaaaaggt tcgggaagcg caacaccatc tggctgtttg gccggccac cacgggcaag  1020 accaacatcg cggaagccat cgcccacgcc gtgcccttct acggctgcgt caactggacc  1080
aatgagaact ttccccttcaa tgattgcgtc gacaagatgg tgatctggtg ggaggagggc  1140
```

| | |
|---|---:|
| aagatgacgg ccaaggtcgt ggagtccgcc aaggccattc tcggcggcag caaggtgcgc | 1200 |
| gtggaccaaa agtgcaagtc gtccgcccag atcgacccca cccccgtgat cgtcacctcc | 1260 |
| aacaccaaca tgtgcgccgt gattgacggg aacagcacca ccttcgagca ccagcagccg | 1320 |
| ttgcaggacc ggatgttcaa atttgaactc acccgccgtc tggagcatga ctttggcaag | 1380 |
| gtgacaaagc aggaagtcaa agagttcttc cgctgggcgc aggatcacgt gaccgaggtg | 1440 |
| gcgcatgagt tctacgtcag aaagggtgga gccaacaaaa gacccgcccc cgatgacgcg | 1500 |
| gataaaagcg agcccaagcg ggcctgcccc tcagtcgcgg atccatcgac gtcagacgcg | 1560 |
| gaaggagctc cggtggactt tgccgacagg taccaaaaca aatgttctcg tcacgcgggc | 1620 |
| atgcttcaga tgctgtttcc ctgcaagaca tgcgagagaa tgaatcagaa tttcaacatt | 1680 |
| tgcttcacgc acgggacgag agactgttca gagtgcttcc ccggcgtgtc agaatctcaa | 1740 |
| ccggtcgtca gaaagaggac gtatcggaaa ctctgtgcca ttcatcatct gctggggcgg | 1800 |
| gctcccgaga ttgcttgctc ggcctgcgat ctggtcaacg tggacctgga tgactgtgtt | 1860 |
| tctgagcaat aa | 1872 |

<210> SEQ ID NO 9
<211> LENGTH: 1866
<212> TYPE: DNA
<213> ORGANISM: Artificial Sequence
<220> FEATURE:
<223> OTHER INFORMATION: Synthetic polynucleotide

<400> SEQUENCE: 9

| | |
|---|---:|
| atgccggggt tttacgagat tgtgattaag gtccccagcg accttgacgg gcatctgccc | 60 |
| ggcatttctg acagctttgt gaactgggtg gccgagaagg aatgggagtt gccgccagat | 120 |
| tctgacatgg atctgaatct gattgagcag gcacccctga ccgtggccga aagctgcag | 180 |
| cgcgactttc tgacggaatg gcgccgtgtg agtaaggccc cggaggccct tttctttgtg | 240 |
| caatttgaga agggagagag ctacttccac atgcacgtgc tcgtggaaac caccggggtg | 300 |
| aaatccatgg tttttgggacg tttcctgagt cagattcgcg aaaaactgat tcagagaatt | 360 |
| taccgcggga tcgagccgac tttgccaaac tggttcgcgg tcacaaagac cagaaatggc | 420 |
| gccggaggcg ggaacaaggt ggtggatgag tgctacatcc ccaattactt gctccccaaa | 480 |
| acccagcctg agctccagtg ggcgtggact aatatggaac agtatttaag cgcctgtttg | 540 |
| aatctcacgg agcgtaaacg gttggtggcg cagcatctga cgcacgtgtc gcagacgcag | 600 |
| gagcagaaca aagagaatca gaatcccaat tctgatgcgc cggtgatcag atcaaaaact | 660 |
| tcagccaggt acatggagct ggtcgggtgg ctcgtggaca aggggattac ctcggagaag | 720 |
| cagtggatcc aggaggacca ggcctcatac atctccttca atgcggcctc caactcgcgg | 780 |
| tcccaaatca aggctgcctt ggacaatgcg ggaaagatta tgagcctgac taaaaccgcc | 840 |
| cccgactacc tggtgggcca gcagcccgtg gaggacattt ccagcaatcg gatttataaa | 900 |
| attttggaac taaacgggta cgatccccaa tatgcggctt ccgtctttct gggatgggcc | 960 |
| acgaaaaagt tcggcaagag gaacaccatc tggctgtttg ggcctgcaac taccgggaag | 1020 |
| accaacatcg cggaggccat agcccacact gtgcccttct acgggtgcgt aaactggacc | 1080 |
| aatgagaact ttcccttcaa cgactgtgtc gacaagatgg tgatctggtg ggaggagggg | 1140 |
| aagatgaccg ccaaggtcgt ggagtcggcc aaagccattc tcggaggaag caaggtgcgc | 1200 |
| gtggaccaga aatgcaagtc ctcggcccag atagacccga ctcccgtgat cgtcacctcc | 1260 |
| aacaccaaca tgtgcgccgt gattgacggg aactcaacga ccttcgaaca ccagcagccg | 1320 |

```
ttgcaagacc ggatgttcaa atttgaactc acccgccgtc tggatcatga ctttgggaag    1380
gtcaccaagc aggaagtcaa agactttttc cggtgggcaa aggatcacgt ggttgaggtg    1440
gagcatgaat tctacgtcaa aaagggtgga gccaagaaaa gacccgcccc cagtgacgca    1500
gatataagtg agcccaaacg ggtgcgcgag tcagttgcgc agccatcgac gtcagacgcg    1560
gaagcttcga tcaactacgc agacaggtac caaaacaaat gttctcgtca cgtgggcatg    1620
aatctgatgt gtttccctg cagacaatgc gagagaatga atcagaattc aaatatctgc    1680
ttcactcacg gacagaaaga ctgtttagag tgctttcccg tgtcagaatc tcaacccgtt    1740
tctgtcgtca aaaaggcgta tcagaaactg tgctacattc atcatatcat gggaaaggtg    1800
ccagacgctt gcactgcctg cgatctggtc aatgtggatt tggatgactg catctttgaa    1860
caataa                                                               1866

<210> SEQ ID NO 10
<211> LENGTH: 1875
<212> TYPE: DNA
<213> ORGANISM: Artificial Sequence
<220> FEATURE:
<223> OTHER INFORMATION: Synthetic polynucleotide

<400> SEQUENCE: 10 atgccgggt tctacgagat tgtcctgaag gtcccgagtg acctggacga gcacctgccg      60
ggcatttcta actcgtttgt taactgggtg gccgagaagg aatgggagct gccgccggat    120
tctgacatgg atccgaatct gattgagcag gcacccctga ccgtggccga aaagcttcag    180
cgcgagttcc tggtggagtg gcgccgcgtg agtaaggccc cggaggccct cttttttgtc    240
cagttcgaaa aggggggagac ctacttccac ctgcacgtgc tgattgagac catcgggggtc    300 aaatccatgg tggtcggccg ctacgtgagc cagattaaag agaagctggt gacccgcatc    360
taccgcgggg tcgagccgca gcttccgaac tggttcgcgg tgaccaaaac gcgaaatggc    420 gccggggggcg ggaacaaggt ggtggacgac tgctacatcc ccaactacct gctccccaag    480
acccagcccg agctccagtg ggcgtggact aacatggacc agtatttaag cgcctgtttg    540
aatctcgcgg agcgtaaacg gctggtggcg cagcatctga cgcacgtgtc gcagacgcag    600
gagcagaaca agagaatca gaacccaat tctgacgcgc cggtcatcag gtcaaaaacc    660
tcagccaggt acatggagct ggtcgggtgg ctggtggacc gcgggatcac gtcagaaaag    720
caatggattc aggaggacca ggcctcgtac atctccttca cgccgcctc caactcgcgg    780 tcccagatca aggccgcgct ggacaatgcc tccaagatca tgagcctgac aaagacggct    840
ccggactacc tggtgggcag caacccgccg gaggacatta ccaaaaatcg gatctaccaa    900
atcctggagc tgaacgggta cgatccgcag tacgcggcct ccgtcttcct gggctgggcg    960
caaaagaagt tcgggaagag gaacaccatc tggctctttg ggccggccac gacgggtaaa   1020
accaacatcg cggaagccat cgcccacgcc gtgcccttct acggctgcgt aaactggacc   1080
aatgagaact ttcccttcaa cgattgcgtc gacaagatgg tgatctggtg ggaggagggc   1140
aagatgacgg ccaaggtcgt ggagagcgcc aaggccattc tgggcggaag caaggtgcgc   1200
gtggaccaaa agtgcaagtc atcggcccag atcgaaccca ctcccgtgat cgtcacctcc   1260
aacaccaaca tgtgcgccgt gattgacggg aacagcacca ccttcgagca tcagcagccg   1320
ctgcaggacc ggatgtttaa atttgaactt acccgccgtt tggaccatga ctttgggaag   1380
gtcaccaaac aggaagtaaa ggactttttc cggtgggctt ccgatcacgt gactgacgtg   1440
```

```
gctcatgagt tctacgtcag aaagggtgga gctaagaaac gccccgcctc caatgacgcg   1500
gatgtaagcg agccaaaacg gcagtgcacg tcacttgcgc agccgacaac gtcagacgcg   1560
gaagcaccgg cggactacgc ggacaggtac caaaacaaat gttctcgtca cgtgggcatg   1620
aatctgatgc ttttccctg taaaacatgc gagagaatga atcaaatttc caatgtctgt   1680
tttacgcatg gtcaaagaga ctgtggggaa tgcttccctg gaatgtcaga atctcaaccc   1740
gtttctgtcg tcaaaaagaa gacttatcag aaactgtgtc caattcatca tatcctggga   1800
agggcacccg agattgcctg ttcggcctgc gatttggcca atgtggactt ggatgactgt   1860
gtttctgagc aataa                                                   1875

<210> SEQ ID NO 11
<211> LENGTH: 1872
<212> TYPE: DNA
<213> ORGANISM: Artificial Sequence
<220> FEATURE:
<223> OTHER INFORMATION: Synthetic polynucleotide

<400> SEQUENCE: 11
atgccggggt tctacgagat cgtgctgaag gtgcccagcg acctggacga gcacctgccc     60
ggcatttctg actcttttgt gagctgggtg gccgagaagg aatgggagct gccgccggat    120
tctgacatgg acttgaatct gattgagcag gcacccctga ccgtggccga aaagctgcaa    180
cgcgagttcc tggtcgagtg gcgccgcgtg agtaaggccc cggaggccct cttctttgtc    240
cagttcgaga aggggacag ctacttccac ctgcacatcc tggtggagac cgtgggcgtc    300
aaatccatgg tggtgggccg ctacgtgagc cagattaaag agaagctggt gacccgcatc    360
taccgcgggg tcgagccgca gcttccgaac tggttcgcgg tgaccaagac gcgtaatggc    420 gccgaggcg ggaacaaggt ggtggacgac tgctacatcc ccaactacct gctccccaag    480
acccagcccg agctccagtg ggcgtggact aacatggacc agtatataag cgcctgtttg    540
aatctcgcga agcgtaaacg gctggtggcg cagcatctga cgcacgtgtc gcagacgcag    600
gagcagaaca aggaaaacca gaaccccaat tctgacgcgc cggtcatcag gtcaaaaacc    660
tccgccaggt acatggagct ggtcgggtgg ctggtggacc gcgggatcac gtcagaaaag    720
caatggatcc aggaggacca ggcgtcctac atctccttca cgccgcctc caactcgcgg    780 tcacaaatca aggccgcgct ggacaatgcc tccaaaatca tgagcctgac aaagacgct    840 ccggactacc tggtgggcca gaacccgccg gaggacattt ccagcaaccg catctaccga    900
atcctcgaga tgaacgggta cgatccgcag tacgcggcct ccgtcttcct gggctgggcg    960
caaaagaagt tcgggaagag gaacaccatc tggctctttg gccggccac gacgggtaaa   1020 accaacatcg cggaagccat cgcccacgcc gtgcccttct acggctgcgt gaactggacc   1080
aatgagaact tccgttcaa cgattgcgtc gacaagatgg tgatctggtg ggaggagggc   1140
aagatgacgg ccaaggtcgt agagagcgcc aaggccatcc tgggcggaag caaggtgcgc   1200
gtggaccaaa agtgcaagtc atcggcccag atcgacccaa ctcccgtgat cgtcacctcc   1260
aacaccaaca tgtgcgcggt catcgacgga aactcgacca ccttcgagca ccaacaacca   1320
ctccaggacc ggatgttcaa gttcgagctc accaagcgcc tggagcacga ctttggcaag   1380
gtcaccaagc aggaagtcaa agactttttc cggtgggcgt cagatcacgt gaccgaggtg   1440
actcacgagt tttacgtcag aaagggtgga gctagaaaga ggcccgcccc caatgacgca   1500
gatataagtg agcccaagcg ggcctgtccg tcagttgcgc agccatcgac gtcagacgcg   1560
gaagctccgg tggactacgc ggacaggtac caaaacaaat gttctcgtca cgtgggtatg   1620
```

| | |
|---|---|
| aatctgatgc tttttccctg ccggcaatgc gagagaatga atcagaatgt ggacatttgc | 1680 |
| ttcacgcacg gggtcatgga ctgtgccgag tgcttccccg tgtcagaatc tcaacccgtg | 1740 |
| tctgtcgtca gaaagcggac gtatcagaaa ctgtgtccga ttcatcacat catggggagg | 1800 |
| gcgcccgagg tggcctgctc ggcctgcgaa ctggccaatg tggacttgga tgactgtgac | 1860 |
| atggaacaat aa | 1872 |

<210> SEQ ID NO 12
<211> LENGTH: 1833
<212> TYPE: DNA
<213> ORGANISM: Artificial Sequence
<220> FEATURE:
<223> OTHER INFORMATION: Synthetic polynucleotide

<400> SEQUENCE: 12

| | |
|---|---|
| atggctacct tctatgaagt cattgttcgc gtcccatttg acgtggagga acatctgcct | 60 |
| ggaatttctg acagctttgt ggactgggta actggtcaaa tttgggagct gcctccagag | 120 |
| tcagatttaa atttgactct ggttgaacag cctcagttga cggtggctga tagaattcgc | 180 |
| cgcgtgttcc tgtacgagtg gaacaaattt tccaagcagg agtccaaatt ctttgtgcag | 240 |
| tttgaaaagg gatctgaata ttttcatctg cacacgcttg tggagacctc cggcatctct | 300 |
| tccatggtcc tcggccgcta cgtgagtcag attcgcgccc agctggtgaa agtggtcttc | 360 |
| cagggaattg aaccccagat caacgactgg gtcgccatca ccaaggtaaa gaagggcgga | 420 |
| gccaataagg tggtggattc tgggtatatt cccgcctacc tgctgccgaa ggtccaaccg | 480 |
| gagcttcagt gggcgtggac aaacctggac gagtataaat tggccgccct gaatctggag | 540 |
| gagcgcaaac ggctcgtcgc gcagtttctg gcagaatcct cgcagcgctc gcaggaggcg | 600 |
| gcttcgcagc gtgagttctc ggctgacccg gtcatcaaaa gcaagacttc ccagaaatac | 660 |
| atggcgctcg tcaactggct cgtggagcac ggcatcactt ccgagaagca gtggatccag | 720 |
| gaaaatcagg agagctacct ctccttcaac tccaccggca actctcggag ccagatcaag | 780 |
| gccgcgctcg acaacgcgac caaaattatg agtctgacaa aaagcgcggt ggactacctc | 840 |
| gtggggagct ccgttcccga ggacatttca aaaaacagaa tctggcaaat ttttgagatg | 900 |
| aatggctacg acccggccta cgcgggatcc atcctctacg ctggtgtca gcgctccttc | 960 |
| aacaagagga acaccgtctg gctctacgga cccgccacga ccggcaagac caacatcgcg | 1020 |
| gaggccatcg cccacactgt gcccttttac ggctgcgtga actggaccaa tgaaaacttt | 1080 |
| ccctttaatg actgtgtgga caaatgctc atttggtggg aggagggaaa gatgaccaac | 1140 |
| aaggtggttg aatccgccaa ggccatcctg gggggctcaa aggtgcgggt cgatcagaaa | 1200 |
| tgtaaatcct ctgttcaaat tgattctacc cctgtcattg taacttccaa tacaaacatg | 1260 |
| tgtgtggtgg tggatgggaa ttccacgacc tttgaacacc agcagccgct ggaggaccgc | 1320 |
| atgttcaaat ttgaactgac taagcggctc ccgccagatt ttggcaagat tactaagcag | 1380 |
| gaagtcaagg acttttttgc ttgggcaaag gtcaatcagg tgccggtgac tcacgagttt | 1440 |
| aaagttccca gggaattggc gggaactaaa ggggcggaga atctctaaa acgcccactg | 1500 |
| ggtgacgtca ccaatactag ctataaaagt ctggagaagc gggccaggct ctcatttgtt | 1560 |
| cccgagacgc ctcgcagttc agacgtgact gttgatcccg ctcctctgcg accgctcaat | 1620 |
| tggaattcaa ggtatgattg caaatgtgac tatcatgctc aatttgacaa catttctaac | 1680 |
| aaatgtgatg aatgtgaata tttgaatcgg ggcaaaaatg gatgtatctg tcacaatgta | 1740 |

| | |
|---|---|
| actcactgtc aaatttgtca tgggattccc ccctgggaaa aggaaaactt gtcagatttt | 1800 |
| ggggattttg acgatgccaa taaagaacag taa | 1833 |

<210> SEQ ID NO 13
<211> LENGTH: 1872
<212> TYPE: DNA
<213> ORGANISM: Artificial Sequence
<220> FEATURE:
<223> OTHER INFORMATION: Synthetic polynucleotide

<400> SEQUENCE: 13

| | |
|---|---|
| atgccgggt tttacgagat tgtgattaag gtccccagcg accttgacga gcatctgccc | 60 |
| ggcatttctg acagctttgt gaactgggtg gccgagaagg aatgggagtt gccgccagat | 120 |
| tctgacatgg atctgaatct gattgagcag gcacccctga ccgtggccga gaagctgcag | 180 |
| cgcgacttcc tggtccagtg gcgccgcgtg agtaaggccc cggaggccct cttctttgtt | 240 |
| cagttcgaga agggcgagtc ctacttccac ctccatattc tggtggagac cacggggggtc | 300 |
| aaatccatgg tgctgggccg cttcctgagt cagattaggg acaagctggt gcagaccatc | 360 |
| taccgcggga tcgagccgac cctgcccaac tggttcgcgg tgaccaagac gcgtaatggc | 420 |
| gccgagggg ggaacaaggt ggtggacgag tgctacatcc ccaactacct cctgcccaag | 480 |
| actcagcccg agctgcagtg ggcgtggact aacatggagg agtatataag cgcgtgttta | 540 |
| aacctggccg agcgcaaacg gctcgtggcg cacgacctga cccacgtcag ccagacccag | 600 |
| gagcagaaca aggagaatct gaaccccaat tctgacgcgc tgtcatccg gtcaaaaacc | 660 |
| tccgcacgct acatggagct ggtcgggtgg ctggtggacc ggggcatcac ctccgagaag | 720 |
| cagtggatcc aggaggacca ggcctcgtac atctccttca cgccgcctc caactcgcgg | 780 |
| tcccagatca aggccgctct ggacaatgcc ggcaagatca tggcgctgac caaatccgcg | 840 |
| cccgactacc tggtaggccc cgctccgccc gccgacatta aaaccaaccg catttaccgc | 900 |
| atcctggagc tgaacggcta cgaccctgcc tacgccggct ccgtctttct cggctgggcc | 960 |
| cagaaaaggt tcggaaaacg caacaccatc tggctgtttg ggccggccac cacgggcaag | 1020 |
| accaacatcg cggaagccat cgcccacgcc gtgcccttct acggctgcgt caactggacc | 1080 |
| aatgagaact ttcccttcaa cgattgcgtc gacaagatgg tgatctggtg ggaggagggc | 1140 |
| aagatgacgg ccaaggtcgt ggagtccgcc aaggccattc tcggcggcag caaggtgcgc | 1200 |
| gtggaccaaa agtgcaagtc gtccgcccag atcgatccca cccccgtgat cgtcacctcc | 1260 |
| aacaccaaca tgtgcgccgt gattgacggg aacagcacca cttcgagca ccagcagccg | 1320 |
| ttgcaggacc ggatgttcaa atttgaactc acccgccgtc tggagcatga ctttggcaag | 1380 |
| gtgacaaagc aggaagtcaa agagttcttc cgctgggcgc aggatcacgt gaccgaggtg | 1440 |
| gcgcatgagt tctacgtcag aaagggtgga gccaacaaga acccgccccc cgatgacgcg | 1500 |
| gataaaagcg agcccaagcg ggcctgcccc tcagtcgcgg atccatcgac gtcagacgcg | 1560 |
| gaaggagctc cggtggactt tgccgacagg taccaaaaca aatgttctcg tcacgcgggc | 1620 |
| atgcttcaga tgctgttccc ctgcaaaaca tgcgagagaa tgaatcagaa tttcaacatt | 1680 |
| tgcttcacgc acgggaccag agactgttca gaatgtttcc ccggcgtgtc agaatctcaa | 1740 |
| ccggtcgtca gaaagaggac gtatcggaaa ctctgtgcca ttcatcatct gctggggcgg | 1800 |
| gctcccgaga ttgcttgctc ggcctgcgat ctggtcaacg tggatctgga tgactgtgtt | 1860 |
| tctgagcaat aa | 1872 |

<210> SEQ ID NO 14
<211> LENGTH: 1872
<212> TYPE: DNA
<213> ORGANISM: Artificial Sequence
<220> FEATURE:
<223> OTHER INFORMATION: Synthetic polynucleotide

<400> SEQUENCE: 14

| | |
|---|---:|
| atgccgggtt tctacgagat cgtgatcaag gtgccgagcg acctggacga gcacctgccg | 60 |
| ggcatttctg actcgtttgt gaactgggtg gccgagaagg aatgggagct gcccccggat | 120 |
| tctgacatgg atctgaatct gatcgagcag gcaccc tga ccgtggccga aagctgcag | 180 |
| cgcgacttcc tggtccaatg cgccgcgtg agtaaggccc cggaggccct gttctttgtt | 240 |
| cagttcgaga agggcgagag ctacttccac cttcacgttc tggtggagac cacggggg tc | 300 |
| aagtccatgg tgctaggccg cttcctgagt cagattcggg agaagctggt ccagaccatc | 360 |
| taccgcgggg tcgagcccac gctgcccaac tggttcgcgg tgaccaagac gcgtaatggc | 420 |
| gccggcgggg gaacaaggt ggtggacgag tgctacatcc ccaactacct cctgcccaag | 480 |
| acccagcccg agctgcagtg ggcgtggact aacatggagg agtatataag cgcgtgtttg | 540 |
| aacctggccg aacgcaaacg gctcgtggcg cagcacctga cccacgtcag ccagacgcag | 600 |
| gagcagaaca aggagaatct gaaccccaat tctgacgcgc ccgtgatcag gtcaaaaacc | 660 |
| tccgcgcgct acatggagct ggtcgggtgg ctggtggacc ggggcatcac ctccgagaag | 720 |
| cagtggatcc aggaggacca ggcctcgtac atctccttca cgccgcctc caactcgcgg | 780 |
| tcccagatca aggccgcgct ggacaatgcc ggcaagatca tggcgctgac caaatccgcg | 840 |
| cccgactacc tggtggggcc ctcgctgccc gcggacatta aaccaaccg catctaccgc | 900 |
| atcctggagc tgaacgggta cgatcctgcc tacgccggct ccgtctttct cggctgggcc | 960 |
| cagaaaaagt tcgggaagcg caacaccatc tggctgtttg ggcccgccac caccggcaag | 1020 |
| accaacattg cggaagccat cgcccacgcc gtgcccttct acggctgcgt caactggacc | 1080 |
| aatgagaact ttcccttcaa cgattgcgtc gacaagatgg tgatctggtg ggaggagggc | 1140 |
| aagatgacgg ccaaggtcgt ggagtccgcc aaggccattc tcggcggcag caaggtgcgc | 1200 |
| gtggaccaaa agtgcaagtc gtccgcccag atcgacccca ccccgtgat cgtcacctcc | 1260 |
| aacaccaaca tgtgcgccgt gattgacggg aacagcacca ccttcgagca ccagcagccg | 1320 |
| ttgcaggacc ggatgttcaa atttgaactc acccgccgtc tggagcacga ctttggcaag | 1380 |
| gtgacgaagc aggaagtcaa agagttcttc cgctgggcca gtgatcacgt gaccgaggtg | 1440 |
| gcgcatgagt tctacgtcag aaagggcgga gccagcaaaa gacccgcccc cgatgacgcg | 1500 |
| gatataagcg agcccaagcg ggcctgcccc tcagtcgcgg atccatcgac gtcagacgcg | 1560 |
| gaaggagctc cggtggactt tgccgacagg taccaaaaca aatgttctcg tcacgcgggc | 1620 |
| atgattcaga tgctgtttcc ctgcaaaacg tgcgagagaa tgaatcagaa tttcaacatt | 1680 |
| tgcttcacac acggggtcag agactgttta gagtgtttcc ccggcgtgtc agaatctcaa | 1740 |
| ccggtcgtca gaaaaaagac gtatcggaaa ctctgcgcga ttcatcatct gctggggcgg | 1800 |
| gcgccccgaga ttgcttgctc ggcctgcgac ctggtcaacg tggacctgga cgactgcgtt | 1860 |
| tctgagcaat aa | 1872 |

<210> SEQ ID NO 15
<211> LENGTH: 1878
<212> TYPE: DNA
<213> ORGANISM: Artificial Sequence
<220> FEATURE:

<223> OTHER INFORMATION: Synthetic polynucleotide

<400> SEQUENCE: 15

```
atgccgggct tctacgagat cgtgatcaag gtgccgagcg acctggacga gcacctgccg      60
ggcatttctg actcgtttgt gaactgggtg gccgagaagg aatgggagct gcccccggat     120
tctgacatgg atcggaatct gatcgagcag gcacccctga ccgtggccga aagctgcag      180
cgcgacttcc tggtccaatg gcgccgcgtg agtaaggccc ggaggcccct cttctttgtt     240
cagttcgaga agggcgagag ctactttcac ctgcacgttc tggtcgagac cacggggggtc    300
aagtccatgg tgctaggccg cttcctgagt cagattcggg aaaagcttgg tccagaccat    360
ctacccgcgg ggtcgagccc caccttgccc aactggttcg cggtgaccaa agacgcggta    420
atggcgccgg cgggggggaa caaggtggtg gacgagtgct acatccccaa ctacctcctg    480
cccaagactc agcccgagct gcagtgggcg tggactaaca tggaggagta tataagcgcg    540
tgcttgaacc tggccgagcg caaacggctc gtggcgcagc acctgaccca cgtcagccag    600
acgcaggagc agaacaagga gaatctgaac cccaattctg acgcgccgt gatcaggtca     660
aaaacctccg cgcgctatat ggagctggtc gggtggctgg tggaccgggg catcacctcc    720
gagaagcagt ggatccagga ggaccaggcc tcgtacatct ccttcaacgc cgcctccaac    780
tcgcggtccc agatcaaggc cgcgctggac aatgccggca agatcatggc gctgaccaaa    840
tccgcgcccg actacctggt gggccctcg ctgcccgcgg acattaccca gaaccgcatc    900
taccgcatcc tcgctctcaa cggctacgac cctgcctacg ccggctccgt ctttctcggc    960
tgggctcaga aaaagttcgg gaaacgcaac accatctggc tgtttggacc cgccaccacc   1020
ggcaagacca acattgcgga agccatcgcc cacgccgtgc ccttctacgg ctgcgtcaac   1080
tggaccaatg agaactttcc cttcaatgat tgcgtcgaca agatggtgat ctggtgggag   1140
gagggcaaga tgacggccaa ggtcgtggag tccgccaagg ccattctcgg cggcagcaag   1200
gtgcgcgtgg accaaaagtg caagtcgtcc gcccagatcg accccacccc cgtgatcgtc   1260
acctccaaca ccaacatgtg cgccgtgatt gacgggaaca gcaccacctt cgagcaccag   1320
cagcctctcc aggaccggat gtttaagttc gaactcaccc gccgtctgga gcacgacttt   1380
ggcaaggtga caaagcagga agtcaaagag ttcttccgct gggccagtga tcacgtgacc   1440
gaggtggcgc atgagtttta cgtcagaaag ggcggagcca gcaaaagacc cgcccccgat   1500
gacgcggata aagcgagcc caagcgggcc tgcccctcag tcgcggatcc atcgacgtca   1560
gacgcggaag gagctccggt ggactttgcc gacaggtacc aaaacaaatg ttctcgtcac   1620
gcgggcatgc ttcagatgct gtttccctgc aaaacgtgcg agagaatgaa tcagaatttc   1680
aacatttgct tcacacacgg ggtcagagac tgctcagagt gtttccccgg cgtgtcagaa   1740
tctcaaccgg tcgtcagaaa gaggacgtat cggaaactct gtgcgattca tcatctgctg   1800
gggcgggctc ccgagattgc ttgctcggcc tgcgatctgg tcaacgtgga cctggatgac   1860
tgtgtttctg agcaataa                                                  1878
```

<210> SEQ ID NO 16
<211> LENGTH: 1878
<212> TYPE: DNA
<213> ORGANISM: Artificial Sequence
<220> FEATURE:
<223> OTHER INFORMATION: Synthetic polynucleotide

<400> SEQUENCE: 16

```
atgccgggct tctacgagat cgtgatcaag gtgccgagcg acctggacga gcacctgccg      60
```

```
ggcatttctg actcgtttgt gaactgggtg gccgagaagg aatgggagct gcccccggat        120
tctgacatgg atcggaatct gatcgagcag gcacccctga ccgtggccga gaagctgcag        180
cgcgacttcc tggtccaatg gcgccgcgtg agtaaggccc ggaggccct cttctttgtt         240 cagttcgaga agggcgagag ctactttcac ctgcacgttc tggtcgagac cacgggggtc        300
aagtccatgg tgctaggccg cttcctgagt cagattcggg aaaagcttgg tccagaccat        360
ctacccgcgg ggtcgagccc caccttgccc aactggttcg cggtgaccaa agacgcggta        420
atggcgccgg cggggggggaa caaggtggtg gacgagtgct acatccccaa ctacctcctg       480
cccaagactc agcccgagct gcagtgggcg tggactaaca tggaggagta tataagcgcg        540
tgcttgaacc tggccgagcg caaacggctc gtggcgcagc acctgaccca cgtcagccag        600
acgcaggagc agaacaagga gaatctgaac cccaattctg acgcgccgt gatcaggtca        660 aaaacctccg cgcgctatat ggagctggtc gggtggctgg tggaccgggg catcacctcc        720
gagaagcagt ggatccagga ggaccaggcc tcgtacatct ccttcaacgc cgcctccaac       780
tcgcggtccc agatcaaggc cgcgctggac aatgccggca gatcatggc gctgaccaaa       840 tccgcgcccg actacctggt ggggccctcg ctgcccgcgg acattaccca gaaccgcatc       900
taccgcatcc tcgctctcaa cggctacgac cctgcctacg ccggctccgt ctttctcggc       960
tgggctcaga aaaagttcgg gaaacgcaac accatctggc tgtttggacc cgccaccacc      1020
ggcaagacca acattgcgga agccatcgcc cacgccgtgc ccttctacgg ctgcgtcaac      1080
tggaccaatg agaactttcc cttcaatgat tgcgtcgaca agatggtgat ctggtgggag      1140
gagggcaaga tgacggccaa ggtcgtggag tccgccaagg ccattctcgg cggcagcaag      1200
gtgcgcgtgg accaaaagtg caagtcgtcc gcccagatcg accccacccc cgtgatcgtc      1260
acctccaaca ccaacatgtg cgccgtgatt gacgggaaca gcaccacctt cgagcaccag      1320
cagcctctcc aggaccggat gtttaagttc gaactcaccc gccgtctgga gcacgacttt      1380
ggcaaggtga caaagcagga agtcaaagag ttcttccgct gggccagtga tcacgtgacc      1440
gaggtggcgc atgagttta cgtcagaaag ggcggagcca gcaaaagacc cgcccccgat      1500
gacgcggata aaagcgagcc caagcgggcc tgcccctcag tcgcggatcc atcgacgtca      1560
gacgcggaag gagctccggt ggactttgcc gacaggtacc aaaacaaatg ttctcgtcac      1620
gcgggcatgc ttcagatgct gtttccctgc aaaacgtgcg agagaatgaa tcagaatttc      1680
aacatttgct tcacacacgg ggtcagagac tgctcagagt gtttccccgg cgtgtcagaa      1740
tctcaaccgg tcgtcagaaa gaggacgtat cggaaactct gtgcgattca tcatctgctg      1800
gggcgggctc ccgagattgc ttgctcggcc tgcgatctgg tcaacgtgga cctggatgac      1860
tgtgtttctg agcaataa                                                     1878
```

<210> SEQ ID NO 17
<211> LENGTH: 1869
<212> TYPE: DNA
<213> ORGANISM: Artificial Sequence
<220> FEATURE:
<223> OTHER INFORMATION: Synthetic polynucleotide

<400> SEQUENCE: 17

```
atgccgggct ctacgagat cgtgatcaag gtgccgagcg acctggacga gcacctgccg        60
ggcatttctg actcgtttgt gaactgggtg gccgagaagg aatgggagct gcccccggat       120
tctgacatgg atcggaatct gatcgagcag gcacccctga ccgtggccga gaagctgcag      180
```

```
cgcgacttcc tggtccactg gcgccgcgtg agtaaggccc cggaggccct cttctttgtt        240
cagttcgaga agggcgagtc ctactttcac ctgcacgttc tggtcgagac cacggggtc         300 aagtccatgg tcctgggccg cttcctgagt cagatcagag acaggctggt gcagaccatc        360
taccgcgggg tagagcccac gctgcccaac tggttcgcgg tgaccaagac gcgaaatggc        420
gccggcgggg ggaacaaggt ggtggacgag tgctacatcc ccaactacct cctgcccaag        480
acgcagcccg agctgcagtg ggcgtggact aacatggagg agtatataag cgcgtgtctg        540
aacctcgcgg agcgtaaacg gctcgtggcg cagcacctga cccacgtcag ccagacgcag        600
gagcagaaca aggagaatct gaacccgaat tctgacgcgc ccgtgatcag gtcaaaaacc        660
tccgcgcgct acatggagct ggtcgggtgg ctggtggacc ggggcatcac ctccgagaag        720
cagtggatcc aggaggacca ggcctcgtac atctccttca acgccgcctc caactcgcgg        780
tcccagatca aggccgcgct ggacaatgcc ggaaagatca tggcgctgac caaatccgcg        840
cccgactacc tggtaggccc gtccttaccc gcggacatta aggccaaccg catctaccgc        900
atcctggagc tcaacggcta cgaccccgcc tacgccggct ccgtcttcct gggctgggcg        960
cagaaaaagt tcggtaaaag gaatacaatt tggctgttcg ggcccgccac caccggcaag       1020
accaacatcg cggaagccat cgcccacgcc gtgcccttct acggctgcgt caactggacc       1080
aatgagaact ttcccttcaa cgattgcgtc gacaagatgg tgatctggtg ggaggagggc       1140
aagatgaccc ccaaggtcgt ggagtccgcc aaggccattc tgggcggaag caaggtgcgc       1200
gtcgaccaaa agtgcaagtc ctcggcccag atcgacccca cgcccgtgat cgtcacctcc       1260
aacaccaaca tgtgcgccgt gatcgacggg aacagcacca ccttcgagca ccagcagccc       1320
ctgcaggacc gcatgttcaa gttcgagctc acccgccgtc tggagcacga ctttggcaag       1380
gtgaccaagc aggaagtcaa agagttcttc cgctgggctc aggatcacgt gactgaggtg       1440
acgcatgagt tctacgtcag aaagggcgga gccaccaaaa gacccgcccc cagtgacgcg       1500
gatataagcg agcccaagcg ggcctgcccc tcagttgcgg agccatcgac gtcagacgcg       1560
gaagcaccgg tggactttgc ggacaggtac caaaacaaat gttctcgtca cgcgggcatg       1620
cttcagatgc tgtttccctg caagacatgc gagagaatga atcagaattt caacgtctgc       1680
ttcacgcacg gggtcagaga ctgctcagag tgcttccccg gcgcgtcaga atctcaacct       1740
gtcgtcagaa aaaagacgta tcagaaactg tgcgcgattc atcatctgct ggggcgggca       1800
cccgagattg cgtgttcggc ctgcgatctc gtcaacgtgg acttggatga ctgtgtttct       1860
gagcaataa                                                                1869
```

<210> SEQ ID NO 18
<211> LENGTH: 1869
<212> TYPE: DNA
<213> ORGANISM: Artificial Sequence
<220> FEATURE:
<223> OTHER INFORMATION: Synthetic polynucleotide

<400> SEQUENCE: 18

```
atgccgggct ctacgagat cgtgatcaag gtgccgagcg acctggacga gcacctgccg         60
ggcatttctg actcgtttgt gaactgggtg gccgagaagg aatgggagct gccccccggat      120 tctgacatgg atcggaatct gatcgagcag gcaccctga ccgtggccga aagctgcag         180 cgcgacttcc tggtccactg gcgccgcgtg agtaaggccc cggaggccct cttctttgtt       240
cagttcgaga agggcgagtc ctacttccac ctccacgttc tcgtcgagac cacggggtc        300 aagtccatgg tcctgggccg cttcctgagt cagatcagag acaggctggt gcagaccatc       360
```

```
taccgcgggg tcgagcccac gctgcccaac tggttcgcgg tgaccaagac gcgaaatggc    420
gccggcgggg ggaacaaggt ggtggacgag tgctacatcc ccaactacct cctgcccaag    480
acccagcccg agctgcagtg ggcgtggact aacatggagg agtatataag cgcgtgtcta    540
aacctcgcgg agcgtaaacg gctcgtggcg cagcacctga cccacgtcag ccagacgcag    600
gagcagaaca aggagaatct gaacccgaat tctgacgcgc ccgtgatcag gtcaaaaacc    660
tccgcgcgct acatggagct ggtcgggtgg ctggtggacc ggggcatcac ctccgagaag    720
cagtggatcc aggaggacca ggcctcgtac atctccttca cgccgcctc caactcgcgg    780 tcccagatca aggccgcgct ggacaatgcc ggaaagatca tggcgctgac caaatccgcg    840
cccgactacc tggtaggccc gtccttaccc gcggacatta aggccaaccg catctaccgc    900
atcctggagc tcaacggcta cgaccccgcc tacgccggct ccgtcttcct gggctgggcg    960
cagaaaaagt tcggtaaacg caacaccatc tggctgtttg ggcccgccac caccggcaag   1020
accaacatcg cggaagccat agcccacgcc gtgcccttct acggctgcgt gaactggacc   1080
aatgagaact ttcccttcaa cgattgcgtc gacaagatgg tgatctggtg ggaggagggc   1140
aagatgaccg ccaaggtcgt ggagtccgcc aaggccattc tgggcggaag caaggtgcgc   1200
gtggaccaaa agtgcaagtc ctcggcccag atcgaccccc cgcccgtgat cgtcacctcc   1260
aacaccaaca tgtgcgccgt gatcgacggg aacagcacca ccttcgagca ccagcagccg   1320
ctgcaggacc gcatgttcaa gttcgagctc acccgccgtc tggagcacga ctttggcaag   1380
gtgaccaagc aggaagtcaa agagttcttc cgctgggctc aggatcacgt gactgaggtg   1440
gcgcatgagt tctacgtcag aaagggcgga gccaccaaaa gacccgcccc cagtgacgcg   1500
gatataagcg agcccaagcg ggcctgcccc tcagttccgg agccatcgac gtcagacgcg   1560
gaagcaccgg tggactttgc ggacaggtac caaaacaaat gttctcgtca cgcgggcatg   1620
cttcagatgc tgtttccctg caagacatgc gagagaatga atcagaattt caacgtctgc   1680
ttcacgcacg gggtcagaga ctgctcagag tgcttccccg gcgcgtcaga atctcaaccc   1740
gtcgtcagaa aaaagacgta tcagaaactg tgcgcgattc atcatctgct ggggcgggca   1800
cccgagattg cgtgttcggc ctgcgatctc gtcaacgtgg acttggatga ctgtgtttct   1860
gagcaataa                                                           1869
```

<210> SEQ ID NO 19
<211> LENGTH: 1866
<212> TYPE: DNA
<213> ORGANISM: Artificial Sequence
<220> FEATURE:
<223> OTHER INFORMATION: Synthetic polynucleotide

<400> SEQUENCE: 19

```
atgccggggt tctacgaggt ggtgatcaag gtgcccagcg acctggacga gcacctgccc     60
ggcatttctg actcctttgt gaactgggtg gccgagaagg aatgggagtt gccccccggat   120 tctgacatgg atcagaatct gattgagcag gcaccctga ccgtggccga aagctgcag    180 cgcgagttcc tggtggaatg gcgccgagtg agtaaatttc tggaggccaa gttttttgtg    240
cagtttgaaa aggggactc gtactttcat ttgcatattc tgattgaaat taccggcgtg    300
aaatccatgg tggtgggccg ctacgtgagt cagattaggg ataaactgat ccagcgcatc    360
taccgcgggg tcgagcccca gctgcccaac tggttcgcgg tcacaaagac ccgaaatggc    420
gccggaggcg ggaacaaggt ggtggacgag tgctacatcc ccaactacct gctccccaag    480
```

```
gtccagcccg agcttcagtg ggcgtggact aacatggagg agtatataag cgcctgtttg    540
aacctcgcgg agcgtaaacg gctcgtggcg cagcacctga cgcacgtctc ccagacccag    600
gagggcgaca aggagaatct gaacccgaat tctgacgcgc cggtgatccg gtcaaaaacc    660
tccgccaggt acatggagct ggtcgggtgg ctggtggaca agggcatcac gtccgagaag    720
cagtggatcc aggaggacca ggcctcgtac atctccttca cgcggcctc caactcccgg    780
tcgcagatca aggcggccct ggacaatgcc tccaaaatca tgagcctcac caaaacggct    840
ccggactatc tcatcgggca gcagcccgtg ggggacatta ccaccaaccg gatctacaaa    900
atcctggaac tgaacgggta cgaccccag tacgccgcct ccgtctttct cggctgggcc    960
cagaaaaagt ttggaaagcg caacaccatc tggctgtttg ggcccgccac caccggcaag   1020
accaacatcg cggaagccat cgcccacgcg gtccccttct acggctgcgt caactggacc   1080
aatgagaact ttcccttcaa cgactgcgtc gacaaaatgg tgatttggtg ggaggagggc   1140
aagatgaccg ccaaggtcgt agagtccgcc aaggccattc tgggcggcag caaggtgcgc   1200
gtggaccaaa aatgcaaggc tctgcgcag atcgaccca cccccgtgat cgtcacctcc   1260
aacaccaaca tgtgcgccgt gattgacggg aacagcacca ccttcgagca ccagcagccc   1320
ctgcaggacc ggatgttcaa gtttgaactc acccgccgcc tcgaccacga ctttggcaag   1380
gtcaccaagc aggaagtcaa ggactttttc cggtgggcgg ctgatcacgt gactgacgtg   1440
gctcatgagt tttacgtcac aaagggtgga gctaagaaaa ggcccgcccc ctctgacgag   1500
gatataagcg agcccaagcg gccgcgcgtg tcatttgcgc agccggagac gtcagacgcg   1560
gaagctcccg gagacttcgc cgacaggtac caaaacaaat gttctcgtca cgcgggtatg   1620
ctgcagatgc tctttcctg caagacgtgc gagagaatga atcagaattc caacgtctgc   1680
ttcacgcacg gtcagaaaga ttgcggggag tgctttcccg gtcagaatc tcaaccggtt   1740
tctgtcgtca gaaaaacgta tcagaaactg tgcatccttc atcagctccg gggggcaccc   1800
gagatcgcct gctctgcttg cgaccaactc aaccccgatt tggacgattg ccaatttgag   1860
caataa                                                              1866
```

<210> SEQ ID NO 20
<211> LENGTH: 1872
<212> TYPE: DNA
<213> ORGANISM: Artificial Sequence
<220> FEATURE:
<223> OTHER INFORMATION: Synthetic polynucleotide

<400> SEQUENCE: 20

```
atgccgggat tctacgagat tgtcctgaag gtgcccagcg acctggacga gcacctgcct     60
ggcatttctg actctttgt aaactgggtg gcggagaagg aatgggagct gccgccggat    120
tctgacatgg atctgaatct gattgagcag gcaccctaa ccgtggccga aaagctgcaa    180
cgcgaattcc tggtcgagtg gcgccgcgtg agtaaggccc ggaggccct cttctttgtt    240
cagttcgaga aggggacag ctacttccac ctacacattc tggtggagac cgtgggcgtg    300
aaatccatgg tggtgggccg ctacgtgagc cagattaaag agaagctggt gacccgcatc    360
taccgcgggg tcgagccgca gcttccgaac tggttcgcgg tgaccaagac gcgtaatggc    420
gccggaggcg ggaacaaggt ggtggacgac tgctacatcc ccaactacct gctccccaag    480
acccagcccg agctccagtg ggcgtggact aatatggacc agtatttaag cgcctgtttg    540
aatctcgcgg agcgtaaacg gctggtggcg cagcatctga cgcacgtgtc gcagacgcag    600
gagcagaaca agagaaacca gaatcccaat tctgacgcgc cggtgatcag atcaaaaacc    660
```

```
tccgcgaggt acatggagct ggtcgggtgg ctggtggacc gcgggatcac gtcagaaaag    720
caatggatcc aggaggacca ggcctcttac atctccttca acgccgcctc caactcgcgg    780
tcacaaatca aggccgcact ggacaatgcc tccaaattta tgagcctgac aaaaacggct    840
ccggactacc tggtgggaaa caacccgccg gaggacatta ccagcaaccg gatctacaaa    900
atcctcgaga tgaacgggta cgatccgcag tacgcggcct ccgtcttcct gggctgggcg    960
caaaagaagt tcgggaagag gaacaccatc tggctctttg gccggccac gacgggtaaa    1020 accaacatcg ctgaagctat cgcccacgcc gtgccctttt acggctgcgt gaactggacc    1080
aatgagaact ttccgttcaa cgattgcgtc gacaagatgg tgatctggtg ggaggagggc    1140
aagatgacgg ccaaggtcgt ggagtccgcc aaggccattc tgggcggaag caaggtgcgc    1200
gtggaccaaa agtgcaagtc atcggcccag atcgacccaa ctcccgtcat cgtcacctcc    1260
aacaccaaca tgtgcgcggt catcgacgga aattccacca ccttcgagca ccaacaacca    1320
ctccaagacc ggatgttcaa gttcgagctc accaagcgcc tggagcacga ctttggcaag    1380
gtcaccaagc aggaagtcaa ggactttttc cggtgggcgt cagatcacgt gactgaggtg    1440
tctcacgagt tttacgtcag aaagggtgga gctagaaaga ggcccgcccc caatgacgca    1500
gatataagtg agcccaagcg ggcctgtccg tcagttgcgc agccatcgac gtcagacgcg    1560
gaagctccgg tggactacgc ggacaggtac caaaacaaat gttctcgtca cgtgggcatg    1620
aatctgatgc ttttttccctg ccggcaatgc gagagaatga atcagaatgt ggacatttgc    1680
ttcacgcacg gggtcatgga ctgtgccgag tgcttccccg tgtcagaatc tcaacccgtg    1740
tctgtcgtca gaaagcggac atatcagaaa ctgtgtccga ttcatcacat catggggagg    1800
gcgcccgagg tggcttgttc ggcctgcgat ctggccaatg tggacttgga tgactgtgac    1860
atggagcaat aa                                                        1872
```

<210> SEQ ID NO 21
<211> LENGTH: 623
<212> TYPE: PRT
<213> ORGANISM: Artificial Sequence
<220> FEATURE:
<223> OTHER INFORMATION: Synthetic polypeptide

<400> SEQUENCE: 21

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140
```

```
Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
            165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
            195                 200                 205

Pro Asn Ser Asp Ala Pro Val Ile Arg Ser Lys Thr Ser Ala Arg Tyr
            210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
            275                 280                 285

Pro Pro Ala Asp Ile Lys Thr Asn Arg Ile Tyr Arg Ile Leu Glu Leu
290                 295                 300

Asn Gly Tyr Glu Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
            325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
            450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
            485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
            515                 520                 525

Asp Arg Tyr Gln Asn Lys Cys Ser Arg His Ala Gly Met Leu Gln Met
            530                 535                 540

Leu Phe Pro Cys Lys Thr Cys Glu Arg Met Asn Gln Asn Phe Asn Ile
545                 550                 555                 560
```

```
Cys Phe Thr His Gly Thr Arg Asp Cys Ser Glu Cys Phe Pro Gly Val
                565                 570                 575

Ser Glu Ser Gln Pro Val Val Arg Lys Arg Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
    610                 615                 620

<210> SEQ ID NO 22
<211> LENGTH: 621
<212> TYPE: PRT
<213> ORGANISM: Artificial Sequence
<220> FEATURE:
<223> OTHER INFORMATION: Synthetic polypeptide

<400> SEQUENCE: 22

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300
```

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
            485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
            565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
610                 615                 620

<210> SEQ ID NO 23
<211> LENGTH: 624
<212> TYPE: PRT
<213> ORGANISM: Artificial Sequence
<220> FEATURE:
<223> OTHER INFORMATION: Synthetic polypeptide

<400> SEQUENCE: 23

Met Pro Gly Phe Tyr Glu Ile Val Leu Lys Val Pro Ser Asp Leu Asp
1               5                   10                  15

Glu His Leu Pro Gly Ile Ser Asn Ser Phe Val Asn Trp Val Ala Glu
            20                  25                  30

Lys Glu Trp Glu Leu Pro Pro Asp Ser Asp Met Asp Pro Asn Leu Ile
        35                  40                  45

```
Glu Gln Ala Pro Leu Thr Val Ala Glu Lys Leu Gln Arg Glu Phe Leu
    50                  55                  60
Val Glu Trp Arg Arg Val Ser Lys Ala Pro Glu Ala Leu Phe Phe Val
65                  70                  75                  80
Gln Phe Glu Lys Gly Glu Thr Tyr Phe His Leu His Val Leu Ile Glu
                85                  90                  95
Thr Ile Gly Val Lys Ser Met Val Val Gly Arg Tyr Val Ser Gln Ile
                100                 105                 110
Lys Glu Lys Leu Val Thr Arg Ile Tyr Arg Gly Val Glu Pro Gln Leu
            115                 120                 125
Pro Asn Trp Phe Ala Val Thr Lys Thr Arg Asn Gly Ala Gly Gly Gly
    130                 135                 140
Asn Lys Val Val Asp Asp Cys Tyr Ile Pro Asn Tyr Leu Leu Pro Lys
145                 150                 155                 160
Thr Gln Pro Glu Leu Gln Trp Ala Trp Thr Asn Met Asp Gln Tyr Leu
                165                 170                 175
Ser Ala Cys Leu Asn Leu Ala Glu Arg Lys Arg Leu Val Ala Gln His
                180                 185                 190
Leu Thr His Val Ser Gln Thr Gln Glu Gln Asn Lys Glu Asn Gln Asn
            195                 200                 205
Pro Asn Ser Asp Ala Pro Val Ile Arg Ser Lys Thr Ser Ala Arg Tyr
    210                 215                 220
Met Glu Leu Val Gly Trp Leu Val Asp Arg Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Ser Lys
                260                 265                 270
Ile Met Ser Leu Thr Lys Thr Ala Pro Asp Tyr Leu Val Gly Ser Asn
            275                 280                 285
Pro Pro Glu Asp Ile Thr Lys Asn Arg Ile Tyr Gln Ile Leu Glu Leu
    290                 295                 300
Asn Gly Tyr Asp Pro Gln Tyr Ala Ala Ser Val Phe Leu Gly Trp Ala
305                 310                 315                 320
Gln Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Ala Val Pro
                340                 345                 350
Phe Tyr Gly Cys Val Asn Trp Thr Asn Glu Asn Phe Pro Phe Asn Asp
            355                 360                 365
Cys Val Asp Lys Met Val Ile Trp Trp Glu Glu Gly Lys Met Thr Ala
    370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Glu Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
    435                 440                 445
Glu Leu Thr Arg Arg Leu Asp His Asp Phe Gly Lys Val Thr Lys Gln
450                 455                 460
Glu Val Lys Asp Phe Phe Arg Trp Ala Ser Asp His Val Thr Asp Val
```

```
                    465                 470                 475                 480
Ala His Glu Phe Tyr Val Arg Lys Gly Gly Ala Lys Lys Arg Pro Ala
                485                 490                 495

Ser Asn Asp Ala Asp Val Ser Glu Pro Lys Arg Gln Cys Thr Ser Leu
                500                 505                 510

Ala Gln Pro Thr Thr Ser Asp Ala Glu Ala Pro Ala Asp Tyr Ala Asp
                515                 520                 525

Arg Tyr Gln Asn Lys Cys Ser Arg His Val Gly Met Asn Leu Met Leu
                530                 535                 540

Phe Pro Cys Lys Thr Cys Glu Arg Met Asn Gln Ile Ser Asn Val Cys
545                 550                 555                 560

Phe Thr His Gly Gln Arg Asp Cys Gly Glu Cys Phe Pro Gly Met Ser
                565                 570                 575

Glu Ser Gln Pro Val Ser Val Val Lys Lys Thr Tyr Gln Lys Leu
                580                 585                 590

Cys Pro Ile His His Ile Leu Gly Arg Ala Pro Glu Ile Ala Cys Ser
                595                 600                 605

Ala Cys Asp Leu Ala Asn Val Asp Leu Asp Asp Cys Val Ser Glu Gln
                610                 615                 620
```

<210> SEQ ID NO 24
<211> LENGTH: 623
<212> TYPE: PRT
<213> ORGANISM: Artificial Sequence
<220> FEATURE:
<223> OTHER INFORMATION: Synthetic polypeptide

<400> SEQUENCE: 24

```
Met Pro Gly Phe Tyr Glu Ile Val Leu Lys Val Pro Ser Asp Leu Asp
1               5                   10                  15

Glu His Leu Pro Gly Ile Ser Asp Ser Phe Val Ser Trp Val Ala Glu
                20                  25                  30

Lys Glu Trp Glu Leu Pro Pro Asp Ser Asp Met Asp Leu Asn Leu Ile
                35                  40                  45

Glu Gln Ala Pro Leu Thr Val Ala Glu Lys Leu Gln Arg Glu Phe Leu
        50                  55                  60

Val Glu Trp Arg Arg Val Ser Lys Ala Pro Glu Ala Leu Phe Phe Val
65                  70                  75                  80

Gln Phe Glu Lys Gly Asp Ser Tyr Phe His Leu His Ile Leu Val Glu
                85                  90                  95

Thr Val Gly Val Lys Ser Met Val Val Gly Arg Tyr Val Ser Gln Ile
                100                 105                 110

Lys Glu Lys Leu Val Thr Arg Ile Tyr Arg Gly Val Glu Pro Gln Leu
                115                 120                 125

Pro Asn Trp Phe Ala Val Thr Lys Thr Arg Asn Gly Ala Gly Gly
                130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Gln Asn
                195                 200                 205

Pro Asn Ser Asp Ala Pro Val Ile Arg Ser Lys Thr Ser Ala Arg Tyr
```

```
            210                 215                 220
Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
                260                 265                 270

Ile Met Ser Leu Thr Lys Thr Ala Pro Asp Tyr Leu Val Gly Gln Asn
            275                 280                 285

Pro Pro Glu Asp Ile Ser Ser Asn Arg Ile Tyr Arg Ile Leu Glu Met
        290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
                340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
        370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

Glu Leu Thr Lys Arg Leu Glu His Asp Phe Gly Lys Val Thr Lys Gln
        450                 455                 460

Glu Val Lys Asp Phe Phe Arg Trp Ala Ser Asp His Val Thr Glu Val
465                 470                 475                 480

Thr His Glu Phe Tyr Val Arg Lys Gly Gly Ala Arg Lys Arg Pro Ala
                485                 490                 495

Pro Asn Asp Ala Asp Ile Ser Glu Pro Lys Arg Ala Cys Pro Ser Val
                500                 505                 510

Ala Gln Pro Ser Thr Ser Asp Ala Glu Ala Pro Val Asp Tyr Ala Asp
            515                 520                 525

Arg Tyr Gln Asn Lys Cys Ser Arg His Val Gly Met Asn Leu Met Leu
        530                 535                 540

Phe Pro Cys Arg Gln Cys Glu Arg Met Asn Gln Asn Val Asp Ile Cys
545                 550                 555                 560

Phe Thr His Gly Val Met Asp Cys Ala Glu Cys Phe Pro Val Ser Glu
                565                 570                 575

Ser Gln Pro Val Ser Val Val Arg Lys Arg Thr Tyr Gln Lys Leu Cys
                580                 585                 590

Pro Ile His His Ile Met Gly Arg Ala Pro Glu Val Ala Cys Ser Ala
            595                 600                 605

Cys Glu Leu Ala Asn Val Asp Leu Asp Asp Cys Asp Met Glu Gln
        610                 615                 620

<210> SEQ ID NO 25
```

<211> LENGTH: 610
<212> TYPE: PRT
<213> ORGANISM: Artificial Sequence
<220> FEATURE:
<223> OTHER INFORMATION: Synthetic polypeptide

<400> SEQUENCE: 25

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
        195                 200                 205

Asp Pro Val Ile Lys Ser Lys Thr Ser Gln Lys Tyr Met Ala Leu Val
    210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
        275                 280                 285

Ile Ser Lys Asn Arg Ile Trp Gln Ile Phe Glu Met Asn Gly Tyr Asp
    290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
        355                 360                 365

Met Leu Ile Trp Trp Glu Glu Gly Lys Met Thr Asn Lys Val Val Glu
    370                 375                 380
```

```
Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
            405                 410                 415

Asn Thr Asn Met Cys Val Val Asp Gly Asn Ser Thr Thr Phe Glu
            420                 425                 430

His Gln Gln Pro Leu Glu Asp Arg Met Phe Lys Phe Glu Leu Thr Lys
            435                 440                 445

Arg Leu Pro Pro Asp Phe Gly Lys Ile Thr Lys Gln Glu Val Lys Asp
    450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
            515                 520                 525

Val Thr Val Asp Pro Ala Pro Leu Arg Pro Leu Asn Trp Asn Ser Arg
    530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
                565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Asp Ala Asn Lys
            595                 600                 605

Glu Gln
    610

<210> SEQ ID NO 26
<211> LENGTH: 623
<212> TYPE: PRT
<213> ORGANISM: Artificial Sequence
<220> FEATURE:
<223> OTHER INFORMATION: Synthetic polypeptide

<400> SEQUENCE: 26

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125
```

```
Pro Asn Trp Phe Ala Val Thr Lys Thr Arg Asn Gly Ala Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala His Asp
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
        275                 280                 285

Pro Pro Ala Asp Ile Lys Thr Asn Arg Ile Tyr Arg Ile Leu Glu Leu
290                 295                 300

Asn Gly Tyr Asp Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Leu Gln Met
530                 535                 540
```

```
Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
            565                 570                 575

Ser Glu Ser Gln Pro Val Val Arg Lys Arg Thr Tyr Arg Lys Leu Cys
            580                 585                 590

Ala Ile His His Leu Leu Gly Arg Ala Pro Glu Ile Ala Cys Ser Ala
            595                 600                 605

Cys Asp Leu Val Asn Val Asp Leu Asp Asp Cys Val Ser Glu Gln
            610                 615                 620

<210> SEQ ID NO 27
<211> LENGTH: 623
<212> TYPE: PRT
<213> ORGANISM: Artificial Sequence
<220> FEATURE:
<223> OTHER INFORMATION: Synthetic polypeptide

<400> SEQUENCE: 27

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285
```

Leu Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                485                 490                 495

Pro Asp Asp Ala Asp Ile Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Ile Gln Met
530                 535                 540

Leu Phe Pro Cys Lys Thr Cys Glu Arg Met Asn Gln Asn Phe Asn Ile
545                 550                 555                 560

Cys Phe Thr His Gly Val Arg Asp Cys Leu Glu Cys Phe Pro Gly Val
                565                 570                 575

Ser Glu Ser Gln Pro Val Val Arg Lys Lys Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
610                 615                 620

<210> SEQ ID NO 28
<211> LENGTH: 625
<212> TYPE: PRT
<213> ORGANISM: Artificial Sequence
<220> FEATURE:
<223> OTHER INFORMATION: Synthetic polypeptide

<400> SEQUENCE: 28

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

```
Lys Glu Trp Glu Leu Pro Pro Asp Ser Asp Met Asp Arg Asn Leu Ile
             35                  40                  45
Glu Gln Ala Pro Leu Thr Val Ala Glu Lys Leu Gln Arg Asp Phe Leu
 50                  55                  60
Val Gln Trp Arg Arg Val Ser Lys Ala Pro Glu Ala Leu Phe Phe Val
 65                  70                  75                  80
Gln Phe Glu Lys Gly Glu Ser Tyr Phe His Leu His Val Leu Val Glu
                 85                  90                  95
Thr Thr Gly Val Lys Ser Met Val Leu Gly Arg Phe Leu Ser Gln Ile
                100                 105                 110
Arg Glu Lys Leu Gly Pro Asp His Leu Pro Ala Gly Ser Ser Pro Thr
            115                 120                 125
Leu Pro Asn Trp Phe Ala Val Thr Lys Asp Ala Val Met Ala Pro Ala
130                 135                 140
Gly Gly Asn Lys Val Val Asp Glu Cys Tyr Ile Pro Asn Tyr Leu Leu
145                 150                 155                 160
Pro Lys Thr Gln Pro Glu Leu Gln Trp Ala Trp Thr Asn Met Glu Glu
                165                 170                 175
Tyr Ile Ser Ala Cys Leu Asn Leu Ala Glu Arg Lys Arg Leu Val Ala
                180                 185                 190
Gln His Leu Thr His Val Ser Gln Thr Gln Glu Gln Asn Lys Glu Asn
            195                 200                 205
Leu Asn Pro Asn Ser Asp Ala Pro Val Ile Arg Ser Lys Thr Ser Ala
210                 215                 220
Arg Tyr Met Glu Leu Val Gly Trp Leu Val Asp Arg Gly Ile Thr Ser
225                 230                 235                 240
Glu Lys Gln Trp Ile Gln Glu Asp Gln Ala Ser Tyr Ile Ser Phe Asn
                245                 250                 255
Ala Ala Ser Asn Ser Arg Ser Gln Ile Lys Ala Ala Leu Asp Asn Ala
                260                 265                 270
Gly Lys Ile Met Ala Leu Thr Lys Ser Ala Pro Asp Tyr Leu Val Gly
            275                 280                 285
Pro Ser Leu Pro Ala Asp Ile Thr Gln Asn Arg Ile Tyr Arg Ile Leu
290                 295                 300
Ala Leu Asn Gly Tyr Asp Pro Ala Tyr Ala Gly Ser Val Phe Leu Gly
305                 310                 315                 320
Trp Ala Gln Lys Lys Phe Gly Lys Arg Asn Thr Ile Trp Leu Phe Gly
                325                 330                 335
Pro Ala Thr Thr Gly Lys Thr Asn Ile Ala Glu Ala Ile Ala His Ala
            340                 345                 350
Val Pro Phe Tyr Gly Cys Val Asn Trp Thr Asn Glu Asn Phe Pro Phe
            355                 360                 365
Asn Asp Cys Val Asp Lys Met Val Ile Trp Trp Glu Glu Gly Lys Met
370                 375                 380
Thr Ala Lys Val Val Glu Ser Ala Lys Ala Ile Leu Gly Gly Ser Lys
385                 390                 395                 400
Val Arg Val Asp Gln Lys Cys Lys Ser Ser Ala Gln Ile Asp Pro Thr
                405                 410                 415
Pro Val Ile Val Thr Ser Asn Thr Asn Met Cys Ala Val Ile Asp Gly
                420                 425                 430
Asn Ser Thr Thr Phe Glu His Gln Gln Pro Leu Gln Asp Arg Met Phe
            435                 440                 445
Lys Phe Glu Leu Thr Arg Arg Leu Glu His Asp Phe Gly Lys Val Thr
```

-continued

```
            450                 455                 460
Lys Gln Glu Val Lys Glu Phe Phe Arg Trp Ala Ser Asp His Val Thr
465                 470                 475                 480

Glu Val Ala His Glu Phe Tyr Val Arg Lys Gly Gly Ala Ser Lys Arg
                485                 490                 495

Pro Ala Pro Asp Ala Asp Lys Ser Glu Pro Lys Arg Ala Cys Pro
            500                 505                 510

Ser Val Ala Asp Pro Ser Thr Ser Asp Ala Glu Gly Ala Pro Val Asp
            515                 520                 525

Phe Ala Asp Arg Tyr Gln Asn Lys Cys Ser Arg His Ala Gly Met Leu
            530                 535                 540

Gln Met Leu Phe Pro Cys Lys Thr Cys Glu Arg Met Asn Gln Asn Phe
545                 550                 555                 560

Asn Ile Cys Phe Thr His Gly Val Arg Asp Cys Ser Glu Cys Phe Pro
                565                 570                 575

Gly Val Ser Glu Ser Gln Pro Val Val Arg Lys Arg Thr Tyr Arg Lys
                580                 585                 590

Leu Cys Ala Ile His His Leu Leu Gly Arg Ala Pro Glu Ile Ala Cys
                595                 600                 605

Ser Ala Cys Asp Leu Val Asn Val Asp Leu Asp Asp Cys Val Ser Glu
            610                 615                 620

Gln
625

<210> SEQ ID NO 29
<211> LENGTH: 622
<212> TYPE: PRT
<213> ORGANISM: Artificial Sequence
<220> FEATURE:
<223> OTHER INFORMATION: Synthetic polypeptide

<400> SEQUENCE: 29

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Arg Asn Leu Ile
            35                  40                  45

Glu Gln Ala Pro Leu Thr Val Ala Glu Lys Leu Arg Asp Phe Leu Val
        50                  55                  60

Gln Trp Arg Arg Val Ser Lys Ala Pro Glu Ala Leu Phe Phe Val Gln
65                  70                  75                  80

Phe Glu Lys Gly Glu Ser Tyr Phe His Leu His Val Leu Val Glu Thr
                85                  90                  95

Thr Gly Val Lys Ser Met Val Leu Gly Arg Phe Leu Ser Gln Ile Arg
                100                 105                 110

Glu Lys Leu Val Gln Thr Ile Tyr Arg Gly Ile Glu Pro Thr Leu Pro
            115                 120                 125

Asn Trp Phe Ala Val Thr Lys Thr Arg Asn Gly Ala Gly Gly Gly Asn
        130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Glu Tyr Ile Ser
                165                 170                 175

Ala Cys Leu Asn Leu Ala Glu Arg Lys Arg Leu Val Ala Gln His Leu
```

```
            180                 185                 190
Thr His Val Ser Gln Thr Gln Glu Gln Asn Lys Glu Asn Leu Asn Pro
            195                 200                 205
Asn Ser Asp Ala Pro Val Ile Arg Ser Lys Thr Ser Ala Arg Tyr Met
            210                 215                 220
Glu Leu Val Gly Trp Leu Val Asp Arg Gly Ile Thr Ser Glu Lys Gln
225                 230                 235                 240
Trp Ile Gln Glu Asp Gln Ala Ser Tyr Ile Ser Phe Asn Ala Ala Ser
                245                 250                 255
Asn Ser Arg Ser Gln Ile Lys Ala Ala Leu Asp Asn Ala Gly Lys Ile
            260                 265                 270
Met Ala Leu Thr Lys Ser Ala Pro Asp Tyr Leu Val Gly Pro Ser Leu
            275                 280                 285
Pro Val Asp Ile Thr Gln Asn Arg Ile Tyr Arg Ile Leu Gln Leu Asn
            290                 295                 300
Gly Tyr Asp Pro Ala Tyr Ala Gly Ser Val Phe Leu Gly Trp Ala Gln
305                 310                 315                 320
Lys Lys Phe Gly Lys Arg Asn Thr Ile Trp Leu Phe Gly Pro Ala Thr
                325                 330                 335
Thr Gly Lys Thr Asn Ile Ala Glu Ala Ile Ala His Ala Val Pro Phe
            340                 345                 350
Tyr Gly Cys Val Asn Trp Thr Asn Glu Asn Phe Pro Phe Asn Asp Cys
            355                 360                 365
Val Asp Lys Met Val Ile Trp Trp Glu Glu Gly Lys Met Thr Ala Lys
            370                 375                 380
Val Val Glu Ser Ala Lys Ala Ile Leu Gly Gly Ser Lys Val Arg Val
385                 390                 395                 400
Asp Gln Lys Cys Lys Ser Ser Ala Gln Ile Asp Pro Thr Pro Val Ile
                405                 410                 415
Val Thr Ser Asn Thr Asn Met Cys Ala Val Ile Asp Gly Asn Ser Thr
            420                 425                 430
Thr Phe Glu His Gln Gln Pro Leu Gln Asp Arg Met Phe Lys Phe Glu
            435                 440                 445
Leu Thr Arg Arg Leu Glu His Asp Phe Gly Lys Val Thr Lys Gln Glu
            450                 455                 460
Val Lys Glu Phe Phe Arg Trp Ala Ser Asp His Val Thr Glu Val Ala
465                 470                 475                 480
His Glu Phe Tyr Val Arg Lys Gly Gly Ala Ser Lys Arg Pro Ala Pro
                485                 490                 495
Asp Asp Ala Asp Lys Ser Glu Pro Lys Arg Ala Cys Pro Ser Val Ala
            500                 505                 510
Asp Pro Ser Thr Ser Asp Ala Glu Gly Ala Pro Val Asp Phe Ala Asp
            515                 520                 525
Arg Tyr Gln Asn Lys Cys Ser Arg His Ala Gly Met Leu Gln Met Leu
            530                 535                 540
Leu Pro Cys Lys Thr Cys Glu Arg Met Asn Gln Asn Phe Asn Ile Cys
545                 550                 555                 560
Phe Thr His Gly Val Arg Asp Cys Ser Glu Cys Phe Pro Gly Val Ser
                565                 570                 575
Glu Ser Gln Pro Val Val Arg Lys Arg Thr Tyr Arg Lys Leu Cys Ala
            580                 585                 590
Ile His His Leu Leu Gly Arg Ala Pro Glu Ile Ala Cys Ser Ala Cys
            595                 600                 605
```

```
Asp Leu Val Asn Val Asp Leu Asp Asp Cys Val Ser Glu Gln
        610                 615                 620

<210> SEQ ID NO 30
<211> LENGTH: 622
<212> TYPE: PRT
<213> ORGANISM: Artificial Sequence
<220> FEATURE:
<223> OTHER INFORMATION: Synthetic polypeptide

<400> SEQUENCE: 30

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val His Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Asp Arg Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285

Leu Pro Ala Asp Ile Lys Ala Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350
```

Phe Tyr Gly Cys Val Asn Trp Thr Asn Glu Asn Phe Pro Phe Asn Asp
             355                 360                 365

Cys Val Asp Lys Met Val Ile Trp Trp Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
                435                 440                 445

Glu Leu Thr Arg Arg Leu Glu His Asp Phe Gly Lys Val Thr Lys Gln
                450                 455                 460

Glu Val Lys Glu Phe Phe Arg Trp Ala Gln Asp His Val Thr Glu Val
465                 470                 475                 480

Thr His Glu Phe Tyr Val Arg Lys Gly Gly Ala Thr Lys Arg Pro Ala
                485                 490                 495

Pro Ser Asp Ala Asp Ile Ser Glu Pro Lys Arg Ala Cys Pro Ser Val
                500                 505                 510

Ala Glu Pro Ser Thr Ser Asp Ala Glu Ala Pro Val Asp Phe Ala Asp
                515                 520                 525

Arg Tyr Gln Asn Lys Cys Ser Arg His Ala Gly Met Leu Gln Met Leu
                530                 535                 540

Phe Pro Cys Lys Thr Cys Glu Arg Met Asn Gln Asn Phe Asn Val Cys
545                 550                 555                 560

Phe Thr His Gly Val Arg Asp Cys Ser Glu Cys Phe Pro Gly Ala Ser
                565                 570                 575

Glu Ser Gln Pro Val Val Arg Lys Lys Thr Tyr Gln Lys Leu Cys Ala
                580                 585                 590

Ile His His Leu Leu Gly Arg Ala Pro Glu Ile Ala Cys Ser Ala Cys
                595                 600                 605

Asp Leu Val Asn Val Asp Leu Asp Asp Cys Val Ser Glu Gln
                610                 615                 620

<210> SEQ ID NO 31
<211> LENGTH: 622
<212> TYPE: PRT
<213> ORGANISM: Artificial Sequence
<220> FEATURE:
<223> OTHER INFORMATION: Synthetic polypeptide

<400> SEQUENCE: 31

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Arg Asn Leu Ile
            35                  40                  45

Glu Gln Ala Pro Leu Thr Val Ala Glu Lys Leu Gln Arg Asp Phe Leu
        50                  55                  60

Val His Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

-continued

```
Thr Thr Gly Val Lys Ser Met Val Leu Gly Arg Phe Leu Ser Gln Ile
            100                 105                 110

Arg Asp Arg Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285

Leu Pro Ala Asp Ile Lys Ala Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Thr Lys Arg Pro Ala
                485                 490                 495

Pro Ser Asp Ala Asp Ile Ser Glu Pro Lys Arg Ala Cys Pro Ser Val
            500                 505                 510
```

```
Pro Glu Pro Ser Thr Ser Asp Ala Glu Ala Pro Val Asp Phe Ala Asp
        515                 520                 525

Arg Tyr Gln Asn Lys Cys Ser Arg His Ala Gly Met Leu Gln Met Leu
    530                 535                 540

Phe Pro Cys Lys Thr Cys Glu Arg Met Asn Gln Asn Phe Asn Val Cys
545                 550                 555                 560

Phe Thr His Gly Val Arg Asp Cys Ser Glu Cys Phe Pro Gly Ala Ser
                565                 570                 575

Glu Ser Gln Pro Val Val Arg Lys Lys Thr Tyr Gln Lys Leu Cys Ala
            580                 585                 590

Ile His His Leu Leu Gly Arg Ala Pro Glu Ile Ala Cys Ser Ala Cys
        595                 600                 605

Asp Leu Val Asn Val Asp Leu Asp Asp Cys Val Ser Glu Gln
    610                 615                 620

<210> SEQ ID NO 32
<211> LENGTH: 621
<212> TYPE: PRT
<213> ORGANISM: Artificial Sequence
<220> FEATURE:
<223> OTHER INFORMATION: Synthetic polypeptide

<400> SEQUENCE: 32

Met Pro Gly Phe Tyr Glu Val Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Gln Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Phe Leu Glu Ala Lys Phe Phe Val
65                  70                  75                  80

Gln Phe Glu Lys Gly Asp Ser Tyr Phe His Leu His Ile Leu Ile Glu
                85                  90                  95

Ile Thr Gly Val Lys Ser Met Val Val Gly Arg Tyr Val Ser Gln Ile
            100                 105                 110

Arg Asp Lys Leu Ile Gln Arg Ile Tyr Arg Gly Val Glu Pro Gln Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Val Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gly Asp Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255
```

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Ile Gly Gln Gln
        275                 280                 285

Pro Val Gly Asp Ile Thr Thr Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ala Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Ala Asp His Val Thr Asp Val
465                 470                 475                 480

Ala His Glu Phe Tyr Val Thr Lys Gly Gly Ala Lys Lys Arg Pro Ala
                485                 490                 495

Pro Ser Asp Glu Asp Ile Ser Glu Pro Lys Arg Pro Arg Val Ser Phe
            500                 505                 510

Ala Gln Pro Glu Thr Ser Asp Ala Glu Ala Pro Gly Asp Phe Ala Asp
        515                 520                 525

Arg Tyr Gln Asn Lys Cys Ser Arg His Ala Gly Met Leu Gln Met Leu
    530                 535                 540

Phe Pro Cys Lys Thr Cys Glu Arg Met Asn Gln Asn Ser Asn Val Cys
545                 550                 555                 560

Phe Thr His Gly Gln Lys Asp Cys Gly Glu Cys Phe Pro Gly Ser Glu
                565                 570                 575

Ser Gln Pro Val Ser Val Val Arg Lys Thr Tyr Gln Lys Leu Cys Ile
            580                 585                 590

Leu His Gln Leu Arg Gly Ala Pro Glu Ile Ala Cys Ser Ala Cys Asp
        595                 600                 605

Gln Leu Asn Pro Asp Leu Asp Asp Cys Gln Phe Glu Gln
    610                 615                 620

<210> SEQ ID NO 33
<211> LENGTH: 623
<212> TYPE: PRT
<213> ORGANISM: Artificial Sequence
<220> FEATURE:
<223> OTHER INFORMATION: Synthetic polypeptide

<400> SEQUENCE: 33

```
Met Pro Gly Phe Tyr Glu Ile Val Leu Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
                35                  40                  45

Glu Gln Ala Pro Leu Thr Val Ala Glu Lys Leu Gln Arg Glu Phe Leu
50                  55                  60

Val Glu Trp Arg Arg Val Ser Lys Ala Pro Glu Ala Leu Phe Phe Val
65                  70                  75                  80

Gln Phe Glu Lys Gly Asp Ser Tyr Phe His Leu His Ile Leu Val Glu
                85                  90                  95

Thr Val Gly Val Lys Ser Met Val Val Gly Arg Tyr Val Ser Gln Ile
            100                 105                 110

Lys Glu Lys Leu Val Thr Arg Ile Tyr Arg Gly Val Glu Pro Gln Leu
                115                 120                 125

Pro Asn Trp Phe Ala Val Thr Lys Thr Arg Asn Gly Ala Gly Gly Gly
            130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
                195                 200                 205

Pro Asn Ser Asp Ala Pro Val Ile Arg Ser Lys Thr Ser Ala Arg Tyr
            210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Phe Met Ser Leu Thr Lys Thr Ala Pro Asp Tyr Leu Val Gly Asn Asn
                275                 280                 285

Pro Pro Glu Asp Ile Thr Ser Asn Arg Ile Tyr Lys Ile Leu Glu Met
            290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
                355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
```

```
              420                 425                 430
Thr Thr Phe Glu His Gln Gln Pro Leu Gln Asp Arg Met Phe Lys Phe
        435                 440                 445
Glu Leu Thr Lys Arg Leu Glu His Asp Phe Gly Lys Val Thr Lys Gln
450                 455                 460
Glu Val Lys Asp Phe Phe Arg Trp Ala Ser Asp His Val Thr Glu Val
465                 470                 475                 480
Ser His Glu Phe Tyr Val Arg Lys Gly Gly Ala Arg Lys Arg Pro Ala
                485                 490                 495
Pro Asn Asp Ala Asp Ile Ser Glu Pro Lys Arg Ala Cys Pro Ser Val
            500                 505                 510
Ala Gln Pro Ser Thr Ser Asp Ala Glu Ala Pro Val Asp Tyr Ala Asp
        515                 520                 525
Arg Tyr Gln Asn Lys Cys Ser Arg His Val Gly Met Asn Leu Met Leu
    530                 535                 540
Phe Pro Cys Arg Gln Cys Glu Arg Met Asn Gln Asn Val Asp Ile Cys
545                 550                 555                 560
Phe Thr His Gly Val Met Asp Cys Ala Glu Cys Phe Pro Val Ser Glu
                565                 570                 575
Ser Gln Pro Val Ser Val Val Arg Lys Arg Thr Tyr Gln Lys Leu Cys
            580                 585                 590
Pro Ile His His Ile Met Gly Arg Ala Pro Glu Val Ala Cys Ser Ala
        595                 600                 605
Cys Asp Leu Ala Asn Val Asp Leu Asp Asp Cys Asp Met Glu Gln
    610                 615                 620

<210> SEQ ID NO 34
<211> LENGTH: 621
<212> TYPE: PRT
<213> ORGANISM: Artificial Sequence
<220> FEATURE:
<223> OTHER INFORMATION: Synthetic polypeptide

<400> SEQUENCE: 34

Met Pro Gly Phe Tyr Glu Ile Val Ile Lys Val Pro Ser Asp Leu Asp
1               5                   10                  15
Glu His Leu Pro Gly Ile Ser Asp Ser Phe Val Ser Trp Val Ala Glu
            20                  25                  30
Lys Glu Trp Glu Leu Pro Pro Asp Ser Asp Met Asp Leu Asn Leu Ile
        35                  40                  45
Glu Gln Ala Pro Leu Thr Val Ala Glu Lys Leu Gln Arg Asp Phe Leu
    50                  55                  60
Val Gln Trp Arg Arg Val Ser Lys Ala Pro Glu Ala Leu Phe Phe Val
65                  70                  75                  80
Gln Phe Glu Lys Gly Glu Ser Tyr Phe His Leu His Ile Leu Val Glu
                85                  90                  95
Thr Thr Gly Val Lys Ser Met Val Leu Gly Arg Phe Leu Ser Gln Ile
            100                 105                 110
Arg Asp Lys Leu Val Gln Thr Ile Tyr Arg Gly Ile Glu Pro Thr Leu
        115                 120                 125
Pro Asn Trp Phe Ala Val Thr Lys Thr Arg Asn Gly Ala Gly Gly Gly
    130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Glu Tyr Ile
```

```
                165                 170                 175
Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590
```

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
    610                 615                 620

<210> SEQ ID NO 35
<211> LENGTH: 623
<212> TYPE: PRT
<213> ORGANISM: Artificial Sequence
<220> FEATURE:
<223> OTHER INFORMATION: Synthetic polypeptide

<400> SEQUENCE: 35

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
        275                 280                 285

Pro Pro Ala Asp Ile Lys Thr Asn Arg Ile Tyr Arg Ile Leu Glu Leu
    290                 295                 300

Asn Gly Tyr Glu Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

```
Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ala Gln Ile Asp Pro Thr Pro Val
        405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Leu Gln Met
    530                 535                 540

Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
                565                 570                 575

Ser Glu Ser Gln Pro Val Val Arg Lys Arg Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Cys Val Ser Glu Gln
    610                 615                 620

<210> SEQ ID NO 36
<211> LENGTH: 614
<212> TYPE: PRT
<213> ORGANISM: Artificial Sequence
<220> FEATURE:
<223> OTHER INFORMATION: Synthetic polypeptide

<400> SEQUENCE: 36

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80
```

```
Gln Phe Glu Lys Gly Glu Ser Tyr Phe His Met His Val Leu Val Glu
                    85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
                180                 185                 190

Leu Thr His Val Ser Gln Thr Gln Glu Gln Asn Lys Glu Asn Gln Asn
                195                 200                 205

Pro Asn Ser Asp Ala Pro Val Ile Arg Ser Lys Thr Ser Ala Arg Tyr
210                 215                 220

Met Ala Leu Val Asn Trp Leu Val Glu His Gly Ile Thr Ser Glu Lys
225                 230                 235                 240

Gln Trp Ile Gln Glu Asn Gln Glu Ser Tyr Leu Ser Phe Asn Ser Thr
                245                 250                 255

Gly Asn Ser Arg Ser Gln Ile Lys Ala Ala Leu Asp Asn Ala Thr Lys
                260                 265                 270

Ile Met Ser Leu Thr Lys Ser Ala Val Asp Tyr Leu Val Gly Ser Ser
                275                 280                 285

Val Pro Glu Asp Ile Ser Lys Asn Arg Ile Trp Gln Ile Phe Glu Met
290                 295                 300

Asn Gly Tyr Asp Pro Ala Tyr Ala Gly Ser Ile Leu Tyr Gly Trp Cys
305                 310                 315                 320

Gln Arg Ser Phe Asn Lys Arg Asn Thr Val Trp Leu Tyr Gly Pro Ala
                325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
                355                 360                 365

Cys Val Asp Lys Met Leu Ile Trp Trp Glu Glu Gly Lys Met Thr Asn
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Val Gln Ile Asp Ser Thr Pro Val
                405                 410                 415

Ile Val Thr Ser Asn Thr Asn Met Cys Val Val Asp Gly Asn Ser Ser
                420                 425                 430

Thr Thr Phe Glu His Gln Gln Pro Leu Glu Asp Arg Met Phe Lys Phe
                435                 440                 445

Glu Leu Thr Lys Arg Leu Pro Pro Asp Phe Gly Lys Ile Thr Lys Gln
450                 455                 460

Glu Val Lys Asp Phe Phe Ala Trp Ala Lys Val Asn Gln Val Pro Val
465                 470                 475                 480

Thr His Glu Phe Lys Val Pro Arg Glu Leu Ala Gly Thr Lys Gly Ala
                485                 490                 495
```

```
Glu Lys Ser Leu Lys Arg Pro Leu Gly Asp Val Thr Asn Thr Ser Tyr
                500                 505                 510

Lys Ser Leu Glu Lys Arg Ala Arg Leu Ser Phe Val Pro Glu Thr Pro
            515                 520                 525

Arg Ser Ser Asp Val Thr Val Asp Pro Ala Pro Leu Arg Pro Leu Asn
        530                 535                 540

Trp Asn Ser Arg Tyr Asp Cys Lys Cys Asp Tyr His Ala Gln Phe Asp
545                 550                 555                 560

Asn Ile Ser Asn Lys Cys Asp Glu Cys Glu Tyr Leu Asn Arg Gly Lys
                565                 570                 575

Asn Gly Cys Ile Cys His Asn Val Thr His Cys Gln Ile Cys His Gly
            580                 585                 590

Ile Pro Pro Trp Glu Lys Glu Asn Leu Ser Asp Phe Gly Asp Phe Asp
        595                 600                 605

Asp Ala Asn Lys Glu Gln
    610
```

<210> SEQ ID NO 37
<211> LENGTH: 614
<212> TYPE: PRT
<213> ORGANISM: Artificial Sequence
<220> FEATURE:
<223> OTHER INFORMATION: Synthetic polypeptide

<400> SEQUENCE: 37

```
Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Ala Leu Val Asn Trp Leu Val Glu His Gly Ile Thr Ser Glu Lys
225                 230                 235                 240
```

Gln Trp Ile Gln Glu Asn Gln Glu Ser Tyr Leu Ser Phe Asn Ser Thr
                245                 250                 255

Gly Asn Ser Arg Ser Gln Ile Lys Ala Ala Leu Asp Asn Ala Thr Lys
            260                 265                 270

Ile Met Ser Leu Thr Lys Ser Ala Val Asp Tyr Leu Val Gly Ser Ser
        275                 280                 285

Val Pro Glu Asp Ile Ser Lys Asn Arg Ile Trp Gln Ile Phe Glu Met
290                 295                 300

Asn Gly Tyr Asp Pro Ala Tyr Ala Gly Ser Ile Leu Tyr Gly Trp Cys
305                 310                 315                 320

Gln Arg Ser Phe Asn Lys Arg Asn Thr Val Trp Leu Tyr Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Leu Ile Trp Trp Glu Gly Lys Met Thr Asn
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Val Gln Ile Asp Ser Thr Pro Val
                405                 410                 415

Ile Val Thr Ser Asn Thr Asn Met Cys Val Val Asp Gly Asn Ser
            420                 425                 430

Thr Thr Phe Glu His Gln Gln Pro Leu Glu Asp Arg Met Phe Lys Phe
        435                 440                 445

Glu Leu Thr Lys Arg Leu Pro Pro Asp Phe Gly Lys Ile Thr Lys Gln
450                 455                 460

Glu Val Lys Asp Phe Phe Ala Trp Ala Lys Val Asn Gln Val Pro Val
465                 470                 475                 480

Thr His Glu Phe Lys Val Pro Arg Glu Leu Ala Gly Thr Lys Gly Ala
                485                 490                 495

Glu Lys Ser Leu Lys Arg Pro Leu Gly Asp Val Thr Asn Thr Ser Tyr
            500                 505                 510

Lys Ser Leu Glu Lys Arg Ala Arg Leu Ser Phe Val Pro Glu Thr Pro
        515                 520                 525

Arg Ser Ser Asp Val Thr Val Asp Pro Ala Pro Leu Arg Pro Leu Asn
530                 535                 540

Trp Asn Ser Arg Tyr Asp Cys Lys Cys Asp Tyr His Ala Gln Phe Asp
545                 550                 555                 560

Asn Ile Ser Asn Lys Cys Asp Glu Cys Glu Tyr Leu Asn Arg Gly Lys
                565                 570                 575

Asn Gly Cys Ile Cys His Asn Val Thr His Cys Gln Ile Cys His Gly
            580                 585                 590

Ile Pro Pro Trp Glu Lys Glu Asn Leu Ser Asp Phe Gly Asp Phe Asp
        595                 600                 605

Asp Ala Asn Lys Glu Gln
    610

<210> SEQ ID NO 38
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 38

Leu Ala Arg Gly His Ser Leu
1               5

<210> SEQ ID NO 39
<211> LENGTH: 148
<212> TYPE: DNA
<213> ORGANISM: Artificial Sequence
<220> FEATURE:
<223> OTHER INFORMATION: Synthetic polynucleotide

<400> SEQUENCE: 39

```
hvsbthrkkr gatctactac ctcaacsggt gagggagaka cgcgygagcg agygagysas    60
ycsggcskkc hsgtytcsdg mmskcagmcs bctggaaacc agvsggccsg rstsrctcrc   120
tcgctcrcgc gtmtctccct caccsgtt                                      148
```

<210> SEQ ID NO 40
<211> LENGTH: 306
<212> TYPE: DNA
<213> ORGANISM: Artificial Sequence
<220> FEATURE:
<223> OTHER INFORMATION: Synthetic polynucleotide

<400> SEQUENCE: 40

```
atgccgggct tctacgagat cgtgatcaag gtgccgagcg acctggacga gcacctgccg    60
ggcatttctg actcgtttgt gagctgggtg gccgagaagg aatgggagct gccccccggat  120 tctgacatgg atctgaatct gattgagcag gcacccctga ccgtggccga gaagctgcag   180
cgcgacttcc tggtccaatg gcgccgcgtg agtaaggccc cggaggccct cttctttgtt   240
cagttcgaga agggcgagtc ctacttccac ctccatattc tggtggagac cacgggggtc   300
aaatcc                                                              306
```

<210> SEQ ID NO 41
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 41

```
atggtgctgg ccgcttcct gagtcagatt agggacaagc tggtgcagac catctaccgc     60
gggatcgagc cgaccctgcc caactggttc gcggtgacca agacgcgtaa tggcgccgga   120 gggggaaca aggtggtgga cgagtgctac atccccaact acctcctgcc caagactcag   180
cccgagctgc agtgggcgtg gactaacatg gaggagtata taagcgcctg tttgaacctg   240
gccgagcgca acggctcgt ggcgcagcac ctgacccacg tcagccagac ccaggagcag   300
aacaaggaga atctgaaccc caattctgac gcgcctgtca tccggtcaaa aacctccgcg   360
cgctacatgg agctggtcgg gtggctggtg gaccggggca tcacctccga gaagcagtgg   420
```

<210> SEQ ID NO 42
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 42

```
atccaggagg accaggcctc gtacatctcc ttcaacgccg cttccaactc gcggtcccag     60
```

```
atcaaggccg ctctggacaa tgccggcaag atcatggcgc tgaccaaatc cgcgcccgac    120
tacctggtag gccccgctcc gcccgcggac attaaaacca accgcatcta ccgcatcctg    180
gagctgaacg gctacgaacc tgcctacgcc ggctccgtct ttctcggctg ggcccagaaa    240
aggttcggga agcgcaacac catctggctg tttgggccgg ccaccacggg caagaccaac    300
atcgcggaag ccatcgccca cgccgtgccc ttctacggct gcgtcaactg gaccaatgag    360
aactttccct tcaatgattg c                                              381
```

<210> SEQ ID NO 43
<211> LENGTH: 765
<212> TYPE: DNA
<213> ORGANISM: Artificial Sequence
<220> FEATURE:
<223> OTHER INFORMATION: Synthetic polynucleotide

<400> SEQUENCE: 43

```
gtcgacaaga tggtgatctg gtgggaggag ggcaagatga cggccaaggt cgtggagtcc     60
gccaaggcca ttctcggcgg cagcaaggtg cgcgtggacc aaaagtgcaa gtcgtccgcc    120
cagatcgacc ccacccccgt gatcgtcacc tccaacacca acatgtgcgc cgtgattgac    180
gggaacagca ccaccttcga gcaccagcag ccgttgcagg accggatgtt caaatttgaa    240
ctcacccgcc gtctggagca tgactttggc aaggtgacaa agcaggaagt caaagagttc    300
ttccgctggg cgcaggatca cgtgaccgag gtggcgcatg agttctacgt cagaaagggt    360
ggagccaaca aaagacccgc ccccgatgac gcggataaaa gcgagcccaa gcgggcctgc    420
ccctcagtcg cggatccatc gacgtcagac gcggaaggag ctccggtgga ctttgccgac    480
aggtaccaaa acaaatgttc tcgtcacgcg ggcatgcttc agatgctgtt tccctgcaag    540
acatgcgaga gaatgaatca gaatttcaac atttgcttca cgcacgggac gagagactgt    600
tcagagtgct tccccggcgt gtcagaatct caaccggtcg tcagaaagag gacgtatcgg    660
aaactctgtg ccattcatca tctgctgggg cgggctcccg agattgcttg ctcggcctgc    720
gatctggtca acgtggacct ggatgactgt gtttctgagc aataa                    765
```

<210> SEQ ID NO 44
<211> LENGTH: 495
<212> TYPE: DNA
<213> ORGANISM: Artificial Sequence
<220> FEATURE:
<223> OTHER INFORMATION: Synthetic polynucleotide

<400> SEQUENCE: 44

```
gtcgacaaga tggtgatctg gtgggaggag ggcaagatga cggccaaggt cgtggagtcc     60
gccaaggcca ttctcggcgg cagcaaggtg cgcgtggacc aaaagtgcaa gtcgtccgcc    120
cagatcgacc ccacccccgt gatcgtcacc tccaacacca acatgtgcgc cgtgattgac    180
gggaacagca ccaccttcga gcaccagcag ccgttgcagg accggatgtt caaatttgaa    240
ctcacccgcc gtctggagca tgactttggc aaggtgacaa agcaggaagt caaagagttc    300
ttccgctggg cgcaggatca cgtgaccgag gtggcgcatg agttctacgt cagaaagggt    360
ggagccaaca aaagacccgc ccccgatgac gcggataaaa gcgagcccaa gcgggcctgc    420
ccctcagtcg cggatccatc gacgtcagac gcggaaggag ctccggtgga ctttgccgac    480
aggtaccaaa acaaa                                                     495
```

<210> SEQ ID NO 45

```
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 45
tgttctcgtc acgcgggcat gcttcagatg ctgtttccct gcaagacatg cgagagaatg      60
aatcagaatt tcaacatttg cttcacgcac gggacgagag actgttcaga gtgcttcccc    120
ggcgtgtcag aatctcaacc ggtcgtcaga aagaggacgt atcggaaact ctgtgccatt    180
catcatctgc tggggcgggc tcccgagatt gcttgctcgg cctgcgatct ggtcaacgtg    240
gacctggatg actgtgtttc tgagcaataa                                      270

<210> SEQ ID NO 46
<211> LENGTH: 102
<212> TYPE: PRT
<213> ORGANISM: Artificial Sequence
<220> FEATURE:
<223> OTHER INFORMATION: Synthetic polypeptide

<400> SEQUENCE: 46
```

Met Pro Gly Phe Tyr Glu Ile Val Ile Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser
            100

```
<210> SEQ ID NO 47
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 47
```

Met Val Leu Gly Arg Phe Leu Ser Gln Ile Arg Asp Lys Leu Val Gln
1               5                   10                  15

Thr Ile Tyr Arg Gly Ile Glu Pro Thr Leu Pro Asn Trp Phe Ala Val
            20                  25                  30

Thr Lys Thr Arg Asn Gly Ala Gly Gly Gly Asn Lys Val Val Asp Glu
        35                  40                  45

Cys Tyr Ile Pro Asn Tyr Leu Leu Pro Lys Thr Gln Pro Glu Leu Gln
    50                  55                  60

Trp Ala Trp Thr Asn Met Glu Gly Tyr Ile Ser Ala Cys Leu Asn Leu
65                  70                  75                  80

Ala Glu Arg Lys Arg Leu Val Ala Gln His Leu Thr His Val Ser Gln
                85                  90                  95

Thr Gln Glu Gln Asn Lys Glu Asn Leu Asn Pro Asn Ser Asp Ala Pro
            100                 105                 110

```
Val Ile Arg Ser Lys Thr Ser Ala Arg Tyr Met Glu Leu Val Gly Trp
            115                 120                 125

Leu Val Asp Arg Gly Ile Thr Ser Glu Lys Gln Trp
        130                 135                 140

<210> SEQ ID NO 48
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 48

Ile Gln Glu Asp Gln Ala Ser Tyr Ile Ser Phe Asn Ala Ala Ser Asn
1               5                   10                  15

Ser Arg Ser Gln Ile Lys Ala Ala Leu Asp Asn Ala Gly Lys Ile Met
            20                  25                  30

Ala Leu Thr Lys Ser Ala Pro Asp Tyr Leu Val Gly Pro Ala Pro Pro
        35                  40                  45

Ala Asp Ile Lys Thr Asn Arg Ile Tyr Arg Ile Leu Glu Leu Asn Gly
    50                  55                  60

Tyr Glu Pro Ala Tyr Ala Gly Ser Val Phe Leu Gly Trp Ala Gln Lys
65                  70                  75                  80

Arg Phe Gly Lys Arg Asn Thr Ile Trp Leu Phe Gly Pro Ala Thr Thr
                85                  90                  95

Gly Lys Thr Asn Ile Ala Glu Ala Ile Ala His Ala Val Pro Phe Tyr
            100                 105                 110

Gly Cys Val Asn Trp Thr Asn Glu Asn Phe Pro Phe Asn Asp Cys
        115                 120                 125

<210> SEQ ID NO 49
<211> LENGTH: 254
<212> TYPE: PRT
<213> ORGANISM: Artificial Sequence
<220> FEATURE:
<223> OTHER INFORMATION: Synthetic polypeptide

<400> SEQUENCE: 49

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Ala Gln Ile Asp Pro Thr Pro Val Ile
        35                  40                  45

Val Thr Ser Asn Thr Asn Met Cys Ala Val Ile Asp Gly Asn Ser Thr
    50                  55                  60

Thr Phe Glu His Gln Gln Pro Leu Gln Asp Arg Met Phe Lys Phe Glu
65                  70                  75                  80

Leu Thr Arg Arg Leu Glu His Asp Phe Gly Lys Val Thr Lys Gln Glu
                85                  90                  95

Val Lys Glu Phe Phe Arg Trp Ala Gln Asp His Val Thr Glu Val Ala
            100                 105                 110

His Glu Phe Tyr Val Arg Lys Gly Gly Ala Asn Lys Arg Pro Ala Pro
        115                 120                 125

Asp Asp Ala Asp Lys Ser Glu Pro Lys Arg Ala Cys Pro Ser Val Ala
    130                 135                 140

Asp Pro Ser Thr Ser Asp Ala Glu Gly Ala Pro Val Asp Phe Ala Asp
```

```
            145                 150                 155                 160

Arg Tyr Gln Asn Lys Cys Ser Arg His Ala Gly Met Leu Gln Met Leu
                165                 170                 175

Phe Pro Cys Lys Thr Cys Glu Arg Met Asn Gln Asn Phe Asn Ile Cys
                180                 185                 190

Phe Thr His Gly Thr Arg Asp Cys Ser Glu Cys Phe Pro Gly Val Ser
                195                 200                 205

Glu Ser Gln Pro Val Val Arg Lys Arg Thr Tyr Arg Lys Leu Cys Ala
        210                 215                 220

Ile His His Leu Leu Gly Arg Ala Pro Glu Ile Ala Cys Ser Ala Cys
225                 230                 235                 240

Asp Leu Val Asn Val Asp Leu Asp Asp Cys Val Ser Glu Gln
                245                 250

<210> SEQ ID NO 50
<211> LENGTH: 165
<212> TYPE: PRT
<213> ORGANISM: Artificial Sequence
<220> FEATURE:
<223> OTHER INFORMATION: Synthetic polypeptide

<400> SEQUENCE: 50

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
                20                  25                  30

Asp Gln Lys Cys Lys Ser Ser Ala Gln Ile Asp Pro Thr Pro Val Ile
            35                  40                  45

Val Thr Ser Asn Thr Asn Met Cys Ala Val Ile Asp Gly Asn Ser Thr
        50                  55                  60

Thr Phe Glu His Gln Gln Pro Leu Gln Asp Arg Met Phe Lys Phe Glu
65                  70                  75                  80

Leu Thr Arg Arg Leu Glu His Asp Phe Gly Lys Val Thr Lys Gln Glu
                85                  90                  95

Val Lys Glu Phe Phe Arg Trp Ala Gln Asp His Val Thr Glu Val Ala
                100                 105                 110

His Glu Phe Tyr Val Arg Lys Gly Gly Ala Asn Lys Arg Pro Ala Pro
            115                 120                 125

Asp Asp Ala Asp Lys Ser Glu Pro Lys Arg Ala Cys Pro Ser Val Ala
        130                 135                 140

Asp Pro Ser Thr Ser Asp Ala Glu Gly Ala Pro Val Asp Phe Ala Asp
145                 150                 155                 160

Arg Tyr Gln Asn Lys
                165

<210> SEQ ID NO 51
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 51

Cys Ser Arg His Ala Gly Met Leu Gln Met Leu Phe Pro Cys Lys Thr
1               5                   10                  15

Cys Glu Arg Met Asn Gln Asn Phe Asn Ile Cys Phe Thr His Gly Thr
                20                  25                  30
```

Arg Asp Cys Ser Glu Cys Phe Pro Gly Val Ser Glu Ser Gln Pro Val
35                  40                  45

Val Arg Lys Arg Thr Tyr Arg Lys Leu Cys Ala Ile His His Leu Leu
50                  55                  60

Gly Arg Ala Pro Glu Ile Ala Cys Ser Ala Cys Asp Leu Val Asn Val
65                  70                  75                  80

Asp Leu Asp Asp Cys Val Ser Glu Gln
                85

<210> SEQ ID NO 52
<211> LENGTH: 306
<212> TYPE: DNA
<213> ORGANISM: Artificial Sequence
<220> FEATURE:
<223> OTHER INFORMATION: Synthetic polynucleotide

<400> SEQUENCE: 52 acgccgggt tttacgagat tgtgattaag gtccccagcg accttgacga gcatctgccc        60
ggcatttctg acagctttgt gaactgggtg gccgagaagg aatgggagtt gccgccagat      120
tctgacatgg atctgaatct gattgagcag gcacccctga ccgtggccga gaagctgcag      180
cgcgactttc tgacggaatg gcgccgtgtg agtaaggccc cggaggccct tttctttgtg      240
caatttgaga agggagagag ctacttccac atgcacgtgc tcgtggaaac caccggggtg      300
aaatcc                                                                306

<210> SEQ ID NO 53
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 53
atggttttgg gacgtttcct gagtcagatt cgcgaaaaac tgattcagag aatttaccgc       60
gggatcgagc cgactttgcc aaactggttc gcggtcacaa agaccagaaa tggcgccgga      120
ggcgggaaca aggtggtgga tgagtgctac atccccaatt acttgctccc caaaacccag      180
cctgagctcc agtgggcgtg gactaatatg aacagtatt taagcgcctg tttgaatctc      240
acggagcgta acggttggt ggcgcagcat ctgacgcacg tgtcgcagac gcaggagcag      300
aacaaagaga tcagaatcc caattctgat gcgccggtga tcagatcaaa aacttcagcc      360
aggtacatgg agctggtcgg gtggctcgtg gacaagggga ttacctcgga gaagcagtgg      420

<210> SEQ ID NO 54
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 54
atccaggagg accaggcctc atacatctcc ttcaatgcgg cctccaactc gcggtcccaa       60
atcaaggctg ccttggacaa tgcgggaaag attatgagcc tgactaaaac cgccccgac      120 tacctggtgg gccagcagcc cgtggaggac atttccagca tcggattta taaaattttg      180 gaactaaacg ggtacgatcc ccaatatgcg gcttccgtct ttctgggatg ggccacgaaa      240
aagttcggca agaggaacac catctggctg tttgggcctg caactaccgg gaagaccaac      300
atcgcggagg ccatagccca cactgtgccc ttctacgggt gcgtaaactg gaccaatgag      360

```
aactttccct tcaacgactg t                                              381
```

<210> SEQ ID NO 55
<211> LENGTH: 759
<212> TYPE: DNA
<213> ORGANISM: Artificial Sequence
<220> FEATURE:
<223> OTHER INFORMATION: Synthetic polynucleotide

<400> SEQUENCE: 55

```
gtcgacaaga tggtgatctg gtgggaggag gggaagatga ccgccaaggt cgtggagtcg    60
gccaaagcca ttctcggagg aagcaaggtg cgcgtggacc agaaatgcaa gtcctcggcc   120
cagatagacc cgactcccgt gatcgtcacc tccaacacca acatgtgcgc cgtgattgac   180
gggaactcaa cgaccttcga acaccagcag ccgttgcaag accggatgtt caaatttgaa   240
ctcacccgcc gtctggatca tgactttggg aaggtcacca agcaggaagt caaagacttt   300
ttccggtggg caaggatca cgtggttgag gtggagcatg aattctacgt caaaaagggt   360
ggagccaaga aaagacccgc ccccagtgac gcagatataa gtgagcccaa acgggtgcgc   420
gagtcagttg cgcagccatc gacgtcagac gcggaagctt cgatcaacta cgcagacagg   480
taccaaaaca atgttctcg tcacgtgggc atgaatctga tgctgtttcc ctgcagacaa   540
tgcgagagaa tgaatcagaa ttcaaatatc tgcttcactc acggacagaa agactgttta   600
gagtgctttc ccgtgtcaga atctcaaccc gtttctgtcg tcaaaaaggc gtatcagaaa   660
ctgtgctaca ttcatcatat catgggaaag gtgccagacg cttgcactgc ctgcgatctg   720
gtcaatgtgg atttggatga ctgcatcttt gaacaataa                          759
```

<210> SEQ ID NO 56
<211> LENGTH: 492
<212> TYPE: DNA
<213> ORGANISM: Artificial Sequence
<220> FEATURE:
<223> OTHER INFORMATION: Synthetic polynucleotide

<400> SEQUENCE: 56

```
gtcgacaaga tggtgatctg gtgggaggag gggaagatga ccgccaaggt cgtggagtcg    60
gccaaagcca ttctcggagg aagcaaggtg cgcgtggacc agaaatgcaa gtcctcggcc   120
cagatagacc cgactcccgt gatcgtcacc tccaacacca acatgtgcgc cgtgattgac   180
gggaactcaa cgaccttcga acaccagcag ccgttgcaag accggatgtt caaatttgaa   240
ctcacccgcc gtctggatca tgactttggg aaggtcacca agcaggaagt caaagacttt   300
ttccggtggg caaggatca cgtggttgag gtggagcatg aattctacgt caaaaagggt   360
ggagccaaga aaagacccgc ccccagtgac gcagatataa gtgagcccaa acgggtgcgc   420
gagtcagttg cgcagccatc gacgtcagac gcggaagctt cgatcaacta cgcagacagg   480
taccaaaaca aa                                                        492
```

<210> SEQ ID NO 57
<211> LENGTH: 267
<212> TYPE: DNA
<213> ORGANISM: Artificial Sequence
<220> FEATURE:
<223> OTHER INFORMATION: Synthetic polynucleotide

<400> SEQUENCE: 57

```
tgttctcgtc acgtgggcat gaatctgatg ctgtttccct gcagacaatg cgagagaatg    60
```

```
aatcagaatt caaatatctg cttcactcac ggacagaaag actgtttaga gtgctttccc    120
gtgtcagaat ctcaacccgt ttctgtcgtc aaaaaggcgt atcagaaact gtgctacatt    180
catcatatca tgggaaaggt gccagacgct tgcactgcct gcgatctggt caatgtggat    240
ttggatgact gcatctttga acaataa                                        267
```

```
<210> SEQ ID NO 58
<211> LENGTH: 102
<212> TYPE: PRT
<213> ORGANISM: Artificial Sequence
<220> FEATURE:
<223> OTHER INFORMATION: Synthetic polypeptide

<400> SEQUENCE: 58
```

Thr Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser
            100

```
<210> SEQ ID NO 59
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 59
```

Met Val Leu Gly Arg Phe Leu Ser Gln Ile Arg Glu Lys Leu Ile Gln
1               5                   10                  15

Arg Ile Tyr Arg Gly Ile Glu Pro Thr Leu Pro Asn Trp Phe Ala Val
            20                  25                  30

Thr Lys Thr Arg Asn Gly Ala Gly Gly Gly Asn Lys Val Val Asp Glu
        35                  40                  45

Cys Tyr Ile Pro Asn Tyr Leu Leu Pro Lys Thr Gln Pro Glu Leu Gln
    50                  55                  60

Trp Ala Trp Thr Asn Met Glu Gln Tyr Leu Ser Ala Cys Leu Asn Leu
65                  70                  75                  80

Thr Glu Arg Lys Arg Leu Val Ala Gln His Leu Thr His Val Ser Gln
                85                  90                  95

Thr Gln Glu Gln Asn Lys Glu Asn Gln Asn Pro Asn Ser Asp Ala Pro
            100                 105                 110

Val Ile Arg Ser Lys Thr Ser Ala Arg Tyr Met Glu Leu Val Gly Trp
        115                 120                 125

Leu Val Asp Lys Gly Ile Thr Ser Glu Lys Gln Trp
    130                 135                 140

```
<210> SEQ ID NO 60
<211> LENGTH: 127
```

```
<212> TYPE: PRT
<213> ORGANISM: Artificial Sequence
<220> FEATURE:
<223> OTHER INFORMATION: Synthetic polypeptide

<400> SEQUENCE: 60

Ile Gln Glu Asp Gln Ala Ser Tyr Ile Ser Phe Asn Ala Ala Ser Asn
1               5                   10                  15

Ser Arg Ser Gln Ile Lys Ala Ala Leu Asp Asn Ala Gly Lys Ile Met
            20                  25                  30

Ser Leu Thr Lys Thr Ala Pro Asp Tyr Leu Val Gly Gln Gln Pro Val
        35                  40                  45

Glu Asp Ile Ser Ser Asn Arg Ile Tyr Lys Ile Leu Glu Leu Asn Gly
50                  55                  60

Tyr Asp Pro Gln Tyr Ala Ala Ser Val Phe Leu Gly Trp Ala Thr Lys
65                  70                  75                  80

Lys Phe Gly Lys Arg Asn Thr Ile Trp Leu Phe Gly Pro Ala Thr Thr
                85                  90                  95

Gly Lys Thr Asn Ile Ala Glu Ala Ile Ala His Thr Val Pro Phe Tyr
            100                 105                 110

Gly Cys Val Asn Trp Thr Asn Glu Asn Phe Pro Phe Asn Asp Cys
        115                 120                 125

<210> SEQ ID NO 61
<211> LENGTH: 252
<212> TYPE: PRT
<213> ORGANISM: Artificial Sequence
<220> FEATURE:
<223> OTHER INFORMATION: Synthetic polypeptide

<400> SEQUENCE: 61

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Ala Gln Ile Asp Pro Thr Pro Val Ile
            35                  40                  45

Val Thr Ser Asn Thr Asn Met Cys Ala Val Ile Asp Gly Asn Ser Thr
50                  55                  60

Thr Phe Glu His Gln Gln Pro Leu Gln Asp Arg Met Phe Lys Phe Glu
65                  70                  75                  80

Leu Thr Arg Arg Leu Asp His Asp Phe Gly Lys Val Thr Lys Gln Glu
                85                  90                  95

Val Lys Asp Phe Phe Arg Trp Ala Lys Asp His Val Val Glu Val Glu
            100                 105                 110

His Glu Phe Tyr Val Lys Lys Gly Gly Ala Lys Lys Arg Pro Ala Pro
            115                 120                 125

Ser Asp Ala Asp Ile Ser Glu Pro Lys Arg Val Arg Glu Ser Val Ala
            130                 135                 140

Gln Pro Ser Thr Ser Asp Ala Glu Ala Ser Ile Asn Tyr Ala Asp Arg
145                 150                 155                 160

Tyr Gln Asn Lys Cys Ser Arg His Val Gly Met Asn Leu Met Leu Phe
                165                 170                 175

Pro Cys Arg Gln Cys Glu Arg Met Asn Gln Asn Ser Asn Ile Cys Phe
            180                 185                 190

Thr His Gly Gln Lys Asp Cys Leu Glu Cys Phe Pro Val Ser Glu Ser
            195                 200                 205
```

```
Gln Pro Val Ser Val Lys Lys Ala Tyr Gln Lys Leu Cys Tyr Ile
    210                 215                 220

His His Ile Met Gly Lys Val Pro Asp Ala Cys Thr Ala Cys Asp Leu
225                 230                 235                 240

Val Asn Val Asp Leu Asp Asp Cys Ile Phe Glu Gln
                245                 250

<210> SEQ ID NO 62
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 62

Val Asp Lys Met Val Ile Trp Trp Glu Gly Lys Met Thr Ala Lys
1               5                   10                  15

Val Val Glu Ser Ala Lys Ala Ile Leu Gly Gly Ser Lys Val Arg Val
                20                  25                  30

Asp Gln Lys Cys Lys Ser Ser Ala Gln Ile Asp Pro Thr Pro Val Ile
            35                  40                  45

Val Thr Ser Asn Thr Asn Met Cys Ala Val Ile Asp Gly Asn Ser Thr
50                  55                  60

Thr Phe Glu His Gln Gln Pro Leu Gln Asp Arg Met Phe Lys Phe Glu
65                  70                  75                  80

Leu Thr Arg Arg Leu Asp His Asp Phe Gly Lys Val Thr Lys Gln Glu
                85                  90                  95

Val Lys Asp Phe Phe Arg Trp Ala Lys Asp His Val Val Glu Val Glu
            100                 105                 110

His Glu Phe Tyr Val Lys Lys Gly Gly Ala Lys Lys Arg Pro Ala Pro
        115                 120                 125

Ser Asp Ala Asp Ile Ser Glu Pro Lys Arg Val Arg Glu Ser Val Ala
    130                 135                 140

Gln Pro Ser Thr Ser Asp Ala Glu Ala Ser Ile Asn Tyr Ala Asp Arg
145                 150                 155                 160

Tyr Gln Asn Lys

<210> SEQ ID NO 63
<211> LENGTH: 88
<212> TYPE: PRT
<213> ORGANISM: Artificial Sequence
<220> FEATURE:
<223> OTHER INFORMATION: Synthetic polypeptide

<400> SEQUENCE: 63

Cys Ser Arg His Val Gly Met Asn Leu Met Leu Phe Pro Cys Arg Gln
1               5                   10                  15

Cys Glu Arg Met Asn Gln Asn Ser Asn Ile Cys Phe Thr His Gly Gln
                20                  25                  30

Lys Asp Cys Leu Glu Cys Phe Pro Val Ser Glu Ser Gln Pro Val Ser
            35                  40                  45

Val Val Lys Lys Ala Tyr Gln Lys Leu Cys Tyr Ile His His Ile Met
50                  55                  60

Gly Lys Val Pro Asp Ala Cys Thr Ala Cys Asp Leu Val Asn Val Asp
65                  70                  75                  80

Leu Asp Asp Cys Ile Phe Glu Gln
                85
```

<210> SEQ ID NO 64
<211> LENGTH: 306
<212> TYPE: DNA
<213> ORGANISM: Artificial Sequence
<220> FEATURE:
<223> OTHER INFORMATION: Synthetic polynucleotide

<400> SEQUENCE: 64

```
atgccggggt tctacgagat tgtcctgaag gtcccgagtg acctggacga gcacctgccg      60
ggcatttcta actcgtttgt taactgggtg gccgagaagg aatgggagct gccgccggat     120
tctgacatgg atccgaatct gattgagcag gcacccctga ccgtggccga aaagcttcag     180
cgcgagttcc tggtggagtg gcgccgcgtg agtaaggccc cggaggccct cttttttgtc     240
cagttcgaaa aggggagac ctacttccac ctgcacgtgc tgattgagac catcggggtc      300
aaatcc                                                                306
```

<210> SEQ ID NO 65
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 65

```
atggtggtcg gccgctacgt gagccagatt aaagagaagc tggtgacccg catctaccgc      60
ggggtcgagc cgcagcttcc gaactggttc gcggtgacca aaacgcgaaa tggcgccggg     120
ggcgggaaca aggtggtgga cgactgctac atccccaact acctgctccc caagacccag     180
cccgagctcc agtgggcgtg gactaacatg gaccagtatt taagcgcctg tttgaatctc     240
gcggagcgta acggctggt ggcgcagcat ctgacgcacg tgtcgcagac gcaggagcag      300
aacaaagaga tcagaaccc caattctgac gcgccggtca tcaggtcaaa aacctcagcc      360
aggtacatgg agctggtcgg gtggctggtg gaccgcggga tcacgtcaga aaagcaatgg     420
```

<210> SEQ ID NO 66
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 66

```
attcaggagg accaggcctc gtacatctcc ttcaacgccg cctccaactc gcggtcccag      60
atcaaggccg cgctggacaa tgcctccaag atcatgagcc tgacaaagac ggctccggac     120
tacctggtgg gcagcaaccc gccggaggac attaccaaaa atcggatcta ccaaatcctg     180
gagctgaacg gtacgatcc gcagtacgcg gcctccgtct tcctgggctg ggcgcaaaag     240
aagttcggga agaggaacac catctggctc tttgggccgg ccacgacggg taaaaccaac     300
atcgcggaag ccatcgccca cgccgtgccc ttctacggct gcgtaaactg gaccaatgag     360
aactttcccct tcaacgattg c                                              381
```

<210> SEQ ID NO 67
<211> LENGTH: 768
<212> TYPE: DNA
<213> ORGANISM: Artificial Sequence
<220> FEATURE:
<223> OTHER INFORMATION: Synthetic polynucleotide

<400> SEQUENCE: 67

```
gtcgacaaga tggtgatctg gtgggaggag ggcaagatga cggccaaggt cgtggagagc    60
gccaaggcca ttctgggcgg aagcaaggtg cgcgtggacc aaaagtgcaa gtcatcggcc   120
cagatcgaac ccactcccgt gatcgtcacc tccaacacca acatgtgcgc cgtgattgac   180
gggaacagca ccaccttcga gcatcagcag ccgctgcagg accggatgtt taaatttgaa   240
cttacccgcc gtttggacca tgactttggg aaggtcacca acaggaagt aaaggacttt    300
ttccggtggg cttccgatca cgtgactgac gtggctcatg agttctacgt cagaaagggt   360
ggagctaaga aacgccccgc ctccaatgac gcggatgtaa gcgagccaaa acggcagtgc   420
acgtcacttg cgcagccgac aacgtcagac gcggaagcac cggcggacta cgcggacagg   480
taccaaaaca aatgttctcg tcacgtgggc atgaatctga tgcttttcc ctgtaaaaca    540
tgcgagagaa tgaatcaaat ttccaatgtc tgttttacgc atggtcaaag agactgtggg   600
gaatgcttcc ctggaatgtc agaatctcaa cccgtttctg tcgtcaaaaa gaagacttat   660
cagaaactgt gtccaattca tcatatcctg ggaagggcac ccgagattgc ctgttcggcc   720
tgcgatttgg ccaatgtgga cttggatgac tgtgtttctg agcaataa                768
```

<210> SEQ ID NO 68
<211> LENGTH: 492
<212> TYPE: DNA
<213> ORGANISM: Artificial Sequence
<220> FEATURE:
<223> OTHER INFORMATION: Synthetic polynucleotide

<400> SEQUENCE: 68

```
gtcgacaaga tggtgatctg gtgggaggag ggcaagatga cggccaaggt cgtggagagc    60
gccaaggcca ttctgggcgg aagcaaggtg cgcgtggacc aaaagtgcaa gtcatcggcc   120
cagatcgaac ccactcccgt gatcgtcacc tccaacacca acatgtgcgc cgtgattgac   180
gggaacagca ccaccttcga gcatcagcag ccgctgcagg accggatgtt taaatttgaa   240
cttacccgcc gtttggacca tgactttggg aaggtcacca acaggaagt aaaggacttt    300
ttccggtggg cttccgatca cgtgactgac gtggctcatg agttctacgt cagaaagggt   360
ggagctaaga aacgccccgc ctccaatgac gcggatgtaa gcgagccaaa acggcagtgc   420
acgtcacttg cgcagccgac aacgtcagac gcggaagcac cggcggacta cgcggacagg   480
taccaaaaca aa                                                       492
```

<210> SEQ ID NO 69
<211> LENGTH: 276
<212> TYPE: DNA
<213> ORGANISM: Artificial Sequence
<220> FEATURE:
<223> OTHER INFORMATION: Synthetic polynucleotide

<400> SEQUENCE: 69

```
tgttctcgtc acgtgggcat gaatctgatg cttttcccct gtaaaacatg cgagagaatg    60
aatcaaattt ccaatgtctg ttttacgcat ggtcaaagag actgtgggga atgcttccct   120
ggaatgtcag aatctcaacc cgtttctgtc gtcaaaaaga agacttatca gaaactgtgt   180
ccaattcatc atatcctggg aagggcaccc gagattgcct gttcggcctg cgatttggcc   240
aatgtggact tggatgactg tgtttctgag caataa                             276
```

<210> SEQ ID NO 70
<211> LENGTH: 102

```
<212> TYPE: PRT
<213> ORGANISM: Artificial Sequence
<220> FEATURE:
<223> OTHER INFORMATION: Synthetic polypeptide

<400> SEQUENCE: 70

Met Pro Gly Phe Tyr Glu Ile Val Leu Lys Val Pro Ser Asp Leu Asp
1               5                   10                  15

Glu His Leu Pro Gly Ile Ser Asn Ser Phe Val Asn Trp Val Ala Glu
            20                  25                  30

Lys Glu Trp Glu Leu Pro Pro Asp Ser Asp Met Asp Pro Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Glu Thr Tyr Phe His Leu His Val Leu Ile Glu
                85                  90                  95

Thr Ile Gly Val Lys Ser
            100

<210> SEQ ID NO 71
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 71

Met Val Val Gly Arg Tyr Val Ser Gln Ile Lys Glu Lys Leu Val Thr
1               5                   10                  15

Arg Ile Tyr Arg Gly Val Glu Pro Gln Leu Pro Asn Trp Phe Ala Val
            20                  25                  30

Thr Lys Thr Arg Asn Gly Ala Gly Gly Asn Lys Val Val Asp Asp
        35                  40                  45

Cys Tyr Ile Pro Asn Tyr Leu Leu Pro Lys Thr Gln Pro Glu Leu Gln
    50                  55                  60

Trp Ala Trp Thr Asn Met Asp Gln Tyr Leu Ser Ala Cys Leu Asn Leu
65                  70                  75                  80

Ala Glu Arg Lys Arg Leu Val Ala Gln His Leu Thr His Val Ser Gln
                85                  90                  95

Thr Gln Glu Gln Asn Lys Glu Asn Gln Asn Pro Asn Ser Asp Ala Pro
            100                 105                 110

Val Ile Arg Ser Lys Thr Ser Ala Arg Tyr Met Glu Leu Val Gly Trp
        115                 120                 125

Leu Val Asp Arg Gly Ile Thr Ser Glu Lys Gln Trp
    130                 135                 140

<210> SEQ ID NO 72
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 72

Ile Gln Glu Asp Gln Ala Ser Tyr Ile Ser Phe Asn Ala Ala Ser Asn
1               5                   10                  15

Ser Arg Ser Gln Ile Lys Ala Ala Leu Asp Asn Ala Ser Lys Ile Met
```

-continued

```
                20                  25                  30
Ser Leu Thr Lys Thr Ala Pro Asp Tyr Leu Val Gly Ser Asn Pro Pro
                35                  40                  45

Glu Asp Ile Thr Lys Asn Arg Ile Tyr Gln Ile Leu Glu Leu Asn Gly
 50                  55                  60

Tyr Asp Pro Gln Tyr Ala Ala Ser Val Phe Leu Gly Trp Ala Gln Lys
 65                  70                  75                  80

Lys Phe Gly Lys Arg Asn Thr Ile Trp Leu Phe Gly Pro Ala Thr Thr
                85                  90                  95

Gly Lys Thr Asn Ile Ala Glu Ala Ile Ala His Ala Val Pro Phe Tyr
                100                 105                 110

Gly Cys Val Asn Trp Thr Asn Glu Asn Phe Pro Phe Asn Asp Cys
                115                 120                 125
```

<210> SEQ ID NO 73
<211> LENGTH: 255
<212> TYPE: PRT
<213> ORGANISM: Artificial Sequence
<220> FEATURE:
<223> OTHER INFORMATION: Synthetic polypeptide

<400> SEQUENCE: 73

```
Val Asp Lys Met Val Ile Trp Trp Glu Gly Lys Met Thr Ala Lys
 1               5                  10                  15

Val Val Glu Ser Ala Lys Ala Ile Leu Gly Gly Ser Lys Val Arg Val
                20                  25                  30

Asp Gln Lys Cys Lys Ser Ser Ala Gln Ile Glu Pro Thr Pro Val Ile
                35                  40                  45

Val Thr Ser Asn Thr Asn Met Cys Ala Val Ile Asp Gly Asn Ser Thr
 50                  55                  60

Thr Phe Glu His Gln Gln Pro Leu Gln Asp Arg Met Phe Lys Phe Glu
 65                  70                  75                  80

Leu Thr Arg Arg Leu Asp His Asp Phe Gly Lys Val Thr Lys Gln Glu
                85                  90                  95

Val Lys Asp Phe Phe Arg Trp Ala Ser Asp His Val Thr Asp Val Ala
                100                 105                 110

His Glu Phe Tyr Val Arg Lys Gly Gly Ala Lys Lys Arg Pro Ala Ser
                115                 120                 125

Asn Asp Ala Asp Val Ser Glu Pro Lys Arg Gln Cys Thr Ser Leu Ala
 130                 135                 140

Gln Pro Thr Thr Ser Asp Ala Glu Ala Pro Ala Asp Tyr Ala Asp Arg
 145                 150                 155                 160

Tyr Gln Asn Lys Cys Ser Arg His Val Gly Met Asn Leu Met Leu Phe
                165                 170                 175

Pro Cys Lys Thr Cys Glu Arg Met Asn Gln Ile Ser Asn Val Cys Phe
                180                 185                 190

Thr His Gly Gln Arg Asp Cys Gly Glu Cys Phe Pro Gly Met Ser Glu
                195                 200                 205

Ser Gln Pro Val Ser Val Val Lys Lys Thr Tyr Gln Lys Leu Cys
                210                 215                 220

Pro Ile His His Ile Leu Gly Arg Ala Pro Glu Ile Ala Cys Ser Ala
 225                 230                 235                 240

Cys Asp Leu Ala Asn Val Asp Leu Asp Asp Cys Val Ser Glu Gln
                245                 250                 255
```

<210> SEQ ID NO 74
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 74

```
Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Ala Gln Ile Glu Pro Thr Pro Val Ile
        35                  40                  45

Val Thr Ser Asn Thr Asn Met Cys Ala Val Ile Asp Gly Asn Ser Thr
    50                  55                  60

Thr Phe Glu His Gln Gln Pro Leu Gln Asp Arg Met Phe Lys Phe Glu
65                  70                  75                  80

Leu Thr Arg Arg Leu Asp His Asp Phe Gly Lys Val Thr Lys Gln Glu
                85                  90                  95

Val Lys Asp Phe Phe Arg Trp Ala Ser Asp His Val Thr Asp Val Ala
            100                 105                 110

His Glu Phe Tyr Val Arg Lys Gly Gly Ala Lys Lys Arg Pro Ala Ser
        115                 120                 125

Asn Asp Ala Asp Val Ser Glu Pro Lys Arg Gln Cys Thr Ser Leu Ala
    130                 135                 140

Gln Pro Thr Thr Ser Asp Ala Glu Ala Pro Ala Asp Tyr Ala Asp Arg
145                 150                 155                 160

Tyr Gln Asn Lys
```

<210> SEQ ID NO 75
<211> LENGTH: 91
<212> TYPE: PRT
<213> ORGANISM: Artificial Sequence
<220> FEATURE:
<223> OTHER INFORMATION: Synthetic polypeptide

<400> SEQUENCE: 75

```
Cys Ser Arg His Val Gly Met Asn Leu Met Leu Phe Pro Cys Lys Thr
1               5                   10                  15

Cys Glu Arg Met Asn Gln Ile Ser Asn Val Cys Phe Thr His Gly Gln
            20                  25                  30

Arg Asp Cys Gly Glu Cys Phe Pro Gly Met Ser Glu Ser Gln Pro Val
        35                  40                  45

Ser Val Val Lys Lys Lys Thr Tyr Gln Lys Leu Cys Pro Ile His His
    50                  55                  60

Ile Leu Gly Arg Ala Pro Glu Ile Ala Cys Ser Ala Cys Asp Leu Ala
65                  70                  75                  80

Asn Val Asp Leu Asp Asp Cys Val Ser Glu Gln
                85                  90
```

<210> SEQ ID NO 76
<211> LENGTH: 306
<212> TYPE: DNA
<213> ORGANISM: Artificial Sequence
<220> FEATURE:
<223> OTHER INFORMATION: Synthetic polynucleotide

<400> SEQUENCE: 76

```
acgccggggt tctacgagat cgtgctgaag gtgcccagcg acctggacga gcacctgccc    60
ggcatttctg actcttttgt gagctgggtg gccgagaagg aatgggagct gccgccggat   120
tctgacatgg acttgaatct gattgagcag gcacccctga ccgtggccga aaagctgcaa   180
cgcgagttcc tggtcgagtg gcgccgcgtg agtaaggccc cggaggccct cttctttgtc   240
cagttcgaga aggggacag ctacttccac ctgcacatcc tggtggagac cgtgggcgtc    300
aaatcc                                                              306
```

<210> SEQ ID NO 77
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 77

```
atggtggtgg ccgctacgt gagccagatt aaagagaagc tggtgacccg catctaccgc    60
ggggtcgagc cgcagcttcc gaactggttc gcggtgacca agacgcgtaa tggcgccgga   120
ggcgggaaca aggtggtgga cgactgctac atccccaact acctgctccc caagacccag   180
cccgagctcc agtgggcgtg gactaacatg gaccagtata taagcgcctg tttgaatctc   240
gcggagcgta acggctggt ggcgcagcat ctgacgcacg tgtcgcagac gcaggagcag    300
aacaaggaaa accagaaccc caattctgac gcgccggtca tcaggtcaaa aacctccgcc   360
aggtacatgg agctggtcgg gtggctggtg gaccgcggga tcacgtcaga aaagcaatgg   420
```

<210> SEQ ID NO 78
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 78

```
atccaggagg accaggcgtc ctacatctcc ttcaacgccg cctccaactc gcggtcacaa    60
atcaaggccg cgctggacaa tgcctccaaa atcatgagcc tgacaaagac ggctccggac   120
tacctggtgg gccagaaccc gccggaggac atttccagca accgcatcta ccgaatcctg   180
gagatgaacg gtacgatcc gcagtacgcg gcctccgtct tcctgggctg gcgcaaaag    240 aagttcggga agaggaacac catctggctc tttgggccgg ccacgacggg taaaaccaac   300
atcgcggaag ccatcgccca cgccgtgccc ttctacggct gcgtgaactg gaccaatgag   360
aactttccgt tcaacgattg c                                             381
```

<210> SEQ ID NO 79
<211> LENGTH: 765
<212> TYPE: DNA
<213> ORGANISM: Artificial Sequence
<220> FEATURE:
<223> OTHER INFORMATION: Synthetic polynucleotide

<400> SEQUENCE: 79

```
gtcgacaaga tggtgatctg gtgggaggag ggcaagatga cggccaaggt cgtagagagc    60
gccaaggcca tcctgggcgg aagcaaggtg cgcgtggacc aaaagtgcaa gtcatcggcc   120
cagatcgacc caactcccgt gatcgtcacc tccaacacca acatgtgcgc ggtcatcgac   180
ggaaactcga ccaccttcga gcaccaacaa ccactccagg accggatgtt caagttcgag   240
ctcaccaagc gcctggagca cgactttggc aaggtcacca agcaggaagt caaagacttt   300
```

```
ttccggtggg cgtcagatca cgtgaccgag gtgactcacg agttttacgt cagaaagggt    360
ggagctagaa agaggcccgc ccccaatgac gcagatataa gtgagcccaa gcgggcctgt    420
ccgtcagttg cgcagccatc gacgtcagac gcggaagctc cggtggacta cgcggacagg    480
taccaaaaca aatgttctcg tcacgtgggt atgaatctga tgcttttttcc ctgccggcaa    540 tgcgagagaa tgaatcagaa tgtggacatt tgcttcacgc acggggtcat ggactgtgcc    600
gagtgcttcc ccgtgtcaga atctcaaccc gtgtctgtcg tcagaaagcg gacgtatcag    660
aaactgtgtc cgattcatca catcatgggg agggcgcccg aggtggcctg ctcggcctgc    720
gaactggcca atgtggactt ggatgactgt gacatggaac aataa                    765
```

<210> SEQ ID NO 80
<211> LENGTH: 492
<212> TYPE: DNA
<213> ORGANISM: Artificial Sequence
<220> FEATURE:
<223> OTHER INFORMATION: Synthetic polynucleotide

<400> SEQUENCE: 80

```
gtcgacaaga tggtgatctg gtgggaggag ggcaagatga cggccaaggt cgtagagagc     60
gccaaggcca tcctgggcgg aagcaaggtg cgcgtggacc aaaagtgcaa gtcatcggcc    120
cagatcgacc caactcccgt gatcgtcacc tccaacacca catgtgcgc ggtcatcgac     180 ggaaactcga ccaccttcga gcaccaacaa ccactccagg accggatgtt caagttcgag    240
ctcaccaagc gcctggagca cgactttggc aaggtcacca gcaggaagt caaagacttt     300 ttccggtggg cgtcagatca cgtgaccgag gtgactcacg agttttacgt cagaaagggt    360
ggagctagaa agaggcccgc ccccaatgac gcagatataa gtgagcccaa gcgggcctgt    420
ccgtcagttg cgcagccatc gacgtcagac gcggaagctc cggtggacta cgcggacagg    480
taccaaaaca aa                                                         492
```

<210> SEQ ID NO 81
<211> LENGTH: 273
<212> TYPE: DNA
<213> ORGANISM: Artificial Sequence
<220> FEATURE:
<223> OTHER INFORMATION: Synthetic polynucleotide

<400> SEQUENCE: 81

```
tgttctcgtc acgtgggtat gaatctgatg cttttttccct gccggcaatg cgagagaatg     60
aatcagaatg tggacatttg cttcacgcac ggggtcatgg actgtgccga gtgcttcccc    120
gtgtcagaat ctcaacccgt gtctgtcgtc agaaagcgga cgtatcagaa actgtgtccg    180
attcatcaca tcatggggag ggcgcccgag gtggcctgct cggcctgcga actggccaat    240
gtggacttgg atgactgtga catggaacaa taa                                  273
```

<210> SEQ ID NO 82
<211> LENGTH: 102
<212> TYPE: PRT
<213> ORGANISM: Artificial Sequence
<220> FEATURE:
<223> OTHER INFORMATION: Synthetic polypeptide

<400> SEQUENCE: 82

Thr Pro Gly Phe Tyr Glu Ile Val Leu Lys Val Pro Ser Asp Leu Asp
1               5                   10                  15

Glu His Leu Pro Gly Ile Ser Asp Ser Phe Val Ser Trp Val Ala Glu

```
            20                  25                  30
Lys Glu Trp Glu Leu Pro Pro Asp Ser Asp Met Asp Leu Asn Leu Ile
         35                  40                  45

Glu Gln Ala Pro Leu Thr Val Ala Glu Lys Leu Gln Arg Glu Phe Leu
 50                  55                  60

Val Glu Trp Arg Arg Val Ser Lys Ala Pro Glu Ala Leu Phe Phe Val
65                  70                  75                  80

Gln Phe Glu Lys Gly Asp Ser Tyr Phe His Leu His Ile Leu Val Glu
             85                  90                  95

Thr Val Gly Val Lys Ser
            100

<210> SEQ ID NO 83
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 83

Met Val Val Gly Arg Tyr Val Ser Gln Ile Lys Glu Lys Leu Val Thr
1               5                   10                  15

Arg Ile Tyr Arg Gly Val Glu Pro Gln Leu Pro Asn Trp Phe Ala Val
             20                  25                  30

Thr Lys Thr Arg Asn Gly Ala Gly Gly Asn Lys Val Asp Asp
         35                  40                  45

Cys Tyr Ile Pro Asn Tyr Leu Leu Pro Lys Thr Gln Pro Glu Leu Gln
 50                  55                  60

Trp Ala Trp Thr Asn Met Asp Gln Tyr Ile Ser Ala Cys Leu Asn Leu
65                  70                  75                  80

Ala Glu Arg Lys Arg Leu Val Ala Gln His Leu Thr His Val Ser Gln
             85                  90                  95

Thr Gln Glu Gln Asn Lys Glu Asn Gln Asn Pro Asn Ser Asp Ala Pro
            100                 105                 110

Val Ile Arg Ser Lys Thr Ser Ala Arg Tyr Met Glu Leu Val Gly Trp
            115                 120                 125

Leu Val Asp Arg Gly Ile Thr Ser Glu Lys Gln Trp
            130                 135                 140

<210> SEQ ID NO 84
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 84

Ile Gln Glu Asp Gln Ala Ser Tyr Ile Ser Phe Asn Ala Ala Ser Asn
1               5                   10                  15

Ser Arg Ser Gln Ile Lys Ala Ala Leu Asp Asn Ala Ser Lys Ile Met
             20                  25                  30

Ser Leu Thr Lys Thr Ala Pro Asp Tyr Leu Val Gly Gln Asn Pro Pro
         35                  40                  45

Glu Asp Ile Ser Ser Asn Arg Ile Tyr Arg Ile Leu Glu Met Asn Gly
 50                  55                  60

Tyr Asp Pro Gln Tyr Ala Ala Ser Val Phe Leu Gly Trp Ala Gln Lys
65                  70                  75                  80
```

Lys Phe Gly Lys Arg Asn Thr Ile Trp Leu Phe Gly Pro Ala Thr Thr
            85                  90                  95

Gly Lys Thr Asn Ile Ala Glu Ala Ile Ala His Ala Val Pro Phe Tyr
            100                 105                 110

Gly Cys Val Asn Trp Thr Asn Glu Asn Phe Pro Phe Asn Asp Cys
        115                 120                 125

<210> SEQ ID NO 85
<211> LENGTH: 254
<212> TYPE: PRT
<213> ORGANISM: Artificial Sequence
<220> FEATURE:
<223> OTHER INFORMATION: Synthetic polypeptide

<400> SEQUENCE: 85

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Ala Gln Ile Asp Pro Thr Pro Val Ile
        35                  40                  45

Val Thr Ser Asn Thr Asn Met Cys Ala Val Ile Asp Gly Asn Ser Thr
    50                  55                  60

Thr Phe Glu His Gln Gln Pro Leu Gln Asp Arg Met Phe Lys Phe Glu
65                  70                  75                  80

Leu Thr Lys Arg Leu Glu His Asp Phe Gly Lys Val Thr Lys Gln Glu
                85                  90                  95

Val Lys Asp Phe Phe Arg Trp Ala Ser Asp His Val Thr Glu Val Thr
            100                 105                 110

His Glu Phe Tyr Val Arg Lys Gly Gly Ala Arg Lys Arg Pro Ala Pro
        115                 120                 125

Asn Asp Ala Asp Ile Ser Glu Pro Lys Arg Ala Cys Pro Ser Val Ala
    130                 135                 140

Gln Pro Ser Thr Ser Asp Ala Glu Ala Pro Val Asp Tyr Ala Asp Arg
145                 150                 155                 160

Tyr Gln Asn Lys Cys Ser Arg His Val Gly Met Asn Leu Met Leu Phe
                165                 170                 175

Pro Cys Arg Gln Cys Glu Arg Met Asn Gln Asn Val Asp Ile Cys Phe
            180                 185                 190

Thr His Gly Val Met Asp Cys Ala Glu Cys Phe Pro Val Ser Glu Ser
        195                 200                 205

Gln Pro Val Ser Val Val Arg Lys Arg Thr Tyr Gln Lys Leu Cys Pro
    210                 215                 220

Ile His His Ile Met Gly Arg Ala Pro Glu Val Ala Cys Ser Ala Cys
225                 230                 235                 240

Glu Leu Ala Asn Val Asp Leu Asp Asp Cys Asp Met Glu Gln
                245                 250

<210> SEQ ID NO 86
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 86

Val Asp Lys Met Val Ile Trp Trp Glu Glu Gly Lys Met Thr Ala Lys
1               5                   10                  15

```
Val Val Glu Ser Ala Lys Ala Ile Leu Gly Gly Ser Lys Val Arg Val
         20                  25                  30

Asp Gln Lys Cys Lys Ser Ser Ala Gln Ile Asp Pro Thr Pro Val Ile
     35                  40                  45

Val Thr Ser Asn Thr Asn Met Cys Ala Val Ile Asp Gly Asn Ser Thr
 50                  55                  60

Thr Phe Glu His Gln Gln Pro Leu Gln Asp Arg Met Phe Lys Phe Glu
 65                  70                  75                  80

Leu Thr Lys Arg Leu Glu His Asp Phe Gly Lys Val Thr Lys Gln Glu
             85                  90                  95

Val Lys Asp Phe Phe Arg Trp Ala Ser Asp His Val Thr Glu Val Thr
            100                 105                 110

His Glu Phe Tyr Val Arg Lys Gly Gly Ala Arg Lys Arg Pro Ala Pro
                115                 120                 125

Asn Asp Ala Asp Ile Ser Glu Pro Lys Arg Ala Cys Pro Ser Val Ala
130                 135                 140

Gln Pro Ser Thr Ser Asp Ala Glu Ala Pro Val Asp Tyr Ala Asp Arg
145                 150                 155                 160

Tyr Gln Asn Lys

<210> SEQ ID NO 87
<211> LENGTH: 90
<212> TYPE: PRT
<213> ORGANISM: Artificial Sequence
<220> FEATURE:
<223> OTHER INFORMATION: Synthetic polypeptide

<400> SEQUENCE: 87

Cys Ser Arg His Val Gly Met Asn Leu Met Leu Phe Pro Cys Arg Gln
1               5                   10                  15

Cys Glu Arg Met Asn Gln Asn Val Asp Ile Cys Phe Thr His Gly Val
            20                  25                  30

Met Asp Cys Ala Glu Cys Phe Pro Val Ser Glu Ser Gln Pro Val Ser
        35                  40                  45

Val Val Arg Lys Arg Thr Tyr Gln Lys Leu Cys Pro Ile His His Ile
    50                  55                  60

Met Gly Arg Ala Pro Glu Val Ala Cys Ser Ala Cys Glu Leu Ala Asn
65                  70                  75                  80

Val Asp Leu Asp Asp Cys Asp Met Glu Gln
            85                  90

<210> SEQ ID NO 88
<211> LENGTH: 303
<212> TYPE: DNA
<213> ORGANISM: Artificial Sequence
<220> FEATURE:
<223> OTHER INFORMATION: Synthetic polynucleotide

<400> SEQUENCE: 88
atggctacct tctatgaagt cattgttcgc gtcccatttg acgtggagga acatctgcct     60
ggaatttctg acagctttgt ggactgggta actggtcaaa tttgggagct gcctccagag    120
tcagatttaa atttgactct ggttgaacag cctcagttga cggtggctga tagaattcgc    180
cgcgtgttcc tgtacgagtg gaacaaattt ccaagcagg agtccaaatt ctttgtgcag    240
tttgaaaagg gatctgaata ttttcatctg cacacgcttg tggagacctc cggcatctct    300
tcc                                                                  303
```

<210> SEQ ID NO 89
<211> LENGTH: 411
<212> TYPE: DNA
<213> ORGANISM: Artificial Sequence
<220> FEATURE:
<223> OTHER INFORMATION: Synthetic polynucleotide

<400> SEQUENCE: 89

| | | | | | |
|---|---|---|---|---|---|
| atggtcctcg | gccgctacgt | gagtcagatt | cgcgcccagc | tggtgaaagt | ggtcttccag | 60 |
| ggaattgaac | cccagatcaa | cgactgggtc | gccatcacca | aggtaaagaa | gggcggagcc | 120 |
| aataaggtgg | tggattctgg | gtatattccc | gcctacctgc | tgccgaaggt | ccaaccggag | 180 |
| cttcagtggg | cgtggacaaa | cctggacgag | tataaattgg | ccgccctgaa | tctggaggag | 240 |
| cgcaaacggc | tcgtcgcgca | gtttctggca | gaatcctcgc | agcgctcgca | ggaggcggct | 300 |
| tcgcagcgtg | agttctcggc | tgacccggtc | atcaaaagca | agacttccca | gaaatacatg | 360 |
| gcgctcgtca | actggctcgt | ggagcacggc | atcacttccg | agaagcagtg | g | 411 |

<210> SEQ ID NO 90
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 90

| | | | | | |
|---|---|---|---|---|---|
| atccaggaaa | atcaggagag | ctacctctcc | ttcaactcca | ccggcaactc | tcggagccag | 60 |
| atcaaggccg | cgctcgacaa | cgcgaccaaa | attatgagtc | tgacaaaaag | cgcggtggac | 120 |
| tacctcgtgg | ggagctccgt | tcccgaggac | atttcaaaaa | acagaatctg | gcaaattttt | 180 |
| gagatgaatg | gctacgaccc | ggcctacgcg | ggatccatcc | tctacggctg | gtgtcagcgc | 240 |
| tccttcaaca | agaggaacac | cgtctggctc | tacggacccg | ccacgaccgg | caagaccaac | 300 |
| atcgcggagg | ccatcgccca | cactgtgccc | ttttacggct | gcgtgaactg | gaccaatgaa | 360 |
| aactttccct | taatgactg | t | | | | 381 |

<210> SEQ ID NO 91
<211> LENGTH: 738
<212> TYPE: DNA
<213> ORGANISM: Artificial Sequence
<220> FEATURE:
<223> OTHER INFORMATION: Synthetic polynucleotide

<400> SEQUENCE: 91

| | | | | | |
|---|---|---|---|---|---|
| gtggacaaaa | tgctcatttg | gtgggaggag | ggaaagatga | ccaacaaggt | ggttgaatcc | 60 |
| gccaaggcca | tcctgggggg | ctcaaaggtg | cgggtcgatc | agaaatgtaa | atcctctgtt | 120 |
| caaattgatt | ctaccccctgt | cattgtaact | tccaatacaa | acatgtgtgt | ggtggtggat | 180 |
| gggaattcca | cgacctttga | acaccagcag | ccgctgaggg | accgcatgtt | caaatttgaa | 240 |
| ctgactaagc | ggctcccgcc | agattttggc | aagattacta | agcaggaagt | caaggacttt | 300 |
| tttgcttggg | caaaggtcaa | tcaggtgccg | gtgactcacg | agtttaaagt | tcccagggaa | 360 |
| ttggcgggaa | ctaaggggc | ggagaaatct | ctaaaacgcc | cactgggtga | cgtcaccaat | 420 |
| actagctata | aaagtctgga | gaagcgggcc | aggctctcat | tgttcccga | gacgcctcgc | 480 |
| agttcagacg | tgactgttga | tcccgctcct | ctgcgaccgc | tcaattggaa | ttcaaggtat | 540 |
| gattgcaaat | gtgactatca | tgctcaattt | gacaacattt | ctaacaaatg | tgatgaatgt | 600 |

```
gaatatttga atcggggcaa aaatggatgt atctgtcaca atgtaactca ctgtcaaatt      660
tgtcatggga ttccccctg ggaaaaggaa aacttgtcag attttgggga ttttgacgat       720
gccaataaag aacagtaa                                                    738
```

<210> SEQ ID NO 92
<211> LENGTH: 549
<212> TYPE: DNA
<213> ORGANISM: Artificial Sequence
<220> FEATURE:
<223> OTHER INFORMATION: Synthetic polynucleotide

<400> SEQUENCE: 92

```
gtggacaaaa tgctcatttg gtgggaggag ggaaagatga ccaacaaggt ggttgaatcc       60
gccaaggcca tcctgggggg ctcaaaggtg cgggtcgatc agaaatgtaa atcctctgtt      120
caaattgatt ctaccccctgt cattgtaact ccaatacaa acatgtgtgt ggtggtggat      180
gggaattcca cgacctttga acaccagcag ccgctggagg accgcatgtt caaatttgaa      240
ctgactaagc ggctcccgcc agattttggc aagattacta agcaggaagt caaggacttt      300
tttgcttggg caaaggtcaa tcaggtgccg gtgactcacg agtttaaagt tcccagggaa      360
ttggcgggaa ctaaggggc ggagaaatct ctaaaacgcc cactgggtga cgtcaccaat       420
actagctata aagtctggaa gaagcgggcc aggctctcat tgttcccga gacgcctcgc      480 agttcagacg tgactgttga tcccgctcct ctgcgaccgc tcaattggaa ttcaaggtat      540
gattgcaaa                                                              549
```

<210> SEQ ID NO 93
<211> LENGTH: 189
<212> TYPE: DNA
<213> ORGANISM: Artificial Sequence
<220> FEATURE:
<223> OTHER INFORMATION: Synthetic polynucleotide

<400> SEQUENCE: 93

```
tgtgactatc atgctcaatt tgacaacatt tctaacaaat gtgatgaatg tgaatatttg       60
aatcggggca aaatggatg tatctgtcac aatgtaactc actgtcaaat tgtcatggg       120 attccccct gggaaaagga aaacttgtca gattttgggg attttgacga tgccaataaa      180
gaacagtaa                                                              189
```

<210> SEQ ID NO 94
<211> LENGTH: 101
<212> TYPE: PRT
<213> ORGANISM: Artificial Sequence
<220> FEATURE:
<223> OTHER INFORMATION: Synthetic polypeptide

<400> SEQUENCE: 94

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80
```

```
Phe Glu Lys Gly Ser Glu Tyr Phe His Leu His Thr Leu Val Glu Thr
                85                  90                  95

Ser Gly Ile Ser Ser
            100
```

<210> SEQ ID NO 95
<211> LENGTH: 137
<212> TYPE: PRT
<213> ORGANISM: Artificial Sequence
<220> FEATURE:
<223> OTHER INFORMATION: Synthetic polypeptide

<400> SEQUENCE: 95

```
Met Val Leu Gly Arg Tyr Val Ser Gln Ile Arg Ala Gln Leu Val Lys
1               5                   10                  15

Val Val Phe Gln Gly Ile Glu Pro Gln Ile Asn Asp Trp Val Ala Ile
                20                  25                  30

Thr Lys Val Lys Lys Gly Gly Ala Asn Lys Val Val Asp Ser Gly Tyr
            35                  40                  45

Ile Pro Ala Tyr Leu Leu Pro Lys Val Gln Pro Glu Leu Gln Trp Ala
        50                  55                  60

Trp Thr Asn Leu Asp Glu Tyr Lys Leu Ala Ala Leu Asn Leu Glu Glu
65                  70                  75                  80

Arg Lys Arg Leu Val Ala Gln Phe Leu Ala Glu Ser Ser Gln Arg Ser
                85                  90                  95

Gln Glu Ala Ala Ser Gln Arg Glu Phe Ser Ala Asp Pro Val Ile Lys
            100                 105                 110

Ser Lys Thr Ser Gln Lys Tyr Met Ala Leu Val Asn Trp Leu Val Glu
        115                 120                 125

His Gly Ile Thr Ser Glu Lys Gln Trp
    130                 135
```

<210> SEQ ID NO 96
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 96

```
Ile Gln Glu Asn Gln Glu Ser Tyr Leu Ser Phe Asn Ser Thr Gly Asn
1               5                   10                  15

Ser Arg Ser Gln Ile Lys Ala Ala Leu Asp Asn Ala Thr Lys Ile Met
                20                  25                  30

Ser Leu Thr Lys Ser Ala Val Asp Tyr Leu Val Gly Ser Ser Val Pro
            35                  40                  45

Glu Asp Ile Ser Lys Asn Arg Ile Trp Gln Ile Phe Glu Met Asn Gly
        50                  55                  60

Tyr Asp Pro Ala Tyr Ala Gly Ser Ile Leu Tyr Gly Trp Cys Gln Arg
65                  70                  75                  80

Ser Phe Asn Lys Arg Asn Thr Val Trp Leu Tyr Gly Pro Ala Thr Thr
                85                  90                  95

Gly Lys Thr Asn Ile Ala Glu Ala Ile Ala His Thr Val Pro Phe Tyr
            100                 105                 110

Gly Cys Val Asn Trp Thr Asn Glu Asn Phe Pro Phe Asn Asp Cys
        115                 120                 125
```

<210> SEQ ID NO 97

```
<211> LENGTH: 245
<212> TYPE: PRT
<213> ORGANISM: Artificial Sequence
<220> FEATURE:
<223> OTHER INFORMATION: Synthetic polypeptide

<400> SEQUENCE: 97

Val Asp Lys Met Leu Ile Trp Trp Glu Glu Gly Lys Met Thr Asn Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Val Gln Ile Asp Ser Thr Pro Val Ile
        35                  40                  45

Val Thr Ser Asn Thr Asn Met Cys Val Val Asp Gly Asn Ser Thr
    50                  55                  60

Thr Phe Glu His Gln Gln Pro Leu Glu Asp Arg Met Phe Lys Phe Glu
65                  70                  75                  80

Leu Thr Lys Arg Leu Pro Pro Asp Phe Gly Lys Ile Thr Lys Gln Glu
                85                  90                  95

Val Lys Asp Phe Phe Ala Trp Ala Lys Val Asn Gln Val Pro Val Thr
            100                 105                 110

His Glu Phe Lys Val Pro Arg Glu Leu Ala Gly Thr Lys Gly Ala Glu
        115                 120                 125

Lys Ser Leu Lys Arg Pro Leu Gly Asp Val Thr Asn Thr Ser Tyr Lys
130                 135                 140

Ser Leu Glu Lys Arg Ala Arg Leu Ser Phe Val Pro Glu Thr Pro Arg
145                 150                 155                 160

Ser Ser Asp Val Thr Val Asp Pro Ala Pro Leu Arg Pro Leu Asn Trp
                165                 170                 175

Asn Ser Arg Tyr Asp Cys Lys Cys Asp Tyr His Ala Gln Phe Asp Asn
            180                 185                 190

Ile Ser Asn Lys Cys Asp Glu Cys Glu Tyr Leu Asn Arg Gly Lys Asn
        195                 200                 205

Gly Cys Ile Cys His Asn Val Thr His Cys Gln Ile Cys His Gly Ile
    210                 215                 220

Pro Pro Trp Glu Lys Glu Asn Leu Ser Asp Phe Gly Asp Phe Asp Asp
225                 230                 235                 240

Ala Asn Lys Glu Gln
                245

<210> SEQ ID NO 98
<211> LENGTH: 183
<212> TYPE: PRT
<213> ORGANISM: Artificial Sequence
<220> FEATURE:
<223> OTHER INFORMATION: Synthetic polypeptide

<400> SEQUENCE: 98

Val Asp Lys Met Leu Ile Trp Trp Glu Glu Gly Lys Met Thr Asn Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Val Gln Ile Asp Ser Thr Pro Val Ile
        35                  40                  45

Val Thr Ser Asn Thr Asn Met Cys Val Val Asp Gly Asn Ser Thr
    50                  55                  60

Thr Phe Glu His Gln Gln Pro Leu Glu Asp Arg Met Phe Lys Phe Glu
```

```
                65                  70                  75                  80
Leu Thr Lys Arg Leu Pro Pro Asp Phe Gly Lys Ile Thr Lys Gln Glu
                    85                  90                  95

Val Lys Asp Phe Phe Ala Trp Ala Lys Val Asn Gln Val Pro Val Thr
                100                 105                 110

His Glu Phe Lys Val Pro Arg Glu Leu Ala Gly Thr Lys Gly Ala Glu
                115                 120                 125

Lys Ser Leu Lys Arg Pro Leu Gly Asp Val Thr Asn Thr Ser Tyr Lys
130                 135                 140

Ser Leu Glu Lys Arg Ala Arg Leu Ser Phe Val Pro Glu Thr Pro Arg
145                 150                 155                 160

Ser Ser Asp Val Thr Val Asp Pro Ala Pro Leu Arg Pro Leu Asn Trp
                165                 170                 175

Asn Ser Arg Tyr Asp Cys Lys
                180

<210> SEQ ID NO 99
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 99

Cys Asp Tyr His Ala Gln Phe Asp Asn Ile Ser Asn Lys Cys Asp Glu
1               5                   10                  15

Cys Glu Tyr Leu Asn Arg Gly Lys Asn Gly Cys Ile Cys His Asn Val
                20                  25                  30

Thr His Cys Gln Ile Cys His Gly Ile Pro Pro Trp Glu Lys Glu Asn
            35                  40                  45

Leu Ser Asp Phe Gly Asp Phe Asp Asp Ala Asn Lys Glu Gln
        50                  55                  60

<210> SEQ ID NO 100
<211> LENGTH: 306
<212> TYPE: DNA
<213> ORGANISM: Artificial Sequence
<220> FEATURE:
<223> OTHER INFORMATION: Synthetic polynucleotide

<400> SEQUENCE: 100
atgccggggt tttacgagat tgtgattaag gtccccagcg accttgacga gcatctgccc        60
ggcatttctg acagctttgt gaactgggtg gccgagaagg aatgggagtt gccgccagat       120
tctgacatgg atctgaatct gattgagcag gcacccctga ccgtggccga gaagctgcag       180
cgcgacttcc tggtccagtg gcgccgcgtg agtaaggccc cggaggccct cttctttgtt       240
cagttcgaga agggcgagtc ctacttccac ctccatattc tggtggagac cacgggggtc       300
aaatcc                                                                  306

<210> SEQ ID NO 101
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 101
atggtgctgg gccgcttcct gagtcagatt agggacaagc tggtgcagac catctaccgc        60
```

```
gggatcgagc cgaccctgcc caactggttc gcggtgacca agacgcgtaa tggcgccgga    120
ggggggaaca aggtggtgga cgagtgctac atccccaact acctcctgcc caagactcag    180
cccgagctgc agtgggcgtg gactaacatg gaggagtata aagcgcgtg tttaaacctg     240 gccgagcgca acggctcgt ggcgcacgac ctgacccacg tcagccagac ccaggagcag     300
aacaaggaga atctgaaccc caattctgac gcgcctgtca tccggtcaaa aacctccgca    360
cgctacatgg agctggtcgg gtggctggtg gaccggggca tcacctccga gaagcagtgg    420
```

<210> SEQ ID NO 102
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 102

```
atccaggagg accaggcctc gtacatctcc ttcaacgccg cctccaactc gcggtcccag     60
atcaaggccg ctctggacaa tgccggcaag atcatggcgc tgaccaaatc cgcgcccgac    120
tacctggtag gccccgctcc gcccgccgac attaaaacca accgcattta ccgcatcctg    180
gagctgaacg gctacgaccc tgcctacgcc ggctccgtct ttctcggctg ggcccagaaa    240
aggttcggaa aacgcaacac catctggctg tttgggccgg ccaccacggg caagaccaac    300
atcgcggaag ccatcgccca cgccgtgccc ttctacggct gcgtcaactg gaccaatgag    360
aactttccct tcaacgattg c                                              381
```

<210> SEQ ID NO 103
<211> LENGTH: 765
<212> TYPE: DNA
<213> ORGANISM: Artificial Sequence
<220> FEATURE:
<223> OTHER INFORMATION: Synthetic polynucleotide

<400> SEQUENCE: 103

```
gtcgacaaga tggtgatctg gtgggaggag ggcaagatga cggccaaggt cgtggagtcc     60
gccaaggcca ttctcggcgg cagcaaggtg cgcgtggacc aaaagtgcaa gtcgtccgcc    120
cagatcgatc ccacccccgt gatcgtcacc tccaacacca acatgtgcgc cgtgattgac    180
gggaacagca ccaccttcga gcaccagcag ccgttcagg accggatgtt caaatttgaa     240
ctcacccgcc gtctggagca tgactttggc aaggtgacaa agcaggaagt caaagagttc    300
ttccgctggg cgcaggatca cgtgaccgag gtggcgcatg agttctacgt cagaaagggt    360
ggagccaaca agagacccgc ccccgatgac gcggataaaa gcgagcccaa gcgggcctgc    420
ccctcagtcg cggatccatc gacgtcgac gcggaaggag ctccggtgga ctttgccgac    480
aggtaccaaa acaaatgttc tcgtcacgcg ggcatgcttc agatgctgtt tccctgcaaa    540
acatgcgaga gaatgaatca gaatttcaac atttgcttca cgcacgggac cagagactgt    600
tcagaatgtt tccccggcgt gtcagaatct caaccggtcg tcagaaagag gacgtatcgg    660
aaactctgtg ccattcatca tctgctgggg cgggctcccg agattgcttg ctcggcctgc    720
gatctggtca acgtggatct ggatgactgt gtttctgagc aataa                    765
```

<210> SEQ ID NO 104
<211> LENGTH: 495
<212> TYPE: DNA
<213> ORGANISM: Artificial Sequence
<220> FEATURE:
<223> OTHER INFORMATION: Synthetic polynucleotide

<400> SEQUENCE: 104

```
gtcgacaaga tggtgatctg gtgggaggag ggcaagatga cggccaaggt cgtggagtcc    60
gccaaggcca ttctcggcgg cagcaaggtg cgcgtggacc aaaagtgcaa gtcgtccgcc   120
cagatcgatc ccaccccgt gatcgtcacc tccaacacca acatgtgcgc cgtgattgac    180
gggaacagca ccaccttcga gcaccagcag ccgttgcagg accggatgtt caaatttgaa   240
ctcacccgcc gtctggagca tgactttggc aaggtgacaa agcaggaagt caaagagttc   300
ttccgctggg cgcaggatca cgtgaccgag gtggcgcatg agttctacgt cagaaagggt   360
ggagccaaca agagacccgc ccccgatgac gcggataaaa gcgagcccaa gcgggcctgc   420
ccctcagtcg cggatccatc gacgtcagac gcggaaggag ctccggtgga ctttgccgac   480
aggtaccaaa acaaa                                                    495
```

<210> SEQ ID NO 105
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 105

```
tgttctcgtc acgcgggcat gcttcagatg ctgtttccct gcaaaacatg cgagagaatg    60
aatcagaatt tcaacatttg cttcacgcac gggaccagag actgttcaga atgtttcccc   120
ggcgtgtcag aatctcaacc ggtcgtcaga aagaggacgt atcggaaact ctgtgccatt   180
catcatctgc tggggcgggc tcccgagatt gcttgctcgg cctgcgatct ggtcaacgtg   240
gatctggatg actgtgtttc tgagcaataa                                    270
```

<210> SEQ ID NO 106
<211> LENGTH: 102
<212> TYPE: PRT
<213> ORGANISM: Artificial Sequence
<220> FEATURE:
<223> OTHER INFORMATION: Synthetic polypeptide

<400> SEQUENCE: 106

```
Met Pro Gly Phe Tyr Glu Ile Val Ile Lys Val Pro Ser Asp Leu Asp
1               5                   10                  15
Glu His Leu Pro Gly Ile Ser Asp Ser Phe Val Asn Trp Val Ala Glu
                20                  25                  30
Lys Glu Trp Glu Leu Pro Pro Asp Ser Asp Met Asp Leu Asn Leu Ile
            35                  40                  45
Glu Gln Ala Pro Leu Thr Val Ala Glu Lys Leu Gln Arg Asp Phe Leu
        50                  55                  60
Val Gln Trp Arg Arg Val Ser Lys Ala Pro Glu Ala Leu Phe Phe Val
65                  70                  75                  80
Gln Phe Glu Lys Gly Glu Ser Tyr Phe His Leu His Ile Leu Val Glu
                85                  90                  95
Thr Thr Gly Val Lys Ser
            100
```

<210> SEQ ID NO 107
<211> LENGTH: 140
<212> TYPE: PRT
<213> ORGANISM: Artificial Sequence
<220> FEATURE:
<223> OTHER INFORMATION: Synthetic polypeptide -continued

```
<400> SEQUENCE: 107

Met Val Leu Gly Arg Phe Leu Ser Gln Ile Arg Asp Lys Leu Val Gln
1               5                   10                  15

Thr Ile Tyr Arg Gly Ile Glu Pro Thr Leu Pro Asn Trp Phe Ala Val
            20                  25                  30

Thr Lys Thr Arg Asn Gly Ala Gly Gly Asn Lys Val Val Asp Glu
        35                  40                  45

Cys Tyr Ile Pro Asn Tyr Leu Leu Pro Lys Thr Gln Pro Glu Leu Gln
50                  55                  60

Trp Ala Trp Thr Asn Met Glu Glu Tyr Ile Ser Ala Cys Leu Asn Leu
65                  70                  75                  80

Ala Glu Arg Lys Arg Leu Val Ala His Asp Leu Thr His Val Ser Gln
                85                  90                  95

Thr Gln Glu Gln Asn Lys Glu Asn Leu Asn Pro Asn Ser Asp Ala Pro
            100                 105                 110

Val Ile Arg Ser Lys Thr Ser Ala Arg Tyr Met Glu Leu Val Gly Trp
        115                 120                 125

Leu Val Asp Arg Gly Ile Thr Ser Glu Lys Gln Trp
    130                 135                 140

<210> SEQ ID NO 108
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 108

Ile Gln Glu Asp Gln Ala Ser Tyr Ile Ser Phe Asn Ala Ala Ser Asn
1               5                   10                  15

Ser Arg Ser Gln Ile Lys Ala Ala Leu Asp Asn Ala Gly Lys Ile Met
            20                  25                  30

Ala Leu Thr Lys Ser Ala Pro Asp Tyr Leu Val Gly Pro Ala Pro Pro
        35                  40                  45

Ala Asp Ile Lys Thr Asn Arg Ile Tyr Arg Ile Leu Glu Leu Asn Gly
    50                  55                  60

Tyr Asp Pro Ala Tyr Ala Gly Ser Val Phe Leu Gly Trp Ala Gln Lys
65                  70                  75                  80

Arg Phe Gly Lys Arg Asn Thr Ile Trp Leu Phe Gly Pro Ala Thr Thr
                85                  90                  95

Gly Lys Thr Asn Ile Ala Glu Ala Ile Ala His Ala Val Pro Phe Tyr
            100                 105                 110

Gly Cys Val Asn Trp Thr Asn Glu Asn Phe Pro Phe Asn Asp Cys
        115                 120                 125

<210> SEQ ID NO 109
<211> LENGTH: 254
<212> TYPE: PRT
<213> ORGANISM: Artificial Sequence
<220> FEATURE:
<223> OTHER INFORMATION: Synthetic polypeptide

<400> SEQUENCE: 109

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30
```

```
Asp Gln Lys Cys Lys Ser Ser Ala Gln Ile Asp Pro Thr Pro Val Ile
            35                  40                  45

Val Thr Ser Asn Thr Asn Met Cys Ala Val Ile Asp Gly Asn Ser Thr
     50                  55                  60

Thr Phe Glu His Gln Gln Pro Leu Gln Asp Arg Met Phe Lys Phe Glu
 65                  70                  75                  80

Leu Thr Arg Arg Leu Glu His Asp Phe Gly Lys Val Thr Lys Gln Glu
                 85                  90                  95

Val Lys Glu Phe Phe Arg Trp Ala Gln Asp His Val Thr Glu Val Ala
                100                 105                 110

His Glu Phe Tyr Val Arg Lys Gly Gly Ala Asn Lys Arg Pro Ala Pro
            115                 120                 125

Asp Asp Ala Asp Lys Ser Glu Pro Lys Arg Ala Cys Pro Ser Val Ala
130                 135                 140

Asp Pro Ser Thr Ser Asp Ala Glu Gly Ala Pro Val Asp Phe Ala Asp
145                 150                 155                 160

Arg Tyr Gln Asn Lys Cys Ser Arg His Ala Gly Met Leu Gln Met Leu
                165                 170                 175

Phe Pro Cys Lys Thr Cys Glu Arg Met Asn Gln Asn Phe Asn Ile Cys
            180                 185                 190

Phe Thr His Gly Thr Arg Asp Cys Ser Glu Cys Phe Pro Gly Val Ser
            195                 200                 205

Glu Ser Gln Pro Val Val Arg Lys Arg Thr Tyr Arg Lys Leu Cys Ala
            210                 215                 220

Ile His His Leu Leu Gly Arg Ala Pro Glu Ile Ala Cys Ser Ala Cys
225                 230                 235                 240

Asp Leu Val Asn Val Asp Leu Asp Asp Cys Val Ser Glu Gln
                245                 250

<210> SEQ ID NO 110
<211> LENGTH: 165
<212> TYPE: PRT
<213> ORGANISM: Artificial Sequence
<220> FEATURE:
<223> OTHER INFORMATION: Synthetic polypeptide

<400> SEQUENCE: 110

Val Asp Lys Met Val Ile Trp Trp Glu Glu Gly Lys Met Thr Ala Lys
 1               5                  10                  15

Val Val Glu Ser Ala Lys Ala Ile Leu Gly Gly Ser Lys Val Arg Val
             20                  25                  30

Asp Gln Lys Cys Lys Ser Ser Ala Gln Ile Asp Pro Thr Pro Val Ile
            35                  40                  45

Val Thr Ser Asn Thr Asn Met Cys Ala Val Ile Asp Gly Asn Ser Thr
     50                  55                  60

Thr Phe Glu His Gln Gln Pro Leu Gln Asp Arg Met Phe Lys Phe Glu
 65                  70                  75                  80

Leu Thr Arg Arg Leu Glu His Asp Phe Gly Lys Val Thr Lys Gln Glu
                 85                  90                  95

Val Lys Glu Phe Phe Arg Trp Ala Gln Asp His Val Thr Glu Val Ala
                100                 105                 110

His Glu Phe Tyr Val Arg Lys Gly Gly Ala Asn Lys Arg Pro Ala Pro
            115                 120                 125

Asp Asp Ala Asp Lys Ser Glu Pro Lys Arg Ala Cys Pro Ser Val Ala
130                 135                 140
```

Asp Pro Ser Thr Ser Asp Ala Glu Gly Ala Pro Val Asp Phe Ala Asp
145                 150                 155                 160

Arg Tyr Gln Asn Lys
            165

<210> SEQ ID NO 111
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 111

Cys Ser Arg His Ala Gly Met Leu Gln Met Leu Phe Pro Cys Lys Thr
1               5                   10                  15

Cys Glu Arg Met Asn Gln Asn Phe Asn Ile Cys Phe Thr His Gly Thr
                20                  25                  30

Arg Asp Cys Ser Glu Cys Phe Pro Gly Val Ser Glu Ser Gln Pro Val
            35                  40                  45

Val Arg Lys Arg Thr Tyr Arg Lys Leu Cys Ala Ile His His Leu Leu
    50                  55                  60

Gly Arg Ala Pro Glu Ile Ala Cys Ser Ala Cys Asp Leu Val Asn Val
65                  70                  75                  80

Asp Leu Asp Asp Cys Val Ser Glu Gln
                85

<210> SEQ ID NO 112
<211> LENGTH: 306
<212> TYPE: DNA
<213> ORGANISM: Artificial Sequence
<220> FEATURE:
<223> OTHER INFORMATION: Synthetic polynucleotide

<400> SEQUENCE: 112
acgccgggtt tctacgagat cgtgatcaag gtgccgagcg acctggacga gcacctgccg      60
ggcatttctg actcgtttgt gaactgggtg gccgagaagg aatgggagct gcccccggat     120
tctgacatgg atctgaatct gatcgagcag gcacccctga ccgtggccga aagctgcag     180 cgcgacttcc tggtccaatg cgccgcgtg agtaaggccc cggaggccct gttctttgtt     240
cagttcgaga agggcgagag ctacttccac cttcacgttc tggtggagac cacggggggtc    300 aagtcc                                                               306

<210> SEQ ID NO 113
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 113
atggtgctag gccgcttcct gagtcagatt cgggagaagc tggtccagac catctaccgc      60
ggggtcgagc ccacgctgcc caactggttc gcggtgacca agacgcgtaa tggcgccggc     120
ggggggaaca aggtggtgga cgagtgctac atccccaact acctcctgcc caagacccag     180
cccgagctgc agtgggcgtg gactaacatg gaggagtata agcgcgtg tttgaacctg       240 gccgaacgca acggctcgt ggcgcagcac ctgacccacg tcagccagac gcaggagcag     300
aacaaggaga atctgaaccc caattctgac gcgcccgtga tcaggtcaaa aacctccgcg     360
cgctacatgg agctggtcgg gtggctggtg gaccggggca tcacctccga gaagcagtgg    420

<210> SEQ ID NO 114
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 114
atccaggagg accaggcctc gtacatctcc ttcaacgccg cctccaactc gcggtcccag     60
atcaaggccg cgctggacaa tgccggcaag atcatggcgc tgaccaaatc cgcgcccgac    120
tacctggtgg ggccctcgct gcccgcggac attaaaacca accgcatcta ccgcatcctg    180
gagctgaacg gtacgatcc tgcctacgcc ggctccgtct ttctcggctg ggcccagaaa    240
aagttcggga agcgcaacac catctggctg tttgggcccg ccaccaccgg caagaccaac    300
attgcggaag ccatcgccca cgccgtgccc ttctacggct cgtcaactg gaccaatgag    360 aactttccct tcaacgattg c                                              381

<210> SEQ ID NO 115
<211> LENGTH: 765
<212> TYPE: DNA
<213> ORGANISM: Artificial Sequence
<220> FEATURE:
<223> OTHER INFORMATION: Synthetic polynucleotide

<400> SEQUENCE: 115
gtcgacaaga tggtgatctg gtgggaggag ggcaagatga cggccaaggt cgtggagtcc     60
gccaaggcca ttctcggcgg cagcaaggtg cgcgtggacc aaaagtgcaa gtcgtccgcc    120
cagatcgacc ccacccccgt gatcgtcacc tccaacacca acatgtgcgc cgtgattgac    180
gggaacagca ccaccttcga gcaccagcag ccgttgcagg accggatgtt caaatttgaa    240
ctcacccgcc gtctggagca cgactttggc aaggtgacga agcaggaagt caaagagttc    300
ttccgctggg ccagtgatca cgtgaccgag gtggcgcatg agttctacgt cagaaagggc    360
ggagccagca aaagacccgc ccccgatgac gcggatataa gcgagcccaa gcgggcctgc    420
ccctcagtcg cggatccatc gacgtcagac gcggaaggag ctccggtgga ctttgccgac    480
aggtaccaaa acaaatgttc tcgtcacgcg gcatgattc agatgctgtt ccctgcaaa    540 acgtgcgaga gaatgaatca gaatttcaac atttgcttca cacacggggt cagagactgt    600
ttagagtgtt tccccggcgt gtcagaatct caaccggtcg tcagaaaaaa gacgtatcgg    660
aaactctgcg cgattcatca tctgctgggg cgggcgcccg agattgcttg ctcggcctgc    720
gacctggtca acgtggacct ggacgactgc gtttctgagc aataa                     765

<210> SEQ ID NO 116
<211> LENGTH: 495
<212> TYPE: DNA
<213> ORGANISM: Artificial Sequence
<220> FEATURE:
<223> OTHER INFORMATION: Synthetic polynucleotide

<400> SEQUENCE: 116
gtcgacaaga tggtgatctg gtgggaggag ggcaagatga cggccaaggt cgtggagtcc     60
gccaaggcca ttctcggcgg cagcaaggtg cgcgtggacc aaaagtgcaa gtcgtccgcc    120
cagatcgacc ccacccccgt gatcgtcacc tccaacacca acatgtgcgc cgtgattgac    180
gggaacagca ccaccttcga gcaccagcag ccgttgcagg accggatgtt caaatttgaa    240

```
ctcacccgcc gtctggagca cgactttggc aaggtgacga agcaggaagt caaagagttc    300
ttccgctggg ccagtgatca cgtgaccgag gtggcgcatg agttctacgt cagaaagggc    360
ggagccagca aaagacccgc ccccgatgac gcggatataa gcgagcccaa gcgggcctgc    420
ccctcagtcg cggatccatc gacgtcagac gcggaaggag ctccggtgga ctttgccgac    480
aggtaccaaa acaaa                                                     495

<210> SEQ ID NO 117
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 117
tgttctcgtc acgcgggcat gattcagatg ctgtttccct gcaaaacgtg cgagagaatg    60
aatcagaatt tcaacatttg cttcacacac ggggtcagag actgtttaga gtgtttcccc    120
ggcgtgtcag aatctcaacc ggtcgtcaga aaaagacgt atcggaaact ctgcgcgatt     180
catcatctgc tggggcgggc gcccgagatt gcttgctcgg cctgcgacct ggtcaacgtg    240
gacctggacg actgcgtttc tgagcaataa                                    270

<210> SEQ ID NO 118
<211> LENGTH: 102
<212> TYPE: PRT
<213> ORGANISM: Artificial Sequence
<220> FEATURE:
<223> OTHER INFORMATION: Synthetic polypeptide

<400> SEQUENCE: 118

Thr Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser
            100

<210> SEQ ID NO 119
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 119

Met Val Leu Gly Arg Phe Leu Ser Gln Ile Arg Glu Lys Leu Val Gln
1               5                   10                  15

Thr Ile Tyr Arg Gly Val Glu Pro Thr Leu Pro Asn Trp Phe Ala Val
            20                  25                  30

Thr Lys Thr Arg Asn Gly Ala Gly Gly Gly Asn Lys Val Val Asp Glu
```

```
            35                  40                  45

Cys Tyr Ile Pro Asn Tyr Leu Leu Pro Lys Thr Gln Pro Glu Leu Gln
 50                  55                  60

Trp Ala Trp Thr Asn Met Glu Glu Tyr Ile Ser Ala Cys Leu Asn Leu
 65                  70                  75                  80

Ala Glu Arg Lys Arg Leu Val Ala Gln His Leu Thr His Val Ser Gln
                 85                  90                  95

Thr Gln Glu Gln Asn Lys Glu Asn Leu Asn Pro Asn Ser Asp Ala Pro
                100                 105                 110

Val Ile Arg Ser Lys Thr Ser Ala Arg Tyr Met Glu Leu Val Gly Trp
                115                 120                 125

Leu Val Asp Arg Gly Ile Thr Ser Glu Lys Gln Trp
                130                 135                 140

<210> SEQ ID NO 120
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 120

Ile Gln Glu Asp Gln Ala Ser Tyr Ile Ser Phe Asn Ala Ala Ser Asn
 1                   5                  10                  15

Ser Arg Ser Gln Ile Lys Ala Ala Leu Asp Asn Ala Gly Lys Ile Met
                 20                  25                  30

Ala Leu Thr Lys Ser Ala Pro Asp Tyr Leu Val Gly Pro Ser Leu Pro
                 35                  40                  45

Ala Asp Ile Lys Thr Asn Arg Ile Tyr Arg Ile Leu Glu Leu Asn Gly
 50                  55                  60

Tyr Asp Pro Ala Tyr Ala Gly Ser Val Phe Leu Gly Trp Ala Gln Lys
 65                  70                  75                  80

Lys Phe Gly Lys Arg Asn Thr Ile Trp Leu Phe Gly Pro Ala Thr Thr
                 85                  90                  95

Gly Lys Thr Asn Ile Ala Glu Ala Ile Ala His Ala Val Pro Phe Tyr
                100                 105                 110

Gly Cys Val Asn Trp Thr Asn Glu Asn Phe Pro Phe Asn Asp Cys
                115                 120                 125

<210> SEQ ID NO 121
<211> LENGTH: 254
<212> TYPE: PRT
<213> ORGANISM: Artificial Sequence
<220> FEATURE:
<223> OTHER INFORMATION: Synthetic polypeptide

<400> SEQUENCE: 121

Val Asp Lys Met Val Ile Trp Trp Glu Glu Gly Lys Met Thr Ala Lys
 1                   5                  10                  15

Val Val Glu Ser Ala Lys Ala Ile Leu Gly Gly Ser Lys Val Arg Val
                 20                  25                  30

Asp Gln Lys Cys Lys Ser Ser Ala Gln Ile Asp Pro Thr Pro Val Ile
                 35                  40                  45

Val Thr Ser Asn Thr Asn Met Cys Ala Val Ile Asp Gly Asn Ser Thr
 50                  55                  60

Thr Phe Glu His Gln Gln Pro Leu Gln Asp Arg Met Phe Lys Phe Glu
 65                  70                  75                  80
```

```
Leu Thr Arg Arg Leu Glu His Asp Phe Gly Lys Val Thr Lys Gln Glu
            85                  90                  95

Val Lys Glu Phe Phe Arg Trp Ala Ser Asp His Val Thr Glu Val Ala
        100                 105                 110

His Glu Phe Tyr Val Arg Lys Gly Gly Ala Ser Lys Arg Pro Ala Pro
            115                 120                 125

Asp Asp Ala Asp Ile Ser Glu Pro Lys Arg Ala Cys Pro Ser Val Ala
130                 135                 140

Asp Pro Ser Thr Ser Asp Ala Glu Gly Ala Pro Val Asp Phe Ala Asp
145                 150                 155                 160

Arg Tyr Gln Asn Lys Cys Ser Arg His Ala Gly Met Ile Gln Met Leu
                165                 170                 175

Phe Pro Cys Lys Thr Cys Glu Arg Met Asn Gln Asn Phe Asn Ile Cys
            180                 185                 190

Phe Thr His Gly Val Arg Asp Cys Leu Glu Cys Phe Pro Gly Val Ser
            195                 200                 205

Glu Ser Gln Pro Val Val Arg Lys Lys Thr Tyr Arg Lys Leu Cys Ala
        210                 215                 220

Ile His His Leu Leu Gly Arg Ala Pro Glu Ile Ala Cys Ser Ala Cys
225                 230                 235                 240

Asp Leu Val Asn Val Asp Leu Asp Asp Cys Val Ser Glu Gln
                245                 250

<210> SEQ ID NO 122
<211> LENGTH: 165
<212> TYPE: PRT
<213> ORGANISM: Artificial Sequence
<220> FEATURE:
<223> OTHER INFORMATION: Synthetic polypeptide

<400> SEQUENCE: 122

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Ala Gln Ile Asp Pro Thr Pro Val Ile
        35                  40                  45

Val Thr Ser Asn Thr Asn Met Cys Ala Val Ile Asp Gly Asn Ser Thr
    50                  55                  60

Thr Phe Glu His Gln Gln Pro Leu Gln Asp Arg Met Phe Lys Phe Glu
65                  70                  75                  80

Leu Thr Arg Arg Leu Glu His Asp Phe Gly Lys Val Thr Lys Gln Glu
            85                  90                  95

Val Lys Glu Phe Phe Arg Trp Ala Ser Asp His Val Thr Glu Val Ala
        100                 105                 110

His Glu Phe Tyr Val Arg Lys Gly Gly Ala Ser Lys Arg Pro Ala Pro
            115                 120                 125

Asp Asp Ala Asp Ile Ser Glu Pro Lys Arg Ala Cys Pro Ser Val Ala
130                 135                 140

Asp Pro Ser Thr Ser Asp Ala Glu Gly Ala Pro Val Asp Phe Ala Asp
145                 150                 155                 160

Arg Tyr Gln Asn Lys
                165

<210> SEQ ID NO 123
<211> LENGTH: 89
```

<212> TYPE: PRT
<213> ORGANISM: Artificial Sequence
<220> FEATURE:
<223> OTHER INFORMATION: Synthetic polypeptide

<400> SEQUENCE: 123

```
Cys Ser Arg His Ala Gly Met Ile Gln Met Leu Phe Pro Cys Lys Thr
1               5                   10                  15
Cys Glu Arg Met Asn Gln Asn Phe Asn Ile Cys Phe Thr His Gly Val
            20                  25                  30
Arg Asp Cys Leu Glu Cys Phe Pro Gly Val Ser Glu Ser Gln Pro Val
        35                  40                  45
Val Arg Lys Lys Thr Tyr Arg Lys Leu Cys Ala Ile His His Leu Leu
50                  55                  60
Gly Arg Ala Pro Glu Ile Ala Cys Ser Ala Cys Asp Leu Val Asn Val
65                  70                  75                  80
Asp Leu Asp Asp Cys Val Ser Glu Gln
                85
```

<210> SEQ ID NO 124
<211> LENGTH: 306
<212> TYPE: DNA
<213> ORGANISM: Artificial Sequence
<220> FEATURE:
<223> OTHER INFORMATION: Synthetic polynucleotide

<400> SEQUENCE: 124

```
atgccgggct ctacgagat cgtgatcaag gtgccgagcg acctggacga gcacctgccg    60
ggcatttctg actcgtttgt gaactgggtg gccgagaagg aatgggagct gccccggat   120
tctgacatgg atcggaatct gatcgagcag gcacccctga ccgtggccga gaagctgcag   180
cgcgacttcc tggtccaatg cgccgcgtg agtaaggccc cggaggccct cttctttgtt   240
cagttcgaga agggcgagag ctactttcac ctgcacgttc tggtcgagac cacgggggtc   300
aagtcc                                                              306
```

<210> SEQ ID NO 125
<211> LENGTH: 426
<212> TYPE: DNA
<213> ORGANISM: Artificial Sequence
<220> FEATURE:
<223> OTHER INFORMATION: Synthetic polynucleotide

<400> SEQUENCE: 125

```
atggtgctag ccgcttcct gagtcagatt cggaaaaagc ttggtccaga ccatctaccc     60
gcggggtcga gccccacctt gcccaactgg ttcgcggtga ccaaagacgc ggtaatggcg   120
ccggcggggg ggaacaaggt ggtggacgag tgctacatcc ccaactacct cctgcccaag   180
actcagcccg agctgcagtg ggcgtggact aacatggagg agtatataag cgcgtgcttg   240
aacctggccg agcgcaaacg gctcgtggcg cagcacctga cccacgtcag ccagacgcag   300
gagcagaaca aggagaatct gaaccccaat tctgacgcgc ccgtgatcag gtcaaaaacc   360
tccgcgcgct atatggagct ggtcgggtgg ctggtggacc ggggcatcac ctccgagaag   420
cagtgg                                                              426
```

<210> SEQ ID NO 126
<211> LENGTH: 420
<212> TYPE: DNA
<213> ORGANISM: Artificial Sequence
<220> FEATURE:

<223> OTHER INFORMATION: Synthetic polynucleotide

<400> SEQUENCE: 126

| | | | | | |
|---|---|---|---|---|---|
| atggtgctag | gccgcttcct | gagtcagatt | cgggaaaagc | tggtccagac | catctaccgc | 60 |
| ggggtcgagc | ccaccttgcc | caactggttc | gcggtgacca | agacgcgtaa | tggcgccggg | 120 |
| gggggaaca | aggtggtgga | cgagtgctac | atccccaact | acctcctgcc | caagactcag | 180 |
| cccgagctgc | agtgggcgtg | gactaacatg | gaggagtata | taagcgcgtg | cttgaacctg | 240 |
| gccgagcgca | acggctcgt | ggcgcagcac | ctgacccacg | tcagccagac | gcaggagcag | 300 |
| aacaaggaga | tctgaaccc | caattctgac | gcgcccgtga | tcaggtcaaa | aacctccgcg | 360 |
| cgctatatgg | agctggtcgg | gtggctggtg | gaccggggca | tcacctccga | aagcagtgg | 420 |

<210> SEQ ID NO 127
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 127

| | | | | | |
|---|---|---|---|---|---|
| atccaggagg | accaggcctc | gtacatctcc | ttcaacgccg | cctccaactc | gcggtcccag | 60 |
| atcaaggccg | cgctggacaa | tgccggcaag | atcatggcgc | tgaccaaatc | cgcgcccgac | 120 |
| tacctggtgg | ggccctcgct | gcccgcggac | attacccaga | accgcatcta | ccgcatcctc | 180 |
| gctctcaacg | gctacgaccc | tgcctacgcc | ggctccgtct | ttctcggctg | ggctcagaaa | 240 |
| aagttcggga | acgcaacac | catctggctg | tttggacccg | ccaccaccgg | caagaccaac | 300 |
| attgcggaag | ccatcgccca | cgccgtgccc | ttctacggct | gcgtcaactg | gaccaatgag | 360 |
| aactttccct | tcaatgattg | c | | | | 381 |

<210> SEQ ID NO 128
<211> LENGTH: 765
<212> TYPE: DNA
<213> ORGANISM: Artificial Sequence
<220> FEATURE:
<223> OTHER INFORMATION: Synthetic polynucleotide

<400> SEQUENCE: 128

| | | | | | |
|---|---|---|---|---|---|
| gtcgacaaga | tggtgatctg | gtgggaggag | ggcaagatga | cggccaaggt | cgtggagtcc | 60 |
| gccaaggcca | ttctcggcgg | cagcaaggtg | cgcgtggacc | aaaagtgcaa | gtcgtccgcc | 120 |
| cagatcgacc | ccaccccgt | gatcgtcacc | tccaacacca | catgtgcgc | cgtgattgac | 180 |
| gggaacagca | ccaccttcga | gcaccagcag | cctctccagg | accggatgtt | taagttcgaa | 240 |
| ctcacccgcc | gtctggagca | cgactttggc | aaggtgacaa | agcaggaagt | caaagagttc | 300 |
| ttccgctggg | ccagtgatca | cgtgaccgag | gtggcgcatg | agttttacgt | cagaaagggc | 360 |
| ggagccagca | aaagacccgc | ccccgatgac | gcggataaaa | gcgagcccaa | gcgggcctgc | 420 |
| ccctcagtcg | cggatccatc | gacgtcgac | gcggaaggag | ctccggtgga | ctttgccgac | 480 |
| aggtaccaaa | acaaatgttc | tcgtcacgcg | ggcatgcttc | agatgctgtt | tccctgcaaa | 540 |
| acgtgcgaga | gaatgaatca | gaatttcaac | atttgcttca | cacacggggt | cagagactgc | 600 |
| tcagagtgtt | tccccggcgt | gtcagaatct | caaccggtcg | tcagaaagag | gacgtatcgg | 660 |
| aaactctgtg | cgattcatca | tctgctgggg | cgggctcccg | agattgcttg | ctcggcctgc | 720 |
| gatctggtca | acgtggacct | ggatgactgt | gtttctgagc | aataa | | 765 |

<210> SEQ ID NO 129
<211> LENGTH: 495
<212> TYPE: DNA
<213> ORGANISM: Artificial Sequence
<220> FEATURE:
<223> OTHER INFORMATION: Synthetic polynucleotide

<400> SEQUENCE: 129

```
gtcgacaaga tggtgatctg gtgggaggag ggcaagatga cggccaaggt cgtggagtcc      60
gccaaggcca ttctcggcgg cagcaaggtg cgcgtggacc aaaagtgcaa gtcgtccgcc     120
cagatcgacc ccaccccccgt gatcgtcacc tccaacacca acatgtgcgc cgtgattgac    180
gggaacagca ccaccttcga gcaccagcag cctctccagg accggatgtt taagttcgaa     240
ctcacccgcc gtctggagca cgactttggc aaggtgacaa agcaggaagt caaagagttc     300
ttccgctggg ccagtgatca cgtgaccgag gtggcgcatg agttttacgt cagaaagggc     360
ggagccagca aaagacccgc ccccgatgac gcggataaaa gcgagcccaa gcgggcctgc     420
ccctcagtcg cggatccatc gacgtcagac gcggaaggag ctccggtgga ctttgccgac     480
aggtaccaaa acaaa                                                     495
```

<210> SEQ ID NO 130
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 130

```
tgttctcgtc acgcgggcat gcttcagatg ctgtttccct gcaaaacgtg cgagagaatg      60
aatcagaatt tcaacatttg cttcacacac ggggtcagag actgctcaga gtgtttcccc     120
ggcgtgtcag aatctcaacc ggtcgtcaga aagaggacgt atcggaaact ctgtgcgatt     180
catcatctgc tggggcgggc tcccgagatt gcttgctcgg cctgcgatct ggtcaacgtg     240
gacctggatg actgtgtttc tgagcaataa                                     270
```

<210> SEQ ID NO 131
<211> LENGTH: 102
<212> TYPE: PRT
<213> ORGANISM: Artificial Sequence
<220> FEATURE:
<223> OTHER INFORMATION: Synthetic polypeptide

<400> SEQUENCE: 131

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser
            100

<210> SEQ ID NO 132
<211> LENGTH: 142
<212> TYPE: PRT
<213> ORGANISM: Artificial Sequence
<220> FEATURE:
<223> OTHER INFORMATION: Synthetic polypeptide

<400> SEQUENCE: 132

```
Met Val Leu Gly Arg Phe Leu Ser Gln Ile Arg Glu Lys Leu Gly Pro
1               5                   10                  15

Asp His Leu Pro Ala Gly Ser Ser Pro Thr Leu Pro Asn Trp Phe Ala
            20                  25                  30

Val Thr Lys Asp Ala Val Met Ala Pro Ala Gly Gly Asn Lys Val Val
        35                  40                  45

Asp Glu Cys Tyr Ile Pro Asn Tyr Leu Leu Pro Lys Thr Gln Pro Glu
    50                  55                  60

Leu Gln Trp Ala Trp Thr Asn Met Glu Glu Tyr Ile Ser Ala Cys Leu
65                  70                  75                  80

Asn Leu Ala Glu Arg Lys Arg Leu Val Ala Gln His Leu Thr His Val
                85                  90                  95

Ser Gln Thr Gln Glu Gln Asn Lys Glu Asn Leu Asn Pro Asn Ser Asp
            100                 105                 110

Ala Pro Val Ile Arg Ser Lys Thr Ser Ala Arg Tyr Met Glu Leu Val
        115                 120                 125

Gly Trp Leu Val Asp Arg Gly Ile Thr Ser Glu Lys Gln Trp
    130                 135                 140
```

<210> SEQ ID NO 133
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 133

```
Met Val Leu Gly Arg Phe Leu Ser Gln Ile Arg Glu Lys Leu Val Gln
1               5                   10                  15

Thr Ile Tyr Arg Gly Val Glu Pro Thr Leu Pro Asn Trp Phe Ala Val
            20                  25                  30

Thr Lys Thr Arg Asn Gly Ala Gly Gly Gly Asn Lys Val Val Asp Glu
        35                  40                  45

Cys Tyr Ile Pro Asn Tyr Leu Leu Pro Lys Thr Gln Pro Glu Leu Gln
    50                  55                  60

Trp Ala Trp Thr Asn Met Glu Glu Tyr Ile Ser Ala Cys Leu Asn Leu
65                  70                  75                  80

Ala Glu Arg Lys Arg Leu Val Ala Gln His Leu Thr His Val Ser Gln
                85                  90                  95

Thr Gln Glu Gln Asn Lys Glu Asn Leu Asn Pro Asn Ser Asp Ala Pro
            100                 105                 110

Val Ile Arg Ser Lys Thr Ser Ala
        115                 120
```

<210> SEQ ID NO 134
<211> LENGTH: 147
<212> TYPE: PRT
<213> ORGANISM: Artificial Sequence
<220> FEATURE:
<223> OTHER INFORMATION: Synthetic polypeptide

<400> SEQUENCE: 134

```
Arg Tyr Met Glu Leu Val Gly Trp Leu Val Asp Arg Gly Ile Thr Ser
1               5                   10                  15

Glu Lys Gln Trp Ile Gln Glu Asp Gln Ala Ser Tyr Ile Ser Phe Asn
            20                  25                  30

Ala Ala Ser Asn Ser Arg Ser Gln Ile Lys Ala Ala Leu Asp Asn Ala
        35                  40                  45

Gly Lys Ile Met Ala Leu Thr Lys Ser Ala Pro Asp Tyr Leu Val Gly
    50                  55                  60

Pro Ser Leu Pro Ala Asp Ile Thr Gln Asn Arg Ile Tyr Arg Ile Leu
65                  70                  75                  80

Ala Leu Asn Gly Tyr Asp Pro Ala Tyr Ala Gly Ser Val Phe Leu Gly
                85                  90                  95

Trp Ala Gln Lys Lys Phe Gly Lys Arg Asn Thr Ile Trp Leu Phe Gly
            100                 105                 110

Pro Ala Thr Thr Gly Lys Thr Asn Ile Ala Glu Ala Ile Ala His Ala
            115                 120                 125

Val Pro Phe Tyr Gly Cys Val Asn Trp Thr Asn Glu Asn Phe Pro Phe
    130                 135                 140

Asn Asp Cys
145
```

<210> SEQ ID NO 135
<211> LENGTH: 254
<212> TYPE: PRT
<213> ORGANISM: Artificial Sequence
<220> FEATURE:
<223> OTHER INFORMATION: Synthetic polypeptide

<400> SEQUENCE: 135

```
Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Ala Gln Ile Asp Pro Thr Pro Val Ile
            35                  40                  45

Val Thr Ser Asn Thr Asn Met Cys Ala Val Ile Asp Gly Asn Ser Thr
    50                  55                  60

Thr Phe Glu His Gln Gln Pro Leu Gln Asp Arg Met Phe Lys Phe Glu
65                  70                  75                  80

Leu Thr Arg Arg Leu Glu His Asp Phe Gly Lys Val Thr Lys Gln Glu
            85                  90                  95

Val Lys Glu Phe Phe Arg Trp Ala Ser Asp His Val Thr Glu Val Ala
            100                 105                 110

His Glu Phe Tyr Val Arg Lys Gly Gly Ala Ser Lys Arg Pro Ala Pro
            115                 120                 125

Asp Asp Ala Asp Lys Ser Glu Pro Lys Arg Ala Cys Pro Ser Val Ala
            130                 135                 140

Asp Pro Ser Thr Ser Asp Ala Glu Gly Ala Pro Val Asp Phe Ala Asp
145                 150                 155                 160

Arg Tyr Gln Asn Lys Cys Ser Arg His Ala Gly Met Leu Gln Met Leu
                165                 170                 175

Phe Pro Cys Lys Thr Cys Glu Arg Met Asn Gln Asn Phe Asn Ile Cys
            180                 185                 190

Phe Thr His Gly Val Arg Asp Cys Ser Glu Cys Phe Pro Gly Val Ser
            195                 200                 205
```

```
Glu Ser Gln Pro Val Val Arg Lys Arg Thr Tyr Arg Lys Leu Cys Ala
    210                 215                 220

Ile His His Leu Leu Gly Arg Ala Pro Glu Ile Ala Cys Ser Ala Cys
225                 230                 235                 240

Asp Leu Val Asn Val Asp Leu Asp Asp Cys Val Ser Glu Gln
                245                 250

<210> SEQ ID NO 136
<211> LENGTH: 165
<212> TYPE: PRT
<213> ORGANISM: Artificial Sequence
<220> FEATURE:
<223> OTHER INFORMATION: Synthetic polypeptide

<400> SEQUENCE: 136

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Ala Gln Ile Asp Pro Thr Pro Val Ile
        35                  40                  45

Val Thr Ser Asn Thr Asn Met Cys Ala Val Ile Asp Gly Asn Ser Thr
    50                  55                  60

Thr Phe Glu His Gln Gln Pro Leu Gln Asp Arg Met Phe Lys Phe Glu
65                  70                  75                  80

Leu Thr Arg Arg Leu Glu His Asp Phe Gly Lys Val Thr Lys Gln Glu
                85                  90                  95

Val Lys Glu Phe Phe Arg Trp Ala Ser Asp His Val Thr Glu Val Ala
            100                 105                 110

His Glu Phe Tyr Val Arg Lys Gly Gly Ala Ser Lys Arg Pro Ala Pro
        115                 120                 125

Asp Asp Ala Asp Lys Ser Glu Pro Lys Arg Ala Cys Pro Ser Val Ala
    130                 135                 140

Asp Pro Ser Thr Ser Ala Glu Gly Ala Pro Val Asp Phe Ala Asp
145                 150                 155                 160

Arg Tyr Gln Asn Lys
                165

<210> SEQ ID NO 137
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 137

Cys Ser Arg His Ala Gly Met Leu Gln Met Leu Phe Pro Cys Lys Thr
1               5                   10                  15

Cys Glu Arg Met Asn Gln Asn Phe Asn Ile Cys Phe Thr His Gly Val
            20                  25                  30

Arg Asp Cys Ser Glu Cys Phe Pro Gly Val Ser Glu Ser Gln Pro Val
        35                  40                  45

Val Arg Lys Arg Thr Tyr Arg Lys Leu Cys Ala Ile His His Leu Leu
    50                  55                  60

Gly Arg Ala Pro Glu Ile Ala Cys Ser Ala Cys Asp Leu Val Asn Val
65                  70                  75                  80

Asp Leu Asp Asp Cys Val Ser Glu Gln
```

<210> SEQ ID NO 138
<211> LENGTH: 306
<212> TYPE: DNA
<213> ORGANISM: Artificial Sequence
<220> FEATURE:
<223> OTHER INFORMATION: Synthetic polynucleotide

<400> SEQUENCE: 138

```
atgccgggct tctacgagat cgtgatcaag gtgccgagcg acctggacga gcacctgccg      60
ggcatttctg actcgtttgt gaactgggtg gccgagaagg aatgggagct gcccccggat     120
tctgacatgg atcggaatct gatcgagcag gcacccctga ccgtggccga aagctgcag     180
cgcgacttcc tggtccactg gcgccgcgtg agtaaggccc cggaggccct cttctttgtt     240
cagttcgaga agggcgagtc ctactttcac ctgcacgttc tggtcgagac cacggggtc     300
aagtcc                                                                 306
```

<210> SEQ ID NO 139
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 139

```
atggtcctgg gccgcttcct gagtcagatc agagacaggc tggtgcagac catctaccgc      60
ggggtagagc ccacgctgcc caactggttc gcggtgacca agacgcgaaa tggcgccggc     120
gggggaaca aggtggtgga cgagtgctac atccccaact acctcctgcc caagacgcag     180
cccgagctgc agtgggcgtg gactaacatg gaggagtata taagcgcgtg tctgaacctc     240
gcggagcgta acggctcgt ggcgcagcac ctgacccacg tcagccagac gcaggagcag     300
aacaaggaga tctgaaccc gaattctgac gcgcccgtga tcaggtcaaa aacctccgcg     360
cgctacatgg agctggtcgg gtggctggtg accggggca tcacctccga aagcagtgg     420
```

<210> SEQ ID NO 140
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 140

```
atccaggagg accaggcctc gtacatctcc ttcaacgccg cctccaactc gcggtcccag      60
atcaaggccg cgctggacaa tgccggaaag atcatggcgc tgaccaaatc cgcgcccgac     120
tacctggtag gcccgtcctt acccgcggac attaaggcca accgcatcta ccgcatcctg     180
gagctcaacg gctacgaccc cgcctacgcc ggctccgtct tcctgggctg ggcgcagaaa     240
aagttcggta aaaggaatac aatttggctg ttcgggcccg ccaccaccgg caagaccaac     300
atcgcggaag ccatcgccca cgccgtgccc ttctacggct gcgtcaactg gaccaatgag     360
aactttccct tcaacgattg c                                                381
```

<210> SEQ ID NO 141
<211> LENGTH: 762
<212> TYPE: DNA
<213> ORGANISM: Artificial Sequence
<220> FEATURE:
<223> OTHER INFORMATION: Synthetic polynucleotide

<400> SEQUENCE: 141

```
gtcgacaaga tggtgatctg gtgggaggag ggcaagatga ccgccaaggt cgtggagtcc      60
gccaaggcca ttctgggcgg aagcaaggtg cgcgtcgacc aaaagtgcaa gtcctcggcc     120
cagatcgacc ccacgcccgt gatcgtcacc tccaacacca acatgtgcgc cgtgatcgac     180
gggaacagca ccaccttcga gcaccagcag ccccctgcagg accgcatgtt caagttcgag    240
ctcacccgcc gtctggagca cgactttggc aaggtgacca agcaggaagt caaagagttc     300
ttccgctggg ctcaggatca cgtgactgag gtgacgcatg agttctacgt cagaaagggc     360
ggagccacca aaagacccgc ccccagtgac gcggatataa gcgagcccaa gcgggcctgc     420
ccctcagttg cggagccatc gacgtcagac gcggaagcac cggtggactt tgcggacagg     480
taccaaaaca atgttctcg tcacgcgggc atgcttcaga tgctgtttcc ctgcaagaca      540
tgcgagagaa tgaatcagaa tttcaacgtc tgcttcacgc acggggtcag agactgctca     600
gagtgcttcc ccggcgcgtc agaatctcaa cctgtcgtca gaaaaaagac gtatcagaaa     660
ctgtgcgcga ttcatcatct gctggggcgg gcacccgaga ttgcgtgttc ggcctgcgat     720
ctcgtcaacg tggacttgga tgactgtgtt tctgagcaat aa                         762
```

<210> SEQ ID NO 142
<211> LENGTH: 492
<212> TYPE: DNA
<213> ORGANISM: Artificial Sequence
<220> FEATURE:
<223> OTHER INFORMATION: Synthetic polynucleotide

<400> SEQUENCE: 142

```
gtcgacaaga tggtgatctg gtgggaggag ggcaagatga ccgccaaggt cgtggagtcc      60
gccaaggcca ttctgggcgg aagcaaggtg cgcgtcgacc aaaagtgcaa gtcctcggcc     120
cagatcgacc ccacgcccgt gatcgtcacc tccaacacca acatgtgcgc cgtgatcgac     180
gggaacagca ccaccttcga gcaccagcag ccccctgcagg accgcatgtt caagttcgag    240
ctcacccgcc gtctggagca cgactttggc aaggtgacca agcaggaagt caaagagttc     300
ttccgctggg ctcaggatca cgtgactgag gtgacgcatg agttctacgt cagaaagggc     360
ggagccacca aaagacccgc ccccagtgac gcggatataa gcgagcccaa gcgggcctgc     420
ccctcagttg cggagccatc gacgtcagac gcggaagcac cggtggactt tgcggacagg     480
taccaaaaca aa                                                         492
```

<210> SEQ ID NO 143
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 143

```
tgttctcgtc acgcgggcat gcttcagatg ctgtttccct gcaagacatg cgagagaatg      60
aatcagaatt tcaacgtctg cttcacgcac ggggtcagag actgctcaga gtgcttcccc    120
ggcgcgtcag aatctcaacc tgtcgtcaga aaaaagacgt atcagaaact gtgcgcgatt    180
catcatctgc tggggcgggc acccgagatt gcgtgttcgg cctgcgatct cgtcaacgtg    240
gacttggatg actgtgtttc tgagcaataa                                     270
```

<210> SEQ ID NO 144

```
<211> LENGTH: 102
<212> TYPE: PRT
<213> ORGANISM: Artificial Sequence
<220> FEATURE:
<223> OTHER INFORMATION: Synthetic polypeptide

<400> SEQUENCE: 144

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val His Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser
            100

<210> SEQ ID NO 145
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 145

Met Val Leu Gly Arg Phe Leu Ser Gln Ile Arg Asp Arg Leu Val Gln
1               5                   10                  15

Thr Ile Tyr Arg Gly Val Glu Pro Thr Leu Pro Asn Trp Phe Ala Val
            20                  25                  30

Thr Lys Thr Arg Asn Gly Ala Gly Gly Asn Lys Val Val Asp Glu
        35                  40                  45

Cys Tyr Ile Pro Asn Tyr Leu Leu Pro Lys Thr Gln Pro Glu Leu Gln
    50                  55                  60

Trp Ala Trp Thr Asn Met Glu Glu Tyr Ile Ser Ala Cys Leu Asn Leu
65                  70                  75                  80

Ala Glu Arg Lys Arg Leu Val Ala Gln His Leu Thr His Val Ser Gln
                85                  90                  95

Thr Gln Glu Gln Asn Lys Glu Asn Leu Asn Pro Asn Ser Asp Ala Pro
            100                 105                 110

Val Ile Arg Ser Lys Thr Ser Ala Arg Tyr Met Glu Leu Val Gly Trp
        115                 120                 125

Leu Val Asp Arg Gly Ile Thr Ser Glu Lys Gln Trp
    130                 135                 140

<210> SEQ ID NO 146
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 146

Ile Gln Glu Asp Gln Ala Ser Tyr Ile Ser Phe Asn Ala Ala Ser Asn
1               5                   10                  15
```

Ser Arg Ser Gln Ile Lys Ala Ala Leu Asp Asn Ala Gly Lys Ile Met
         20                  25                  30

Ala Leu Thr Lys Ser Ala Pro Asp Tyr Leu Val Gly Pro Ser Leu Pro
         35                  40                  45

Ala Asp Ile Lys Ala Asn Arg Ile Tyr Arg Ile Leu Glu Leu Asn Gly
50                   55                  60

Tyr Asp Pro Ala Tyr Ala Gly Ser Val Phe Leu Gly Trp Ala Gln Lys
65                   70                  75                  80

Lys Phe Gly Lys Arg Asn Thr Ile Trp Leu Phe Gly Pro Ala Thr Thr
             85                  90                  95

Gly Lys Thr Asn Ile Ala Glu Ala Ile Ala His Ala Val Pro Phe Tyr
         100                 105                 110

Gly Cys Val Asn Trp Thr Asn Glu Asn Phe Pro Phe Asn Asp Cys
         115                 120                 125

<210> SEQ ID NO 147
<211> LENGTH: 253
<212> TYPE: PRT
<213> ORGANISM: Artificial Sequence
<220> FEATURE:
<223> OTHER INFORMATION: Synthetic polypeptide

<400> SEQUENCE: 147

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
             20                  25                  30

Asp Gln Lys Cys Lys Ser Ser Ala Gln Ile Asp Pro Thr Pro Val Ile
         35                  40                  45

Val Thr Ser Asn Thr Asn Met Cys Ala Val Ile Asp Gly Asn Ser Thr
50                   55                  60

Thr Phe Glu His Gln Gln Pro Leu Gln Asp Arg Met Phe Lys Phe Glu
65                   70                  75                  80

Leu Thr Arg Arg Leu Glu His Asp Phe Gly Lys Val Thr Lys Gln Glu
             85                  90                  95

Val Lys Glu Phe Phe Arg Trp Ala Gln Asp His Val Thr Glu Val Thr
         100                 105                 110

His Glu Phe Tyr Val Arg Lys Gly Gly Ala Thr Lys Arg Pro Ala Pro
         115                 120                 125

Ser Asp Ala Asp Ile Ser Glu Pro Lys Arg Ala Cys Pro Ser Val Ala
         130                 135                 140

Glu Pro Ser Thr Ser Asp Ala Glu Ala Pro Val Asp Phe Ala Asp Arg
145                 150                 155                 160

Tyr Gln Asn Lys Cys Ser Arg His Ala Gly Met Leu Gln Met Leu Phe
                165                 170                 175

Pro Cys Lys Thr Cys Glu Arg Met Asn Gln Asn Phe Asn Val Cys Phe
             180                 185                 190

Thr His Gly Val Arg Asp Cys Ser Glu Cys Phe Pro Gly Ala Ser Glu
         195                 200                 205

Ser Gln Pro Val Val Arg Lys Lys Thr Tyr Gln Lys Leu Cys Ala Ile
         210                 215                 220

His His Leu Leu Gly Arg Ala Pro Glu Ile Ala Cys Ser Ala Cys Asp
225                 230                 235                 240

Leu Val Asn Val Asp Leu Asp Asp Cys Val Ser Glu Gln
                245                 250

<210> SEQ ID NO 148
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 148

```
Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Ala Gln Ile Asp Pro Thr Pro Val Ile
        35                  40                  45

Val Thr Ser Asn Thr Asn Met Cys Ala Val Ile Asp Gly Asn Ser Thr
    50                  55                  60

Thr Phe Glu His Gln Gln Pro Leu Gln Asp Arg Met Phe Lys Phe Glu
65                  70                  75                  80

Leu Thr Arg Arg Leu Glu His Asp Phe Gly Lys Val Thr Lys Gln Glu
                85                  90                  95

Val Lys Glu Phe Phe Arg Trp Ala Gln Asp His Val Thr Glu Val Thr
            100                 105                 110

His Glu Phe Tyr Val Arg Lys Gly Gly Ala Thr Lys Arg Pro Ala Pro
        115                 120                 125

Ser Asp Ala Asp Ile Ser Glu Pro Lys Arg Ala Cys Pro Ser Val Ala
    130                 135                 140

Glu Pro Ser Thr Ser Asp Ala Glu Ala Pro Val Asp Phe Ala Asp Arg
145                 150                 155                 160

Tyr Gln Asn Lys
```

<210> SEQ ID NO 149
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 149

```
Cys Ser Arg His Ala Gly Met Leu Gln Met Leu Phe Pro Cys Lys Thr
1               5                   10                  15

Cys Glu Arg Met Asn Gln Asn Phe Asn Val Cys Phe Thr His Gly Val
            20                  25                  30

Arg Asp Cys Ser Glu Cys Phe Pro Gly Ala Ser Glu Ser Gln Pro Val
        35                  40                  45

Val Arg Lys Lys Thr Tyr Gln Lys Leu Cys Ala Ile His His Leu Leu
    50                  55                  60

Gly Arg Ala Pro Glu Ile Ala Cys Ser Ala Cys Asp Leu Val Asn Val
65                  70                  75                  80

Asp Leu Asp Asp Cys Val Ser Glu Gln
                85
```

<210> SEQ ID NO 150
<211> LENGTH: 306
<212> TYPE: DNA
<213> ORGANISM: Artificial Sequence
<220> FEATURE:
<223> OTHER INFORMATION: Synthetic polynucleotide

<400> SEQUENCE: 150

```
atgccgggct tctacgagat cgtgatcaag gtgccgagcg acctggacga gcacctgccg    60
ggcatttctg actcgtttgt gaactgggtg gccgagaagg aatgggagct gccccggat    120 tctgacatgg atcggaatct gatcgagcag gcacccctga ccgtggccga gaagctgcag   180
cgcgacttcc tggtccactg gcgccgcgtg agtaaggccc cggaggccct cttctttgtt   240
cagttcgaga agggcgagtc ctacttccac ctccacgttc tcgtcgagac cacgggggtc   300
aagtcc                                                              306
```

```
<210> SEQ ID NO 151
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 151
atggtcctgg ccgcttcct gagtcagatc agagacaggc tggtgcagac catctaccgc    60
ggggtcgagc ccacgctgcc caactggttc gcggtgacca agacgcgaaa tggcgccggc   120 gggggaaca aggtggtgga cgagtgctac atccccaact acctcctgcc caagacccag    180
cccgagctgc agtgggcgtg gactaacatg gaggagtata agcgcgtg tctaaacctc     240 gcggagcgta acggctcgt ggcgcagcac ctgacccacg tcagccagac gcaggagcag    300
aacaaggaga atctgaaccc gaattctgac gcgcccgtga tcaggtcaaa aacctccgcg   360
cgctacatgg agctggtcgg gtggctggtg gaccggggca tcacctccga gaagcagtgg   420
```

```
<210> SEQ ID NO 152
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 152
atccaggagg accaggcctc gtacatctcc ttcaacgccg cctccaactc gcggtcccag    60
atcaaggccg cgctggacaa tgccggaaag atcatggcgc tgaccaaatc cgcgcccgac   120
tacctggtag gcccgtcctt acccgcggac attaaggcca accgcatcta ccgcatcctg   180
gagctcaacg gctacgaccc cgcctacgcc ggctccgtct tcctgggctg ggcgcagaaa   240
aagttcggta acgcaacac catctggctg tttgggcccg ccaccaccgg caagaccaac    300
atcgcggaag ccatagccca cgccgtgccc ttctacggct gcgtgaactg gaccaatgag   360 aactttcccct tcaacgattg c                                            381
```

```
<210> SEQ ID NO 153
<211> LENGTH: 762
<212> TYPE: DNA
<213> ORGANISM: Artificial Sequence
<220> FEATURE:
<223> OTHER INFORMATION: Synthetic polynucleotide

<400> SEQUENCE: 153
gtcgacaaga tggtgatctg gtgggaggag ggcaagatga ccgccaaggt cgtggagtcc    60
gccaaggcca ttctgggcgg aagcaaggtg cgcgtggacc aaaagtgcaa gtcctcggcc   120
cagatcgacc ccacgcccgt gatcgtcacc tccaacacca acatgtgcgc cgtgatcgac   180
gggaacagca ccaccttcga gcaccagcag ccgctgcagg accgcatgtt caagttcgag    240
```

```
ctcacccgcc gtctggagca cgactttggc aaggtgacca agcaggaagt caaagagttc    300
ttccgctggg ctcaggatca cgtgactgag gtggcgcatg agttctacgt cagaaagggc    360
ggagccacca aaagacccgc ccccagtgac gcggatataa gcgagcccaa gcgggcctgc    420
ccctcagttc cggagccatc gacgtcagac gcggaagcac cggtggactt tgcggacagg    480
taccaaaaca atgttctcg tcacgcgggc atgcttcaga tgctgtttcc ctgcaagaca    540
tgcgagagaa tgaatcagaa tttcaacgtc tgcttcacgc acggggtcag agactgctca    600
gagtgcttcc ccggcgcgtc agaatctcaa cccgtcgtca gaaaaagac gtatcagaaa     660 ctgtgcgcga ttcatcatct gctggggcgg cacccgaga ttgcgtgttc ggcctgcgat     720
ctcgtcaacg tggacttgga tgactgtgtt tctgagcaat aa                       762
```

<210> SEQ ID NO 154
<211> LENGTH: 492
<212> TYPE: DNA
<213> ORGANISM: Artificial Sequence
<220> FEATURE:
<223> OTHER INFORMATION: Synthetic polynucleotide

<400> SEQUENCE: 154

```
gtcgacaaga tggtgatctg gtgggaggag ggcaagatga ccgccaaggt cgtggagtcc     60
gccaaggcca ttctgggcgg aagcaaggtg cgcgtggacc aaaagtgcaa gtcctcggcc    120
cagatcgacc ccacgcccgt gatcgtcacc tccaacacca catgtgcgc cgtgatcgac    180 gggaacagca ccaccttcga gcaccagcag ccgctgcagg accgcatgtt caagttcgag    240
ctcacccgcc gtctggagca cgactttggc aaggtgacca agcaggaagt caaagagttc    300
ttccgctggg ctcaggatca cgtgactgag gtggcgcatg agttctacgt cagaaagggc    360
ggagccacca aaagacccgc ccccagtgac gcggatataa gcgagcccaa gcgggcctgc    420
ccctcagttc cggagccatc gacgtcagac gcggaagcac cggtggactt tgcggacagg    480
taccaaaaca aa                                                        492
```

<210> SEQ ID NO 155
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 155

```
tgttctcgtc acgcgggcat gcttcagatg ctgtttccct gcaagacatg cgagagaatg     60
aatcagaatt tcaacgtctg cttcacgcac ggggtcagag actgctcaga gtgcttcccc    120
ggcgcgtcag aatctcaacc cgtcgtcaga aaaagacgt atcagaaact gtgcgcgatt    180
catcatctgc tggggcgggc acccgagatt gcgtgttcgg cctgcgatct cgtcaacgtg    240
gacttggatg actgtgtttc tgagcaataa                                     270
```

<210> SEQ ID NO 156
<211> LENGTH: 102
<212> TYPE: PRT
<213> ORGANISM: Artificial Sequence
<220> FEATURE:
<223> OTHER INFORMATION: Synthetic polypeptide

<400> SEQUENCE: 156

Met Pro Gly Phe Tyr Glu Ile Val Ile Lys Val Pro Ser Asp Leu Asp
1               5                   10                  15

```
Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val His Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser
            100

<210> SEQ ID NO 157
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 157

Met Val Leu Gly Arg Phe Leu Ser Gln Ile Arg Asp Arg Leu Val Gln
1               5                   10                  15

Thr Ile Tyr Arg Gly Val Glu Pro Thr Leu Pro Asn Trp Phe Ala Val
            20                  25                  30

Thr Lys Thr Arg Asn Gly Ala Gly Gly Asn Lys Val Val Asp Glu
        35                  40                  45

Cys Tyr Ile Pro Asn Tyr Leu Leu Pro Lys Thr Gln Pro Glu Leu Gln
    50                  55                  60

Trp Ala Trp Thr Asn Met Glu Glu Tyr Ile Ser Ala Cys Leu Asn Leu
65                  70                  75                  80

Ala Glu Arg Lys Arg Leu Val Ala Gln His Leu Thr His Val Ser Gln
                85                  90                  95

Thr Gln Glu Gln Asn Lys Glu Asn Leu Asn Pro Asn Ser Asp Ala Pro
            100                 105                 110

Val Ile Arg Ser Lys Thr Ser Ala Arg Tyr Met Glu Leu Val Gly Trp
        115                 120                 125

Leu Val Asp Arg Gly Ile Thr Ser Glu Lys Gln Trp
    130                 135                 140

<210> SEQ ID NO 158
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 158

Ile Gln Glu Asp Gln Ala Ser Tyr Ile Ser Phe Asn Ala Ala Ser Asn
1               5                   10                  15

Ser Arg Ser Gln Ile Lys Ala Ala Leu Asp Asn Ala Gly Lys Ile Met
            20                  25                  30

Ala Leu Thr Lys Ser Ala Pro Asp Tyr Leu Val Gly Pro Ser Leu Pro
        35                  40                  45

Ala Asp Ile Lys Ala Asn Arg Ile Tyr Arg Ile Leu Glu Leu Asn Gly
    50                  55                  60

Tyr Asp Pro Ala Tyr Ala Gly Ser Val Phe Leu Gly Trp Ala Gln Lys
65                  70                  75                  80
```

-continued

```
Lys Phe Gly Lys Arg Asn Thr Ile Trp Leu Phe Gly Pro Ala Thr Thr
                 85                  90                  95
Gly Lys Thr Asn Ile Ala Glu Ala Ile Ala His Ala Val Pro Phe Tyr
            100                 105                 110
Gly Cys Val Asn Trp Thr Asn Glu Asn Phe Pro Phe Asn Asp Cys
        115                 120                 125
```

<210> SEQ ID NO 159
<211> LENGTH: 253
<212> TYPE: PRT
<213> ORGANISM: Artificial Sequence
<220> FEATURE:
<223> OTHER INFORMATION: Synthetic polypeptide

<400> SEQUENCE: 159

```
Val Asp Lys Met Val Ile Trp Trp Glu Glu Gly Lys Met Thr Ala Lys
1               5                   10                  15
Val Val Glu Ser Ala Lys Ala Ile Leu Gly Gly Ser Lys Val Arg Val
            20                  25                  30
Asp Gln Lys Cys Lys Ser Ser Ala Gln Ile Asp Pro Thr Pro Val Ile
        35                  40                  45
Val Thr Ser Asn Thr Asn Met Cys Ala Val Ile Asp Gly Asn Ser Thr
    50                  55                  60
Thr Phe Glu His Gln Gln Pro Leu Gln Asp Arg Met Phe Lys Phe Glu
65                  70                  75                  80
Leu Thr Arg Arg Leu Glu His Asp Phe Gly Lys Val Thr Lys Gln Glu
                85                  90                  95
Val Lys Glu Phe Phe Arg Trp Ala Gln Asp His Val Thr Glu Val Ala
            100                 105                 110
His Glu Phe Tyr Val Arg Lys Gly Gly Ala Thr Lys Arg Pro Ala Pro
        115                 120                 125
Ser Asp Ala Asp Ile Ser Glu Pro Lys Arg Ala Cys Pro Ser Val Pro
    130                 135                 140
Glu Pro Ser Thr Ser Asp Ala Glu Ala Pro Val Asp Phe Ala Asp Arg
145                 150                 155                 160
Tyr Gln Asn Lys Cys Ser Arg His Ala Gly Met Leu Gln Met Leu Phe
                165                 170                 175
Pro Cys Lys Thr Cys Glu Arg Met Asn Gln Asn Phe Asn Val Cys Phe
            180                 185                 190
Thr His Gly Val Arg Asp Cys Ser Glu Cys Phe Pro Gly Ala Ser Glu
        195                 200                 205
Ser Gln Pro Val Val Arg Lys Lys Thr Tyr Gln Lys Leu Cys Ala Ile
    210                 215                 220
His His Leu Leu Gly Arg Ala Pro Glu Ile Ala Cys Ser Ala Cys Asp
225                 230                 235                 240
Leu Val Asn Val Asp Leu Asp Asp Cys Val Ser Glu Gln
                245                 250
```

<210> SEQ ID NO 160
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 160

```
Val Asp Lys Met Val Ile Trp Trp Glu Glu Gly Lys Met Thr Ala Lys
```

```
                1               5                   10                  15
Val Val Glu Ser Ala Lys Ala Ile Leu Gly Gly Ser Lys Val Arg Val
                20                  25                  30

Asp Gln Lys Cys Lys Ser Ser Ala Gln Ile Asp Pro Thr Pro Val Ile
                35                  40                  45

Val Thr Ser Asn Thr Asn Met Cys Ala Val Ile Asp Gly Asn Ser Thr
    50                  55                  60

Thr Phe Glu His Gln Gln Pro Leu Gln Asp Arg Met Phe Lys Phe Glu
65                  70                  75                  80

Leu Thr Arg Arg Leu Glu His Asp Phe Gly Lys Val Thr Lys Gln Glu
                85                  90                  95

Val Lys Glu Phe Phe Arg Trp Ala Gln Asp His Val Thr Glu Val Ala
                100                 105                 110

His Glu Phe Tyr Val Arg Lys Gly Gly Ala Thr Lys Arg Pro Ala Pro
                115                 120                 125

Ser Asp Ala Asp Ile Ser Glu Pro Lys Arg Ala Cys Pro Ser Val Pro
            130                 135                 140

Glu Pro Ser Thr Ser Asp Ala Glu Ala Pro Val Asp Phe Ala Asp Arg
145                 150                 155                 160

Tyr Gln Asn Lys

<210> SEQ ID NO 161
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 161

Cys Ser Arg His Ala Gly Met Leu Gln Met Leu Phe Pro Cys Lys Thr
1               5                   10                  15

Cys Glu Arg Met Asn Gln Asn Phe Asn Val Cys Phe Thr His Gly Val
                20                  25                  30

Arg Asp Cys Ser Glu Cys Phe Pro Gly Ala Ser Glu Ser Gln Pro Val
            35                  40                  45

Val Arg Lys Lys Thr Tyr Gln Lys Leu Cys Ala Ile His His Leu Leu
        50                  55                  60

Gly Arg Ala Pro Glu Ile Ala Cys Ser Ala Cys Asp Leu Val Asn Val
65                  70                  75                  80

Asp Leu Asp Asp Cys Val Ser Glu Gln
                85

<210> SEQ ID NO 162
<211> LENGTH: 306
<212> TYPE: DNA
<213> ORGANISM: Artificial Sequence
<220> FEATURE:
<223> OTHER INFORMATION: Synthetic polynucleotide

<400> SEQUENCE: 162
atgccggggt tctacgaggt ggtgatcaag gtgcccagcg acctggacga gcacctgccc      60
ggcatttctg actcctttgt gaactgggtg gccgagaagg aatgggagtt gccccccggat    120 tctgacatgg atcagaatct gattgagcag gcacccctga ccgtggccga aagctgcag     180 cgcgagttcc tggtggaatg cgccgagtg agtaaattc tggaggccaa gttttttgtg      240
cagtttgaaa aggggactc gtactttcat ttgcatattc tgattgaaat taccggcgtg     300
``` aaatcc                                                                   306

<210> SEQ ID NO 163
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 163
atggtggtgg gccgctacgt gagtcagatt agggataaac tgatccagcg catctaccgc    60
ggggtcgagc cccagctgcc caactggttc gcggtcacaa agacccgaaa tggcgccgga   120
ggcgggaaca aggtggtgga cgagtgctac atccccaact acctgctccc caaggtccag   180
cccgagcttc agtgggcgtg gactaacatg gaggagtata taagcgcctg tttgaacctc   240
gcggagcgta acggctcgt ggcgcagcac ctgacgcacg tctcccagac ccaggagggc    300
gacaaggaga atctgaaccc gaattctgac gcgccggtga tccggtcaaa aacctccgcc   360
aggtacatgg agctggtcgg gtggctggtg gacaagggca tcacgtccga aagcagtgg    420

<210> SEQ ID NO 164
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 164
atccaggagg accaggcctc gtacatctcc ttcaacgcgg cctccaactc ccggtcgcag    60
atcaaggcgg ccctggacaa tgcctccaaa atcatgagcc tcaccaaaac ggctccggac   120
tatctcatcg ggcagcagcc cgtgggggac attaccacca accggatcta caaaatcctg   180
gaactgaacg ggtacgaccc ccagtacgcc gcctccgtct ttctcggctg ggcccagaaa   240
aagtttggaa agcgcaacac catctggctg tttgggcccg ccaccaccgg caagaccaac   300
atcgcggaag ccatcgccca cgcggtcccc ttctacggct gcgtcaactg gaccaatgag   360
aactttcccct tcaacgactg c                                             381

<210> SEQ ID NO 165
<211> LENGTH: 759
<212> TYPE: DNA
<213> ORGANISM: Artificial Sequence
<220> FEATURE:
<223> OTHER INFORMATION: Synthetic polynucleotide

<400> SEQUENCE: 165
gtcgacaaaa tggtgatttg gtgggaggag ggcaagatga ccgccaaggt cgtagagtcc    60
gccaaggcca ttctgggcgg cagcaaggtg cgcgtggacc aaaaatgcaa ggcctctgcg   120
cagatcgacc ccaccccgt gatcgtcacc tccaacacca catgtgcgc cgtgattgac     180
gggaacagca ccaccttcga gcaccagcag cccctgcagg accggatgtt caagtttgaa   240
ctcacccgcc gcctcgacca cgactttggc aaggtcacca gcaggaagt caaggacttt   300
ttccggtggg cggctgatca cgtgactgac gtggctcatg agttttacgt cacaaagggt   360
ggagctaaga aaaggcccgc cccctctgac gaggatataa gcgagcccaa gcggccgcgc   420
gtgtcatttg cgcagccgga gacgtcagac gcggaagctc ccggagactt cgccgacagg   480
taccaaaaca aatgttctcg tcacgcgggt atgctgcaga tgctctttcc ctgcaagacg   540
tgcgagagaa tgaatcagaa ttccaacgtc tgcttcacgc acgtcagaa agattgcggg   600

```
gagtgctttc ccgggtcaga atctcaaccg gtttctgtcg tcagaaaaac gtatcagaaa      660
ctgtgcatcc ttcatcagct ccggggggca cccgagatcg cctgctctgc ttgcgaccaa      720
ctcaaccccg atttggacga ttgccaattt gagcaataa                             759
```

<210> SEQ ID NO 166
<211> LENGTH: 492
<212> TYPE: DNA
<213> ORGANISM: Artificial Sequence
<220> FEATURE:
<223> OTHER INFORMATION: Synthetic polynucleotide

<400> SEQUENCE: 166

```
gtcgacaaaa tggtgatttg gtgggaggag ggcaagatga ccgccaaggt cgtagagtcc       60
gccaaggcca ttctgggcgg cagcaaggtg cgcgtggacc aaaaatgcaa ggcctctgcg      120
cagatcgacc ccaccccgt gatcgtcacc tccaacacca acatgtgcgc cgtgattgac      180
gggaacagca ccaccttcga gcaccagcag cccctgcagg accggatgtt caagtttgaa      240
ctcacccgcc gcctcgacca cgactttggc aaggtcacca agcaggaagt caaggacttt      300
ttccggtggg cggctgatca cgtgactgac gtggctcatg agttttacgt cacaaagggt      360
ggagctaaga aaaggcccgc cccctctgac gaggatataa gcgagcccaa gcggccgcgc      420
gtgtcatttg cgcagccgga gacgtcagac gcggaagctc ccggagactt cgccgacagg      480
taccaaaaca aa                                                         492
```

<210> SEQ ID NO 167
<211> LENGTH: 267
<212> TYPE: DNA
<213> ORGANISM: Artificial Sequence
<220> FEATURE:
<223> OTHER INFORMATION: Synthetic polynucleotide

<400> SEQUENCE: 167

```
tgttctcgtc acgcgggtat gctgcagatg ctctttccct gcaagacgtg cgagagaatg       60
aatcagaatt ccaacgtctg cttcacgcac ggtcagaaag attgcgggga gtgctttccc      120
gggtcagaat ctcaaccggt ttctgtcgtc agaaaaacgt atcagaaact gtgcatcctt      180
catcagctcc gggggcacc cgagatcgcc tgctctgctt gcgaccaact caaccccgat      240
ttggacgatt gccaatttga gcaataa                                         267
```

<210> SEQ ID NO 168
<211> LENGTH: 102
<212> TYPE: PRT
<213> ORGANISM: Artificial Sequence
<220> FEATURE:
<223> OTHER INFORMATION: Synthetic polypeptide

<400> SEQUENCE: 168

```
Met Pro Gly Phe Tyr Glu Val Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Gln Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Phe Leu Glu Ala Lys Phe Phe Val
65                  70                  75                  80
```

Gln Phe Glu Lys Gly Asp Ser Tyr Phe His Leu His Ile Leu Ile Glu
                85                  90                  95

Ile Thr Gly Val Lys Ser
            100

<210> SEQ ID NO 169
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 169

Met Val Val Gly Arg Tyr Val Ser Gln Ile Arg Asp Lys Leu Ile Gln
1               5                   10                  15

Arg Ile Tyr Arg Gly Val Glu Pro Gln Leu Pro Asn Trp Phe Ala Val
            20                  25                  30

Thr Lys Thr Arg Asn Gly Ala Gly Gly Asn Lys Val Val Asp Glu
        35                  40                  45

Cys Tyr Ile Pro Asn Tyr Leu Leu Pro Lys Val Gln Pro Glu Leu Gln
    50                  55                  60

Trp Ala Trp Thr Asn Met Glu Glu Tyr Ile Ser Ala Cys Leu Asn Leu
65                  70                  75                  80

Ala Glu Arg Lys Arg Leu Val Ala Gln His Leu Thr His Val Ser Gln
                85                  90                  95

Thr Gln Glu Gly Asp Lys Glu Asn Leu Asn Pro Asn Ser Asp Ala Pro
            100                 105                 110

Val Ile Arg Ser Lys Thr Ser Ala Arg Tyr Met Glu Leu Val Gly Trp
        115                 120                 125

Leu Val Asp Lys Gly Ile Thr Ser Glu Lys Gln Trp
    130                 135                 140

<210> SEQ ID NO 170
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 170

Ile Gln Glu Asp Gln Ala Ser Tyr Ile Ser Phe Asn Ala Ala Ser Asn
1               5                   10                  15

Ser Arg Ser Gln Ile Lys Ala Ala Leu Asp Asn Ala Ser Lys Ile Met
            20                  25                  30

Ser Leu Thr Lys Thr Ala Pro Asp Tyr Leu Ile Gly Gln Gln Pro Val
        35                  40                  45

Gly Asp Ile Thr Thr Asn Arg Ile Tyr Lys Ile Leu Glu Leu Asn Gly
    50                  55                  60

Tyr Asp Pro Gln Tyr Ala Ala Ser Val Phe Leu Gly Trp Ala Gln Lys
65                  70                  75                  80

Lys Phe Gly Lys Arg Asn Thr Ile Trp Leu Phe Gly Pro Ala Thr Thr
                85                  90                  95

Gly Lys Thr Asn Ile Ala Glu Ala Ile Ala His Ala Val Pro Phe Tyr
            100                 105                 110

Gly Cys Val Asn Trp Thr Asn Glu Asn Phe Pro Phe Asn Asp Cys
        115                 120                 125

```
<210> SEQ ID NO 171
<211> LENGTH: 252
<212> TYPE: PRT
<213> ORGANISM: Artificial Sequence
<220> FEATURE:
<223> OTHER INFORMATION: Synthetic polypeptide

<400> SEQUENCE: 171

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ala Ser Ala Gln Ile Asp Pro Thr Pro Val Ile
        35                  40                  45

Val Thr Ser Asn Thr Asn Met Cys Ala Val Ile Asp Gly Asn Ser Thr
    50                  55                  60

Thr Phe Glu His Gln Gln Pro Leu Gln Asp Arg Met Phe Lys Phe Glu
65                  70                  75                  80

Leu Thr Arg Arg Leu Asp His Asp Phe Gly Lys Val Thr Lys Gln Glu
                85                  90                  95

Val Lys Asp Phe Phe Arg Trp Ala Ala Asp His Val Thr Asp Val Ala
            100                 105                 110

His Glu Phe Tyr Val Thr Lys Gly Gly Ala Lys Lys Arg Pro Ala Pro
        115                 120                 125

Ser Asp Glu Asp Ile Ser Glu Pro Lys Arg Pro Arg Val Ser Phe Ala
    130                 135                 140

Gln Pro Glu Thr Ser Asp Ala Glu Ala Pro Gly Asp Phe Ala Asp Arg
145                 150                 155                 160

Tyr Gln Asn Lys Cys Ser Arg His Ala Gly Met Leu Gln Met Leu Phe
                165                 170                 175

Pro Cys Lys Thr Cys Glu Arg Met Asn Gln Asn Ser Asn Val Cys Phe
            180                 185                 190

Thr His Gly Gln Lys Asp Cys Gly Glu Cys Phe Pro Gly Ser Glu Ser
        195                 200                 205

Gln Pro Val Ser Val Val Arg Lys Thr Tyr Gln Lys Leu Cys Ile Leu
    210                 215                 220

His Gln Leu Arg Gly Ala Pro Glu Ile Ala Cys Ser Ala Cys Asp Gln
225                 230                 235                 240

Leu Asn Pro Asp Leu Asp Cys Gln Phe Glu Gln
                245                 250

<210> SEQ ID NO 172
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 172

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ala Ser Ala Gln Ile Asp Pro Thr Pro Val Ile
        35                  40                  45

Val Thr Ser Asn Thr Asn Met Cys Ala Val Ile Asp Gly Asn Ser Thr
    50                  55                  60
```

Thr Phe Glu His Gln Gln Pro Leu Gln Asp Arg Met Phe Lys Phe Glu
 65                  70                  75                  80

Leu Thr Arg Arg Leu Asp His Asp Phe Gly Lys Val Thr Lys Gln Glu
                 85                  90                  95

Val Lys Asp Phe Phe Arg Trp Ala Ala Asp His Val Thr Asp Val Ala
            100                 105                 110

His Glu Phe Tyr Val Thr Lys Gly Gly Ala Lys Lys Arg Pro Ala Pro
        115                 120                 125

Ser Asp Glu Asp Ile Ser Glu Pro Lys Arg Pro Arg Val Ser Phe Ala
    130                 135                 140

Gln Pro Glu Thr Ser Asp Ala Glu Ala Pro Gly Asp Phe Ala Asp Arg
145                 150                 155                 160

Tyr Gln Asn Lys

<210> SEQ ID NO 173
<211> LENGTH: 88
<212> TYPE: PRT
<213> ORGANISM: Artificial Sequence
<220> FEATURE:
<223> OTHER INFORMATION: Synthetic polypeptide

<400> SEQUENCE: 173

Cys Ser Arg His Ala Gly Met Leu Gln Met Leu Phe Pro Cys Lys Thr
1               5                   10                  15

Cys Glu Arg Met Asn Gln Asn Ser Asn Val Cys Phe Thr His Gly Gln
                20                  25                  30

Lys Asp Cys Gly Glu Cys Phe Pro Gly Ser Glu Ser Gln Pro Val Ser
            35                  40                  45

Val Val Arg Lys Thr Tyr Gln Lys Leu Cys Ile Leu His Gln Leu Arg
    50                  55                  60

Gly Ala Pro Glu Ile Ala Cys Ser Ala Cys Asp Gln Leu Asn Pro Asp
65                  70                  75                  80

Leu Asp Asp Cys Gln Phe Glu Gln
                85

<210> SEQ ID NO 174
<211> LENGTH: 306
<212> TYPE: DNA
<213> ORGANISM: Artificial Sequence
<220> FEATURE:
<223> OTHER INFORMATION: Synthetic polynucleotide

<400> SEQUENCE: 174
atgccgggat tctacgagat tgtcctgaag gtgcccagcg acctggacga gcacctgcct      60
ggcatttctg actcttttgt aaactgggtg gcggagaagg aatgggagct gccgccggat     120
tctgacatgg atctgaatct gattgagcag gcaccctaa ccgtggccga aaagctgcaa      180
cgcgaattcc tggtcgagtg gcgccgcgtg agtaaggccc cggaggccct cttctttgtt     240
cagttcgaga aggggacag ctacttccac ctacacattc tggtggagac cgtgggcgtg      300
aaatcc                                                                306

<210> SEQ ID NO 175
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 175

```
atggtggtgg gccgctacgt gagccagatt aaagagaagc tggtgacccg catctaccgc    60
ggggtcgagc cgcagcttcc gaactggttc gcggtgacca agacgcgtaa tggcgccgga   120
ggcgggaaca aggtggtgga cgactgctac atccccaact acctgctccc caagacccag   180
cccgagctcc agtgggcgtg gactaatatg gaccagtatt taagcgcctg tttgaatctc   240
gcggagcgta acggctggt ggcgcagcat ctgacgcacg tgtcgcagac gcaggagcag    300
aacaaagaga accagaatcc caattctgac gcgccggtga tcagatcaaa aacctccgcg   360
aggtacatgg agctggtcgg gtggctggtg gaccgcggga tcacgtcaga aaagcaatgg   420
```

<210> SEQ ID NO 176
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 176

```
atccaggagg accaggcctc ttacatctcc ttcaacgccg cctccaactc gcggtcacaa    60
atcaaggccg cactggacaa tgcctccaaa tttatgagcc tgacaaaaac ggctccggac   120
tacctggtgg gaaacaaccc gccggaggac attaccagca accggatcta caaaatcctc   180
gagatgaacg gtacgatcc gcagtacgcg gcctccgtct tcctgggctg ggcgcaaaag   240
aagttcggga agaggaacac catctggctc tttgggccgg ccacgacggg taaaaccaac   300
atcgctgaag ctatcgccca cgccgtgccc ttttacggct gcgtgaactg gaccaatgag   360
aactttccgt tcaacgattg c                                              381
```

<210> SEQ ID NO 177
<211> LENGTH: 765
<212> TYPE: DNA
<213> ORGANISM: Artificial Sequence
<220> FEATURE:
<223> OTHER INFORMATION: Synthetic polynucleotide

<400> SEQUENCE: 177

```
gtcgacaaga tggtgatctg gtgggaggag ggcaagatga cggccaaggt cgtggagtcc    60
gccaaggcca ttctgggcgg aagcaaggtg cgcgtggacc aaaagtgcaa gtcatcggcc   120
cagatcgacc caactcccgt catcgtcacc tccaacacca catgtgcgc ggtcatcgac    180 ggaaattcca ccaccttcga gcaccaacaa ccactccaag accggatgtt caagttcgag   240
ctcaccaagc gcctggagca cgactttggc aaggtcacca agcaggaagt caaggacttt   300
ttccggtggg cgtcagatca cgtgactgag gtgtctcacg agttttacgt cagaaagggt   360
ggagctagaa agaggcccgc ccccaatgac gcagatataa gtgagcccaa gcgggcctgt   420
ccgtcagttg cgcagccatc gacgtcagac gcggaagctc cggtggacta cgcggacagg   480
taccaaaaca aatgttctcg tcacgtgggc atgaatctga tgcttttttcc ctgccggcaa   540 tgcgagagaa tgaatcagaa tgtggacatt tgcttcacgc acgggtcat ggactgtgcc     600 gagtgcttcc ccgtgtcaga atctcaaccc gtgtctgtcg tcagaaagcg gacatatcag   660
aaactgtgtc cgattcatca catcatgggg agggcgcccg aggtggcttg ttcggcctgc   720
gatctggcca atgtggactt ggatgactgt gacatggagc aataa                   765
```

<210> SEQ ID NO 178
<211> LENGTH: 492
<212> TYPE: DNA

<213> ORGANISM: Artificial Sequence
<220> FEATURE:
<223> OTHER INFORMATION: Synthetic polynucleotide

<400> SEQUENCE: 178

```
gtcgacaaga tggtgatctg gtgggaggag ggcaagatga cggccaaggt cgtggagtcc      60
gccaaggcca ttctgggcgg aagcaaggtg cgcgtggacc aaaagtgcaa gtcatcggcc     120
cagatcgacc caactcccgt catcgtcacc tccaacacca acatgtgcgc ggtcatcgac     180
ggaaattcca ccaccttcga gcaccaacaa ccactccaag accggatgtt caagttcgag     240
ctcaccaagc gcctggagca cgactttggc aaggtcacca agcaggaagt caaggacttt     300
ttccggtggg cgtcagatca cgtgactgag gtgtctcacg agttttacgt cagaaagggt     360
ggagctagaa agaggcccgc ccccaatgac gcagatataa gtgagcccaa gcgggcctgt     420
ccgtcagttg cgcagccatc gacgtcagac gcggaagctc cggtggacta cgcggacagg     480
taccaaaaca aa                                                         492
```

<210> SEQ ID NO 179
<211> LENGTH: 273
<212> TYPE: DNA
<213> ORGANISM: Artificial Sequence
<220> FEATURE:
<223> OTHER INFORMATION: Synthetic polynucleotide

<400> SEQUENCE: 179

```
tgttctcgtc acgtgggcat gaatctgatg cttttccct gccggcaatg cgagagaatg       60
aatcagaatg tggacatttg cttcacgcac ggggtcatgg actgtgccga gtgcttcccc     120
gtgtcagaat ctcaacccgt gtctgtcgtc agaaagcgga catatcagaa actgtgtccg     180
attcatcaca tcatggggag ggcgcccgag gtggcttgtt cggcctgcga tctggccaat     240
gtggacttgg atgactgtga catggagcaa taa                                   273
```

<210> SEQ ID NO 180
<211> LENGTH: 102
<212> TYPE: PRT
<213> ORGANISM: Artificial Sequence
<220> FEATURE:
<223> OTHER INFORMATION: Synthetic polypeptide

<400> SEQUENCE: 180

```
Met Pro Gly Phe Tyr Glu Ile Val Leu Lys Val Pro Ser Asp Leu Asp
1               5                   10                  15
Glu His Leu Pro Gly Ile Ser Asp Ser Phe Val Asn Trp Val Ala Glu
            20                  25                  30
Lys Glu Trp Glu Leu Pro Pro Asp Ser Asp Met Asp Leu Asn Leu Ile
        35                  40                  45
Glu Gln Ala Pro Leu Thr Val Ala Glu Lys Leu Gln Arg Glu Phe Leu
    50                  55                  60
Val Glu Trp Arg Arg Val Ser Lys Ala Pro Glu Ala Leu Phe Phe Val
65                  70                  75                  80
Gln Phe Glu Lys Gly Asp Ser Tyr Phe His Leu His Ile Leu Val Glu
                85                  90                  95
Thr Val Gly Val Lys Ser
            100
```

<210> SEQ ID NO 181
<211> LENGTH: 140
<212> TYPE: PRT

<213> ORGANISM: Artificial Sequence
<220> FEATURE:
<223> OTHER INFORMATION: Synthetic polypeptide

<400> SEQUENCE: 181

Met Val Val Gly Arg Tyr Val Ser Gln Ile Lys Glu Lys Leu Val Thr
1               5                   10                  15

Arg Ile Tyr Arg Gly Val Glu Pro Gln Leu Pro Asn Trp Phe Ala Val
            20                  25                  30

Thr Lys Thr Arg Asn Gly Ala Gly Gly Asn Lys Val Asp Asp
        35                  40                  45

Cys Tyr Ile Pro Asn Tyr Leu Leu Pro Lys Thr Gln Pro Glu Leu Gln
50                  55                  60

Trp Ala Trp Thr Asn Met Asp Gln Tyr Leu Ser Ala Cys Leu Asn Leu
65                  70                  75                  80

Ala Glu Arg Lys Arg Leu Val Ala Gln His Leu Thr His Val Ser Gln
                85                  90                  95

Thr Gln Glu Gln Asn Lys Glu Asn Gln Asn Pro Asn Ser Asp Ala Pro
            100                 105                 110

Val Ile Arg Ser Lys Thr Ser Ala Arg Tyr Met Glu Leu Val Gly Trp
            115                 120                 125

Leu Val Asp Arg Gly Ile Thr Ser Glu Lys Gln Trp
            130                 135                 140

<210> SEQ ID NO 182
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 182

Ile Gln Glu Asp Gln Ala Ser Tyr Ile Ser Phe Asn Ala Ala Ser Asn
1               5                   10                  15

Ser Arg Ser Gln Ile Lys Ala Ala Leu Asp Asn Ala Ser Lys Phe Met
            20                  25                  30

Ser Leu Thr Lys Thr Ala Pro Asp Tyr Leu Val Gly Asn Asn Pro Pro
        35                  40                  45

Glu Asp Ile Thr Ser Asn Arg Ile Tyr Lys Ile Leu Glu Met Asn Gly
50                  55                  60

Tyr Asp Pro Gln Tyr Ala Ala Ser Val Phe Leu Gly Trp Ala Gln Lys
65                  70                  75                  80

Lys Phe Gly Lys Arg Asn Thr Ile Trp Leu Phe Gly Pro Ala Thr Thr
                85                  90                  95

Gly Lys Thr Asn Ile Ala Glu Ala Ile Ala His Ala Val Pro Phe Tyr
            100                 105                 110

Gly Cys Val Asn Trp Thr Asn Glu Asn Phe Pro Phe Asn Asp Cys
            115                 120                 125

<210> SEQ ID NO 183
<211> LENGTH: 254
<212> TYPE: PRT
<213> ORGANISM: Artificial Sequence
<220> FEATURE:
<223> OTHER INFORMATION: Synthetic polypeptide

<400> SEQUENCE: 183

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Ala Gln Ile Asp Pro Thr Pro Val Ile
        35                  40                  45

Val Thr Ser Asn Thr Asn Met Cys Ala Val Ile Asp Gly Asn Ser Thr
 50                  55                  60

Thr Phe Glu His Gln Gln Pro Leu Gln Asp Arg Met Phe Lys Phe Glu
65                  70                  75                  80

Leu Thr Lys Arg Leu Glu His Asp Phe Gly Lys Val Thr Lys Gln Glu
                85                  90                  95

Val Lys Asp Phe Phe Arg Trp Ala Ser Asp His Val Thr Glu Val Ser
            100                 105                 110

His Glu Phe Tyr Val Arg Lys Gly Gly Ala Arg Lys Arg Pro Ala Pro
        115                 120                 125

Asn Asp Ala Asp Ile Ser Glu Pro Lys Arg Ala Cys Pro Ser Val Ala
130                 135                 140

Gln Pro Ser Thr Ser Asp Ala Glu Ala Pro Val Asp Tyr Ala Asp Arg
145                 150                 155                 160

Tyr Gln Asn Lys Cys Ser Arg His Val Gly Met Asn Leu Met Leu Phe
                165                 170                 175

Pro Cys Arg Gln Cys Glu Arg Met Asn Gln Asn Val Asp Ile Cys Phe
            180                 185                 190

Thr His Gly Val Met Asp Cys Ala Glu Cys Phe Pro Val Ser Glu Ser
        195                 200                 205

Gln Pro Val Ser Val Arg Lys Arg Thr Tyr Gln Lys Leu Cys Pro
210                 215                 220

Ile His His Ile Met Gly Arg Ala Pro Glu Val Ala Cys Ser Ala Cys
225                 230                 235                 240

Asp Leu Ala Asn Val Asp Leu Asp Asp Cys Asp Met Glu Gln
                245                 250

<210> SEQ ID NO 184
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 184

Val Asp Lys Met Val Ile Trp Trp Glu Glu Gly Lys Met Thr Ala Lys
1               5                   10                  15

Val Val Glu Ser Ala Lys Ala Ile Leu Gly Gly Ser Lys Val Arg Val
            20                  25                  30

Asp Gln Lys Cys Lys Ser Ser Ala Gln Ile Asp Pro Thr Pro Val Ile
        35                  40                  45

Val Thr Ser Asn Thr Asn Met Cys Ala Val Ile Asp Gly Asn Ser Thr
 50                  55                  60

Thr Phe Glu His Gln Gln Pro Leu Gln Asp Arg Met Phe Lys Phe Glu
65                  70                  75                  80

Leu Thr Lys Arg Leu Glu His Asp Phe Gly Lys Val Thr Lys Gln Glu
                85                  90                  95

Val Lys Asp Phe Phe Arg Trp Ala Ser Asp His Val Thr Glu Val Ser
            100                 105                 110

His Glu Phe Tyr Val Arg Lys Gly Gly Ala Arg Lys Arg Pro Ala Pro
        115                 120                 125

```
Asn Asp Ala Asp Ile Ser Glu Pro Lys Arg Ala Cys Pro Ser Val Ala
            130                 135                 140

Gln Pro Ser Thr Ser Asp Ala Glu Ala Pro Val Asp Tyr Ala Asp Arg
145                 150                 155                 160

Tyr Gln Asn Lys

<210> SEQ ID NO 185
<211> LENGTH: 90
<212> TYPE: PRT
<213> ORGANISM: Artificial Sequence
<220> FEATURE:
<223> OTHER INFORMATION: Synthetic polypeptide

<400> SEQUENCE: 185

Cys Ser Arg His Val Gly Met Asn Leu Met Leu Phe Pro Cys Arg Gln
1               5                   10                  15

Cys Glu Arg Met Asn Gln Asn Val Asp Ile Cys Phe Thr His Gly Val
            20                  25                  30

Met Asp Cys Ala Glu Cys Phe Pro Val Ser Glu Ser Gln Pro Val Ser
        35                  40                  45

Val Val Arg Lys Arg Thr Tyr Gln Lys Leu Cys Pro Ile His His Ile
    50                  55                  60

Met Gly Arg Ala Pro Glu Val Ala Cys Ser Ala Cys Asp Leu Ala Asn
65                  70                  75                  80

Val Asp Leu Asp Asp Cys Asp Met Glu Gln
                85                  90

<210> SEQ ID NO 186
<211> LENGTH: 174
<212> TYPE: DNA
<213> ORGANISM: Artificial Sequence
<220> FEATURE:
<223> OTHER INFORMATION: Synthetic polynucleotide

<400> SEQUENCE: 186
aagtccatgg tgctaggccg cttcctgagt cagattcggg aaaagctggt ccagaccatc      60
taccgcgggg tcgagcccac cttgcccaac tggttcgcgg tgaccaagac gcgtaatggc     120 gccgggggg ggaacaaggt ggtggacgag tgctacatcc ccaactacct cctg            174

<210> SEQ ID NO 187
<211> LENGTH: 180
<212> TYPE: DNA
<213> ORGANISM: Artificial Sequence
<220> FEATURE:
<223> OTHER INFORMATION: Synthetic polynucleotide

<400> SEQUENCE: 187
gtcctccatc aaccctaca tcgtgagcag gtggtggaac aaggggggc ggccgcggta       60 atggcgcaga aaccagtggc gcttggtcaa cccgttccac cccgagctgg ggcgcccatc    120
taccagacct ggttcgaaaa gggcttagac tgagtccttc gccggatcgt ggtacctgaa    180
```